United States Patent
Huang et al.

(10) Patent No.: US 10,988,433 B2
(45) Date of Patent: Apr. 27, 2021

(54) CYCLOHEXYL GPR40 AGONISTS FOR THE TREATMENT OF TYPE II DIABETES

(71) Applicant: Janssen Pharmaceutica NV, Beerse (BE)

(72) Inventors: Hui Huang, Blue Bell, PA (US); James C. Lanter, Audubon, PA (US); Sanath K. Meegalla, Garnet Valley, PA (US); Mark R. Player, Phoenixville, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/342,697

(22) PCT Filed: Oct. 24, 2017

(86) PCT No.: PCT/US2017/057979
§ 371 (c)(1),
(2) Date: Apr. 17, 2019

(87) PCT Pub. No.: WO2018/081047
PCT Pub. Date: May 3, 2018

(65) Prior Publication Data
US 2020/0039914 A1   Feb. 6, 2020

Related U.S. Application Data

(60) Provisional application No. 62/561,298, filed on Sep. 21, 2017, provisional application No. 62/412,465, filed on Oct. 25, 2016.

(51) Int. Cl.

| | | |
|---|---|---|
| *C07D 213/64* | (2006.01) | |
| *C07C 59/72* | (2006.01) | |
| *A61P 3/10* | (2006.01) | |
| *C07C 229/42* | (2006.01) | |
| *C07D 257/04* | (2006.01) | |
| *C07D 263/20* | (2006.01) | |
| *C07D 401/12* | (2006.01) | |
| *C07D 401/14* | (2006.01) | |

(52) U.S. Cl.
CPC .............. *C07C 59/72* (2013.01); *A61P 3/10* (2018.01); *C07C 229/42* (2013.01); *C07D 213/64* (2013.01); *C07D 257/04* (2013.01); *C07D 263/20* (2013.01); *C07D 401/12* (2013.01); *C07D 401/14* (2013.01)

(58) Field of Classification Search
CPC ...................................................... C07C 59/72
See application file for complete search history.

(56) References Cited

U.S. PATENT DOCUMENTS 7,582,803 B2   9/2009   Akerman et al.

FOREIGN PATENT DOCUMENTS

| WO | WO 2009/151800 A1 | 12/2009 |
|---|---|---|
| WO | WO 2015/119899 A1 | 8/2015 |

OTHER PUBLICATIONS

Alvarado et al., "Stereoselective α-Fluorination of N-Acyloxazolidinones at Room Temperature within 1 h.", J. Org. Chem., 2014, pp. 6206-6220, vol. 79(13).
Boudewijn L. M. de Jonge, et al., "Discovery of Inhibitors of 4'-Phosphopantetheine Adenylyltransferase (PPAT) to Validate PPAT as a Target for Antibacterial Therapy.", Antimicrobial Agents and Chemotherapy, Dec. 2013, pp. 6005-6015, vol. 57(12)
Briscoe et al., "The Orphan G Protein-coupled Receptor GPR40 Is Activated by Medium and Long Chain Fatty Acids.", J. Biol. Chem., 2003, pp. 11303-11311, vol. 278.
Edfalk et al., "Gpr40 is Expressed in Enteroendocrine Cells and Mediates Free Fatty Acid Stimulation of Incretin Secretion.", Diabetes, 2008, pp. 2280-2287, vol. 57.
Itoh et al., "Free fatty acids regulate insulin secretion from pancreatic β cells through GPR40", Nature, Mar. 13, 2003, pp. 173-176, vol. 422.
Kotarsky et al., "A human cell surface receptor activated by free fatty acids and thiazolidinedione drugs.", Biochem. Biophys. Res. Commun., 2003, pp. 406-410, vol. 301.

(Continued)

*Primary Examiner* — Paul V Ward

(57) ABSTRACT

Disclosed are compounds, compositions and methods for treating of disorders that are affected by the modulation of the GPR40 receptor. Such compounds are represented by Formula (I) as follows:

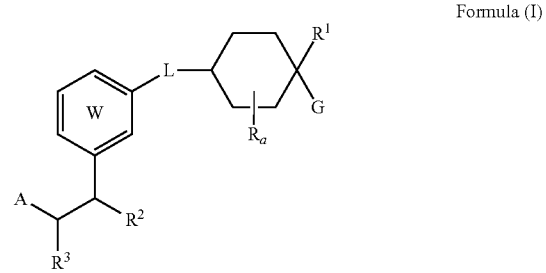

Formula (I)

wherein $R^1$, $R^2$, $R^3$, A, W, L, $R_a$, and G are defined herein: and by Formula (II) as follows:

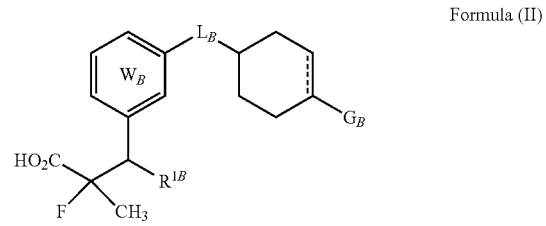

Formula (II)

wherein $R^{1B}$, $W_B$, $L_B$, ¦ , and $G_B$ are defined herein.

44 Claims, No Drawings

(56) References Cited

OTHER PUBLICATIONS

International Search Report relating to International Patent Application No. PCT/US2017/057979, filed Oct. 24, 2017. Date of Mailing of International Search Report: Jan. 31, 2018.

Written Opinion of the International Searching Authority relating to International Patent Application No. PCT/US2017/057979, filed Oct. 24, 2017. Date of Mailing of Written Opinion: Jan. 31, 2018.

CYCLOHEXYL GPR40 AGONISTS FOR THE TREATMENT OF TYPE II DIABETES

CROSS-REFERENCE TO RELATED APPLICATIONS

This Application is a U.S. national stage of PCT Application No. PCT/US2017/057979, filed on Oct. 24, 2017, which claims priority to U.S. Provisional Patent Application No. 62/412,465, filed Oct. 25, 2016, and U.S. Provisional Patent Application No. 62/561,298, filed Sep. 21, 2017, which are hereby incorporated by reference in their entireties.

FIELD OF THE INVENTION

The present invention relates to novel compounds which are GPR40 agonists and are useful for the treatment of disorders that are affected by the modulation of the GPR40 receptor. The invention also relates to pharmaceutical compositions comprising one or more of such compounds, to processes to prepare such compounds and compositions, and to the use of such compounds or pharmaceutical compositions for the treatment of various diseases, syndromes and disorders, including Type II diabetes mellitus, obesity, obesity-related disorders, impaired glucose tolerance, insulin resistance, metabolic syndrome, diabetic nephropathy, nonalcoholic steatohepatitis (NASH), other cardiovascular risk factors such as hypertension and cardiovascular risk factors related to unmanaged cholesterol and/or lipid levels, osteoporosis, inflammation, and eczema, that are related to GPR40 modulation.

BACKGROUND OF THE INVENTION

Diabetes is a rapidly expanding, devastating disease that currently affects over 371 million people in the world, with associated healthcare costs exceeding 470 billion dollars in the USA alone. There are two main types of diabetes. Type 1 diabetes affects ~10% of the patients and is characterized by complete insulinopenia due to autoimmune destruction of the insulin-secreting pancreatic beta cells. Treatment of Type 1 diabetes requires insulin therapy. Type 2 diabetes affects ~90% of the patients and is a polygenic syndrome with not only a hereditary component but also a strong environmental influence. It is caused by insulin resistance and defective insulin secretion. In most individuals, the pancreatic beta cell compensates for obesity-associated insulin resistance by expanding its functional mass and secretion of insulin. In a subset of ~20% of obese subjects, beta cell compensation fails and Type 2 diabetes develops. Two major classes of type 2 diabetes drugs are insulin sensitizers (e.g. metformin, thiazolidinediones) and insulin secretagogues (e.g. sulfonylureas, glinides, glucagon-like peptide-1 (GLP-1)-based drugs). Most of the recently approved drugs belong to the latter category and are based on the GLP-1 mechanism, either by pharmacologically enhancing GLP-1 levels (GLP-1 agonists) or by inhibiting the degradation of endogenous GLP-1 (dipeptidyl-peptidase 4 inhibitors). One advantageous feature of these drugs is that they only stimulate insulin secretion when blood glucose levels are elevated (as opposed to sulfonylureas and glinides), thus minimizing the risk of iatrogenic hypoglycemia. A decade ago, the discovery of the G-protein-coupled receptor GPR40 as a fatty acid receptor specifically expressed in beta cells and which stimulates glucose-dependent insulin secretion, sparked interest in the pharmaceutical industry as a potential therapeutic target to enhance insulin secretion in type 2 diabetes, in a manner similar to GLP-1-based drugs. GPR40, also known as free fatty acid receptor 1 (FFAR1), is one of a family of G-protein coupled receptors that, through receptor deorphanization studies, was shown to be endogenously activated by medium- to long-chain saturated and unsaturated fatty acids (~$C_{12-20}$) (Brisco, et al., 2003, J. Biol. Chem., vol. 278: pgs 11303-11311; Itoh, et al., 2003, Nature, vol. 422, pgs 173-176; Kotarsky et al., 2003, Biochem. Biophys. Res. Commun., vol. 301, pgs 406-410). In humans and rodents, although present in brain and enteroendocrine cells, its expression is particularly high in pancreatic beta cells and enteroendocrine cells in the gut. Operating primarily through Gaq/ii signaling, GPR40 activation of the beta cell leads to an increase in intracellular calcium levels, which in the presence of glucose, ultimately results in augmented insulin secretion. In enteroendocrine cells, GPR40 activation by fatty acids leads to stimulation of incretin secretion (Edfalk, et al., 2008, Diabetes, vol. 57, pgs 2280-2287). Thus, in addition to directly promoting GSIS from islet beta cells, GPR40 activation in enteroendocrine cells provides an indirect means of stimulating GSIS through the actions of released incretins.

Because of the glucose dependency of GPR40-mediated effects on insulin secretion, selective activation of this receptor provides a unique potential therapeutic mechanism by which to treat the diabetic state with minimal risk of hypoglycemic incidents. Given the relatively restricted tissue expression pattern of GPR40, selective GPR40 agonists may offer the additional advantage of providing an improved safety profile relative to the aforementioned therapeutic agents.

Thus, GPR40 agonists of the present invention may provide therapeutic benefit for the treatment of diabetes, particularly Type 2 diabetes, as well as diseases, syndromes and disorders, including obesity, obesity-related disorders, impaired glucose tolerance, insulin resistance, metabolic syndrome, diabetic nephropathy, nonalcoholic steatohepatitis (NASH), cardiovascular risk factors such as hypertension, and cardiovascular risk factors related to unmanaged cholesterol and/or lipid levels, osteoporosis, inflammation, and eczema.

SUMMARY OF THE INVENTION

The present invention is directed to compounds of Formula (I)

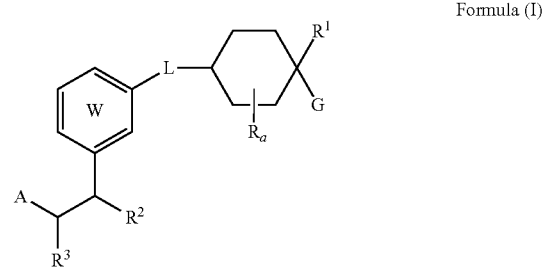

Formula (I)

wherein
G is selected from the group consisting of g1, g2, g3, and g4

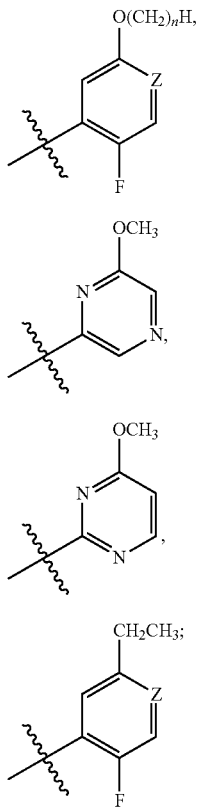

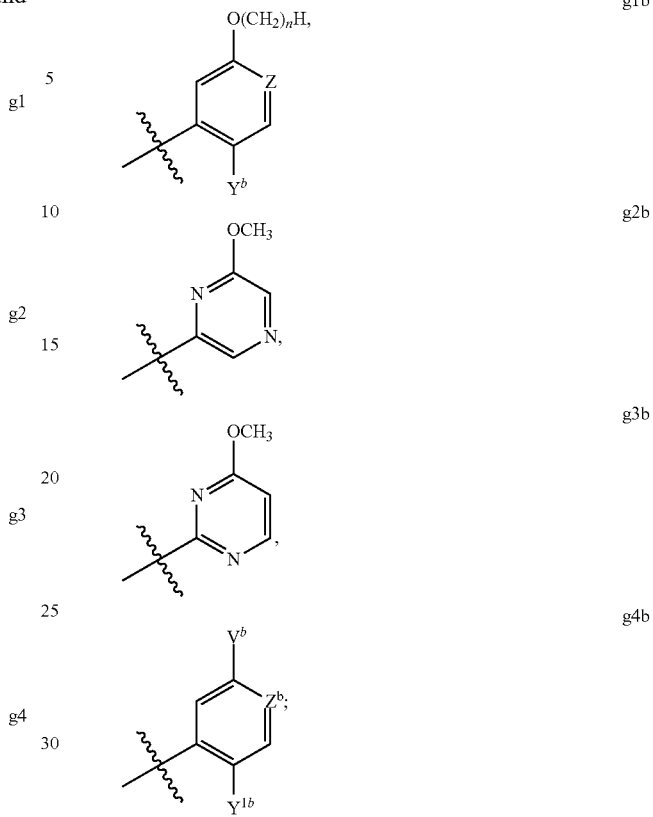

wherein Z is N or CH, and wherein n is an integer from 1 to 3;
$R^1$ is selected from the group consisting of hydrogen, hydroxy, methoxy, and fluoro;
$R_a$ is selected from hydrogen or $C_{1-4}$alkyl;
L is selected from the group consisting of —OCH$_2$—, —NHCH$_2$—, —(CH$_2$)$_2$—, and CH=CH—;
ring W is phenyl or pyridinyl;
$R^2$ is $C_{3-5}$cycloalkyl, methylacetylenyl, or ethoxy;
$R^3$ is hydrogen, methyl, trifluoromethyl, or fluoro;
A is carboxy or 1H-tetrazol-5-yl;
or an enantiomer, diastereomer, or pharmaceutically acceptable salt form thereof.

The present invention is further directed to compounds of Formula (II)

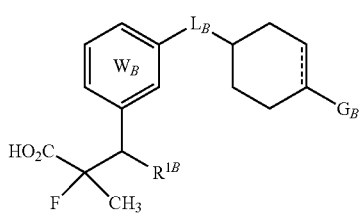

Formula (II)

wherein
$G_B$ is selected from the group consisting of g1b, g2b, g3b, and g4b, wherein
$Z^b$ is N or CH; n is an integer from 1 to 3;
$Y^b$ is independently selected from the group consisting of hydrogen, fluoro, chloro, methyl, trifluoromethoxy, and pyridin-2-ylaminocarbonyl;
$V^b$ is fluoro, trifluoromethoxy, or ethyl;
$Y^{1b}$ is independently selected from the group consisting of hydrogen, fluoro, chloro, methyl, trifluoromethoxy, and pyridin-2-ylaminocarbonyl;
ring $W_B$ is phenyl or pyridinyl, wherein $W_B$ is optionally independently substituted with one substituent selected from fluoro, chloro, or methyl;
$L_B$ is selected from the group consisting of —OCH$_2$—, —CH$_2$O—, —NHCH$_2$—, —(CH$_2$)$_2$—, and —CH=CH—;
┊ is an optional double bond in the $G_B$-substituted cyclohexyl ring;
$R^{1B}$ is $C_{3-5}$cycloalkyl or $C_{1-4}$alkyl;
or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or Formula (II), or a pharmaceutically acceptable salt form thereof.

Also provided are processes for making a pharmaceutical composition comprising, consisting of, and/or consisting essentially of admixing a compound of Formula (I) or Formula (II), and a pharmaceutically acceptable carrier, a pharmaceutically acceptable excipient, and/or a pharmaceutically acceptable diluent.

The present invention further provides methods for treating or ameliorating a disease, syndrome, or condition in a subject, including a mammal and/or human in which the disease, syndrome, or condition is affected by the agonism of the GPR40 receptor, such as Type II diabetes mellitus, using a compound of Formula (I) or Formula (II).

The present invention also is also directed to the use of any of the compounds described herein in the preparation of a medicament wherein the medicament is prepared for treating a disease or condition that is affected by the agonism of the GPR40 receptor, selected from the group consisting of Type II diabetes mellitus, obesity, obesity-related disorders, impaired glucose tolerance, insulin resistance, metabolic syndrome, diabetic nephropathy, diabetic nephropathy, nonalcoholic steatohepatitis (NASH), other cardiovascular risk factors such as hypertension and cardiovascular risk factors related to unmanaged cholesterol and/or lipid levels, osteoporosis, inflammation, and eczema, in a subject in need thereof.

The present invention is also directed to the preparation of substituted cyclohexyl derivatives that act as selective agonists of the GPR40 receptor.

Exemplifying the invention are methods of treating a disorder modulated by the GPR40 receptor selected from the group consisting of Type II diabetes mellitus, obesity, obesity-related disorders, impaired glucose tolerance, insulin resistance, metabolic syndrome, diabetic nephropathy, nonalcoholic steatohepatitis (NASH), cardiovascular risk factors such as hypertension, and cardiovascular risk factors related to unmanaged cholesterol and/or lipid levels, osteoporosis, inflammation, and eczema, comprising administering to a subject in need thereof a therapeutically effective amount of any of the compounds or pharmaceutical compositions described above.

In another embodiment, the present invention is directed to a compound of Formula (I) or Formula (II) for use in the treatment of a disorder affected by the agonism of the GPR40 receptor selected from the group consisting of Type II diabetes mellitus, obesity, obesity-related disorders, impaired glucose tolerance, insulin resistance, metabolic syndrome, diabetic nephropathy, nonalcoholic steatohepatitis (NASH), cardiovascular risk factors such as hypertension, and cardiovascular risk factors related to unmanaged cholesterol and/or lipid levels, osteoporosis, inflammation, and eczema.

In another embodiment, the present invention is directed to a composition comprising a compound of Formula (I) or Formula (II) for the treatment of a disorder affected by the agonism of the GPR40 receptor selected from the group consisting of Type II diabetes mellitus, obesity, obesity-related disorders, impaired glucose tolerance, insulin resistance, metabolic syndrome, diabetic nephropathy, nonalcoholic steatohepatitis (NASH), cardiovascular risk factors such as hypertension, and cardiovascular risk factors related to unmanaged cholesterol and/or lipid levels, osteoporosis, inflammation, and eczema.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, ($C_{1-6}$alkyl)$_2$amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.
The term "formyl" refers to the group —C(=O)H.
The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

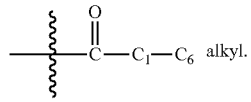

The substituent "L" is oriented such that when an oxygen (O) or nitrogen (N) atom is present, the O or N atom is covalently bound to ring W.

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "GPR40 agonist" is intended to encompass a compound that interacts with the GPR40 receptor to substantially increase its downstream signaling, thereby resulting in physiologic effects such as, but not limited to, insulin secretion in the pancreas.

The term "GPR40 receptor-modulated" is used to refer to the condition of being affected by the modulation of the GPR40 receptor, including but not limited to, the state of being mediated by the GPR40 receptor, for the treatment of a disease or condition such as Type II diabetes or impaired glucose tolerance.

As used herein, unless otherwise noted, the term "disorder modulated by the GPR40 receptor" shall mean any disease, disorder or condition characterized in that at least one of its characteristic symptoms is alleviated or eliminated upon treatment with a GPR40 receptor agonist. Suitable examples include, but are not limited to Type II diabetes mellitus, obesity, obesity-related disorders, impaired glucose tolerance, insulin resistance, metabolic syndrome, diabetic nephropathy, other cardiovascular risk factors such as hypertension and cardiovascular risk factors related to unmanaged cholesterol and/or lipid levels, osteoporosis, inflammation, and eczema; more preferably, Type II diabetes mellitus and impaired glucose tolerance.

As used herein unless otherwise noted, the term "cardiovascular risk factors" shall mean any cardiovascular disease, disorder or condition in which obesity or diabetes (preferably, Type II diabetes) has a role in the initiation or exacerbation of said disorder or condition. Suitable examples include, but are not limited to, hypertension, atherosclerosis and cardiac fibrosis.

As used herein, unless otherwise noted, the term "affect" or "affected" (when referring to a disease, syndrome, condition or disorder that is affected by the agonism of the GPR40 receptor) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of the instant invention are useful in methods for treating or ameliorating a disease, a syndrome, a condition or a disorder that is affected by the agonism of the GPR40 receptor. Such methods comprise, consist of and/or consist essentially of administering to a subject, including an animal, a mammal, and a human in need of such treatment, amelioration and/or prevention, a therapeutically effective amount of a compound of Formula (I) or Formula (II), or an enantiomer, diastereomer, solvate or pharmaceutically acceptable salt thereof.

In particular, the compounds of Formula (I) and Formula (II), or an enantiomer, diastereomer, solvate or pharmaceutically acceptable salt form thereof are useful for treating or ameliorating diseases, syndromes, conditions, or disorders such as Type II diabetes mellitus, obesity, obesity-related disorders, impaired glucose tolerance, insulin resistance, metabolic syndrome, diabetic nephropathy, nonalcoholic steatohepatitis (NASH), other cardiovascular risk factors such as hypertension and cardiovascular risk factors related to unmanaged cholesterol and/or lipid levels, osteoporosis, inflammation, and eczema.

More particularly, the compounds of Formula (I) and Formula (II), or an enantiomer, diastereomer, solvate or pharmaceutically acceptable salt form thereof, are useful for treating or ameliorating Type II diabetes mellitus or impaired glucose tolerance, comprising administering to a subject in need thereof a therapeutically effective amount of a compound of Formula (I) or Formula (II), or an enantiomer, diastereomer, solvate or pharmaceutically acceptable salt form thereof as herein defined.

Embodiments of the present invention include a compound of Formula (I)

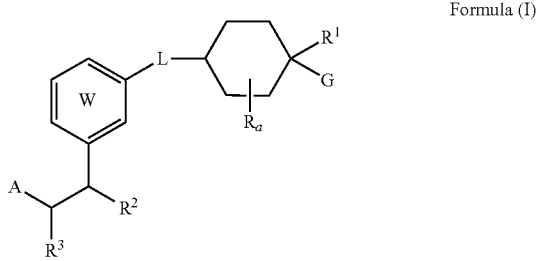

Formula (I)

wherein
aa) G is g1

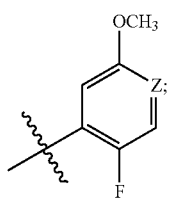

g1 wherein Z is N or CH;
bb) G is 2-fluoro-5-methoxyphenyl, 2-ethoxy-5-fluoropyridin-4-yl, or 5-fluoro-2-methoxypyridin-4-yl;
cc) G is 2-fluoro-5-methoxyphenyl;
dd) $R^1$ is selected from the group consisting of hydrogen, methoxy, hydroxy, and fluoro;
ee) $R^1$ is selected from the group consisting of hydrogen, methoxy, and fluoro;
ff) $R^1$ is hydrogen;
gg) $R_a$ is selected from hydrogen, methyl, or isobutyl;
hh) $R_a$ is hydrogen;

ii) L is selected from the group consisting of —OCH$_2$—, —(CH$_2$)$_2$—, and —CH═CH—;
jj) L is —OCH$_2$—;
kk) $R^2$ is cyclopropyl, methylacetylenyl, or ethoxy;
ll) $R^2$ is C$_{3-5}$cycloalkyl;
mm) $R^2$ is cyclopropyl;
nn) $R^3$ is hydrogen, methyl, or fluoro;
oo) ring W is phenyl;
pp) ring W is pyridinyl
qq) A is carboxy;

and any combination of embodiments aa) through qq) above, provided that it is understood that combinations in which different embodiments of the same substituent would be combined are excluded;

or an enantiomer, diastereomer, or pharmaceutically acceptable salt form thereof.

An embodiment of the present invention includes a compound of Formula (I)

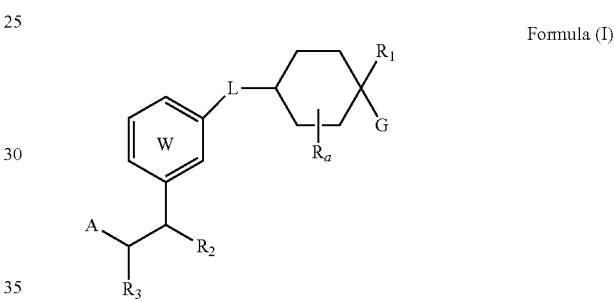

Formula (I)

wherein
G is g1

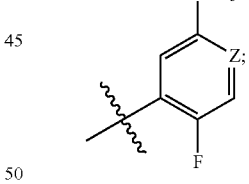

g1 wherein Z is N or CH;
$R^1$ is selected from the group consisting of hydrogen, hydroxy, methoxy, and fluoro;
$R_a$ is selected from hydrogen or C$_{1-4}$alkyl;
L is selected from the group consisting of —OCH$_2$—, —NHCH$_2$—, —(CH$_2$)$_2$—, and —CH═CH—;
ring W is phenyl or pyridinyl;
$R^2$ is C$_{3-5}$cycloalkyl;
$R^3$ is hydrogen, methyl, or fluoro;
A is carboxy or 1H-tetrazol-5-yl;
or an enantiomer, diastereomer, or pharmaceutically acceptable salt form thereof.

An embodiment of the present invention includes a compound of Formula (I)

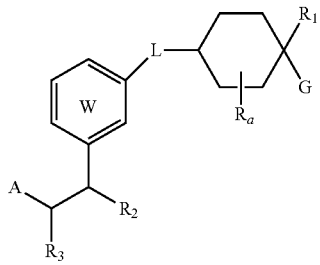

Formula (I)

wherein

G is g1

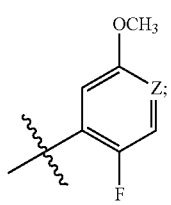

g1 wherein Z is N or CH;

R¹ is selected from the group consisting of hydrogen, methoxy, and fluoro;

$R_a$ is selected from hydrogen, methyl, or isobutyl;

L is selected from the group consisting of —OCH₂—, —(CH₂)₂—, and —CH=CH—;

ring W is phenyl or pyridinyl;

R² is $C_{3-5}$cycloalkyl;

R³ is hydrogen, methyl, or fluoro;

A is carboxy;

or an enantiomer, diastereomer, or pharmaceutically acceptable salt form thereof.

An embodiment of the present invention includes a compound of Formula (I)

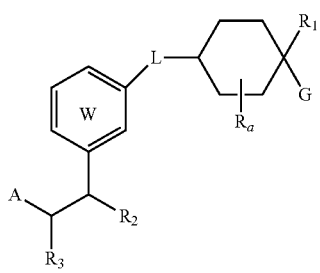

Formula (I)

wherein

G is g1

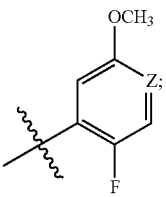

g1 wherein Z is N or CH;

R¹ is selected from the group consisting of hydrogen, methoxy, and fluoro;

$R_a$ is selected from hydrogen, methyl, or isobutyl;

L is selected from the group consisting of —OCH₂—, —(CH₂)₂—, and —CH=CH—;

ring W is phenyl or pyridinyl;

R² is cyclopropyl, methylacetylenyl, or ethoxy;

R³ is hydrogen, methyl, or fluoro;

A is carboxy;

or an enantiomer, diastereomer, or pharmaceutically acceptable salt form thereof.

An embodiment of the present invention includes a compound of Formula (I)

Formula (I)

wherein

G is 2-fluoro-5-methoxyphenyl, 2-ethoxy-5-fluoropyridin-4-yl, or 5-fluoro-2-methoxypyridin-4-yl;

R¹ is selected from the group consisting of hydrogen, methoxy, hydroxy, and fluoro;

$R_a$ is selected from hydrogen, methyl, or isobutyl;

L is selected from the group consisting of —OCH₂—, —NHCH₂—, —(CH₂)₂—, and —CH=CH—;

ring W is phenyl, pyridin-2-yl, pyridin-3-yl, or pyridin-4-yl;

R² is cyclopropyl, methylacetylenyl, or ethoxy;

R³ is hydrogen, methyl, or fluoro;

A is carboxy or 1H-tetrazol-5-yl;

or an enantiomer, diastereomer, or pharmaceutically acceptable salt form thereof.

An embodiment of the present invention includes a compound of Formula (I)

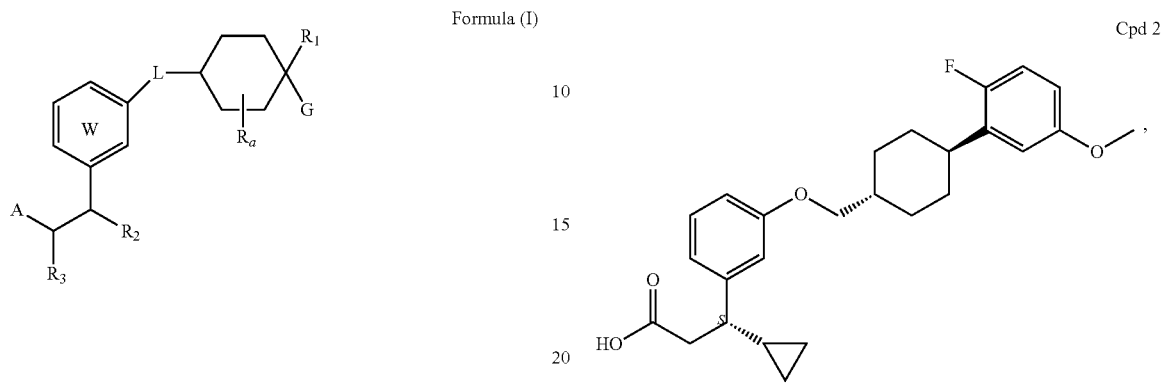

Formula (I)

wherein
G is 2-fluoro-5-methoxyphenyl;
R¹ is hydrogen;
R_a is hydrogen;
L is —OCH₂—;
ring W is phenyl;
R² is cyclopropyl;
R³ is hydrogen, methyl, or fluoro;
A is carboxy;
or an enantiomer, diastereomer, or pharmaceutically acceptable salt form thereof.

A further embodiment of the present invention is directed to the compound of Formula (I) that is (3S)-3-cyclopropyl-3-[3-[[4-(2-fluoro-5-methoxy-phenyl)cyclohexyl]methoxy]phenyl]propanoic acid, Cpd 2.

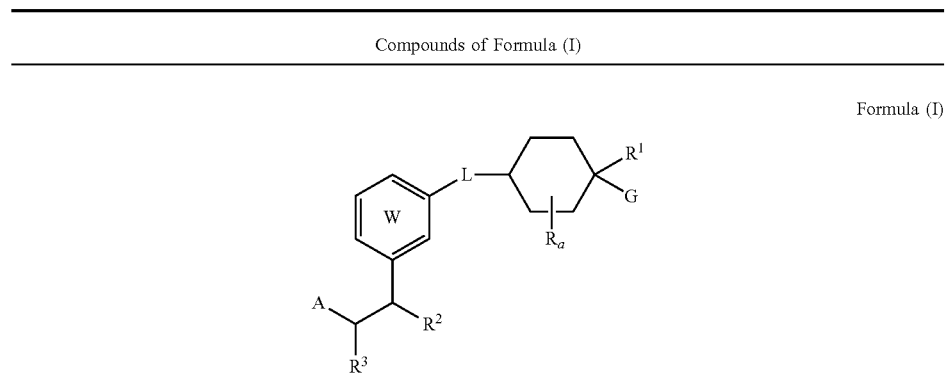

Cpd 2

Additional embodiments of the present invention include compounds of Formula (I) as herein defined, or an enantiomer, diastereomer, solvate, or a pharmaceutically acceptable salt form thereof, wherein the substituents selected from one or more of the variables defined herein are independently selected to be any individual substituent or any subset of substituents from those exemplified in the listing in Table 1, below.

TABLE 1

Compounds of Formula (I)

Formula (I)

| Structure | Cpd No. | Compound Name |
|---|---|---|
| 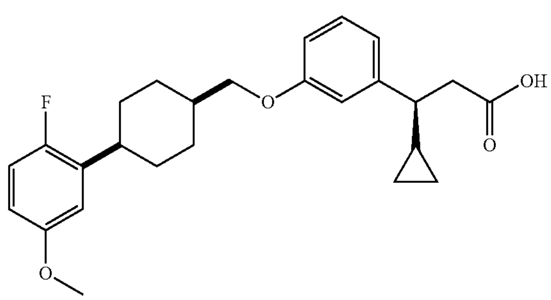 | 1 | (S)-3-cyclopropyl-3-(3-(((1s,4R)-4-(2-fluoro-5-methoxyphenyl)cyclohexyl)methoxy)phenyl)propanoic acid |

TABLE 1-continued

Compounds of Formula (I)

Formula (I)

| Structure | Cpd No. | Compound Name |
|---|---|---|
| | 2 | (S)-3-cyclopropyl-3-(3-(((1r,4S)-4-(2-fluoro-5-methoxyphenyl)cyclohexyl)methoxy)phenyl)propanoic acid |
| | 3 | (S)-3-cyclopropyl-3-(3-(((1s,4R)-4-(2-fluoro-5-methoxyphenyl)-4-hydroxycyclohexyl)methoxy)phenyl)propanoic acid |
| | 4 | 3-cyclopropyl-3-(2-(((1r,4r)-4-(2-fluoro-5-methoxyphenyl)cyclohexyl)methoxy)pyridin-4-yl)propionic acid |
| | 5 | 3-cyclopropyl-3-(2-(((1s,4s)-4-(2-fluoro-5-methoxyphenyl)cyclohexyl)methoxy)pyridin-4-yl)propionic acid |

TABLE 1-continued

Compounds of Formula (I)

Formula (I)

| Structure | Cpd No. | Compound Name |
|---|---|---|
| 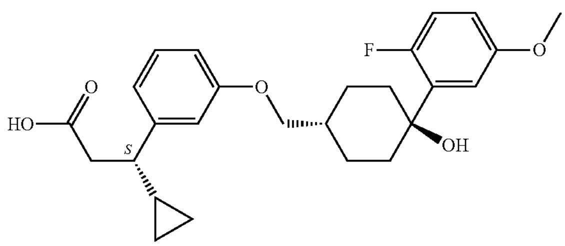 | 6 | (S)-3-cyclopropyl-3-(3-(((1r,4S)-4-(2-fluoro-5-methoxyphenyl)-4-hydroxycyclohexyl)methoxy)phenyl)propanoic acid |
| 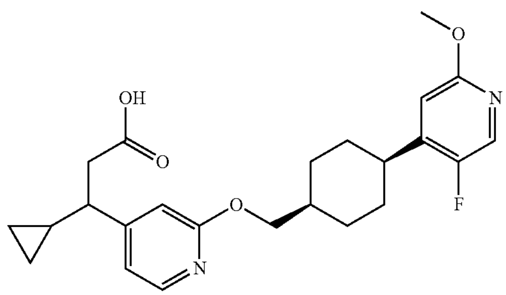 [SMILES: COc1cc([C@H]2CC[C@@H](COc3cc(C(CC(=O)O)C4CC4)ccn3)CC2)c(F)cn1] | 7 | 3-cyclopropyl-3-(2-(((1s,4s)-4-(5-fluoro-2-methoxypyridin-4-yl)cyclohexyl)methoxy)pyridin-4-yl)propionic acid |
| 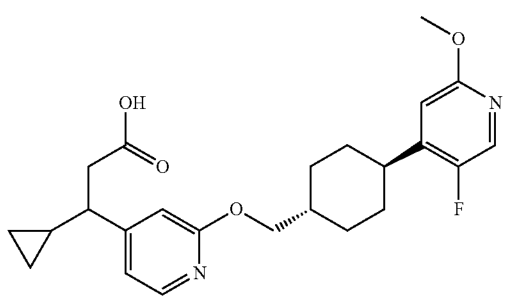 [SMILES: COc1cc([C@H]2CC[C@H](COc3cc(C(CC(=O)O)C4CC4)ccn3)CC2)c(F)cn1] | 8 | 3-cyclopropyl-3-(2-(((1r,4r)-4-(5-fluoro-2-methoxypyridin-4-yl)cyclohexyl)methoxy)pyridin-4-yl)propionic acid |
| 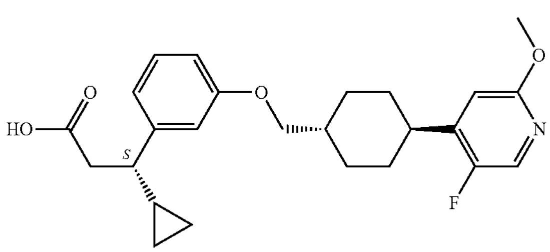 | 9 | (S)-3-cyclopropyl-3-(3-(((1r,4S)-4-(5-fluoro-2-methoxypyridin-4-yl)cyclohexyl)methoxy)phenyl)propanoic acid |

TABLE 1-continued

Compounds of Formula (I)

Formula (I)

| Structure | Cpd No. | Compound Name |
|---|---|---|
| 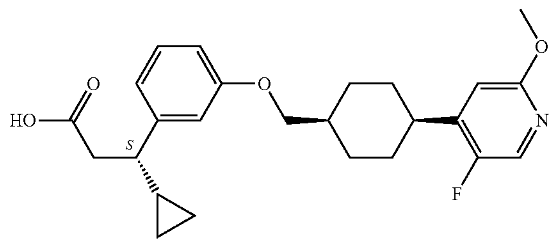 | 10 | (S)-3-cyclopropyl-3-(3-(((1s,4R)-4-(5-fluoro-2-methoxypyridin-4-yl)cyclohexyl)methoxy)phenyl)propanoic acid |
| 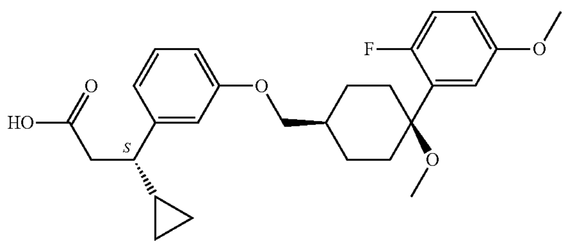 | 11 | (S)-3-cyclopropyl-3-(3-(((1s,4R)-4-(2-fluoro-5-methoxyphenyl)-4-methoxycyclohexyl)methoxy)phenyl)propanoic aicd |
| 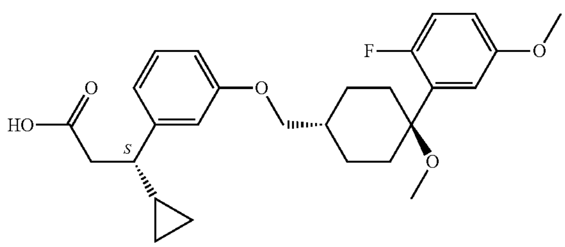 | 12 | (S)-3-cyclopropyl-3-(3-(((1r,4S)-4-(2-fluoro-5-methoxyphenyl)-4-methoxycyclohexyl)methoxy)phenyl)propanoic acid |
| 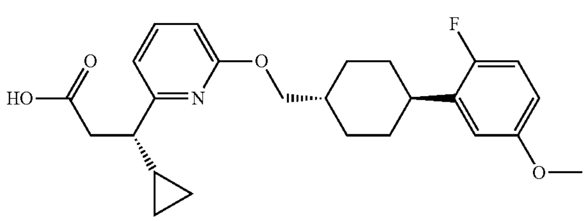 [SMILES: COc1ccc(F)c([C@H]2CC[C@H](COc3cccc([C@@H](CC(=O)O)C4CC4)n3)CC2)c1] | 13 | 3-cyclopropyl-3-(6-(((1r,4r)-4-(2-fluoro-5-methoxyphenyl)cyclohexyl)methoxy)pyridin-2-yl)propionic acid |
| 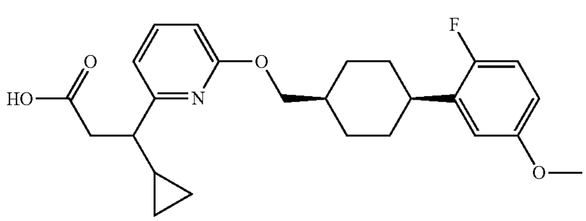 [SMILES: COc1ccc(F)c([C@H]2CC[C@@H](COc3cccc(C(CC(=O)O)C4CC4)n3)CC2)c1] | 14 | 3-cyclopropyl-3-(6-(((1s,4s)-4-(2-fluoro-5-methoxyphenyl)cyclohexyl)methoxy)pyridin-2-yl)propionic acid |

TABLE 1-continued

Compounds of Formula (I)

Formula (I)

| Structure | Cpd No. | Compound Name |
|---|---|---|
| 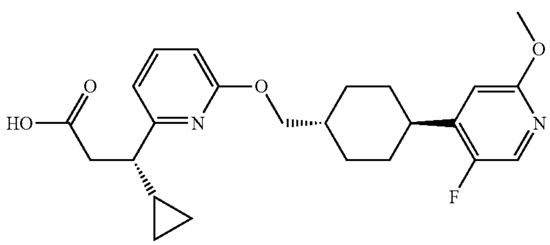 [SMILES: COc1cc([C@H]2CC[C@H](COc3cccc([C@@H](CC(=O)O)C4CC4)n3)CC2)c(F)cn1] | 15 | 3-cyclopropyl-3-(6-(((1r,4r)-4-(5-fluoro-2-methoxy-pyridin-4-yl)cyclohexyl)methoxy)pyridin-2-yl)propionic acid |
| 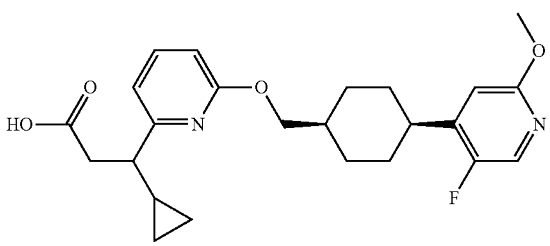 [SMILES: COc1cc([C@H]2CC[C@@H](COc3cccc(C(CC(=O)O)C4CC4)n3)CC2)c(F)cn1] | 16 | 3-cyclopropyl-3-(6-(((1s,4s)-4-(5-fluoro-2-methoxy-pyridin-4-yl)cyclohexyl)methoxy)pyridin-2-yl)propionic acid |
| 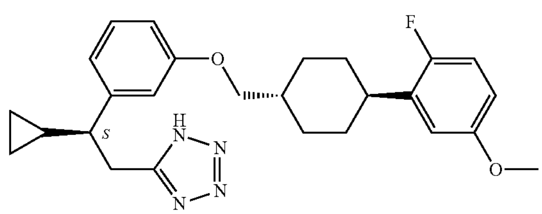 | 17 | 5-((S)-2-cyclopropyl-2-(3-(((1r,4S)-4-(2-fluoro-5-methoxyphenyl)cyclohexyl)methoxy)phenyl)ethyl)-1H-tetrazole |
| 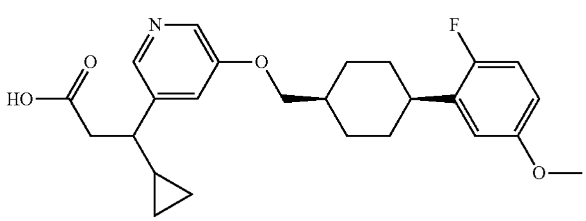 [SMILES: COc1ccc(F)c([C@H]2CC[C@@H](COc3cncc(C(CC(=O)O)C4CC4)c3)CC2)c1] | 18 | 3-cyclopropyl-3-(5-(((1s,4s)-4-(2-fluoro-5-methoxyphenyl)cyclohexyl)methoxy)pyridin-3-yl)propanoic acid |
| 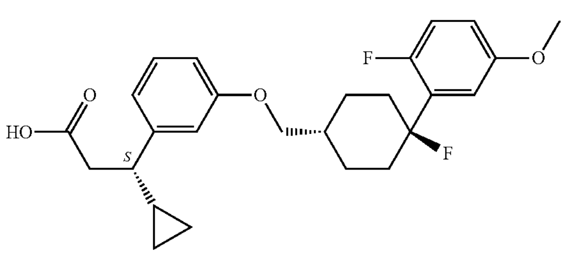 | 19 | (S)-3-cyclopropyl-3-(3-(((1r,4S)-4-fluoro-4-(2-fluoro-5-methoxyphenyl)cyclohexyl)methoxy)phenyl)propanoic acid |

TABLE 1-continued

Compounds of Formula (I)

Formula (I)

| Structure | Cpd No. | Compound Name |
|---|---|---|
|  | 20 | (S)-3-cyclopropyl-3-(3-(((1s,4R)-4-fluoro-4-(2-fluoro-5-methoxyphenyl)cyclohexyl)methoxy)phenyl)propanoic acid |
|  | 21 | 3-cyclopropyl-3-(5-(((1r,4r)-4-(2-fluoro-5-methoxyphenyl)cyclohexyl)methoxy)pyridin-3-yl)propionic acid |
|  | 22 | 3-cyclopropyl-3-(5-(((1r,4r)-4-(5-fluoro-2-methoxy-pyridin-4-yl)cyclohexyl)methoxy)pyridin-3-yl)propionic acid |
|  | 23 | 3-cyclopropyl-3-(5-(((1s,4s)-4-(5-fluoro-2-methoxy-pyridin-4-yl)cyclohexyl)methoxy)pyridin-3-yl)propionic acid |

TABLE 1-continued

Compounds of Formula (I)

Formula (I)

| Structure | Cpd No. | Compound Name |
|---|---|---|
| | 24 | (R)-3-cyclopropyl-3-(2-(((1r,4R)-4-(5-fluoro-2-methoxypyridin-4-yl)cyclohexyl)methoxy)pyridin-4-yl)propanoic acid |
| | 25 | (S)-3-cyclopropyl-3-(2-(((1r,4S)-4-(5-fluoro-2-methoxypyridin-4-yl)cyclohexyl)methoxy)pyridin-4-yl)propanoic acid |
| | 26 | (R)-3-cyclopropyl-3-(2-(((1r,4R)-4-(2-fluoro-5-methoxyphenyl)cyclohexyl)methoxy)pyridin-4-yl)propanoic acid |
| | 27 | (S)-3-cyclopropyl-3-(2-(((1r,4s)-4-(2-fluoro-5-methoxyphenyl)cyclohexyl)methoxy)pyridin-4-yl)propanoic acid |

TABLE 1-continued

Compounds of Formula (I)

Formula (I)

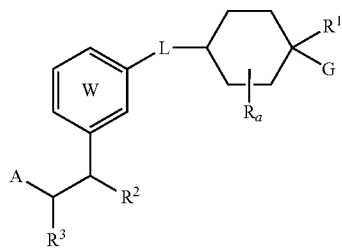

| Structure | Cpd No. | Compound Name |
|---|---|---|
| 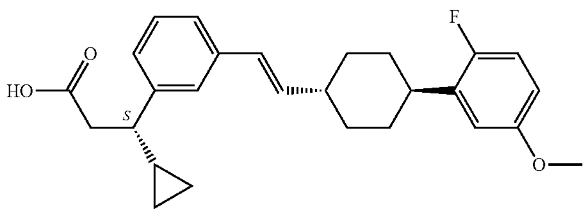 | 28 | (R)-3-cyclopropyl-3-(3-(((1s,4S)-4-(2-fluoro-5-methoxyphenyl)cyclohexyl)methoxy)phenyl)propanoic acid |
| 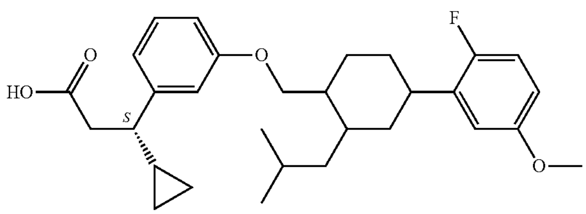 | 29 | (3S)-3-cyclopropyl-3-(3-((4-(2-fluoro-5-methoxyphenyl)-2-isobutylcyclohexyl)methoxy)phenyl)propanoic acid |
| 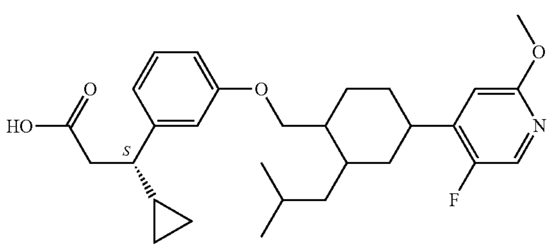 | 30 | (3S)-3-cyclopropyl-3-(3-((4-(5-fluoro-2-methoxypyridin-4-yl)-2-isobutylcyclohexyl)methoxy)phenyl)propanoic acid |
| 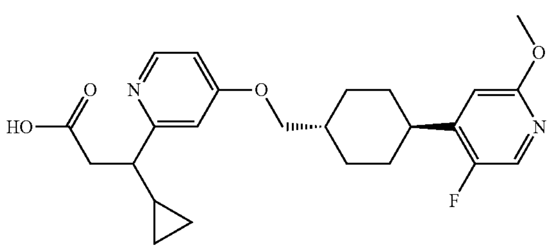 | 31 | 3-cyclopropyl-3-(4-(((1r,4r)-4-(5-fluoro-2-methoxy-pyridin-4-yl)cyclohexyl)methoxy)pyridin-2-yl)propanoic acid |
| 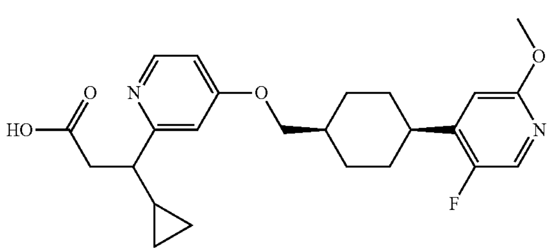 | 32 | 3-cyclopropyl-3-(4-(((1s,4s)-4-(5-fluoro-2-methoxy-pyridin-4-yl)cyclohexyl)methoxy)pyridin-2-yl)propanoic acid |

TABLE 1-continued

Compounds of Formula (I)

Formula (I)

| Structure | Cpd No. | Compound Name |
|---|---|---|
| 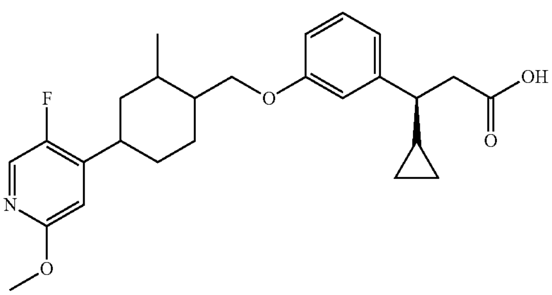 [SMILES: COc1cc(C2CCC(COc3cccc([C@@H](CC(=O)O)C4CC4)c3)C(C)C2)c(F)cn1] | 33 | (3S)-3-cyclopropyl-3-(3-((4-(5-fluoro-2-methoxypyridin-4-yl)-2-methylcyclohexyl)methoxy)phenyl)propanoic acid |
| 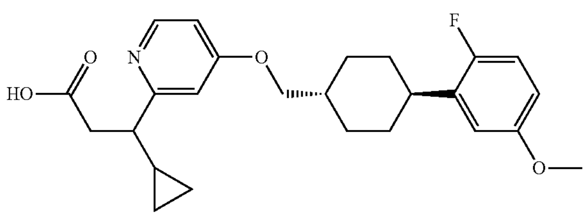 [SMILES: COc1ccc(F)c([C@H]2CC[C@H](COc3ccnc(C(CC(=O)O)C4CC4)c3)CC2)c1] | 34 | 3-cyclopropyl-3-(4-(((1r,4r)-4-(2-fluoro-5-methoxyphenyl)cyclohexyl)methoxy)pyridin-2-yl)propanoic acid |
| 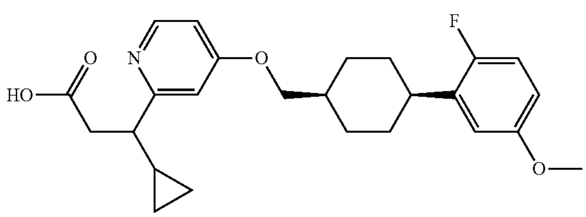 | 35 | 3-cyclopropyl-3-(4-(((1s,4s)-4-(2-fluoro-5-methoxyphenyl)cyclohexyl)methoxy)pyridin-2-yl)propanoic acid |
| 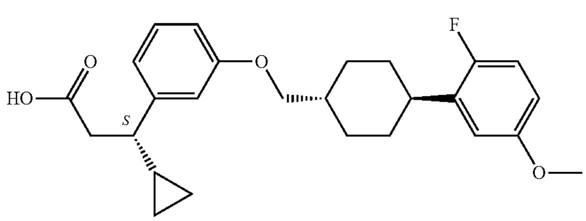 | 36 | (S)-3-cyclopropyl-3-(3-(2-((1r,4R)-4-(2-fluoro-5-methoxyphenyl)cyclohexyl)ethyl)phenyl)propanoic acid |
| 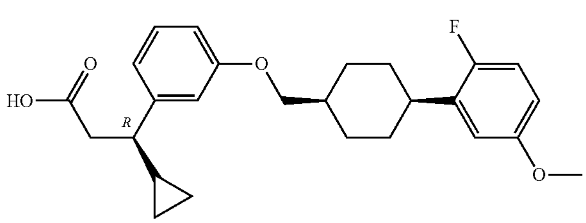 | 37 | (R)-3-cyclopropyl-3-(3-(((1s,4S)-4-(2-fluoro-5-methoxyphenyl)cyclohexyl)methoxy)phenyl)propanoic acid |

TABLE 1-continued

Compounds of Formula (I)

Formula (I)

| Structure | Cpd No. | Compound Name |
|---|---|---|
| 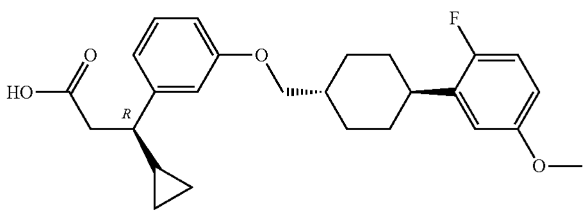 | 38 | (R)-3-cyclopropyl-3-(3-(((1r,4R)-4-(2-fluoro-5-methoxyphenyl)cyclohexyl)methoxy)phenyl)propanoic acid |
| 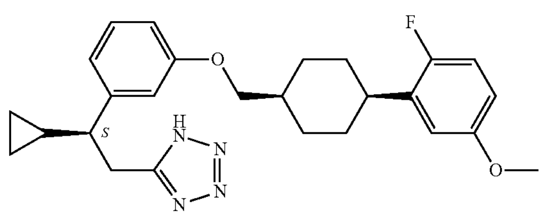 | 39 | 5-((S)-2-cyclopropyl-2-(3-(((1s,4R)-4-(2-fluoro-5-methoxyphenyl)cyclohexyl)methoxy)phenyl)ethyl)-1H-tetrazole |
| 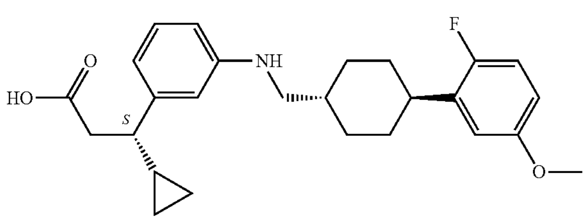 | 40 | (S)-3-cyclopropyl-3-(3-((((1r,4S)-4-(2-fluoro-5-methoxyphenyl)cyclohexyl)methyl)amino)phenyl)propanoic acid |
| 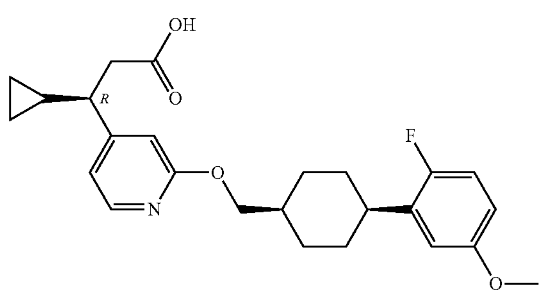 | 41 | (R)-3-cyclopropyl-3-(2-(((1s,4S)-4-(2-fluoro-5-methoxyphenyl)cyclohexyl)methoxy)pyridin-4-yl)propanoic acid |

TABLE 1-continued

Compounds of Formula (I)

Formula (I)

| Structure | Cpd No. | Compound Name |
|---|---|---|
| 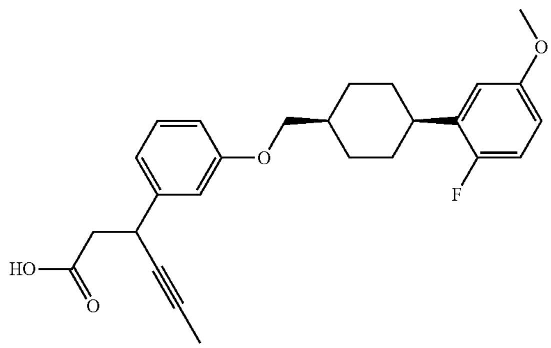 [SMILES: CC#CC(CC(=O)O)c1cccc(OC[C@H]2CC[C@@H](c3cc(OC)ccc3F)CC2)c1] | 42 | 3-(3-(((1s,4s)-4-(2-fluoro-5-methoxyphenyl)cyclohexyl)methoxy)phenyl)hex-4-ynoic acid |
| 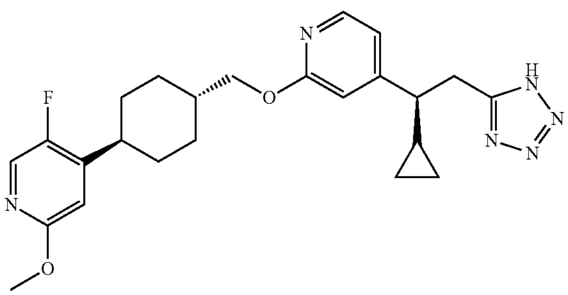 [SMILES: COc1cc([C@H]2CC[C@H](COc3cc([C@@H](Cc4nnn[nH]4)C4CC4)ccn3)CC2)c(F)cn1] | 43 | 4-((1S,4r)-4-(((4-((S)-1-cyclopropyl-2-(1H-tetrazol-5-yl)ethyl)pyridin-2-yl)oxy)methyl)cyclohexyl)-5-fluoro-2-methoxypyridine |
| 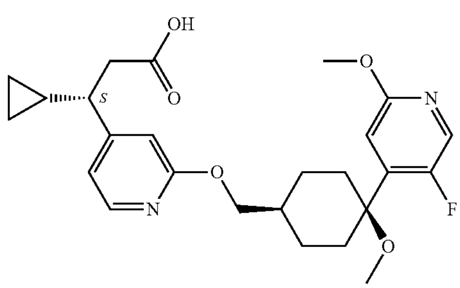 | 44 | (S)-3-cyclopropyl-3-(2-(((1s,4R)-4-(5-fluoro-2-methoxypyridin-4-yl)-4-methoxycyclohexyl)methoxy)pyridin-4-yl)propanoic acid |
| 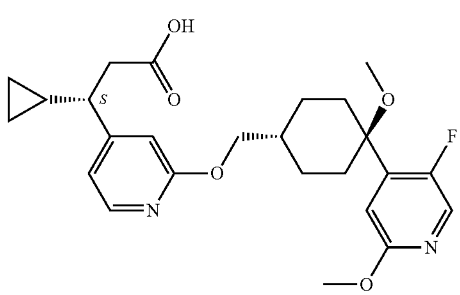 | 45 | (S)-3-cyclopropyl-3-(2-(((1r,4S)-4-(5-fluoro-2-methoxypyridin-4-yl)-4-methoxy cyclohexyl)methoxy)pyridin-4-yl)propanoic acid |

TABLE 1-continued

Compounds of Formula (I)

Formula (I)

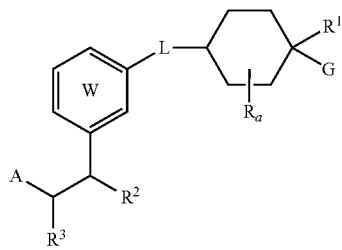

| Structure | Cpd No. | Compound Name |
|---|---|---|
| 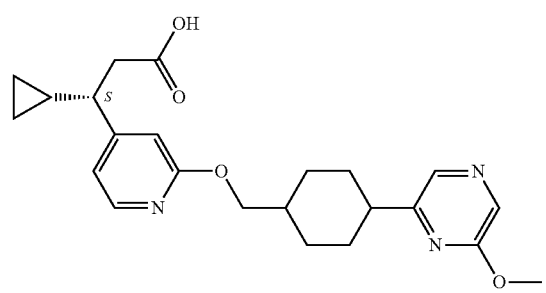 | 46 | (S)-3-cyclopropyl-3-(2-((4-(6-methoxypyrazin-2-yl)cyclohexyl)methoxy)pyridin-4-yl)propanoic acid |
| 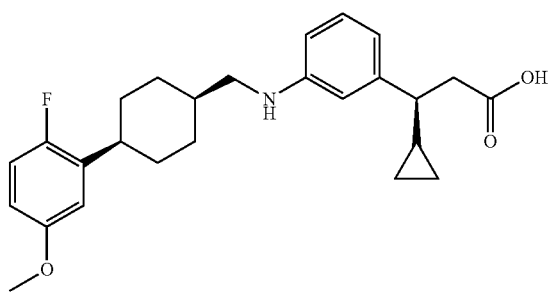 [SMILES: COc1ccc(F)c([C@H]2CC[C@@H](CNc3cccc([C@@H](CC(=O)O)C4CC4)c3)CC2)c1] | 47 | (S)-3-cyclopropyl-3-(3-(((((1s,4R)-4-(2-fluoro-5-methoxyphenyl)cyclohexyl)methyl)amino)phenyl)propanoic acid |
| 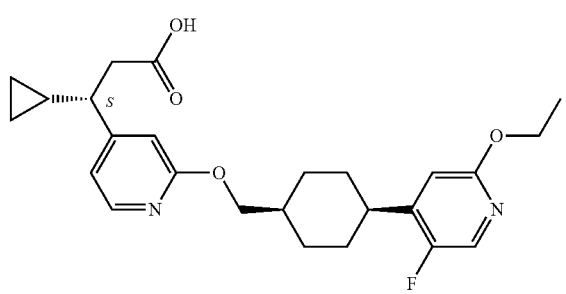 | 48 | (S)-3-cyclopropyl-3-(2-(((1S,4R)-4-(2-ethoxy-5-fluoropyridin-4-yl)cyclohexyl)methoxy)pyridin-4-yl)propanoic acid |
| 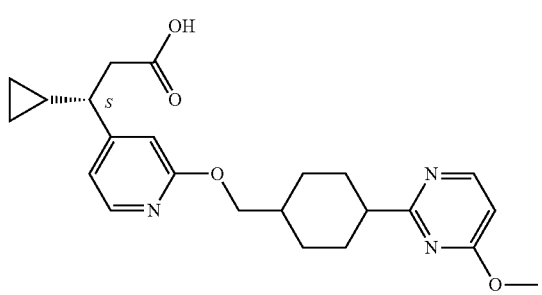 | 49 | (3S)-3-cyclopropyl-3-[2-[[4-(4-methoxypyrimidin-2-yl)cyclohexyl]methoxy]-4-pyridyl]propanoic acid |

TABLE 1-continued

Compounds of Formula (I)

Formula (I)

| Structure | Cpd No. | Compound Name |
|---|---|---|
| 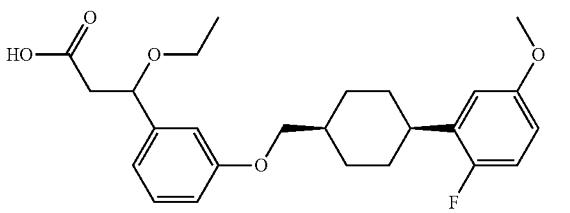 [SMILES: CCOC(CC(=O)O)c1cccc(OC[C@H]2CC[C@@H](c3cc(OC)ccc3F)CC2)c1] | 50 | 3-ethoxy-3-(3-(((1s,4s)-4-(2-fluoro-5-methoxyphenyl)cyclohexyl)methoxy)phenyl)propanoic acid |
| 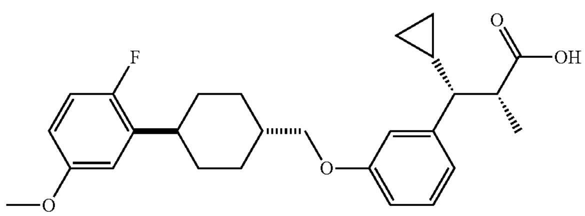 | 51 | (2R,3R)-3-cyclopropyl-3-(3-(((1r,4R)-4-(2-fluoro-5-methoxyphenyl)cyclohexyl)methoxy)phenyl)-2-methylpropanoic acid |
| 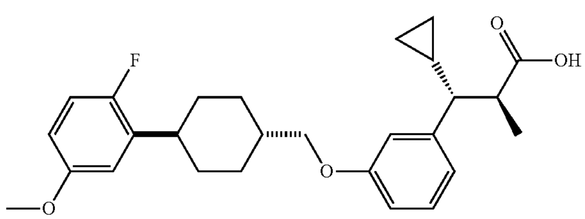 | 52 | (2S,3R)-3-cyclopropyl-3-(3-(((1r,4R)-4-(2-fluoro-5-methoxyphenyl)cyclohexyl)methoxy)phenyl)-2-methylpropanoic acid |
| 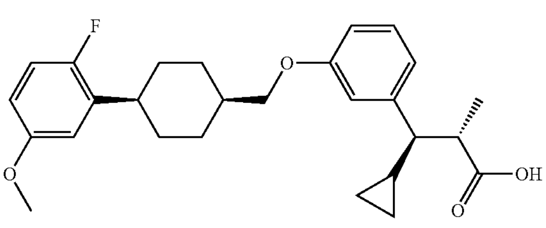 [SMILES: COc1ccc(F)c([C@H]2CC[C@@H](COc3cccc([C@H](C4CC4)[C@H](C)C(=O)O)c3)CC2)c1] | 53 | (2S,3R)-3-cyclopropyl-3-(3-(((1s,4S)-4-(2-fluoro-5-methoxyphenyl)cyclohexyl)methoxy)phenyl)-2-methylpropanoic acid |
| 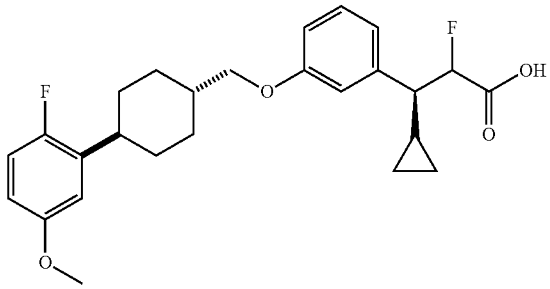 | 54 | (3S)-3-cyclopropyl-2-fluoro-3-(3-(((1r,4S)-4-(2-fluoro-5-methoxyphenyl)cyclohexyl)methoxy)phenyl)propanoic acid |

TABLE 1-continued

Compounds of Formula (I)

Formula (I)

| Structure | Cpd No. | Compound Name |
|---|---|---|
| 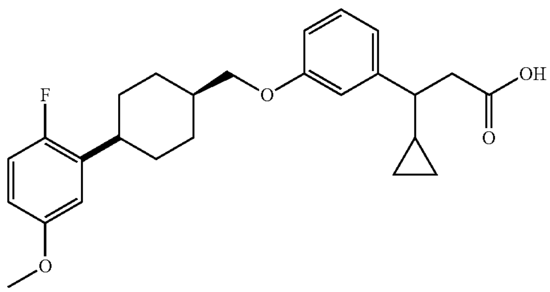 | 55 | 3-cyclopropyl-3-(3-(((1s,4s)-4-(2-fluoro-5-methoxyphenyl)cyclohexyl)methoxy)phenyl)propanoic acid |
| 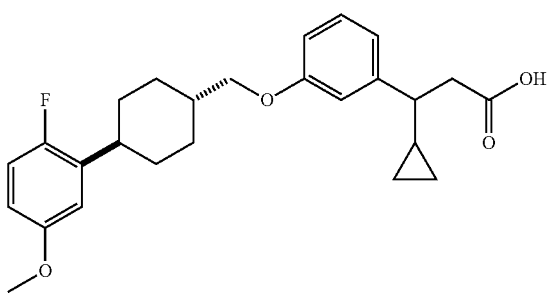 | 56 | 3-cyclopropyl-3-(3-(((1r,4r)-4-(2-fluoro-5-methoxyphenyl)cyclohexyl)methoxy)phenyl)propanoic acid |
| 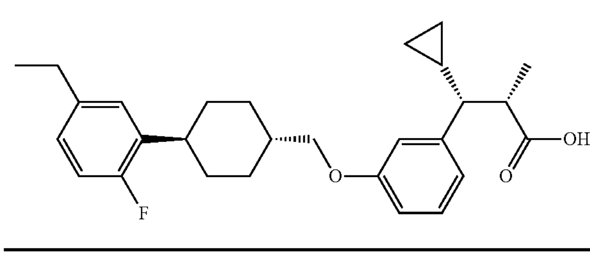 | 57 | (2S,3R)-4-cyclopropyl-3-(3-(((1r,4R)-4-(5-ethyl-2-fluorophenyl)cyclohexyl)methoxy)phenyl)-2-methyl propanoic acid |

Further embodiments of the present invention are directed to a compound of Formula (I)

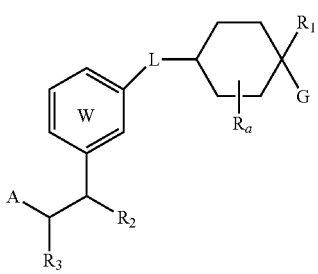

Formula (I)

selected from the group consisting of
(S)-3-cyclopropyl-3-(3-(((1s,4R)-4-(2-fluoro-5-methoxyphenyl)cyclohexyl) methoxy)phenyl)propanoic acid;
(S)-3-cyclopropyl-3-(3-(((1r,4S)-4-(2-fluoro-5-methoxyphenyl)cyclohexyl) methoxy)phenyl) propanoic acid;
(S)-3-cyclopropyl-3-(3-(((1s,4R)-4-(2-fluoro-5-methoxyphenyl)-4-hydroxycyclohexyl) methoxy)phenyl)propanoic acid;
3-cyclopropyl-3-(2-(((1r,4r)-4-(2-fluoro-5-methoxyphenyl)cyclohexyl)methoxy)pyridin-4-yl)propionic acid;
3-cyclopropyl-3-(2-(((1s,4s)-4-(2-fluoro-5-methoxyphenyl)cyclohexyl)methoxy)pyridin-4-yl)propionic acid;
(S)-3-cyclopropyl-3-(3-(((1r,4S)-4-(2-fluoro-5-methoxyphenyl)-4-hydroxycyclohexyl) methoxy)phenyl)propanoic acid;
3-cyclopropyl-3-(2-(((1s,4s)-4-(5-fluoro-2-methoxypyridin-4-yl)cyclohexyl)methoxy)pyridin-4-yl)propionic acid;
3-cyclopropyl-3-(2-(((1r,4r)-4-(5-fluoro-2-methoxypyridin-4-yl)cyclohexyl)methoxy)pyridin-4-yl)propionic acid;
(S)-3-cyclopropyl-3-(3-(((1r,4S)-4-(5-fluoro-2-methoxypyridin-4-yl)cyclohexyl)methoxy)phenyl)propanoic acid;
(S)-3-cyclopropyl-3-(3-(((1s,4R)-4-(5-fluoro-2-methoxypyridin-4-yl)cyclohexyl)methoxy)phenyl)propanoic acid;
(S)-3-cyclopropyl-3-(3-(((1s,4R)-4-(2-fluoro-5-methoxyphenyl)-4-methoxycyclohexyl) methoxy)phenyl)propanoic acid;
(S)-3-cyclopropyl-3-(3-(((1r,4S)-4-(2-fluoro-5-methoxyphenyl)-4-methoxycyclohexyl) methoxy)phenyl)propanoic acid;
3-cyclopropyl-3-(6-(((1r,4r)-4-(2-fluoro-5-methoxyphenyl)cyclohexyl)methoxy)pyridin-2-yl)propionic acid;
3-cyclopropyl-3-(6-(((1s,4s)-4-(2-fluoro-5-methoxyphenyl)cyclohexyl) methoxy)pyridin-2-yl)propionic acid;
3-cyclopropyl-3-(6-(((1r,4r)-4-(5-fluoro-2-methoxypyridin-4-yl)cyclohexyl)methoxy)pyridin-2-yl)propionic acid;
3-cyclopropyl-3-(6-(((1s,4s)-4-(5-fluoro-2-methoxypyridin-4-yl)cyclohexyl)methoxy)pyridin-2-yl)propionic acid;
5-((S)-2-cyclopropyl-2-(3-(((1r,4S)-4-(2-fluoro-5-ethoxyphenyl)cyclohexyl)methoxy)phenyl)ethyl)-1H-tetrazole;
3-cyclopropyl-3-(5-(((1s,4s)-4-(2-fluoro-5-methoxyphenyl)cyclohexyl)methoxy)pyridin-3-yl)propanoic acid;
(S)-3-Cyclopropyl-3-(3-(((1r,4S)-4-fluoro-4-(2-fluoro-5-methoxyphenyl)cyclohexyl)methoxy)phenyl)propanoic acid;
(S)-3-cyclopropyl-3-(3-(((1s,4R)-4-fluoro-4-(2-fluoro-5-methoxyphenyl)cyclohexyl)methoxy)phenyl)propanoic acid;
3-cyclopropyl-3-(5-(((1r,4r)-4-(2-fluoro-5-methoxyphenyl)cyclohexyl)methoxy)pyridin-3-yl)propionic acid;
3-cyclopropyl-3-(5-(((1r,4r)-4-(5-fluoro-2-methoxypyridin-4-yl)cyclohexyl)methoxy)pyridin-3-yl)propionic acid;
3-cyclopropyl-3-(5-(((1s,4s)-4-(5-fluoro-2-methoxypyridin-4-yl)cyclohexyl) methoxy)pyridin-3-yl)propionic acid;
(R)-3-cyclopropyl-3-(2-(((1r,4R)-4-(5-fluoro-2-methoxypyridin-4-yl)cyclohexyl)methoxy)pyridin-4-yl)propanoic acid;
(S)-3-cyclopropyl-3-(2-(((1r,4S)-4-(5-fluoro-2-methoxypyridin-4-yl)cyclohexyl) methoxy)pyridin-4-yl)propanoic acid;
(R)-3-cyclopropyl-3-(2-(((1r,4r)-4-(2-fluoro-5-methoxyphenyl)cyclohexyl)methoxy)pyridin-4-yl)propanoic acid;
(S)-3-cyclopropyl-3-(2-(((1r,4s)-4-(2-fluoro-5-methoxyphenyl)cyclohexyl)methoxy)pyridin-4-yl)propanoic acid;
(R)-3-cyclopropyl-3-(3-(((1s,4S)-4-(2-fluoro-5-methoxyphenyl)cyclohexyl)methoxy)phenyl)propanoic acid;
(3S)-3-cyclopropyl-3-(3-((4-(2-fluoro-5-methoxyphenyl)-2-isobutylcyclohexyl) methoxy)phenyl)propanoic acid;
(3S)-3-cyclopropyl-3-(3-(((4-(5-fluoro-2-methoxypyridin-4-yl)-2-isobutylcyclohexyl) methoxy)phenyl)propanoic acid;
3-cyclopropyl-3-(4-(((1r,4r)-4-(5-fluoro-2-methoxypyridin-4-yl)cyclohexyl)methoxy)pyridin-2-yl)propanoic acid;
3-cyclopropyl-3-(4-(((1s,4s)-4-(5-fluoro-2-methoxypyridin-4-yl)cyclohexyl)methoxy)pyridin-2-yl)propanoic acid;
(3S)-3-cyclopropyl-3-(3-(((4-(5-fluoro-2-methoxypyridin-4-yl)-2-methylcyclohexyl) methoxy)phenyl)propanoic acid;
3-cyclopropyl-3-(4-(((1r,4r)-4-(2-fluoro-5-methoxyphenyl)cyclohexyl)methoxy)pyridin-2-yl)propanoic acid;
3-cyclopropyl-3-(4-(((1s,4s)-4-(2-fluoro-5-methoxyphenyl)cyclohexyl)methoxy)pyridin-2-yl)propanoic acid;
(S)-3-cyclopropyl-3-(3-(2-((1r,4R)-4-(2-fluoro-5-methoxyphenyl)cyclohexyl)ethyl)phenyl) propanoic acid;
(R)-3-cyclopropyl-3-(3-(((1s,4S)-4-(2-fluoro-5-methoxyphenyl)cyclohexyl)methoxy)phenyl)propanoic acid;
(R)-3-cyclopropyl-3-(3-(((1r,4R)-4-(2-fluoro-5-methoxyphenyl)cyclohexyl) methoxy)phenyl)propanoic acid;
5-((S)-2-cyclopropyl-2-(3-(((1s,4R)-4-(2-fluoro-5-methoxyphenyl)cyclohexyl) methoxy)phenyl)ethyl)-1H-tetrazole;
(S)-3-cyclopropyl-3-(3-((((1r,4S)-4-(2-fluoro-5-methoxyphenyl)cyclohexyl)methyl)amino)phenyl)propanoic acid;
(R)-3-cyclopropyl-3-(2-(((1s,4S)-4-(2-fluoro-5-methoxyphenyl)cyclohexyl)methoxy)pyridin-4-yl)propanoic acid;
3-(3-(((1s,4s)-4-(2-fluoro-5-methoxyphenyl)cyclohexyl) methoxy)phenyl)hex-4-ynoic acid;
4-((1S,4r)-4-(((4-((S)-1-cyclopropyl-2-(1H-tetrazol-5-yl)ethyl)pyridin-2-yl)oxy)methyl)cyclohexyl)-5-fluoro-2-methoxypyridine;
(S)-3-cyclopropyl-3-(2-(((1s,4R)-4-(5-fluoro-2-methoxypyridin-4-yl)-4-methoxycyclohexyl) methoxy)pyridin-4-yl) propanoic acid;
(S)-3-cyclopropyl-3-(2-(((1r,4S)-4-(5-fluoro-2-methoxypyridin-4-yl)-4-methoxy cyclohexyl) methoxy)pyridin-4-yl)propanoic acid;
(S)-3-cyclopropyl-3-(2-((4-(6-methoxypyrazin-2-yl)cyclohexyl)methoxy)pyridin-4-yl)propanoic acid;
(S)-3-cyclopropyl-3-(3-((((1s,4R)-4-(2-fluoro-5-methoxyphenyl)cyclohexyl)methyl)amino)phenyl)propanoic acid;
(S)-3-cyclopropyl-3-(2-(((1s,4R)-4-(2-ethoxy-5-fluoropyridin-4-yl)cyclohexyl)methoxy)pyridin-4-yl)propanoic acid;
(3S)-3-cyclopropyl-3-[2-[[4-(4-methoxypyrimidin-2-yl)cyclohexyl]methoxy]-4-pyridyl]propanoic acid;
3-ethoxy-3-(3-(((1s,4s)-4-(2-fluoro-5-methoxyphenyl)cyclohexyl) methoxy)phenyl) propanoic acid;

(2R,3R)-3-cyclopropyl-3-(3-(((1r,4R)-4-(2-fluoro-5-methoxyphenyl)cyclohexyl) methoxy)phenyl)-2-methyl-propanoic acid;
(2S,3R)-3-cyclopropyl-3-(3-(((1r,4R)-4-(2-fluoro-5-methoxyphenyl)cyclohexyl)methoxy)phenyl)-2-methyl-propanoic acid;
(2S,3R)-3-cyclopropyl-3-(3-(((1s,4S)-4-(2-fluoro-5-methoxyphenyl)cyclohexyl) methoxy)phenyl)-2-methyl-propanoic acid;
(3S)-3-cyclopropyl-2-fluoro-3-(3-(((1r,4S)-4-(2-fluoro-5-methoxyphenyl)cyclohexyl) methoxy)phenyl)propanoic acid;
3-cyclopropyl-3-(3-(((1s,4s)-4-(2-fluoro-5-methoxyphenyl)cyclohexyl)methoxy)phenyl)propanoic acid;
3-cyclopropyl-3-(3-(((1r,4r)-4-(2-fluoro-5-methoxyphenyl)cyclohexyl)methoxy)phenyl)propanoic acid; and
(2S,3R)-3-cyclopropyl-3-(3-(((1r,4R)-4-(5-ethyl-2-fluorophenyl)cyclohexyl) methoxy)phenyl)-2-methylpropanoic acid;
or a pharmaceutically acceptable salt form thereof.

Embodiments of the present invention also include a compound of Formula (II)

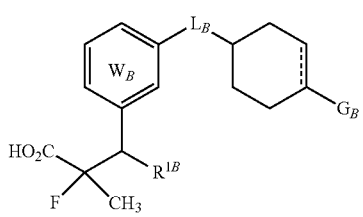

Formula (II)

wherein
aa) $G_B$ is g1b

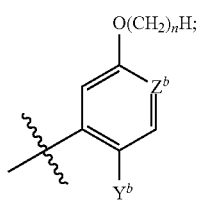

g1b wherein $Z^b$ is N or CH;
bb) $G_B$ is 2-fluoro-5-methoxyphenyl, 2-chloro-5-methoxyphenyl, 2-fluoro-5-methoxypyridin-4-yl, 5-ethyl-2-fluorophenyl, 2,5-difluorophenyl, 2-chloro-5-ethylphenyl, 5-methoxy-2-(pyridin-2-ylcarbamoyl)phenyl, 2-fluoro-5-(trifluoromethoxy)phenyl, 2-ethoxy-5-fluoropyridin-4-yl, or 5-fluoro-2-methoxypyridin-4-yl;
cc) $G_B$ is 2-fluoro-5-methoxyphenyl, 2-chloro-5-methoxyphenyl, or 2-fluoro-5-methoxypyridin-4-yl;
dd) n is 1;
ee) $L_B$ is —OCH$_2$— or —(CH$_2$)$_2$—;
ff) $L_B$ is —OCH$_2$—;
gg) ¦ is absent;
hh) $R^{1B}$ is cyclopropyl;
ii) ring $W_B$ is phenyl;
jj) ring $W_B$ is pyridinyl
and any combination of embodiments aa) through jj) above, provided that it is understood that combinations in which different embodiments of the same substituent would be combined are excluded;
or an enantiomer, diastereomer, or pharmaceutically acceptable salt form thereof.

An embodiment of the present invention includes a compound of Formula (IIa)

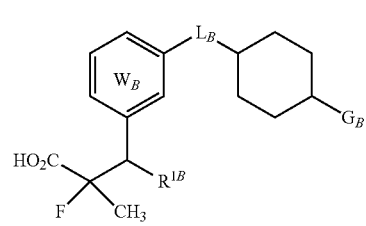

Formula (IIa)

wherein
$G_B$ is g1b; wherein $Z^b$ is N or CH;
n is an integer from 1 to 2;
$Y^b$ is independently selected from the group consisting of fluoro, chloro, trifluoromethyl, and pyridin-2-ylaminocarbonyl;
$L_B$ is —OCH$_2$—, —CH$_2$O—, —NHCH$_2$—, —(CH$_2$)$_2$— and —CH=CH—;
$R^{1B}$ is cyclopropyl;
ring $W_B$ is phenyl or pyridinyl;
or an enantiomer, diastereomer, or pharmaceutically acceptable salt form thereof.

An embodiment of the present invention includes a compound of Formula (IIa)

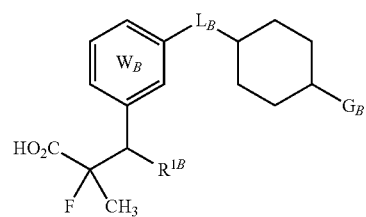

Formula (IIa)

wherein
$G_B$ is 2-fluoro-5-methoxyphenyl, 2-chloro-5-methoxyphenyl, 2-fluoro-5-methoxypyridin-4-yl, 5-ethyl-2-fluorophenyl, 2,5-difluorophenyl, 2-chloro-5-ethylphenyl, 5-methoxy-2-(pyridin-2-ylcarbamoyl)phenyl, 2-fluoro-5-(trifluoromethoxy)phenyl, 2-ethoxy-5-fluoropyridin-4-yl, or 5-fluoro-2-methoxypyridin-4-yl;
$L_B$ is —OCH$_2$—;
$R^{1B}$ is cyclopropyl;
ring $W_B$ is phenyl or pyridinyl;
or an enantiomer, diastereomer, or pharmaceutically acceptable salt form thereof.

An embodiment of the present invention includes a compound of Formula (IIa)

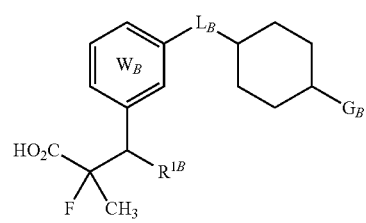

Formula (IIa)

wherein
$G_B$ is 2-fluoro-5-methoxyphenyl, 2-chloro-5-methoxyphenyl, and 2-fluoro-5-methoxypyridin-4-yl;
$L_B$ is —OCH$_2$—;
$R^{1B}$ is cyclopropyl;
ring $W_B$ is phenyl or pyridinyl;
or an enantiomer, diastereomer, or pharmaceutically acceptable salt form thereof.

Additional embodiments of the present invention include compounds of Formula (II) as herein defined, or an enantiomer, diastereomer, solvate, or a pharmaceutically acceptable salt form thereof, wherein the substituents selected from one or more of the variables defined herein are independently selected to be any individual substituent or any subset of substituents from those exemplified in the listing in Table 2, below.

TABLE 2

Formula (II)

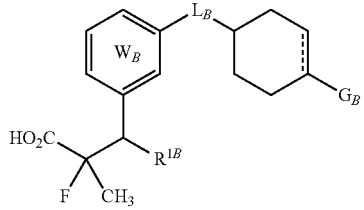

| Strucure | Cpd No. | Compound Name |
|---|---|---|
|  | 58 | (3S)-3-Cyclopropyl-2-fluoro-3-(3-(((1r,4S)-4-(2-fluoro-5-methoxyphenyl)cyclohexyl)methoxy)phenyl)-2-methylpropanoic acid |
|  | 59 | (2R,3S)-3-Cyclopropyl-2-fluoro-3-(3-(((1r,4S)-4-(2-fluoro-5-methoxyphenyl)cyclohexyl)methoxy)phenyl)-2-methylpropanoic acid |
|  | 60 | (2S,3S)-3-Cyclopropyl-2-fluoro-3-(3-(((1r,4S)-4-(2-fluoro-5-methoxyphenyl)cyclohexyl)methoxy)phenyl)-2-methylpropanoic acid |

TABLE 2-continued

Formula (II)

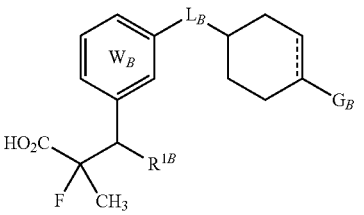

| Strucure | Cpd No. | Compound Name |
|---|---|---|
| 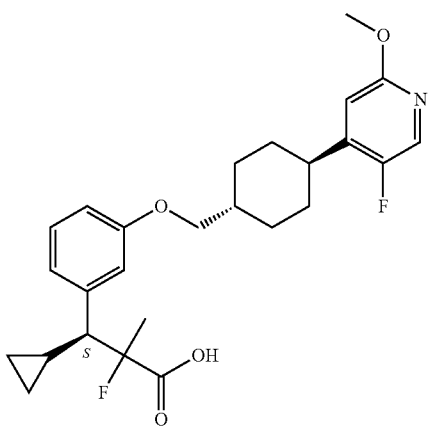 | 61 | (3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid |
| 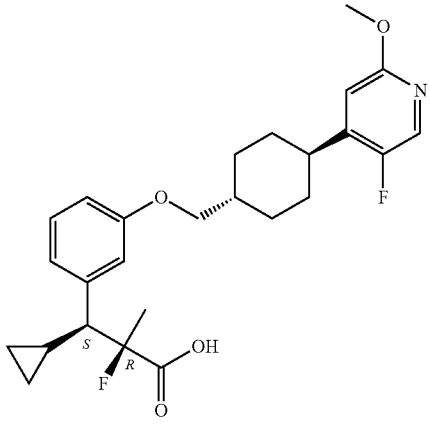 | 62 | (2R,3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid |
| 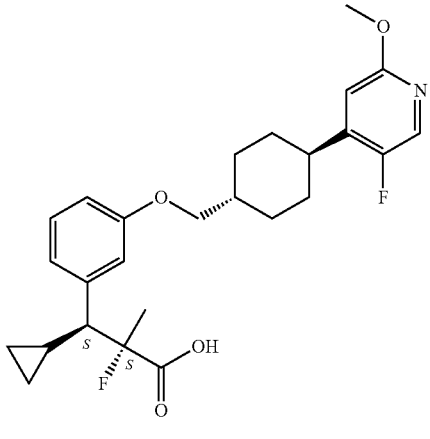 | 63 | (2S,3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid |

TABLE 2-continued
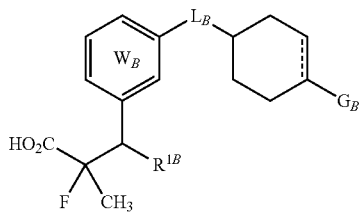
Formula (II)
| Strucure | Cpd No. | Compound Name |
|---|---|---|
|  | 64 | (2R,3S)-3-(3-((4-(2-Chloro-5-methoxyphenyl)cyclohexyl)methoxy)phenyl)-3-cyclopropyl-2-fluoro-2-methylpropanoic acid |
|  | 65 | (3S)-3-(3-((4-(2-Chloro-5-ethylphenyl)cyclohexyl)methoxy)phenyl)-3-cyclopropyl-2-fluoro-2-methylpropanoic acid |
|  | 66 | (3S)-3-Cyclopropyl-2-fluoro-3-(3-((4-(3-methoxyphenyl)cyclohexyl)methoxy)phenyl)-2-methylpropanoic acid |

TABLE 2-continued

Formula (II)

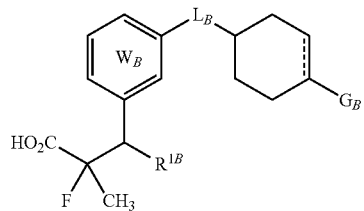

| Strucure | Cpd No. | Compound Name |
|---|---|---|
| (structure) | 67 | (3S)-3-Cyclopropyl-3-(3-((4-(2,5-difluoropyridin-4-yl)cyclohexyl)methoxy)phenyl)-2-fluoro-2-methylpropanoic acid |
| (structure) | 68 | (3S)-3-Cyclopropyl-3-(3-(((1r,4S)-4-(5-ethyl-2-fluorophenyl)cyclohexyl)methoxy)phenyl)-2-fluoro-2-methylpropanoic acid |
| (structure) | 69 | (3S)-3-Cyclopropyl-2-fluoro-3-(3-((4-(2-methoxypyridin-4-yl)cyclohexyl)methoxy)phenyl)-2-methylpropanoic acid |

TABLE 2-continued
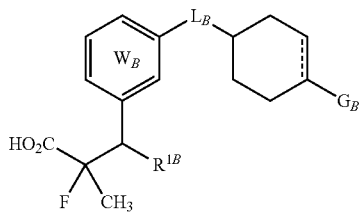
Formula (II)
| Strucure | Cpd No. | Compound Name |
|---|---|---|
| | 70 | (3S)-3-Cyclopropyl-2-fluoro-3-(3-((4-(5-methoxy-2-methylphenyl)cyclohexyl)methoxy)phenyl)-2-methylpropanoic acid |
| | 71 | (3S)-3-Cyclopropyl-2-fluoro-3-(3-((4-(5-methoxy-2-(pyridin-2-ylcarbamoyl)phenyl)cyclohexyl)methoxy)phenyl)-2-methylpropanoic acid |
| | 72 | (3S)-3-Cyclopropyl-2-fluoro-3-(3-((E)-2-((1r,4S)-4-(2-fluoro-5-methoxyphenyl)cyclohexyl)vinyl)phenyl)-2-methylpropanoic acid |

TABLE 2-continued
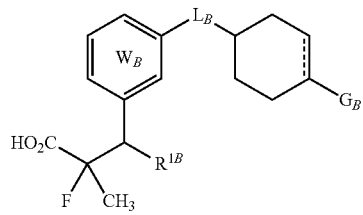
Formula (II)
| Strucure | Cpd No. | Compound Name |
|---|---|---|
| | 73 | (3S)-3-Cyclopropyl-2-fluoro-3-(3-(2-((1r,4R)-4-(2-fluoro-5-methoxyphenyl)cyclohexyl)ethyl)phenyl)-2-methylpropanoic acid |
| | 74 | (2R,3S)-3-Cyclopropyl-2-fluoro-3-(3-(((1r,4S)-4-(2-fluoro-5-(trifluoromethoxy)phenyl)cyclohexyl)methoxy)phenyl)-2-methylpropanoic acid |
| | 75 | (2R,3S)-3-Cyclopropyl-3-(3-((4-(2,5-difluorophenyl)cyclohexyl)methoxy)phenyl)-2-fluoro-2-methylpropanoic acid |

TABLE 2-continued

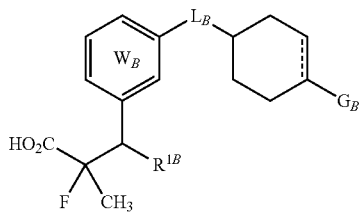

Formula (II)

| Strucure | Cpd No. | Compound Name |
|---|---|---|
| | 76 | (2R,3S)-3-Cyclopropyl-2-fluoro-3-(3-((2'-fluoro-5'-methoxy-2,3,4,5-tetrahydro-[1,1'-biphenyl]-4-yl)methoxy)phenyl)-2-methylpropanoic acid |
| | 77 | (3S)-3-Cyclopropyl-2-fluoro-3-(3-(((((1r,4S)-4-(2-fluoro-5-methoxyphenyl)cyclohexyl)methyl)amino)phenyl)-2-methylpropanoic acid |
| | 78 | (3S)-3-Cyclopropyl-2-fluoro-3-(3-(((4-(2-fluoro-5-methoxyphenyl)cyclohexyl)oxy)methyl)phenyl)-2-methylpropanoic acid |

TABLE 2-continued

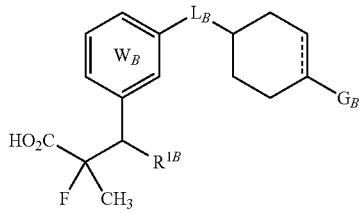
Formula (II)

| Strucure | Cpd No. | Compound Name |
|---|---|---|
|  | 79 | (3S)-3-Cyclopropyl-2-fluoro-3-(2-(((1r,4S)-4-(2-fluoro-5-methoxyphenyl)cyclohexyl)methoxy)pyridin-4-yl)-2-methylpropanoic acid |
|  | 80 | (3S)-3-Cyclopropyl-2-fluoro-3-(2-(((1r,4S)-4-(5-fluoro-2-methoxypyridin-4-yl)cyclohexyl)methoxy)pyridin-4-yl)-2-methylpropanoic acid |

Embodiments of the present invention are also directed to a compound of Formula (II)

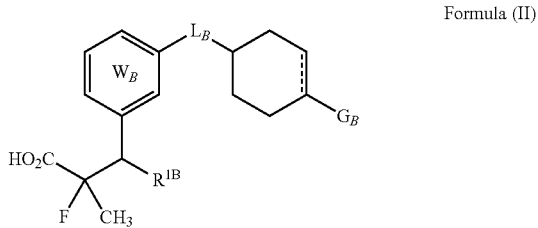
Formula (II)

selected from the group consisting of
(3S)-3-Cyclopropyl-2-fluoro-3-(3-(((1r,4S)-4-(2-fluoro-5-methoxyphenyl)cyclohexyl)methoxy)phenyl)-2-methylpropanoic acid;
(2R,3S)-3-Cyclopropyl-2-fluoro-3-(3-(((1r,4S)-4-(2-fluoro-5-methoxyphenyl)cyclohexyl)methoxy)phenyl)-2-methylpropanoic acid;
(2S,3S)-3-Cyclopropyl-2-fluoro-3-(3-(((1r,4S)-4-(2-fluoro-5-methoxyphenyl)cyclohexyl)methoxy)phenyl)-2-methylpropanoic acid;
(3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid;
(2R,3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid;
(2S,3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid;
(2R,3S)-3-(3-((4-(2-Chloro-5-methoxyphenyl)cyclohexyl)methoxy)phenyl)-3-cyclopropyl-2-fluoro-2-methylpropanoic acid;
(3S)-3-(3-((4-(2-Chloro-5-ethylphenyl)cyclohexyl)methoxy)phenyl)-3-cyclopropyl-2-fluoro-2-methylpropanoic acid;
(3S)-3-Cyclopropyl-2-fluoro-3-(3-((4-(3-methoxyphenyl)cyclohexyl)methoxy)phenyl)-2-methylpropanoic acid;
(3S)-3-Cyclopropyl-3-(3-((4-(2,5-difluoropyridin-4-yl)cyclohexyl)methoxy)phenyl)-2-fluoro-2-methylpropanoic acid;
(3S)-3-Cyclopropyl-3-(3-(((1r,4S)-4-(5-ethyl-2-fluorophenyl)cyclohexyl)methoxy)phenyl)-2-fluoro-2-methylpropanoic acid;
(3S)-3-Cyclopropyl-2-fluoro-3-(3-((4-(2-methoxypyridin-4-yl)cyclohexyl)methoxy)phenyl)-2-methylpropanoic acid;
(3S)-3-Cyclopropyl-2-fluoro-3-(3-((4-(5-methoxy-2-methylphenyl)cyclohexyl)methoxy)phenyl)-2-methylpropanoic acid;
(3S)-3-Cyclopropyl-2-fluoro-3-(3-(((4-(5-methoxy-2-(pyridin-2-ylcarbamoyl)phenyl)cyclohexyl)methoxy)phenyl)-2-methylpropanoic acid;
(3S)-3-Cyclopropyl-2-fluoro-3-(3-((E)-2-((1r,4S)-4-(2-fluoro-5-methoxyphenyl)cyclohexyl)vinyl)phenyl)-2-methylpropanoic acid;

(3S)-3-Cyclopropyl-2-fluoro-3-(3-(2-((1r,4R)-4-(2-fluoro-5-methoxyphenyl)cyclohexyl)ethyl)phenyl)-2-methylpropanoic acid;

(2R,3S)-3-Cyclopropyl-2-fluoro-3-(3-(((1r,4S)-4-(2-fluoro-5-(trifluoromethoxy)phenyl)cyclohexyl)methoxy)phenyl)-2-methylpropanoic acid;

(2R,3S)-3-Cyclopropyl-3-(3-((4-(2,5-difluorophenyl)cyclohexyl)methoxy)phenyl)-2-fluoro-2-methylpropanoic acid;

(2R,3S)-3-Cyclopropyl-2-fluoro-3-(3-((2'-fluoro-5'-methoxy-2,3,4,5-tetrahydro-[1,1'-biphenyl]-4-yl)methoxy)phenyl)-2-methylpropanoic acid;

(3S)-3-Cyclopropyl-2-fluoro-3-(3-((((1r,4S)-4-(2-fluoro-5-methoxyphenyl)cyclohexyl)methyl)amino)phenyl)-2-methylpropanoic acid;

(3S)-3-Cyclopropyl-2-fluoro-3-(3-(((4-(2-fluoro-5-methoxyphenyl)cyclohexyl)oxy)methyl)phenyl)-2-methylpropanoic acid;

(3S)-3-Cyclopropyl-2-fluoro-3-(2-(((1r,4S)-4-(2-fluoro-5-methoxyphenyl)cyclohexyl)methoxy)pyridin-4-yl)-2-methylpropanoic acid; and (3S)-3-Cyclopropyl-2-fluoro-3-(2-(((1r,4S)-4-(5-fluoro-2-methoxypyridin-4-yl)cyclohexyl)methoxy)pyridin-4-yl)-2-methylpropanoic acid;

or a pharmaceutically acceptable salt form thereof.

For use in medicine, salts of compounds of Formula (I) and Formula (II) refer to non-toxic "pharmaceutically acceptable salts." Other salts may, however, be useful in the preparation of compounds of Formula (I) and Formula (II) or of their pharmaceutically acceptable salt forms thereof. Suitable pharmaceutically acceptable salts of compounds of Formula (I) and Formula (II) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) and Formula (II) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I) and Formula (II). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I) and Formula (II).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) and Formula (II) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\% \ (+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\% \ (-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T.W. Greene & P.G.M. Wuts, *Protective Groups in Organic Synthesis*, John Wiley & Sons, 1991; and T.W. Greene & P.G.M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) or Formula (II) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) or Formula (II) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) and Formula (II) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) and Formula (II) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) and Formula (II) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) and Formula (II) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I) or Formula (II).

Advantageously, a compound of Formula (I) or Formula (II) may be administered in a single daily dose, or the total daily dosage may be administered in divided doses of two, three and four times daily.

Optimal dosages of a compound of Formula (I) or Formula (II) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) and Formula (II) may be administered in any of the foregoing compositions and dosage regimens or by means of those compositions and dosage regimens established in the art whenever use of a compound of Formula (I) or Formula (II) is required for a subject in need thereof.

As GPR40 agonists, the compounds of Formula (I) and Formula (II) are useful in methods for treating or preventing a disease, a syndrome, a condition or a disorder in a subject, including an animal, a mammal and a human in which the disease, the syndrome, the condition or the disorder is affected by the modulation, including agonism, of the GPR40 receptor. Such methods comprise, consist of and/or consist essentially of administering to a subject, including an animal, a mammal, and a human, in need of such treatment or prevention, a therapeutically effective amount of a compound, salt or solvate of Formula (I) or Formula (II).

In another embodiment, the present invention is directed to a compound of Formula (I) or Formula (II) for use in the treatment of a disorder affected by the agonism of GPR40 receptor selected from the group consisting of Type 2 diabetes mellitus, obesity, obesity related disorders, impaired glucose tolerance, insulin resistance, metabolic syndrome, diabetic nephropathy, nonalcoholic steatohepatitis (NASH), cardiovascular risk factors such as hypertension, and cardiovascular risk factors related to unmanaged cholesterol and/or lipid levels, osteoporosis, inflammation, and eczema; preferably, Type II diabetes mellitus, metabolic syndrome, and impaired glucose tolerance; more preferably, Type II diabetes mellitus or impaired glucose tolerance.

In another embodiment, the present invention is directed to a compound of Formula (I) or Formula (II) for use in the treatment of Type 2 diabetes mellitus.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
AcOH glacial acetic acid
ADDP azodicarboxylic dipiperidide
aq. aqueous
Bn or Bzl benzyl
BINAP 2,2'-bis(diphenylphosphino)-1,1'-binaphthyl
Boc tert-butyloxycarbonyl
conc. concentrated
dba dibenzylideneacetone
DBU 1,8-diazabicyclo[5.4.0]undec-7-ene
DCC N,N'-dicyclohexyl-carbodiimide
DCE 1,2-dichloroethane
DCM dichloromethane
DEAD diethyl azodicarboxylate
DIBAL diisobutylaluminum hydride
DIPEA or DIEA diisopropyl-ethyl amine
DMA dimethylaniline
DMAP 4-dimethylaminopyridine
DME dimethoxyethane
DMF N,N-dimethylformamide
DMSO dimethylsulfoxide
DPPA diphenylphosphoryl azide
dppf 1,1'-bis(diphenylphosphino)ferrocene
EA ethyl acetate
EDCI 1-ethyl-3-(3-dimethylaminopropyl) carbodiimide
ESI electrospray ionization
EtOAc or EA ethyl acetate
EtOH ethanol
GCMS gas chromatography-mass spectrometry
h or hr(s) hour or hours
HEK human embryonic kidney
HPLC high performance liquid chromatography
LAH lithium aluminum hydride
LDA lithium diisopropylamide
LHMDS lithium bis(trimethylsilyl)amide
MEK methyl ethyl ketone
MeOH methanol
MHz megahertz
min minute or minutes
MS mass spectrometry
Ms methanesulfonyl
NBS N-bromosuccinimide
NIS N-iodosuccinimide
NMM N-methylmorpholine
NMP N-methylpyrrolidone
NMR nuclear magnetic resonance
PCC pyridinium chlorochromate
PE petrolum ether
RP reverse-phase rt or RT room temperature
R$_t$ retention time
Sec second or seconds
SEM-Cl 2-(trimethylsilyl)ethoxymethyl chloride
TBAF tetrabutylammonium fluoride
TBDMS t-butyldimethylsilyl
TBP tributyl phosphate
TEA or Et$_3$N triethylamine
TFA trifluoroacetic acid
THF tetrahydrofuran
TIPS triisopropylsilyl
TLC thin layer chromatography
TMS tetramethylsilane
Ts 4-toluenesulfonyl General Schemes

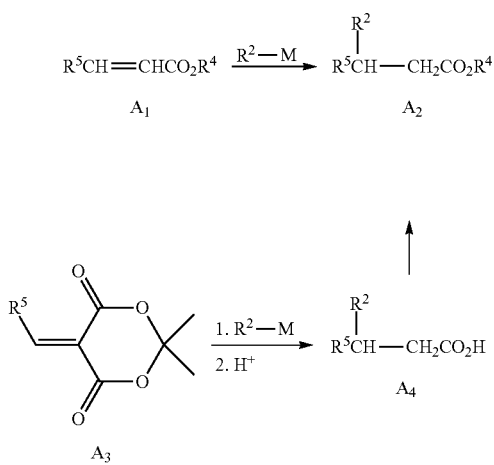

Compound of formula A$_2$ may be prepared as shown in Scheme A. An acrylic ester of formula A$_1$, wherein R$^5$ is 3-hydroxyphenyl, may be used as a substrate for a conjugate addition reaction with a compound of formula R$^2$-M, to obtain a compound of formula A$_2$. The starting acrylate of formula A$_1$ is either commercially available or may be prepared according to the methods described in the scientific literature. A compound of formula R$^2$-M may be (a) a boronic acid to form a compound of formula R$^2$—B(OH)$_2$; (b) a suitably selected boronic ester such as pinacolatoboryl, neopentylglycolatoboryl, and the like; (c) a suitably selected copper reagent or (d) a suitably selected Grignard reagent. One of ordinary skill in the art will understand that a catalyst, optionally in the presence of a ligand, may be required with the use of certain available reagents. In addition, with the use of certain other organometallic reagents, such as a Grignard reagent or a cuprate, the free hydroxyl group may need to be protected with an appropriate hydroxyl protecting group, which may be removed at a later stage in the synthetic sequence. A preferred method for this transformation includes treatment of a compound of formula A$_1$ with a compound of R$^2$-M wherein M is a boronic acid; in the presence of an Rh catalyst such as Rh(COD)Cl$_2$; with a suitable ligand such as BINAP. When optically pure BINAP is employed, an enantiomerically enriched compound of formula A$_2$ may be prepared. A compound of formula A$_2$ may be subjected to chiral separation to obtain an optically pure enantiomer. When a compound of formula A$_3$ is employed in place of the acrylate starting material of formula A$_1$, it is necessary to esterify the resultant carboxylic acid of formula A$_4$ to obtain the desired compound of formula A$_2$. One of ordinary skill in the art will recognize that in certain instances, R$^5$ may be interchanged with R$^2$.

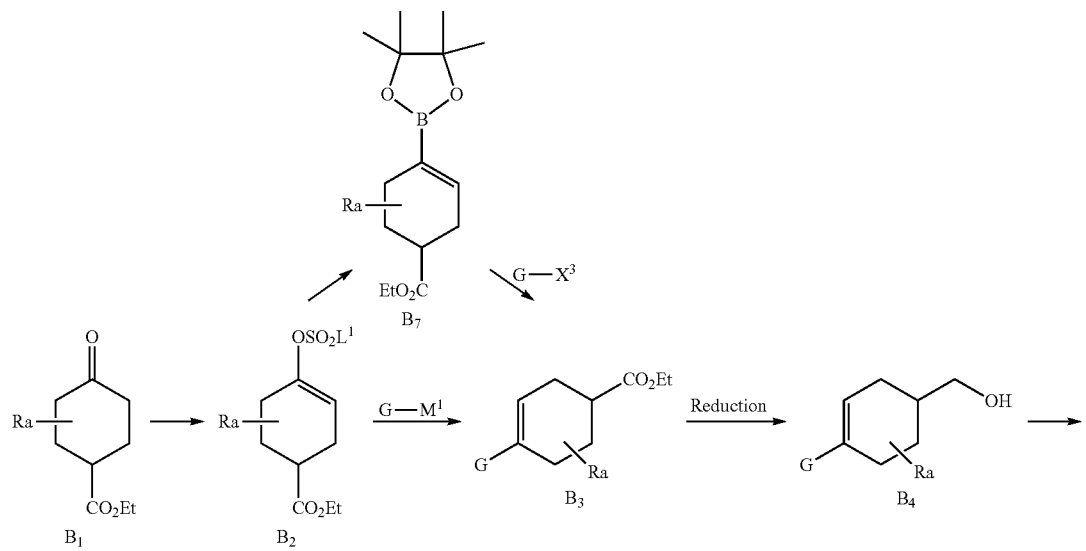

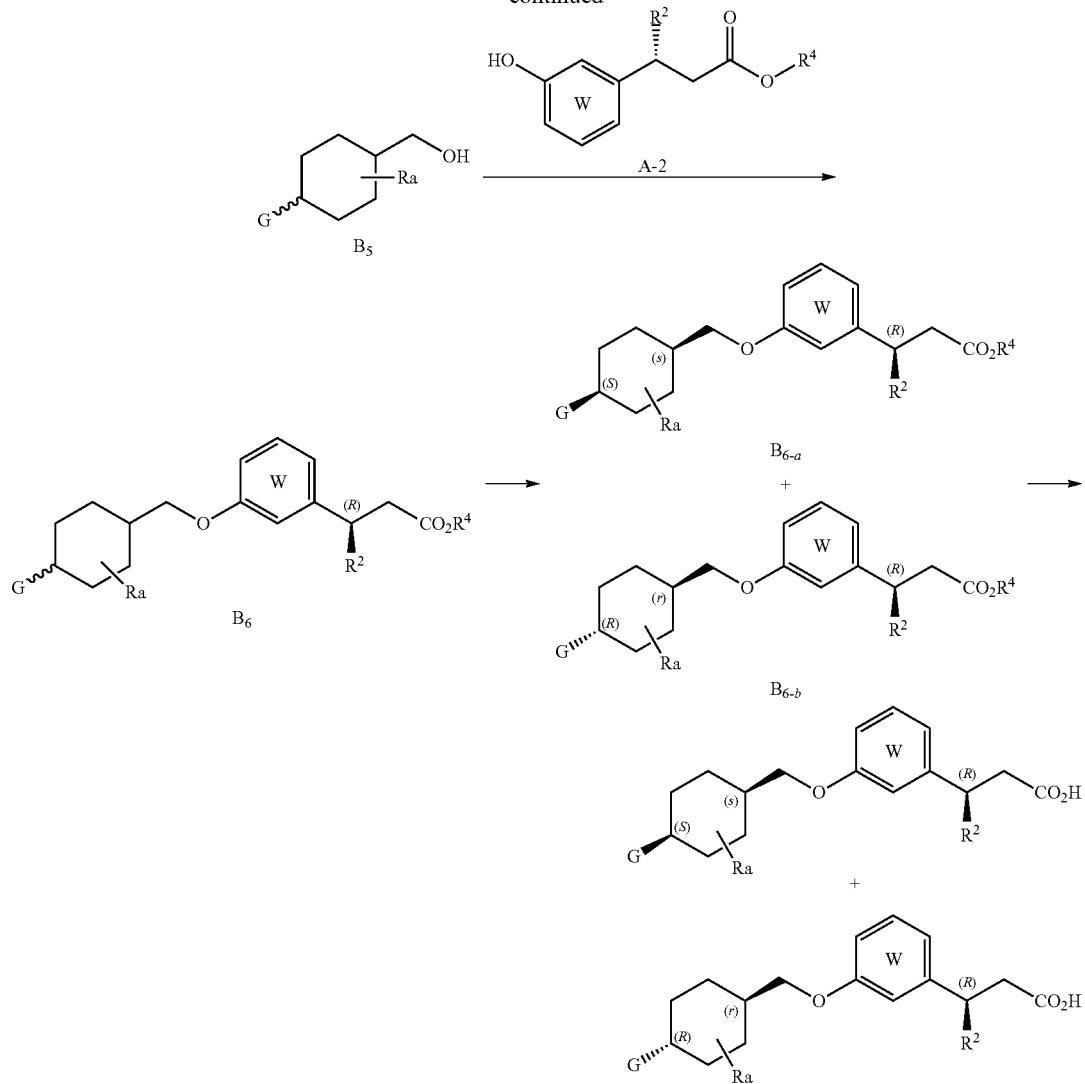

Compound B₁ optionally substituted with R_a, is either commercially available or may be prepared according to the methods described in the scientific literature. Compound B₁ may be converted to its corresponding vinyl perfluorosufonate of formula B₂ via treatment with a suitable base and a perfluorosulfonating agent under appropriate conditions. The preferred method for this transformation includes, but is not limited to, the treatment of compound B₁ with a hindered, tertiary amine base such as DBU and the like, in a solvent such as THF and the like, at a temperature in the range of from about 0 to about 100° C., preferably at about 25° C., in the presence of a perfluorosulfonating agent such as perfluorobutylsulfonyl fluoride, to obtain the corresponding compound of formula B₂ wherein L¹ is C₄F₉. Compounds of formula B₂ wherein L¹ is CF₃ may be prepared from compound B₁ under standard conditions, for example, using the reagents LiHMDS/N-phenyl-bis(trifluoromethanesulfonimide) at about −78° C.

A compound of formula B₂ may be reacted with a suitably substituted compound of formula G-M¹, under suitable coupling conditions, to yield the corresponding compound of formula B₃. A compound of formula G-M¹ may be (a) a boronic acid to form a compound of formula G-B(OH)₂; (b) a suitably selected boronic ester such as pinacolatoboryl, neopentylglycolatoboryl, and the like; (c) a suitably selected trialkylstannyl such as tri(n-butyl)tin, and the like; (d) a suitably selected trialkylsilyl such as triallylsilyl, and the like; or (e) a suitably selected organo zinc reagent such as G-ZnX wherein X is a halide such as chloro, bromo, or iodo.

For example, a compound of formula G-M¹, wherein M¹ is preferably —B(OH)₂ or a boronic ester, may be reacted with a compound of formula B₂ under Suzuki coupling conditions, more particularly in the presence of a suitably selected palladium catalyst such as palladium (II) acetate, palladium (II) chloride, bis(acetonitrile)-dichloro-palladium (II), allylpalladium (II) chloride dimer, tris(dibenzylidineacetone)dipalladium (0) (Pd₂(dba)₃), 2-(di-tert-butylphosphino)biphenyl, dichloro-bis(di-tert-butylphenylphosphine)-palladium (II), [1,1'-bis-(diphenylphosphino)-ferrocene]-palladium (II) dichloride dichloromethane adduct ((dppf)PdCl₂.DCM), tetrakis(triphenylphosphine) palladium(0) (Pd(PPh₃)₄), (1,1'-bis(di-tert-butylphosphino)ferrocene palladium (II) chloride, and the like; optionally in the presence of a suitably selected ligand such as triphenylphosphine, tributylphosphine, tri-o-tolylphosphine, tri(tert-butyl)-phosphine, tricyclohexylphosphine, 1,1'-bis(diphenylphosphino)-ferrocene, 2-(dicyclohexylphosphino)-2',4',6'-tri-i-propyl-1,1'-biphenyl, S-Phos, Ru-Phos, bis[2-(diphenyl-phosphino)phenyl]ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, sodium hydroxide, sodium bicarbonate; potassium phosphate or preferably sodium carbonate; in a suitably selected solvent such as ethanol, THF, DMF, toluene, benzene, DME, water, 1,4-dioxane, or the like, or a combination thereof; at a temperature in the range of from about room temperature to about 180° C.

Alternatively a compound of formula $B_2$ may be converted to a boronic acid or a boronate using standard conditions and then coupled with aryl or heteroaryl halide to furnish the compound of formula $B_3$. A preferred synthetic method includes, but is not limited to, the conversion of the vinylperfluorosulfonate to a boronate of formula $B_7$ and then coupling with a heteroaryl or aryl bromide under Suzuki coupling conditions to obtain a compound of formula $B_3$.

The ester group of a compound of formula $B_3$ may be reduced to its corresponding primary alcohol with a suitable reducing agent such as LAH, DIBAL-H, $B_2H_6$, and the like; in a suitable solvent such as DCM, DCE, THF or diethyl ether; at a temperature ranging from about −78° C. to about 50° C.; to obtain a compound of formula $B_4$. A preferred method for this reduction includes the treatment of a compound of formula $B_3$ with a reducing agent such as LAH; in THF; at a temperature of about 0° C. The alkene function of compound $B_4$ can then be reduced using a suitable method to obtain a compound of formula $B_5$. It is understood that there are many known protocols to effect this conversion. The preferred method for this conversion includes, but is not limited to, a metal-catalyzed hydrogenation of the compound of formula $B_4$. For example, a compound of formula $B_4$ may be hydrogenated in the presence of 5-10% Pd/C, in a solvent such as MeOH, EtOH or the like; at a pressure in the range of from about 1 to about 65 psi, preferably in the range of from about 3 to about 4 psi, to obtain a compound of formula $B_5$ as an isomeric mixture. If desired, the reduction of the alkene functionality may be carried out stereoselectively to obtain the corresponding product enriched with one preferred isomer. For example, a compound of formula $B_4$ may be hydrogenated over Crabtree catalyst in DCM at about 30° C. to obtain a compound of formula $B_5$ enriched with trans isomer. Alternatively, the alkene functionality of a compound of formula $B_3$ may first be reduced to the corresponding ester, followed by reduction of the ester to obtain the compounds of formula $B_5$. The compound of formula $B_6$ may be obtained from the coupling of a compound of formula $B_5$ with a compound of formula $A_2$. When there are no steric interferences, the compound of formula $B_4$ may first be coupled to a compound of formula $A_2$, followed by reduction of the alkene functionality of the resulting product to obtain a compound of formula $B_6$. The coupling reaction may be carried out by first converting the hydroxymethyl group of a compound of formula $B_5$ to a suitable leaving group ($L^2$) such as a halide, tosylate, mesylate, or the like, followed by reaction with a compound of formula $A_2$. For example, the compound of formula $B_5$ may be reacted with a halogenating agent such as $SOCl_2$ or the like; in a solvent such as DCM or DCE; and the resulting product may then be reacted with a compound of formula $A_2$ in the presence of a suitable base such as $Na_2CO_3$, $K_2CO_3$ or $Cs_2CO_3$; in a suitable solvent such as THF, DMF or DMSO; at a suitable temperature. Alternatively, a compound of formula $B_5$ may be directly coupled with a compound of formula $A_2$ under Mitsunobu reaction conditions to obtain a compound of formula $B_6$. A coupling method may include, but is not limited to, the treatment of a mixture of a compound of formula $B_5$ and a compound of formula $A_2$ with a phosphine source such as $PPh_3$ or the like; in the presence of a coupling agent such as DEAD or the like; in a suitable solvent such as THF, DCM, or the like; at a suitable temperature ranging from about 0° C. to about room temperature. A preferred method for this transformation includes the coupling of a compound of formula $B_5$ with a compound of formula $A_2$, in the presence of n-$Bu_3P$ and ADDP; in toluene solvent; at a temperature of about 60° C.; to obtain a compound of formula $B_6$ as an isomeric mixture which may then be separated into its individual isomers using an appropriate separation technique such as supercritical fluid chromatography.

In the final step, the ester functionality of a compound of formula $B_6$ may undergo a conventional saponification to obtain a compound of formula (I). One of ordinary skill in the art will recognize that there are a variety of reagents and reaction conditions available for this conversion. A preferred method for the saponification includes treatment of a compound of formula $B_6$ with an aqueous base such as NaOH, LiOH, or the like; in a mixed solvent such as THF/MeOH, or the like; at about room temperature. It is understood that an alternative to the separation of the isomers of formula $B_6$ is the conversion of the ester mixture to its corresponding carboxylic acid of formula (I), with subsequent isomer separation.

Scheme C

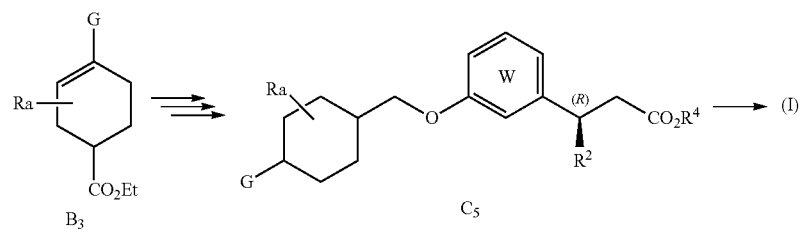

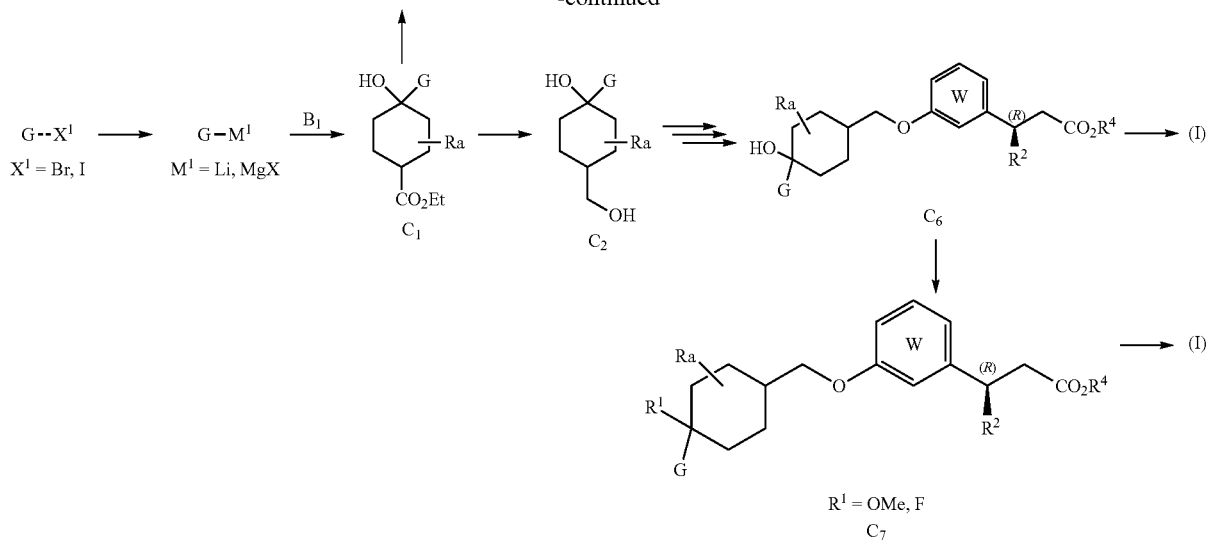

One of ordinary skill in the art will recognize that there are other indirect and direct methods to obtain a compound of formula $B_3$ optionally substituted with $R_a$. For example, a Grignard or Li reagent of formula $G-M^1$, either commercially available or prepared by known methods, may be reacted with a compound of formula $B_1$ to obtain the corresponding tertiary alcohol of formula $C_1$, which may then be dehydrated to obtain a compound of formula $B_3$. For example, an appropriate aryl or heteroaryl halide may be treated with BuLi at about $-78°$ C. to obtain the corresponding G-Li, which may be reacted with a compound of formula $B_1$ to give the compound of formula $C_1$. A compound of formula $C_1$ may be dehydrated at an elevated temperature; in the presence of a suitable catalyst; to give a compound of formula $B_3$. Preferred conditions for this transformation include heating the compound of formula $C_1$ at about 85° C.; in a solvent such as benzene or the like; in the presence of an acid catalyst such as toluenesulfonic acid, or the like; for about 2 h. In addition, the tertiary hydroxyl group of compound $C_1$ may be transformed into other functionalities using conventional synthetic chemistry. For example, the hydroxyl group may be converted to a methoxy group via treatment with NaH/MeI; alternatively, the hydroxyl group may be converted to a fluoride substituent via treatment with a fluorinating agent such as bis(2-methoxyethyl)aminosulfur trifluoride. Optionally, the hydroxyl may be converted to a different functional group at a later stage of the synthetic sequence, provided that there are no interfering, or chemically sensitive, functional groups. The hydroxyl substituent may also remain in the final compound of formula (I).

A synthetic scheme suitable for the preparation of the compounds of formula $D_5$ wherein ring W is pyridinyl and $X^3$ is a halogen preferably F, Cl is shown in Scheme D.

Scheme D

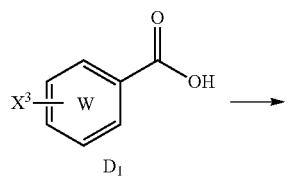

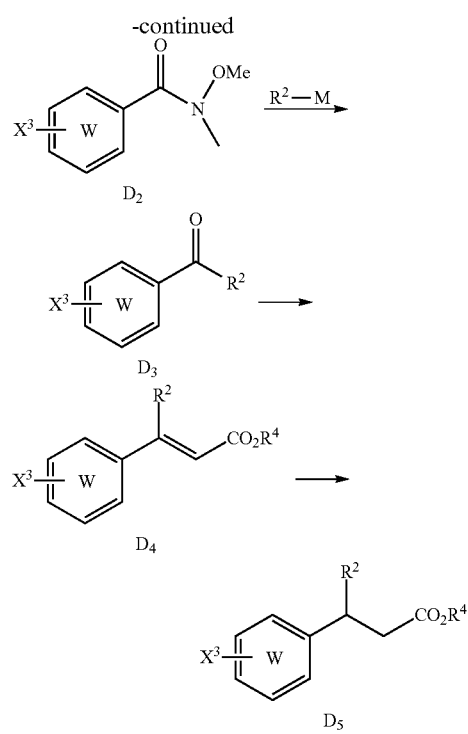

The compounds of formula $D_5$ may be prepared from a ketone of formula $D_3$ which may be obtained from a carboxylic acid of the formula $D_1$. It is understood that there are many direct and indirect methods available for the conversion of a carboxylic acid to a ketone. The preferred method for this transformation includes the conversion of a compound of formula $D_1$ to a Weinreb amide of formula $D_2$, which may then be reacted with an organometallic reagent $R^2$-M. For example, a compound of formula $D_1$ may be coupled with N,O-dimethyl amine using a suitable method, such as a Mitsunobu coupling, to yield the amide of formula $D_2$. The amide of formula $D_2$ may then be reacted with cyclopropyl magnesium bromide in a solvent such as THF and the like; at a temperature in the range of from about $-78°$ C. to about RT; preferably at about 0° C.; to give a compound of formula D₃ wherein R² is cyclopropyl. The compound of formula D₃ may then be olefinated to obtain an α,β unsaturated ester of formula D₄, followed by reduction to a compound of formula D₅. Preferred synthetic methods for this transformation include, but are not limited to, the reaction of ethyl 2-(trimethylsilyl)acetate with a compound of formula D₃; in the presence of a base such as LiHMDS; in a solvent such as THF and the like; at about −78° C. The resulting unsaturated ester of formula D₄ may be reduced under elevated pressure, preferably at about 3.5 atm of H₂ pressure; in the presence of a suitable catalyst such as platinum(IV)oxide; at a temperature in the range of from about RT to about 100° C.; preferably at about 40° C. Alternatively, the reduction may be carried out in the presence of NaBH₄ or the like; in the presence of a catalyst such as NiCl₂·6H₂O, or the like; to furnish a compound of formula D₅.

A compound of formula D₅a wherein W is pyridinyl may then be employed as an intermediate for the preparation of a compound of formula (I), as shown in Scheme E.

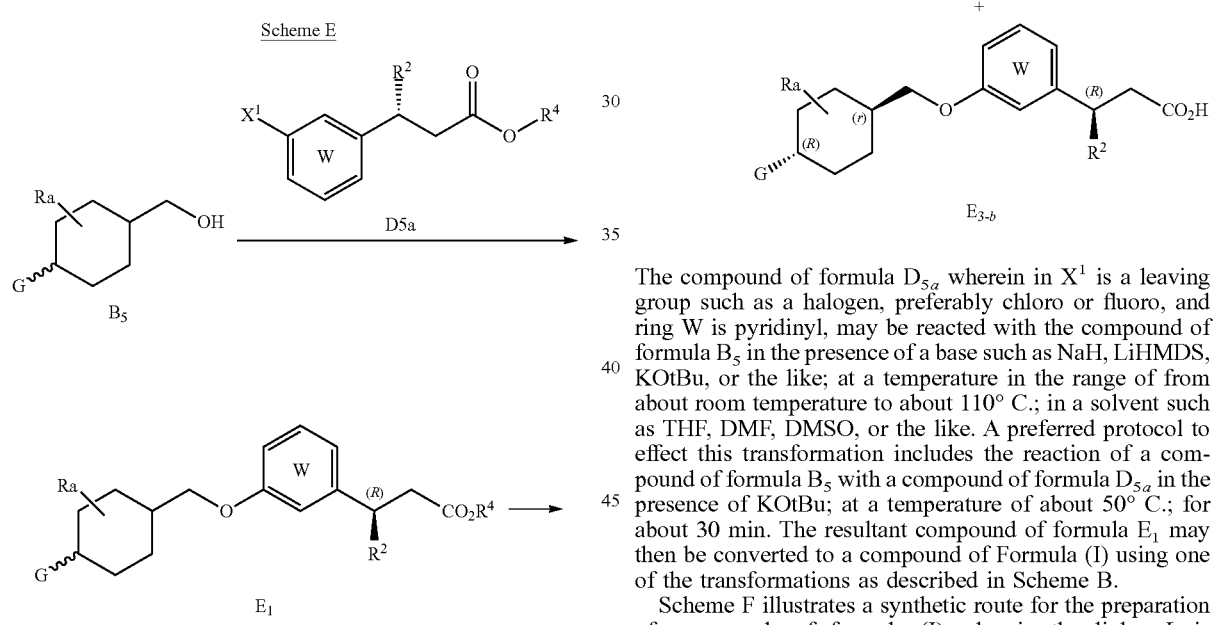

The compound of formula D₅ₐ wherein in X¹ is a leaving group such as a halogen, preferably chloro or fluoro, and ring W is pyridinyl, may be reacted with the compound of formula B₅ in the presence of a base such as NaH, LiHMDS, KOtBu, or the like; at a temperature in the range of from about room temperature to about 110° C.; in a solvent such as THF, DMF, DMSO, or the like. A preferred protocol to effect this transformation includes the reaction of a compound of formula B₅ with a compound of formula D₅ₐ in the presence of KOtBu; at a temperature of about 50° C.; for about 30 min. The resultant compound of formula E₁ may then be converted to a compound of Formula (I) using one of the transformations as described in Scheme B.

Scheme F illustrates a synthetic route for the preparation of compounds of formula (I) wherein the linker L is —NHCH₂—, —(CH₂)₂—, or —CH═CH—.

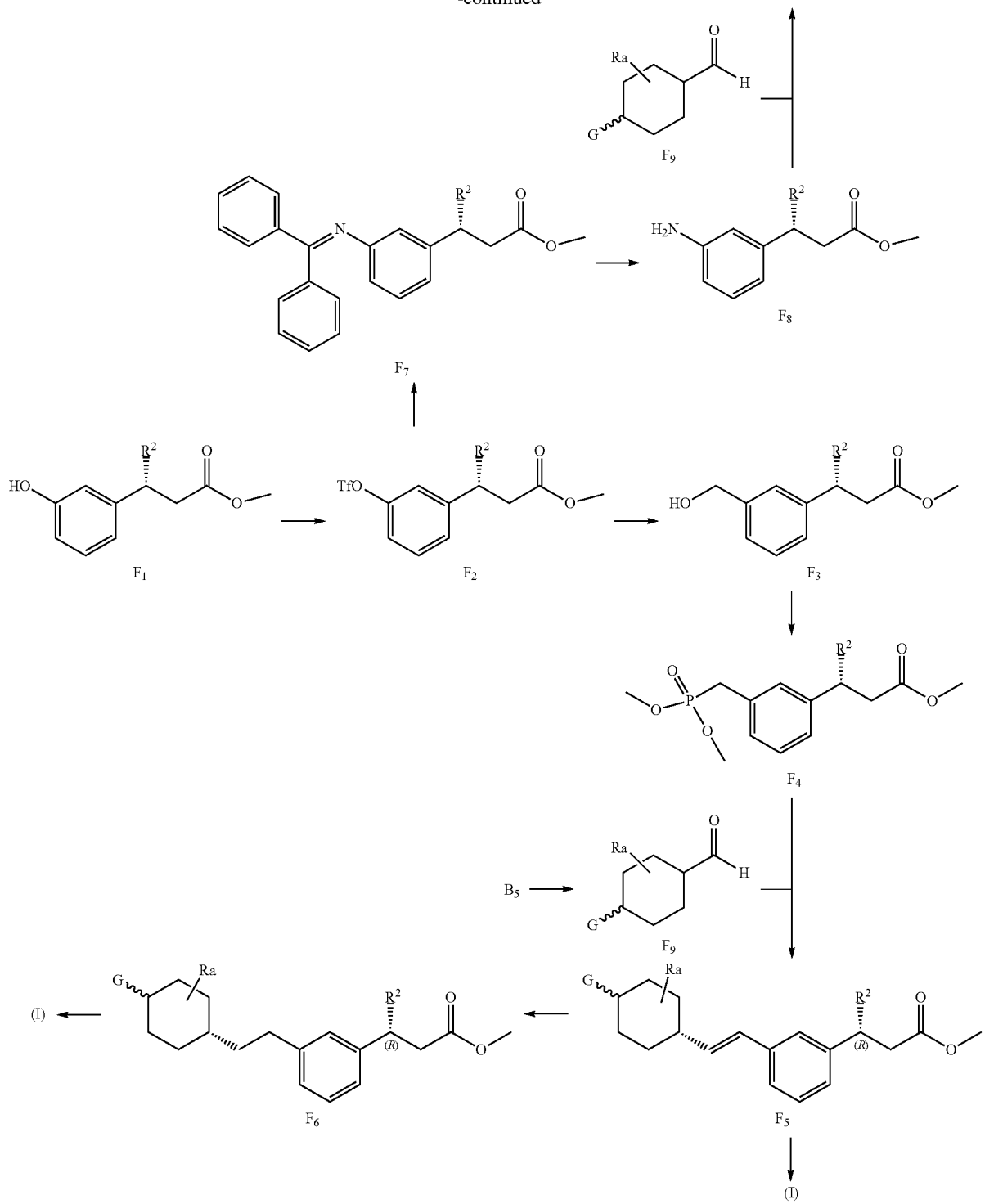

A triflate of formula $F_2$ may be prepared from the phenol of formula $F_1$ using conventional synthetic methods, such as treatment of the phenol of formula $F_1$ with triflic anhydride in the presence of DMAP or $Et_3N$; in a solvent such as DCM, or the like; at a temperature in the range of from about 0° C. to about room temperature, and may be employed in one of various conventional coupling reactions.

The coupling protocols used are well known in the scientific literature. For example, a compound of formula $F_2$ may undergo a Pd-catalyzed coupling reaction, optionally in the presence of an appropriate ligand, with potassium acetoxymethyltrifluoroborate, to obtain the hydroxymethyl compound of formula $F_3$. Alternatively, a compound of formula $F_2$ may be treated with benzophenone imine to afford a diphenylmethyleneamino compound of formula $F_7$, which may afford the amino compound of formula $F_8$ upon removal of the diphenylmethylene moiety. A hydroxymethyl compound of formula $F_3$ may be converted to a phosphonate of formula $F_4$, to be used in a subsequent reaction. Preferred conditions for phosphonate formation include treatment of an alcohol of formula $F_3$ with trimethylphosphite; in the presence of $ZnI_2$; in an aprotic organic solvent such as toluene; at a temperature of about 110° C., overnight. A phosphonate of formula $F_4$ and an aldehyde of formula $F_9$ may undergo a Horner-Wittig reaction to furnish an alkene of formula $F_5$. This reaction may be carried out in the presence of a base such as NaH; with an additive such as 15-crown-5; in a solvent such as THF, or the like; at a temperature in the range of from about 0° C. to about room temperature. The desired aldehyde of formula $F_9$ may be obtained from the corresponding primary alcohol of formula $B_5$ via a partial oxidation using a reagent such as PCC or the like. One of ordinary skill in the art will recognize that there are numerous methods available to effect these transformations. For example, the phosphonate functionality may be replaced by a Wittig salt (phosphonium halide), which may be prepared from a compound of formula $F_3$. Saturation of the alkene linker (L) of the compounds of Formula $F_5$ in the presence of Pd/C under a hydrogen atmosphere may afford a compound of formula $F_6$ wherein L is —$CH_2CH_2$—.

Reductive amination of the aldehyde of formula $F_9$ in the presence of an amine of formula $F_8$ may afford a compound of formula $F_{10}$ wherein L is a aminomethyl linker. Preferred reaction conditions include reduction of the imine (resulting from reaction of an aldehyde of formula $F_9$ with an amine of formula $F_8$ in the presence of a reducing agent such as $NaCNBH_3$ or the like; in a solvent such as DCM; at a temperature of about room temperature. A compounds of formula $F_5$, $F_6$ or $F_{10}$ may subsequently be saponified under standard conditions to obtain a compound of formula (I).

Schemes G and H outline synthetic routes suitable for the preparation of intermediates necessary for the synthesis of compounds of Formula (I), wherein $R^3$ is a substituent other than H.

Scheme G

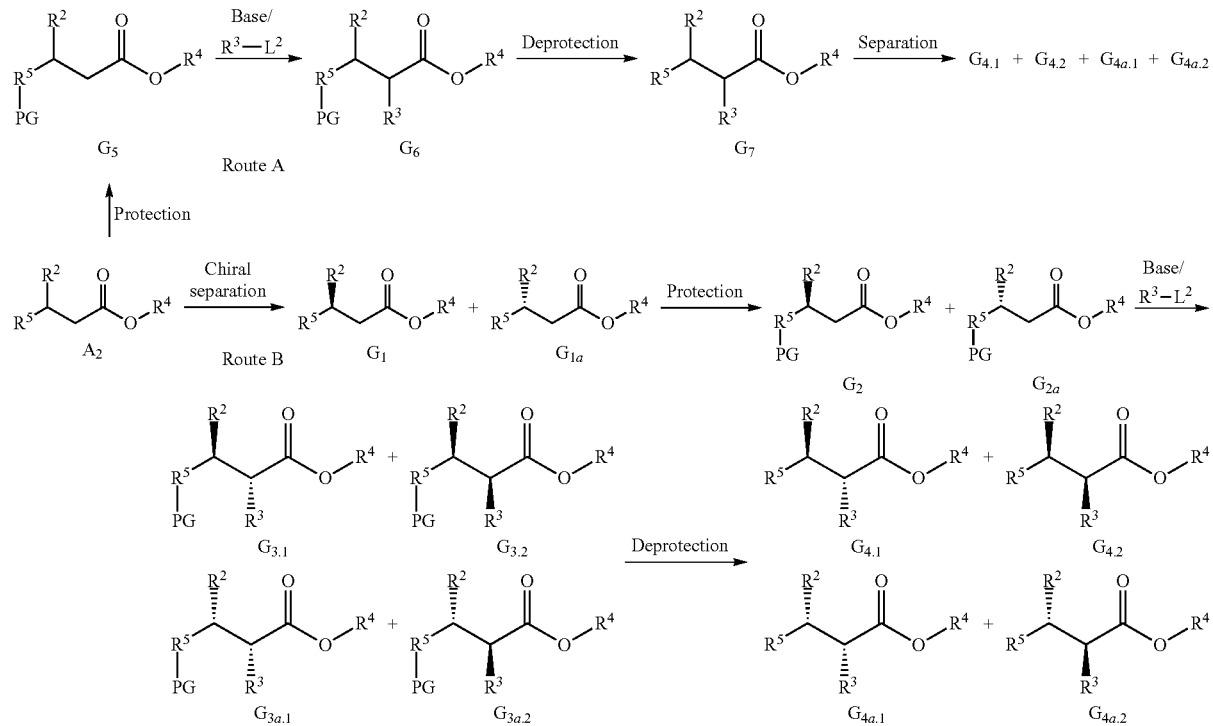

As shown in route B, compounds of formula $A_2$ may be subjected to chiral separation such as SFC to obtain separated enantiomers of the formulae G1 and $G_{1a}$. When a compound of formula G1 and $G_{1a}$ contain a functional group/s that could be sensitive to reaction conditions later in the synthetic scheme, they may be protected with an appropriate protecting group/s at this stage. For instance, when substituent $R^5$ is a phenol, it may be protected as a silyl or benzyl ether, or the like. The preferred method of protecting the phenolic $R^5$ in a compound of formula $G_1$ is via reaction with a silylating agent such as TBSCl, or the like; in a solvent such as DCM, THF, DMF or the like; at a temperature in the range of from about 0 to about 100° C., preferably at a temperature in the range of from about 0 to about 25° C.; for a duration of from about 1 to about 12 h; to obtain compounds of $G_2$ and $G_{2a}$ wherein the protecting group (PG) is TBS. The compounds of formula $G_2$ and $G_{2a}$ may be treated with a suitable base such as LiHMDS, LDA or the like; in a solvent such as THF; at a temperature in the range of from about −78 to about 0° C.; to generate the corresponding enolate which may then be intercepted with an electrophilic reagent $R^3$-$L^2$, wherein $L^2$ is a leaving group, to introduce $R^3$. For example, the compound of formula $G_2$ may be treated with LDA; at a temperature of about −78° C.; in THF; and the resulting anion may be reacted with an electrophile such as MeI or N-fluoro-N-(phenylsulfonyl)

benzenesulfonamide, or the like; to obtain a compound of formula $G_3$ wherein $R^3$ is $CH_3$ or F respectively. The isomeric pairs of the compounds of formulae $G_3$, $G_{3.1/3.2}$ and $G_{3a.1}/G_{3a.2}$ may be deprotected to obtain compound pairs of formulae $G_{4.1/4.2}$ and $G_{4a.1}/G_{4a.2}$. The latter isomeric pairs may be separated by chiral chromatography, such as SCF, to obtain individual compounds of formulae $G_{4.1,\ 4.2,\ 4a.1}$ and $_{4a.2}$. When the protecting group (PG) is TBS, the preferred protocol includes treatment of a compound of formula $G_3$ with a fluoride source, such as TBAF; in a solvent such as THF; at a temperature in the range of from about 0 to about 60° C., preferably at RT; for a reaction duration in the range of from about 1 to 12 h.

Alternatively, the aforementioned chemistry may be carried out starting with a racemic mixture $A_2$, and the individual isomers may be separated at a final step of the synthetic sequence to obtain the individual isomers (Route A).

Another synthetic route for the preparation of phenolic propionic acid esters that bear an α-substituent are shown in Scheme H.

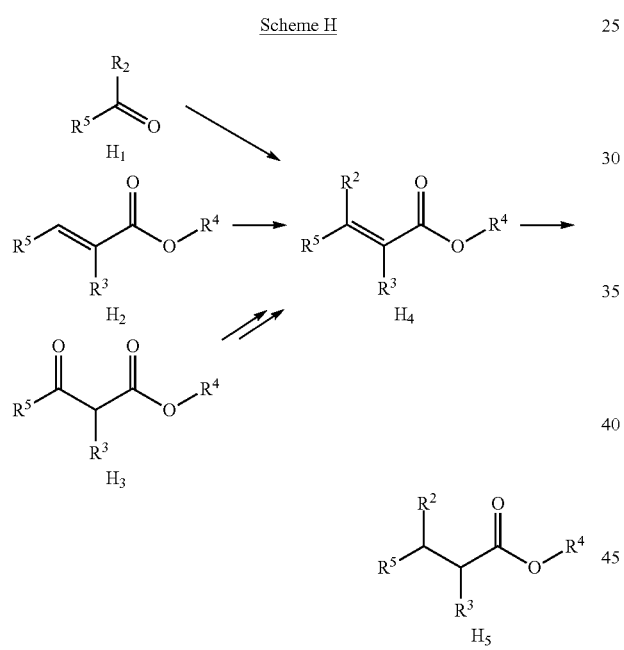

The key step in this synthesis is the hydrogenation of the tetra-substituted alkene $H_4$ wherein $R^5$ is a protected 3-hydroxyphenyl group and $R^3$ is a small substituent such as $CH_3$, F, or $CF_3$. The hydrogenation may be carried out at an elevated $H_2$ pressure in the presence of a Rh or Ru catalyst and a phosphine ligand system. A preferred hydrogenation method includes effecting the reduction in the presence of $(COD)Ru(Me-allyl)_2$, $HBF_4$ and a phosphine ligand such as a Josiphos ligand; in MeOH/DCM; at a temperature of about 80° C.; at a pressure of about 500 psi; to yield the desired compound of formula $H_5$ in a diastereomerically enriched form.

Those of ordinary skill in the art will recognize that a variety of starting materials such as ketones of formula $H_1$, acrylates of formula $H_2$, and keto-esters of formula $H_3$, may be utilized for the preparation of a compound of formula $H_4$ using conventional synthetic protocols. When these compounds are not commercially available they can be prepared according to the standard literature methods.

When necessary, compounds of formula $A_2$, in any synthetic scheme of the present invention, may be replaced with a compound selected from $G_{4.1}$, $G_{4.2}$, $G_{4a.1}$, $G_{4a.2}$, or $H_5$ to obtain a compound of Formula (I) wherein $R^3$ is a substituent other than H.

Scheme I outlines a synthetic route for the preparations of compounds of Formula (I) wherein A is 1H-tetrazol-5-yl.

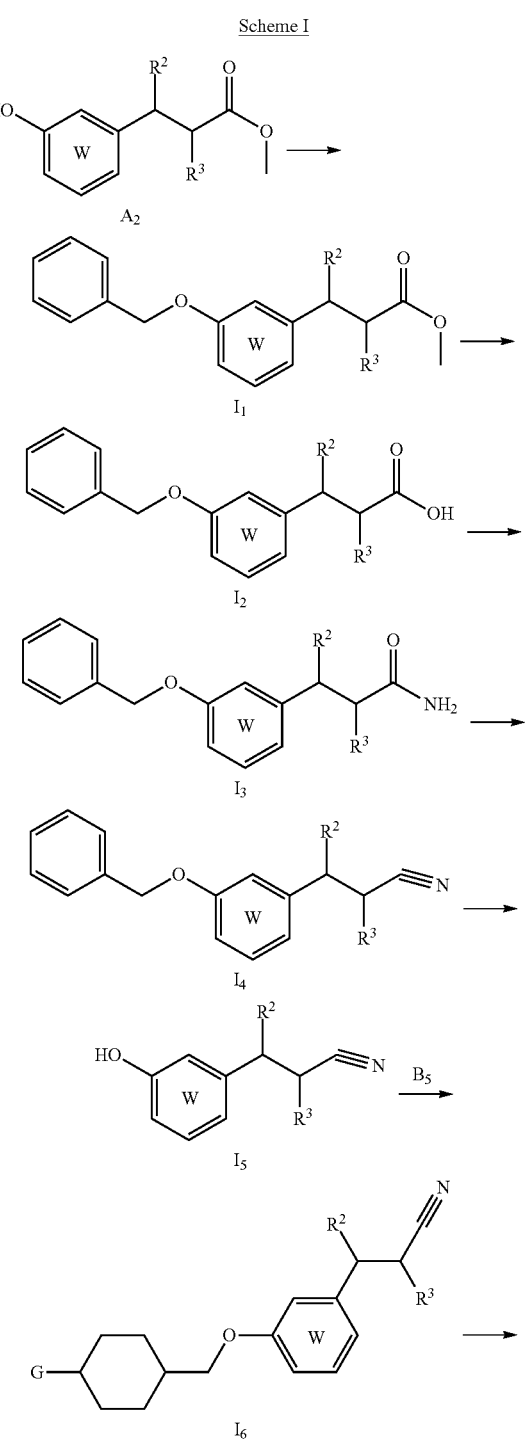

-continued

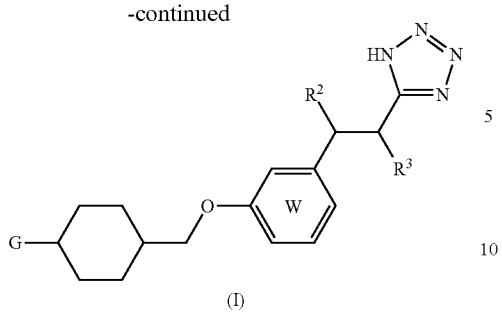

(I)

The phenolic OH of a compound of Formula $A_2$ may be protected with an appropriate protecting group. A preferred method for this transformation includes, but is not limited to, the reaction of compound $A_2$ with benzyl bromide in the presence of a base such as $K_2CO_3$ or the like; in a solvent such as $CH_3CN$; at RT; for 12 h; to obtain compound $I_1$, which may then be subjected to ester hydrolysis as previously described to obtain the corresponding acid $I_2$. One of ordinary skill in the art will recognize that there are many ways of convert acid $I_2$ to an amide, compound $I_3$. A preferred method is via treatment of a mixture of compound 12, $Et_3N$ and $NH_4Cl$ in DCM; with a coupling agent such as O-(7-azabenzotriazol-1-yl)-N,N,N,N-tetramethyluronium hexafluorophosphate; at RT, overnight. Dehydration of the amide $I_3$ may be effected using standard literature methods, such as treatment with trifluoroacetic anhydride/DCM to obtain a nitrile $I_4$, which may then be subjected to removal of the protecting group to obtain the phenolic nitrile $I_5$. One method for phenol deprotection includes exposure of compound $I_4$ to hydrogenolysis; in the presence of 10% $Pd/C/H_2$. The resulting phenol Is may then be coupled to a compound of formula $B_5$, as previously described, to furnish a compound of formula $I_6$, followed by conversion to a tetrazole of Formula (I). It is understood that the chemical literature is replete with methods and protocols to perform this transformation. The addition of a silyl azide, such as $Me_3SiN_3$, in the presence of a suitable catalyst such as bis(tri-n-butyltin) oxide; in a solvent such as toluene or xylene; at an elevated temperature, preferably in the range of from about 70 to 130° C.; is a preferred method for carrying out this conversion.

When it is necessary to have a $R^1$ substituent, the compounds of formula Is may be coupled with a compound of formula $C_2$ as described in Scheme 2 to obtain the compounds of Formula (I). Additionally when a compound of formula $B_5$, the coupling partner of a compound of formula $I_5$, contains a non-interfering $R_a$-substituent, a compound of Formula (I) wherein the $R_a$-substituent is other than hydrogen, may be prepared.

An alternate route for the introduction of $R^3$ substituents to compounds of formula $D_{5a}$ is illustrated in Scheme J.

Scheme J

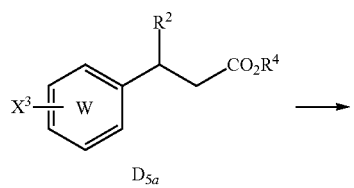

-continued

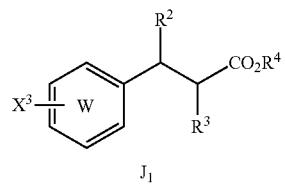

$J_1$ $R^3$ substituents may be introduced to compounds of formula $D_{5a}$ wherein W is pyridinyl, following a similar base-catalyzed enolization and interception of the resulting enolate with a suitable electrophilic reagent $R_3$-$L^2$ wherein $L^2$ is a leaving group such as chloro, bromo, iodo, or the like, using the synthetic methods described in Scheme G, to obtain a compound of formula $J_1$ as an isomeric mixture. A compound of Formula $J_1$ may then be used to afford a compound of Formula (I) using the synthetic methods disclosed in previously described schemes.

An alternate synthetic route to tetrazole-substituted compounds of Formula (I) is shown in Scheme K.

Scheme K

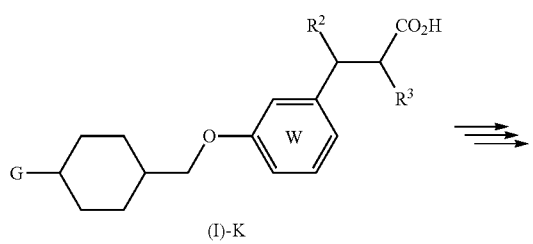

(I)-K

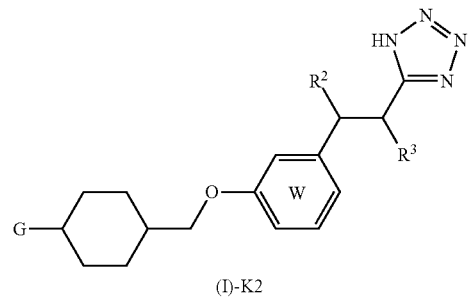

(I)-K2

The starting material for this synthesis is a compound of Formula (I)-K wherein A is $CO_2H$. The acid functionality of the fully assembled molecules of Formula (I)-K may be transformed to the compound of Formula (I)-$K_2$ wherein A is tetrazole the synthetic methods outlined in Scheme I.

The intermediate of formula $L_4$ may be prepared as shown in Scheme L.

Scheme L

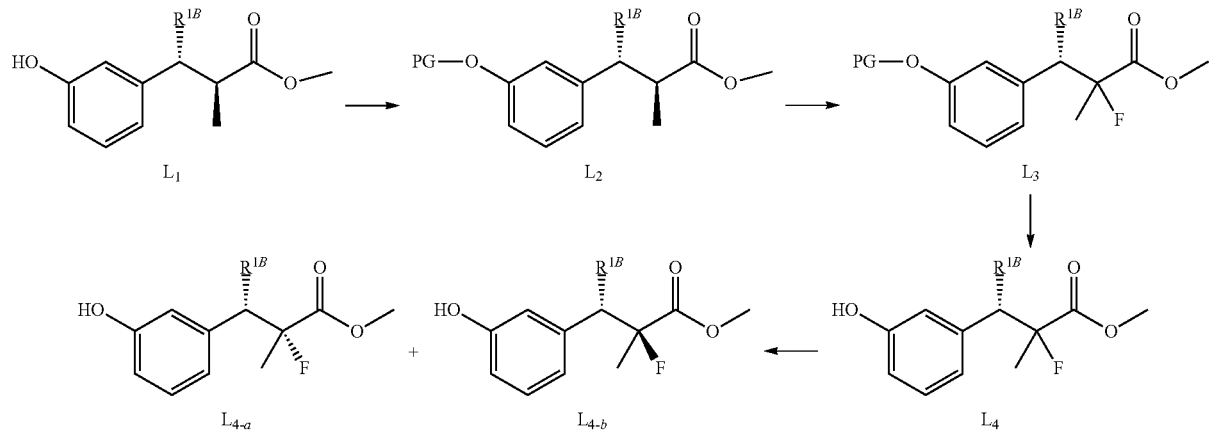

The starting phenol of formula $L_1$, wherein $R^{1B}$ is cyclopropyl is either commercially available or may be prepared according to the methods described in the scientific literature. The phenolic functionality of a compound of formula $L_1$ may be protected (PG is protecting group) by a number of conventional methods available in the scientific literature. A preferred method of protecting the phenolic $L_1$ is via reaction with a silylating agent such as TBSCl, or the like; in a solvent such as DCM, THF, DMF or the like; at a temperature in the range of from about 0 to about 100° C., preferably at a temperature in the range of from about 0 to about 25° C.; for a duration of from about 1 to about 12 h; to obtain a compound of formula $L_2$. The compound of formula $L_2$ may be treated with a suitable base such as LiHMDS, LDA or the like; in a solvent such as THF; at a temperature in the range of from about −78 to about 0° C.; to generate the corresponding enolate which may then be intercepted with an electrophilic reagent such as N-fluoro-N-(phenylsulfonyl)benzenesulfonamide to introduce a fluorine atom to form a compound of formula $L_3$. The compound of formula $L_3$ may be deprotected to obtain a racemic compound mixture of formula $L_4$. When the protecting group (PG) is TBS, the preferred protocol includes treatment of a compound of formula $L_3$ with a fluoride source, such as TBAF; in a solvent such as THF; at a temperature in the range of from about 0 to about 60° C., preferably at RT; for a reaction duration in the range of from about 1 to 12 h. The racemic compound mixture of formula $L_4$ may be separated by chiral chromatography, such as SCF, to obtain individual compounds of formulae $L_{4-a}$ and $L_{4-b}$.

A compound of formula $M_7$ may be prepared as shown in Scheme M.

Scheme M

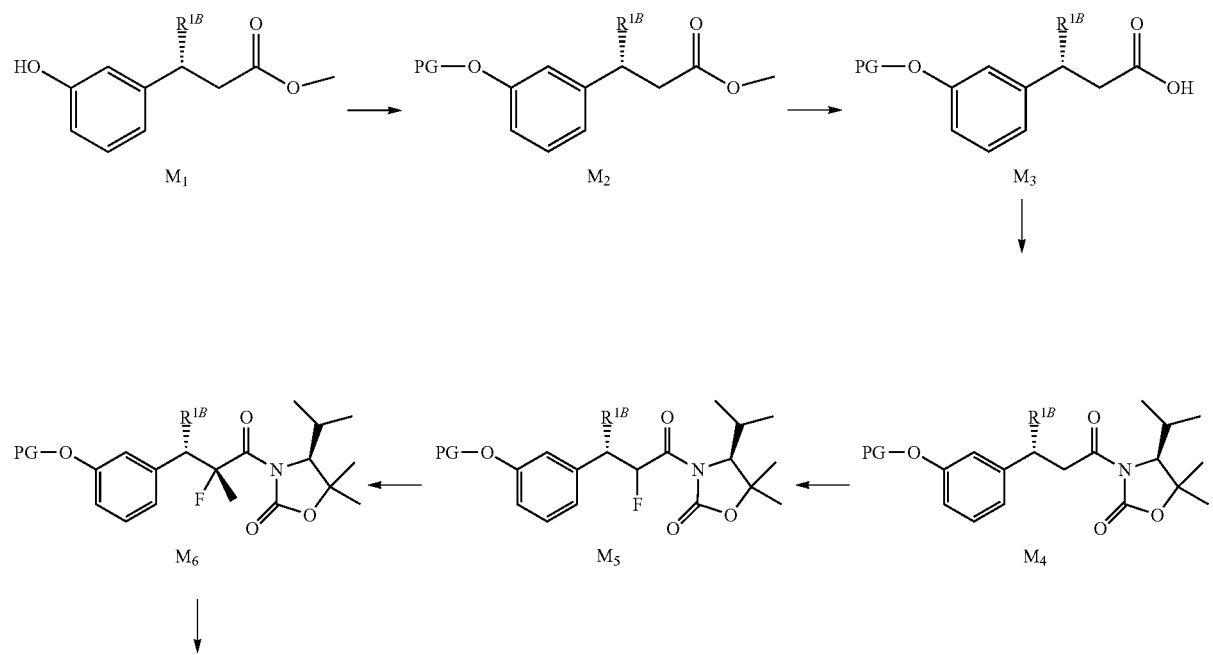

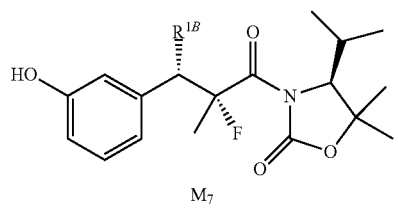

M₇

The fluorine and methyl groups may be introduced to the a carbon to the carboxyl group with high diastereoselection utilizing a chiral auxiliary. The starting phenol of formula $M_1$, wherein $R^{1B}$ is cyclopropyl is either commercially available or may be prepared according to the methods described in the scientific literature. The phenolic OH of a compound of Formula $M_1$ may be protected with an appropriate protecting group (PG). A preferred method for this transformation includes, but is not limited to, the reaction of compound $M_1$ with benzyl bromide in the presence of a base such as $Cs_2CO_3$ or the like; in solvent such as $CH_3CN$; at a temperature in the range of from about rt to about 50° C.; for about 1 h to about 12 h; to obtain compound $M_2$. The ester functionality of a compound of formula $M_2$ may undergo a conventional saponification to obtain a compound of formula $M_3$. One of ordinary skill in the art will recognize that there are a variety of reagents and reaction conditions available for this conversion. A preferred method for the saponification includes treatment of a compound of formula $M_2$ with an aqueous base such as NaOH, LiOH, or the like; in a mixed solvent such as THF/MeOH, or the like; at about room temperature; for about 12 h. One of ordinary skill in the art will recognize that there are many ways of convert the acid of formula $M_3$ to an amide of formula $M_4$. A preferred method is via an acid chloride intermediate. Treatment of the acid of formula $M_3$ in a solvent such as DCM with a chlorinating agent such as oxalyl chloride; in the presence of a catalytic amount of DMF; at about 0° C.; for about 1 h; may be used to obtain an acid chloride intermediate. This intermediate may then be treated with an anion, generated from the reaction of a chiral auxiliary such as (S)-4-isopropyl-5,5-dimethyloxazolidin-2-one and a strong base, such as n-BuLi, LDA or the like; in a solvent such as THF; at a temperature in the range of from about −78 to about RT; to obtain the corresponding amide of formula $M_4$. The compound of formula $M_4$ may be treated with a suitable base such as LiHMDS, LDA or the like; in a solvent such as THF; at a temperature in the range of from about −78 to about 0° C.; to generate the corresponding enolate which may then be intercepted with an electrophilic reagent such as N-fluoro-N-(phenylsulfonyl)benzenesulfonamide to introduce fluorine atom on a compound of formula $M_5$. The compound of formula $M_5$ may be treated with a suitable base such as LiHMDS, LDA or the like; in a solvent such as THF; at a temperature in the range of from about −78 to about 0° C.; to generate the corresponding enolate, which may then be intercepted with an electrophilic reagent such as MeI to obtain a compound of formula $M_6$. The compound of formula $M_6$ may be subjected to removal of the protecting group to obtain the phenol of formula $M_7$. One method for benzyl group removal includes exposure of a compound of formula $M_6$ to hydrogenolysis; in the presence of 10% Pd/C/$H_2$; in a mixed solvent of MeOH and EtOAc.

Scheme N

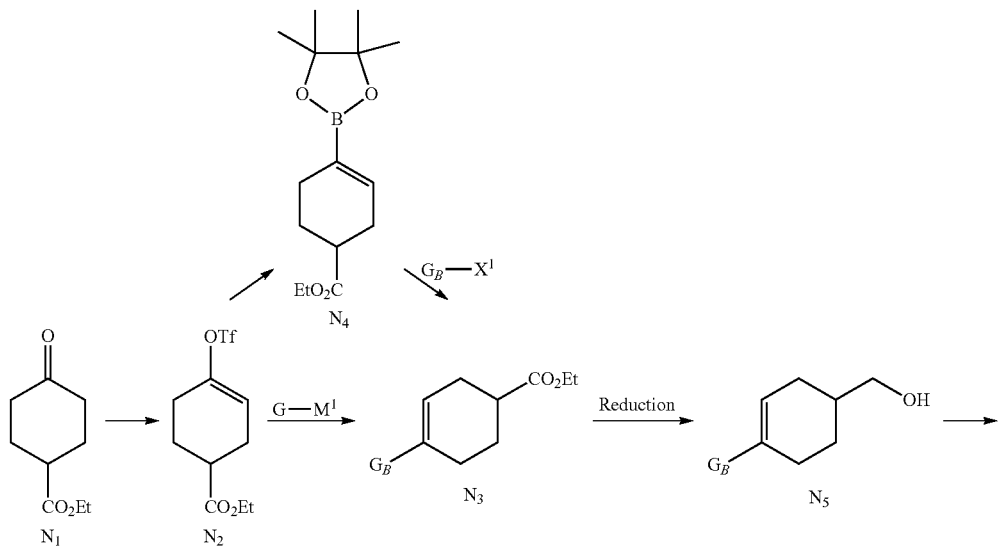

-continued

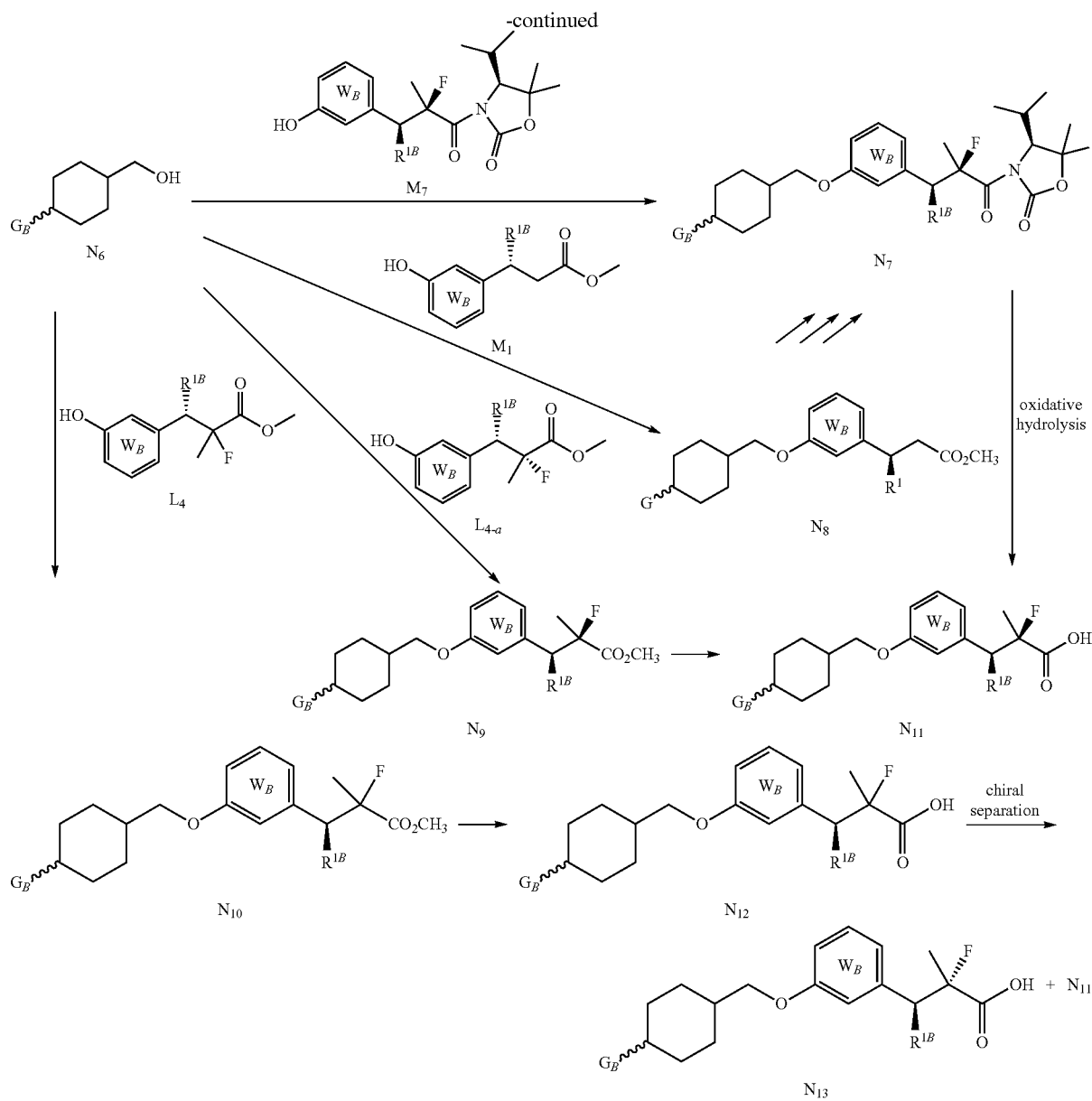

Commercially available compound $N_1$ may be converted to its corresponding vinyl triflate of formula $N_2$ via treatment with a suitable base and a triflating agent under appropriate conditions. The preferred method for this transformation includes, but is not limited to, treatment of a compound $N_1$ with a strong base such as LiHMDS and the like; in a solvent such as THF and the like; at a temperature of about −78° C. in the presence of a triflating agent such as N-phenyl-bis(trifluoromethanesulfonimide), to obtain the corresponding triflate of formula $N_2$.

A compound of formula $N_2$ may be reacted with a suitably substituted compound of formula $G_B$-$M^1$, under suitable coupling conditions, to yield the corresponding compound of formula $N_3$. A compound of formula $G_B$-$M^1$ may be (a) a boronic acid to form a compound of formula $G_B$-B(OH)$_2$; (b) a suitably selected boronic ester such as pinacolatoboryl, neopentylglycolatoboryl, and the like; (c) a suitably selected trialkylstannyl such as tri(n-butyl)tin, and the like; (d) a suitably selected trialkylsilyl such as triallylsilyl, and the like; or (e) a suitably selected organo zinc reagent such as $G_B$-ZnX wherein X is a halide such as chloro, bromo, or iodo. For example, a compound of formula $G_B$-$M^1$, wherein $M^1$ is preferably —B(OH)$_2$ or a boronic ester, may be reacted with a compound of formula $N_2$ under Suzuki coupling conditions, more particularly in the presence of a suitably selected palladium catalyst such as palladium (II) acetate, palladium (II) chloride, bis(acetonitrile)-dichloropalladium(II), allylpalladium (II) chloride dimer, tris(dibenzylidineacetone)dipalladium (0) (Pd$_2$(dba)$_3$), 2-(di-tert-butylphosphino)biphenyl, dichloro-bis(di-tert-butylphenylphosphine)-palladium (II), [1,1′-bis-(diphenylphosphino)-ferrocene]-palladium (II) dichloride dichloromethane adduct ((dppf)PdCl$_2$.DCM), tetrakis(triphenylphosphine) palladium(0) (Pd(PPh$_3$)$_4$), (1,1′-bis(di-tert-butylphosphino)ferrocene palladium (II) chloride, and the like; optionally in the presence of a suitably selected ligand such as triphenylphosphine, tributylphosphine, tri-o-tolylphosphine, tri(tert-butyl)-phosphine, tricyclohexylphosphine, 1,1'-bis(diphenylphosphino)-ferrocene, 2-(dicyclohexylphosphino)-2',4',6'-tri-i-propyl-1,1'-biphenyl, S-Phos, Ru-Phos, bis[2-(diphenyl-phosphino)phenyl]ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, sodium hydroxide, sodium bicarbonate; potassium phosphate or preferably sodium carbonate; in a suitably selected solvent such as ethanol, THF, DMF, toluene, benzene, DME, water, 1,4-dioxane, or the like, or a combination thereof; at a temperature in the range of from about room temperature to about 180° C.

Alternatively, a compound of formula $N_2$ may be converted to a boronic acid or a boronate using standard conditions and then coupled with aryl or heteroaryl halide $G_B$-$X^1$ to furnish the compound of formula $N_3$. A preferred synthetic method includes, but is not limited to, the conversion of the vinyl triflate to a boronate of formula $C_4$ and then coupling with a heteroaryl or aryl bromide under Suzuki coupling conditions to obtain a compound of formula $N_3$.

The ester group of a compound of formula $N_3$ may be reduced to its corresponding primary alcohol with a suitable reducing agent such as LAH, DIBAL-H, $B_2H_6$, and the like; in a suitable solvent such as DCM, DCE, THF or diethyl ether; at a temperature ranging from about −78° C. to about 50° C.; to obtain a compound of formula $N_5$. A preferred method for this reduction includes the treatment of a compound of formula $N_3$ with a reducing agent such as LAH; in THF; at a temperature of about 0° C. The alkene function of compound $N_5$ can then be reduced using a suitable method to obtain a compound of formula $N_6$. It is understood that there are many known protocols to effect this conversion. The preferred method for this conversion includes, but is not limited to, a metal-catalyzed hydrogenation of the compound of formula $N_5$. For example, a compound of formula $N_5$ may be hydrogenated in the presence of 5-10% Pd/C, in a solvent such as MeOH, EtOH or the like; at a pressure in the range of from about 1 to about 65 psi, preferably in the range of from about 3 to about 4 psi, to obtain a compound of formula $N_6$ as an isomeric mixture. If desired, the reduction of the alkene functionality may be carried out stereoselectively to obtain the corresponding product enriched with one preferred isomer. For example, a compound of formula $N_5$ may be hydrogenated over Crabtree catalyst in DCM at about 30° C. to obtain a compound of formula $N_6$ enriched with trans isomer.

The compound of formula $N_6$ may be coupled with compounds of formula $M_7$, $M_1$, $L_{4-a}$ and $L_4$ under Mitsunobu reaction conditions to obtain compounds of formula $N_7$, $N_8$, $N_9$, and $N_{10}$, respectively. A coupling method may include, but is not limited to, the treatment of a mixture of a compound of formula $C_6$ and a phenol with a phosphine source such as $PPh_3$ or the like; in the presence of a coupling agent such as DEAD or the like; in a suitable solvent such as THF, DCM, or the like; at a suitable temperature ranging from about 0° C. to about 60° C. A preferred method for this transformation includes the coupling of a compound of formula $N_6$ with a compound of formula $M_7$, $M_1$, $L_4$-a or $L_4$, in the presence of n-$Bu_3P$ and ADDP; in toluene solvent; at a temperature of about 60° C.

The chiral auxiliary on compound of formula $N_7$ may be removed under oxidative hydrolysis conditions. The preferred method for this conversion includes, but is not limited to, the treatment of the compound of formula $N_7$ with an inorganic base such as LiOH or the like; in the presence of hydrogen peroxide (30% in water); in a solvent such as THF or the like; at a suitable temperature ranging from about 0° C. to about 25° C., to obtain a compound of formula $N_{11}$ with high diastereoselectivity. Alternatively, the compound of formula $N_7$ may be prepared through the compound of formula $N_8$ according to the methods described previously in Scheme B. The ester functionality of compounds of formula $N_9$ and $N_{10}$ may undergo a conventional saponification to obtain compounds of formula NH and $N_{12}$, respectively. A preferred method for the saponification has been described in Scheme M. The compound of formula $N_{12}$ is obtained as an isomeric mixture, which may then be separated into its individual isomers $N_{11}$ and $N_{13}$ using an appropriate separation technique such as supercritical fluid chromatography.

A synthetic scheme suitable for the preparation of the compounds of formula (II) wherein ring $W_B$ is pyridinyl and $X^2$ is a halogen preferably F or Cl, is shown in Scheme O.

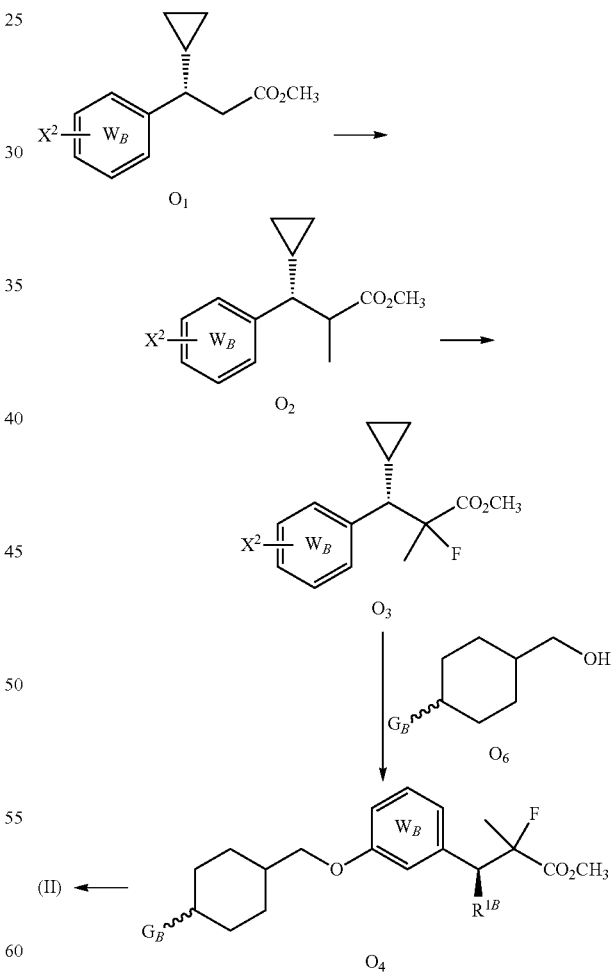

Scheme O

The compounds of formula $O_2$ may be prepared from a compound of formula $O_1$ which is commercially available, according to the methylation method via enolate formation described previously in Scheme M. The method for addition of fluorine atom to the compound of formula $O_2$ to obtain the compound of formula O₃ is described in Scheme L. The compound of formula O₃ wherein in X² is a leaving group such as a halogen, preferably chloro or fluoro, and ring W_B is pyridinyl, may be reacted with the compound of formula N₆ in the presence of a palladium catalyst such as palladium acetate or the like; a phosphorus ligand such as L-(5-[bis(adamantan-1-yl)phosphanyl]-1',3',5'-triphenyl-1'H-1,4'-bipyrazole) or the like; an inorganic base such as cesium carbonate, or the like; at a temperature in the range of from about room temperature to about 100° C.; in a solvent such as dioxane or the like, to obtain the compound of formula O₄. The resultant compound of formula O₄ may then be converted to a compound of formula (II) using one of the ester saponification conditions as described in Scheme M.

Scheme P illustrates a synthetic route for the preparation of compounds of formula (II) wherein the linker L_B is —NHCH₂—, —(CH₂)₂—, or —CH=CH—.

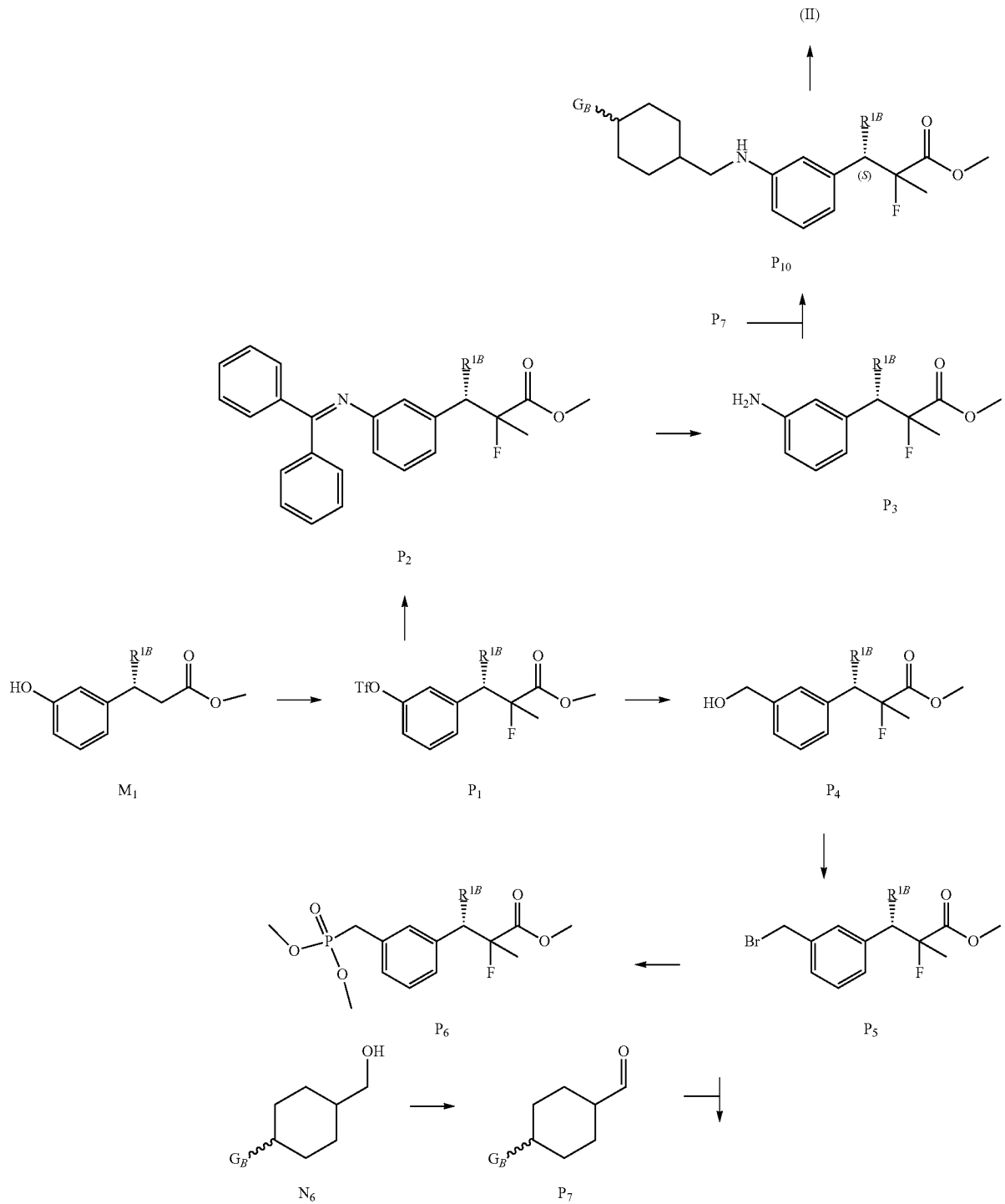

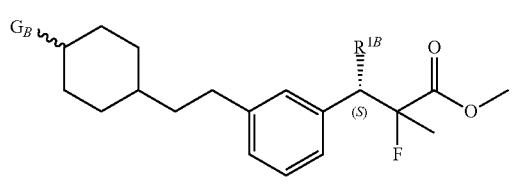

P₉

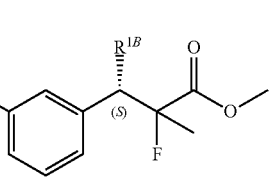

P₈

(II)

(II)

A triflate of formula P₁ may be prepared from the phenol of formula M₁, wherein R^{1B} is cyclopropyl, using conventional synthetic methods, such as treatment of the phenol of formula M₁ with triflic anhydride in the presence of DMAP or Et₃N; in a solvent such as DCM, or the like; at a temperature in the range of from about 0° C. to about room temperature, and may be employed in one of various conventional coupling reactions.

The coupling protocols used are well known in the scientific literature. For example, a compound of formula P₁ may be treated with benzophenone imine to afford a diphenylmethyleneamino compound of formula P₂, which may afford the amino compound of formula P₃ upon removal of the diphenylmethylene moiety. Alternatively, a compound of formula P₁ may undergo a Pd-catalyzed coupling reaction, optionally in the presence of an appropriate ligand, with potassium acetoxymethyltrifluoroborate, to obtain the hydroxymethyl compound of formula P₄. Hydroxymethyl compound of formula P₄ may be converted to a benzyl bromide compound of formula P₅. A preferred method for this transformation includes, but is not limited to, the reaction of compound P₄ with phosphorus(V) tribromide oxide in the presence of DMF; in solvent such as DCM; at a temperature in the range of from about 0° C. to about rt; for about 1 h to about 12 h; to obtain compound P₅. The benzyl bromide compound of formula P₅ then may be converted to a phosphonate compound of formula P₆, to be used in a subsequent reaction. Preferred conditions for phosphonate formation include treatment of compound of formula P₅ with trimethylphosphite, at a temperature of about 110° C., for about 2 h. A phosphonate of formula P₆ and an aldehyde of formula P₇ may undergo a Horner-Wittig reaction to furnish an alkene of formula P₈. This reaction may be carried out in the presence of a base such as NaH; in a solvent such as THF, or the like; at a temperature in the range of from about 0° C. to about room temperature. One of ordinary skill in the art will recognize that there are numerous methods available to effect these transformations. For example, the phosphonate functionality may be replaced by a Wittig salt (phosphonium halide), which may be prepared from a compound of formula P₄. The desired aldehyde of formula P₇ may be obtained from the corresponding primary alcohol of formula N₆ via a partial oxidation using a reagent such as PCC or the like. Saturation of the alkene linker (L_B) of the compounds of Formula P₈ in the presence of Pd/C under a hydrogen atmosphere may afford a compound of formula P₉ wherein L_B is —CH₂CH₂—.

Reductive amination of the aldehyde of formula P₇ in the presence of an amine of formula P₃ may afford a compound of formula P₁₀ wherein L_B is an aminomethyl linker. Preferred reaction conditions include reduction of the intermediate imine (resulting from reaction of an aldehyde of formula P₇ with an amine of formula P₃) in the presence of a reducing agent such as NaCNBH₃ or the like; in the presence of an acid such as acetic acid; in a solvent such as methanol; at a temperature of about room temperature. A compound of formula P₈, P₉ or P₁₀ may subsequently be saponified under standard conditions to obtain a compound of formula (II).

Scheme Q illustrates a synthetic route for the preparation of compounds of formula (II) wherein the linker L_B is —CH₂O—.

Scheme Q

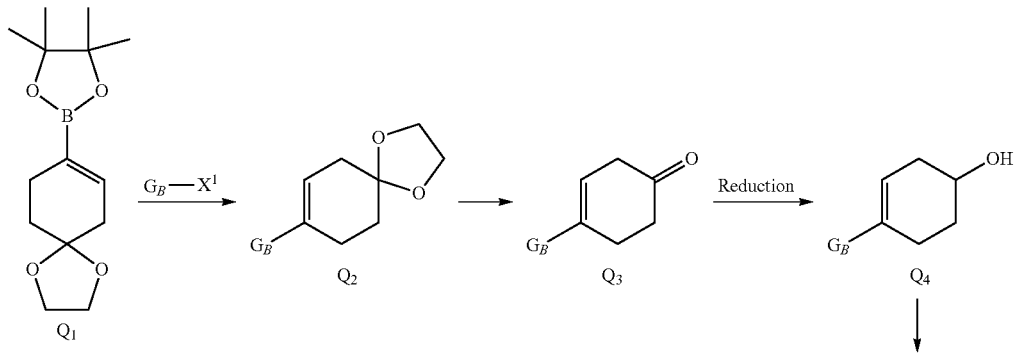

-continued

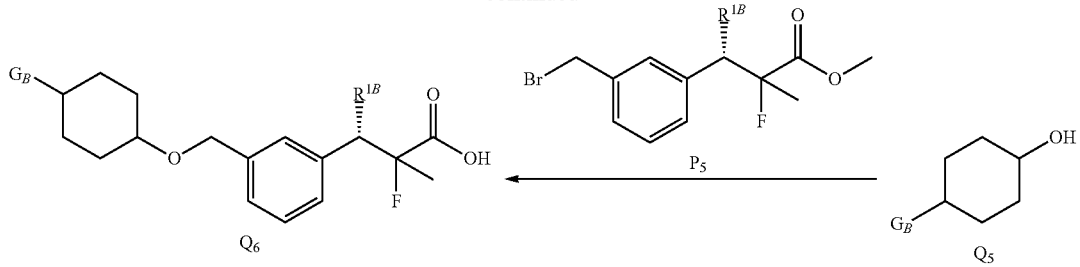

A compound of formula $Q_1$, which is commercially available, may be coupled with aryl or heteroaryl halide $G_B$-$X^1$ under Suzuki coupling conditions to obtain the compound of formula $Q_2$. Upon treatment of an inorganic acid, the acetal of formula $Q_2$ may be converted to the ketone of formula $Q_3$. The preferred method for this conversion includes, but is not limited to, the treatment of the compound of formula $Q_2$ with an inorganic acid such as HCl or the like; in a solvent such as THF or the like; at a suitable temperature ranging from about 0° C. to about 25° C., to obtain a compound of formula $Q_3$. The ketone functionality of formula $Q_3$ may be reduced to its corresponding alcohol with a suitable reducing agent such as $NaBH_4$, and the like; in a suitable solvent such as THF; at a temperature about 25° C.; to obtain a compound of formula $Q_4$. Saturation of the alkene of the compound of Formula $Q_4$ in the presence of Pd/C under a hydrogen atmosphere may afford a compound of formula $Q_5$ according to the methods described in Scheme N. Alkylation of the alcohol of formula $Q_5$ with benzyl bromide compound of formula $P_5$ provides a compound of formula $Q_6$. The preferred method for this transformation includes, but is not limited to, the treatment of the compound of formula $Q_5$ with a strong base such as NaH; in a solvent such as DMF; for about 30 min; at a suitable temperature ranging from about 0° C. to about 25° C.; subsequently addition of the compound formula $P_5$; at a suitable temperature ranging from about 25° C. to about 50° C., to obtain a compound of formula $Q_6$, which is the compound of formula (II) wherein the linker $L_B$ is —$CH_2$O—.

SPECIFIC EXAMPLES

Example 1

(S)-3-Cyclopropyl-3-(3-(((1r,4S)-4-(5-fluoro-2-methoxypyridin-4-yl)cyclohexyl)methoxy)phenyl)propanoic acid Cpd 9

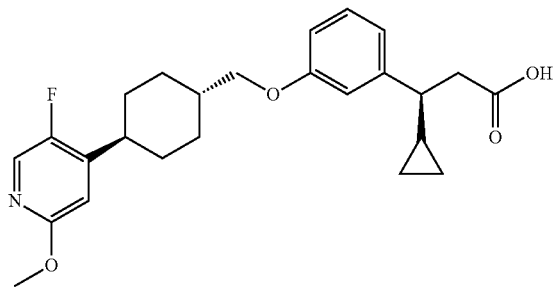 [SMILES: COc1cc([C@H]2CC[C@H](COc3cccc([C@@H](CC(=O)O)C4CC4)c3)CC2)c(F)cn1]

(A) Ethyl 4-(5-fluoro-2-methoxypyridin-4-yl)cyclohex-3-enecarboxylate, 1a

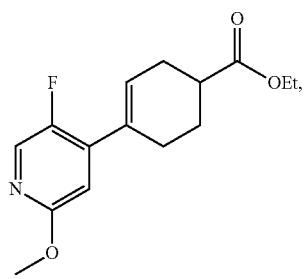

1a

A mixture of ethyl 4-(trifluoromethylsulfonyloxy)cyclohex-3-enecarboxylate (34.0 g, 112 mmol, as prepared in Example 29, Step A), 5-fluoro-2-methoxypyridin-4-ylboronic acid (28.8 g, 168 mmol), 1,1'-bis(diphenylphosphino)ferrocenepalladiumdichloride (2.00 g, 2.45 mmol), triethylamine (34.1 g, 337 mmol) in ethanol (300 mL) was stirred for 2 h at 90° C. The reaction mixture was allowed to cool to RT and treated with 300 mL of water. The resulting mixture was extracted with ethyl acetate (3×300 mL). The organic phases were combined, dried over $Na_2SO_4$ and concentrated. The residue obtained was purified on silica gel with EtOAc/petroleum ether (0-5%) to give the title compound. Mass Spectrum (LCMS, ESI pos.): Calcd. for $C_{15}H_{18}FNO_3$: 280.1 $(M+H)^+$; found: 280.0.

(B) (4-(5-Fluoro-2-methoxypyridin-4-yl)cyclohex-3-en-1-yl)methanol, 1b

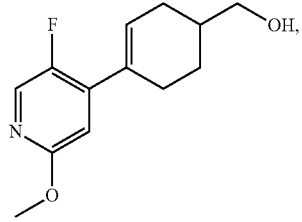

1b

To a solution of ethyl 3-(5-fluoro-2-methoxypyridin-4-yl)cyclohex-3-enecarboxylate, 1a, (15.0 g, 53.7 mmol) in THF (150 mL) was added diisobutylaluminium hydride (163 mL, 163 mmol, 1 M in hexane) at −20° C. The resulting solution was stirred for 0.5 h at −20° C., allowed to warm to RT and stirred 1 h. The reaction was then quenched by the addition of 100 mL of saturated potassium sodium tartrate solution. The resulting solution was extracted with ethyl acetate (3×150 mL). The organic phases were combined, dried over $Na_2SO_4$ and concentrated. The residue obtained was purified on silica gel with EtOAc/petroleum ether (0-40%) to give compound 1b as a yellow oil. Mass Spectrum (LCMS, ESI pos.): Calcd. for $C_{13}H_{16}FNO_2$: 238.1 $(M+H)^+$; found: 237.9.

(C) ((1r,4r)-4-(5-fluoro-2-methoxypyridin-4-yl)cyclohexyl)methanol (1c-1) and ((1s,4s)-4-(5-fluoro-2-methoxypyridin-4-yl)cyclohexyl)methanol (1c-2)

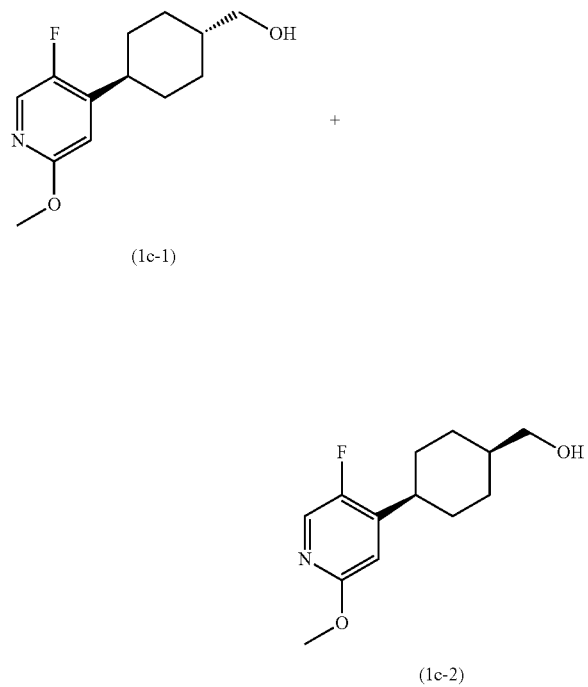

(1c-1)

+

(1c-2)

A mixture of (3-(5-fluoro-2-methoxypyridin-4-yl)cyclohex-3-enyl)methanol, 1b, (6.8 g, 29 mmol) and 10% Pd/C (3.4 g) in MeOH (50 mL) was stirred for 1 h at RT under a $H_2$ (3.5 atm) atmosphere. The reaction mixture was filtered and the filtrate was concentrated. The resulting residue was purified by preparative chiral HPLC on a Chiralpak IC2, 25 cm, 5 μm chiral column using hexane: EtOH (0.1% TFA) gradient (20-90% over 40 min.) to give compounds 1c-1 and 1c-2.

Cpd 1c-1: $^1$H NMR (400 MHz, $CDCl_3$) δ (ppm): 7.89 (s, 1H), 6.59 (d, J=5.1 Hz, 1H), 3.89 (s, 3H), 3.51 (d, J=6.3 Hz, 2H), 2.77 (t, J=12.0 Hz, 1H), 1.92-1.96 (m, 4H), 1.39-1.79 (m, 4H), 1.09-1.26 (m, 2H).

Cpd 1c-2: $^1$H NMR (400 MHz, $CDCl_3$) δ (ppm): 7.88 (s, 1H), 6.59 (d, J=4.8 Hz, 1H), 3.89 (s, 3H), 3.70 (d, J=7.2 Hz, 2H), 2.82-2.90 (m, 1H), 1.91-1.95 (m, 1H), 1.80-1.89 (m, 2H), 1.61-1.79 (m, 7H).

(D) (S)-Methyl 3-cyclopropyl-3-(3-(((1r,4S)-4-(5-fluoro-2-methoxypyridin-4-yl)cyclohexyl)methoxy)phenyl)propanoate, 1d

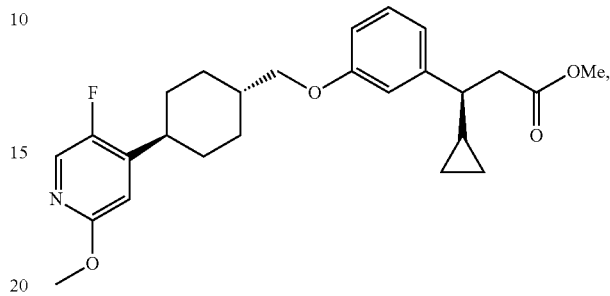

1d

To a solution of ((1r,4r)-4-(5-fluoro-2-methoxypyridin-4-yl)cyclohexyl)methanol, 1c-1 (350 mg, 1.46 mmol), (S)-methyl 3-cyclopropyl-3-(3-hydroxyphenyl)propanoate (322 mg, 1.46 mmol) and tributylphosphine (1.18 g, 5.83 mmol) in toluene (10 mL) was added 1,1'-(azodicarbonyl)-dipiperidine (1.47 g, 5.83 mmol) in toluene at 0° C. The reaction mixture was stirred for 0.5 h at RT first and then at 60° C. overnight. The reaction mixture was allowed to cool to RT and treated with 10 mL of saturated aqueous $NH_4C_1$ solution. The resulting solution was extracted with ethyl acetate (3×10 mL). The organic phases were combined, dried over $Na_2SO_4$ and concentrated. The residue obtained was purified on silica gel with EtOAc/petroleum ether (0-10%) to give the title compound as a yellow oil. Mass Spectrum (LCMS, ESI pos.): Calcd. for $C_{26}H_{32}FNO_4$: 442.2 $(M+H)^+$; found: 442.3.

(E) (S)-3-Cyclopropyl-3-(3-(((1r,4S)-4-(5-fluoro-2-methoxypyridin-4-yl)cyclohexyl) methoxy)phenyl) propanoic acid, Cpd 9

A solution of (S)-methyl 3-cyclopropyl-3-(3-(((1r,4S)-4-(5-fluoro-2-methoxypyridin-4-yl)cyclohexyl)methoxy)phenyl)propanoate, 1d, (270 mg, 0.612 mmol) and $LiOH.H_2O$ (256 mg, 6.10 mmol) in THF (3 mL), water (1 mL) and ethanol (1 mL) was stirred overnight at RT. The mixture was concentrated and diluted with 10 mL of water. The pH of the solution was adjusted to 4~5 with 1M HCl solution. The solids formed were collected by filtration, dried in an oven under reduced pressure, and purified by reverse-phase flash chromatography on a Flash Spherical C18 columns (120 g, 20-35 μm, 100 Å, Agela Technologies), with $CH_3CN/H_2O$ (5% $NH_4HCO_3$) gradient (20-85% over 40 min) to give the title compound 9 as a white solid. $^1$H NMR (300 MHz, DMSO-$d_6$) δ (ppm): 8.03 (d, J=1.9 Hz, 1H), 7.14 (t, J=7.8 Hz, 1H), 6.71-6.81 (m, 4H), 3.78-3.81 (m, 5H), 2.73-2.81 (m, 1H), 2.49-2.50 (m, 2H), 2.21-2.32 (m, 1H), 1.94-1.98 (m, 2H), 1.82-1.85 (m, 3H), 1.47-1.59 (m, 2H), 1.18-1.29 (m, 2H), 0.96-0.97 (m, 1H), 0.41-0.48 (m, 1H), 0.16-0.33 (m, 2H), 0.05-0.11 (m, 1H). (LCMS, ESI pos.): Calcd. for $C_{25}H_{30}FNO_4$: 428.2 $(M+H)^+$; found: 428.3.

Example 2

(S)-3-Cyclopropyl-3-(3-(((1s,4R)-4-(5-fluoro-2-methoxypyridin-4-yl)cyclohexyl)methoxy)phenyl) propanoic acid Cpd 10

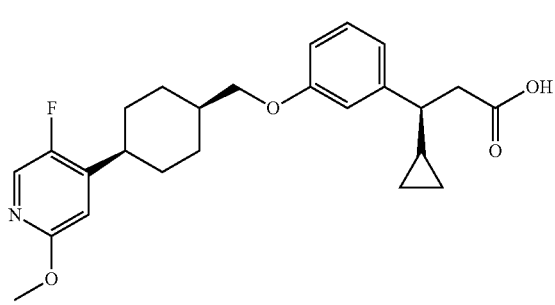 [SMILES: COc1cc([C@H]2CC[C@@H](COc3cccc([C@@H](CC(=O)O)C4CC4)c3)CC2)c(F)cn1]

(A) (S)-Methyl 3-cyclopropyl-3-(3-(((1s,4R)-4-(5-fluoro-2-methoxypyridin-4-yl)cyclohexyl)methoxy) phenyl)propanoate, 2a

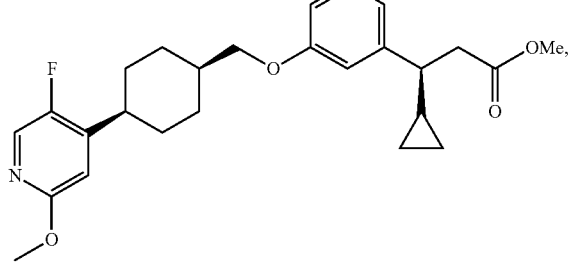

2a

Compound 2a was prepared from ((1s,4s)-4-(5-fluoro-2-methoxypyridin-4-yl)cyclohexyl)methanol (cpd 1c-2) and (S)-methyl 3-cyclopropyl-3-(3-hydroxyphenyl)propanoate according to the methods described in Example 1, Step D. Mass Spectrum (LCMS, ESI pos.): Calcd. for $C_{26}H_{32}FNO_4$: 442.2 (M+H)$^+$; found: 442.3.

(B) (S)-3-Cyclopropyl-3-(3-(((1s,4R)-4-(5-fluoro-2-methoxypyridin-4-yl)cyclohexyl) methoxy)phenyl) propanoic acid, Cpd 10

Compound 10 was prepared from (S)-methyl 3-cyclopropyl-3-(3-(((1s,4R)-4-(5-fluoro-2-methoxypyridin-4-yl)cyclohexyl)methoxy)phenyl)propanoate (cpd 2a) according to the methods described in Example 1, Step E. $^1$H NMR (400 MHz, DMSO-d$_6$) δ (ppm): 8.02 (d, J=1.9 Hz, 1H), 7.15 (t, J=7.8 Hz, 1H), 6.73-6.86 (m, 4H), 4.03 (d, J=7.4 Hz, 2H), 3.79 (s, 3H), 2.82-2.89 (m, 1H), 2.37-2.48 (m, 2H), 2.27-2.29 (m, 1H), 2.15-2.19 (m, 1H), 1.84-1.86 (m, 2H), 1.59-1.70 (m, 6H), 0.89-0.99 (m, 1H), 0.39-0.49 (m, 1H), 0.20-0.29 (m, 2H), 0.02-0.11 (m, 1H); LCMS, ESI pos.: Calcd. for $C_{25}H_{30}FNO_4$: 428.2 (M+H)$^+$; found: 428.3.

Example 3

3-Cyclopropyl-3-(6-(((1r,4r)-4-(2-fluoro-5-methoxyphenyl)cyclohexyl) methoxy)pyridin-2-yl)propanoic acid, Cpd 13

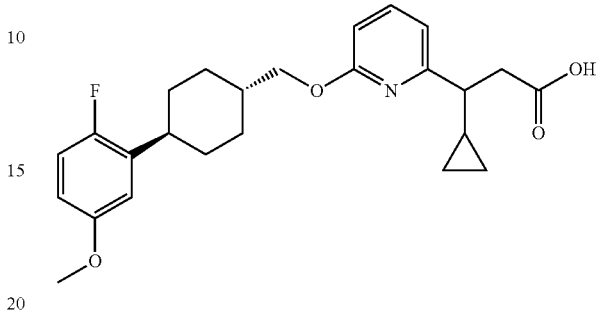

(A) 6-Fluoro-N-methoxy-N-methylpicolinamide, 3a

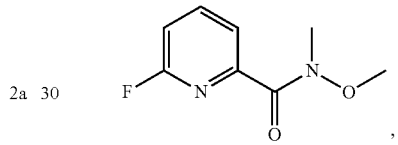

3a

A solution of 6-fluoropicolinic acid (20.0 g, 142 mmol), N,O-dimethylhydroxylamine hydrochloride (16.6 g, 170 mmol), O-(7-azabenzotriazol-1-yl)-N,N,N,N-tetramethyluronium hexafluorophosphate (HATU) (80.8 g, 213 mmol) and triethylamine (59.1 mL, 425 mmol) in dichloromethane (500 mL) was stirred for 24 h at RT and treated with 200 mL of saturated aq. NH$_4$Cl solution. The resulting solution was extracted with dichloromethane (2×500 mL). The organic layers were combined, dried over Na$_2$SO$_4$ and concentrated. The residue obtained was purified on silica gel with EtOAc/petroleum ether (15-50%) to give the title compound as a yellow oil. LCMS, ESI pos.: Calcd. for $C_8H_9FN_2O_2$: 185.0 (M+H)$^+$; found: 184.9.

(B) Cyclopropyl(6-fluoropyridin-2-yl)methanone, 3b

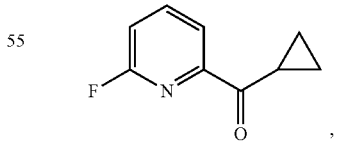

3b

To a solution of compound 3a (25.0 g, 135 mmol) in THF (500 mL), cyclopropylmagnesium bromide (271 mL, 271 mmol, 1 M in THF) was added drop-wise at 0° C. The resulting solution was stirred for 3 h at 0° C. and then treated with 200 mL of saturated aq. NH$_4$Cl solution. The resulting solution was extracted with ethyl acetate (3×400 mL). The organic layers were combined, dried over Na$_2$SO$_4$ and concentrated to give compound 3b. (LCMS, ESI pos.): Calcd. for $C_9H_8FNO$: 166.0 $(M+H)^+$; found: 166.0.

(C) Ethyl 3-cyclopropyl-3-(6-fluoropyridin-2-yl)acrylate, 3c

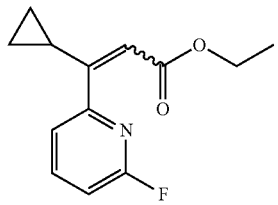

3c

A solution of ethyl 2-(trimethylsilyl)acetate (37.8 g, 236 mmol) in THF (500 mL) was cooled to −78° C. and treated with LiHMDS (236 mL, 236 mmol, 1 M in THF) drop-wise with stirring. The resulting solution was stirred at −78° C. for 30 min and cyclopropyl(6-fluoropyridin-2-yl)methanone 3b (26.0 g, 157 mmol) in THF (30 mL) was added. The resulting solution was stirred at −78° C. for 2 h. The reaction was then quenched by the addition of saturated aq. $NH_4Cl$ (200 mL) and extracted with ethyl acetate (3×500 mL). The separated organic layers were combined, dried over $Na_2SO_4$ and concentrated. The residue obtained was purified on silica gel with EtOAc/petroleum ether (15-50%) to give compound 3c. (LCMS, ESI pos.): Calcd. for $C_{13}H_{14}FNO_2$: 236.1 $(M+H)^+$; found: 236.0.

(D) Ethyl 3-cyclopropyl-3-(6-fluoropyridin-2-yl)propanoate, 3d

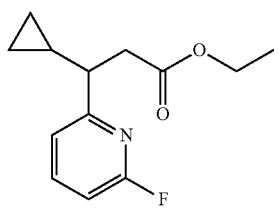

3d

A mixture of ethyl 3-cyclopropyl-3-(6-fluoropyridin-2-yl)propanoate, 3c (15 g, 64 mmol) and platinum(IV)oxide (1.0 g, 1.5 mmol) in ethanol (200 mL) was stirred overnight at 40° C. under a $H_2$ (3.5 atm) atmosphere. The resulting mixture was allowed to cool to RT, filtered and concentrated. The residue obtained was purified by flash chromatography with EtOAc/petroleum ether (20-90%) on silica gel to give compound 3d. LCMS, ESI pos.: Calcd. for $C_{13}H_{16}FNO_2$: 238.1 $(M+H)^+$; found: 237.9.

(E) Ethyl 3-cyclopropyl-3-(6-(((1r,4r)-4-(2-fluoro-5-methoxyphenyl)cyclohexyl)methoxy)pyridin-2-yl)propanoate, 3e

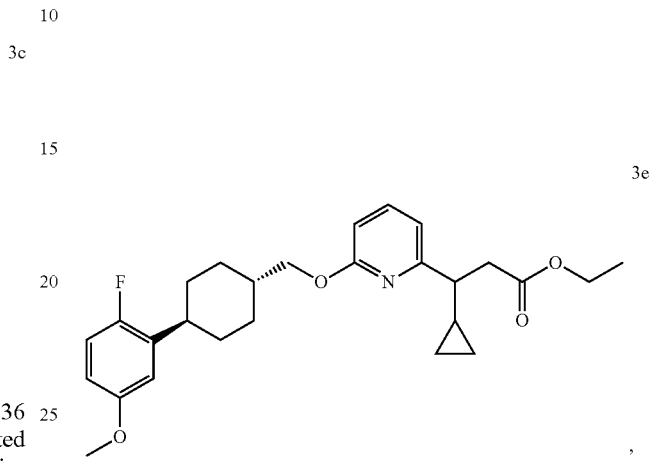

3e

A solution of ((1r,4r)-4-(2-fluoro-5-methoxyphenyl)cyclohexyl)methanol, 8a-1 (165 mg, 0.695 mmol, Example 8, Step A) and ethyl 3-cyclopropyl-3-(6-fluoropyridin-2-yl)propanoate, 3d (150 mg, 0.629 mmol) in THF (1 mL) was stirred for 10 min at 50° C. and treated with potassium tert-butoxide (0.700 mL, 0.700 mmol, 1 M in hexane). The resulting solution was stirred for 30 min at 50° C. The reaction mixture was then allowed to cool to RT and treated with 20 mL of saturated aq. $NaHCO_3$ and extracted with ethyl acetate (3×20 mL). The separated organic layers were combined, dried over $Na_2SO_4$ and concentrated to give compound 3e. LCMS, ESI pos.: Calcd. for $C_{27}H_{34}FNO_4$: 456.2 $(M+H)^+$; found: 456.2.

(F) 3-Cyclopropyl-3-(6-(((1r,4r)-4-(2-fluoro-5-methoxyphenyl)cyclohexyl)methoxy)pyridin-2-yl)propanoic acid, Cpd 13

Compound 13 was prepared from ethyl 3-cyclopropyl-3-(6-(((1r,4r)-4-(2-fluoro-5-methoxyphenyl)cyclohexyl)methoxy)pyridin-2-yl)propanoate, compound 3e, according to the methods described in Example 1, Step E. $^1H$ NMR (400 MHz, $CD_3OD$) δ (ppm): 7.55 (dd, =8.4 Hz, $J_2$=7.6 Hz, 1H), 6.92 (dd, $J_1$=10.0 Hz, $J_2$=8.8 Hz, 1H), 6.77-6.85 (m, 2H), 6.69-6.75 (m, 1H), 6.58 (d, J=7.6 Hz, 1H), 4.10-4.25 (m, 2H), 3.75 (s, 3H), 2.98 (dd, $J_1$=15.6 Hz, $J_2$=9.2 Hz, 1H), 2.79-2.87 (m, 1H), 2.75 (dd, $J_1$=15.6 Hz, $J_2$=5.6 Hz, 1H), 2.30-2.49 (m, 1H), 1.98-2.06 (m, 2H), 1.82-1.95 (m, 3H), 1.50-1.61 (m, 2H), 1.18-1.38 (m, 2H), 1.00-1.11 (m, 1H), 0.53-0.62 (m, 1H), 0.39-0.49 (m, 1H), 0.24-0.33 (m, 2H). (LCMS, ESI pos.): Calcd. for $C_{25}H_{30}FNO_4$: 428.2 $(M+H)^+$; found: 428.3.

Example 4

3-Cyclopropyl-3-(6-(((1s,4s)-4-(2-fluoro-5-methoxyphenyl)cyclohexyl)methoxy)pyridin-2-yl)propanoic acid, Cpd 14

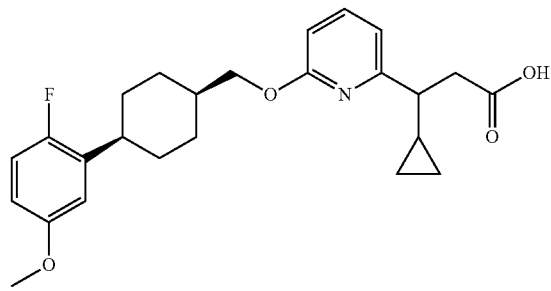 [SMILES: COc1ccc(F)c([C@H]2CC[C@@H](COc3cccc(C(CC(=O)O)C4CC4)n3)CC2)c1]

(A) Ethyl 3-cyclopropyl-3-(6-(((1s,4s)-4-(2-fluoro-5-methoxyphenyl)cyclohexyl)methoxy)pyridin-2-yl)propanoate, 4a

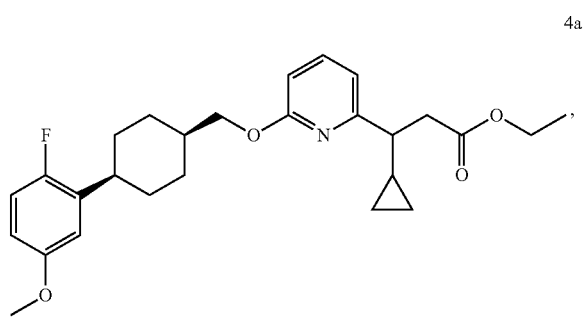 [SMILES: CCOC(=O)CC(c1cccc(OC[C@H]2CC[C@@H](c3cc(OC)ccc3F)CC2)n1)C1CC1]

4a

Compound 4a was prepared from ((1s,4s)-4-(2-fluoro-5-methoxyphenyl)cyclohexyl)methanol, 8a-2 (Example 8, Step A) and ethyl 3-cyclopropyl-3-(6-fluoropyridin-2-yl)propanoate, 3d (Example 3, Step D) according to the methods described in Example 3, Step E. Mass Spectrum (LCMS, ESI pos.): Calcd. for $C_{27}H_{34}FNO_4$: 456.2 (M+H)$^+$; found: 456.3.

(B) 3-Cyclopropyl-3-(6-(((1s,4s)-4-(2-fluoro-5-methoxyphenyl)cyclohexyl)methoxy)pyridin-2-yl)propanoic acid, 14

Compound 14 was prepared from ethyl 3-cyclopropyl-3-(6-(((1s,4s)-4-(2-fluoro-5-methoxyphenyl)cyclohexyl)methoxy)pyridin-2-yl)propanoate, cpd 4a, according to the methods described in Example 3, Step F. $^1$H NMR (400 MHz, CD$_3$OD) δ (ppm): 7.53-7.55 (m, 1H), 6.92 (dd, J, =10.0 Hz, J$_2$=8.8 Hz, 1H), 6.80-6.88 (m, 2H), 6.60-6.71 (m, 1H), 6.58-6.60 (m, 1H), 4.53 (dd, J, =10.8 Hz, J$_2$=8.0 Hz, 1H), 4.38-4.44 (m, 1H), 3.76 (s, 3H), 2.99 (dd, J$_1$=15.6 Hz, J$_2$=9.2 Hz, 1H), 2.85-2.95 (m, 1H), 2.76 (dd, J$_1$=15.6 Hz, J$_2$=5.6 Hz, 1H), 2.32-2.49 (m, 1H), 2.12-2.30 (m, 1H), 1.91-1.97 (m, 2H), 1.59-1.82 (m, 6H), 1.08-1.18 (m, 1H), 0.54-0.62 (m, 1H), 0.40-0.46 (m, 1H), 0.25-0.34 (m, 2H). Mass Spectrum (LCMS, ESI pos.): Calcd. for $C_{25}H_{30}FNO_4$: 428.2 (M+H)$^+$, found 428.2.

Example 5

3-Cyclopropyl-3-(6-(((1r,4r)-4-(5-fluoro-2-methoxypyridin-4-yl)cyclohexyl)methoxy)pyridin-2-yl)propanoic acid, Cpd 15

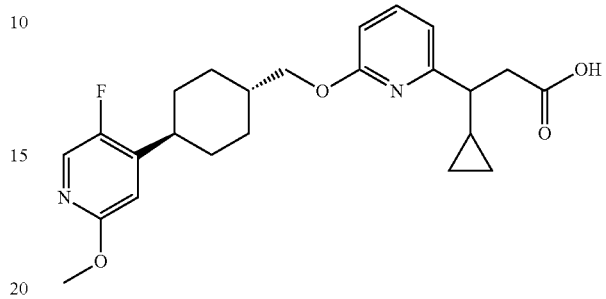

(A) Ethyl 3-cyclopropyl-3-(6-(((1r,4r)-4-(5-fluoro-2-methoxypyridin-4-yl)cyclohexyl)methoxy)pyridin-2-yl)propanoate, 5a

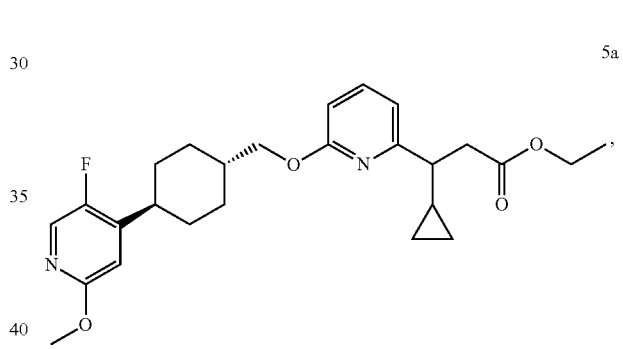

5a

Compound 5a was prepared from ((1r,4r)-4-(5-fluoro-2-methoxypyridin-4-yl)cyclohexyl)methanol, cpd 1c-1, and ethyl 3-cyclopropyl-3-(6-fluoropyridin-2-yl)propanoate, cpd 3d, according to the methods described in Example 3, Step E. Mass Spectrum (LCMS, ESI pos.): Calcd. for $C_{26}H_{33}FN_2O_4$: 457.2 (M+H)$^+$, found 457.1.

(B) 3-Cyclopropyl-3-(6-(((1r,4r)-4-(5-fluoro-2-methoxypyridin-4-yl)cyclohexyl)methoxy)pyridin-2-yl)propanoic acid, Cpd 15

Compound 15 was prepared from ethyl 3-cyclopropyl-3-(6-(((1r,4r)-4-(5-fluoro-2-methoxypyridin-4-yl)cyclohexyl)methoxy)pyridin-2-yl)propanoate, cpd 5a, according to the methods described in Example 3, Step F. $^1$H NMR (400 MHz, CD$_3$OD) δ (ppm): 7.87 (s, 1H), 7.58 (dd, J$_1$=7.6 Hz, J$_2$=8.0 Hz, 1H), 6.87 (d, J=7.2 Hz, 1H), 6.69 (d, J=4.8 Hz, 1H), 6.61 (d, J=8.0 Hz, 1H), 4.12-4.22 (m, 2H), 3.85 (s, 3H), 2.96-2.99 (m, 1H), 2.73-2.83 (m, 2H), 2.39-2.41 (m, 1H), 2.02-2.05 (m, 2H), 1.91-1.95 (m, 3H), 1.50-1.60 (m, 2H), 1.28-1.32 (m, 2H), 1.07-1.08 (m, 1H), 0.58-0.60 (m, 1H), 0.44-0.46 (m, 1H), 0.28-0.32 (m, 2H). Mass Spectrum (LCMS, ESI pos.): Calcd. for $C_{24}H_{29}FN_2O_4$: 429.2 (M+H)$^+$, found 429.1.

Example 6

3-Cyclopropyl-3-(6-(((1s,4s)-4-(5-fluoro-2-methoxy-pyridin-4-yl)cyclohexyl)methoxy)pyridin-2-yl)propanoic acid, Cpd 16

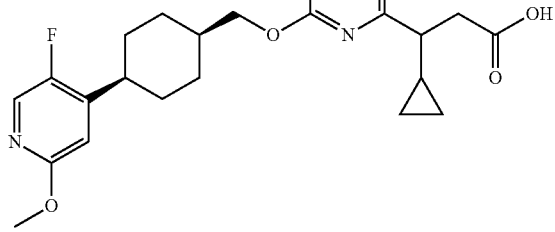

Compound 16 was prepared from ((1 s,4s)-4-(5-fluoro-2-methoxypyridin-4-yl)cyclohexyl)methanol, cpd 1c-2, and ethyl 3-cyclopropyl-3-(6-fluoropyridin-2-yl)propanoate, cpd 3d, (Example 3, Step D) according to the methods described in Example 3, Steps E and F. $^1$H NMR (400 MHz, CD$_3$OD) δ (ppm): 7.86 (s, 1H), 7.56 (dd, J$_1$=8.0 Hz, J$_2$=7.2 Hz, 1H), 6.86 (d, J=7.2 Hz, 1H), 6.75 (d, J=4.8 Hz, 1H), 6.60 (d, J=8.0 Hz, 1H), 4.46-4.52 (m, 1H), 4.40-4.44 (m, 1H), 3.86 (s, 3H), 2.88-3.02 (m, 2H), 2.76 (dd, J$_1$=15.2 Hz, J$_2$=5.6 Hz, 1H), 2.31-2.48 (m, 1H), 2.22-2.06 (m, 1H), 1.92-1.94 (m, 2H), 1.64-1.85 (m, 6H), 1.01-1.12 (m, 1H), 0.55-0.63 (m, 1H), 0.40-0.48 (m, 1H), 0.25-0.35 (m, 2H). Mass Spectrum (LCMS, ESI pos.): Calcd. for C$_{24}$H$_{29}$FN$_2$O$_4$: 429.2 (M+H)$^+$, found 429.1.

(A) Ethyl 3-cyclopropyl-3-(2-fluoropyridin-4-yl)propanoate, 7a

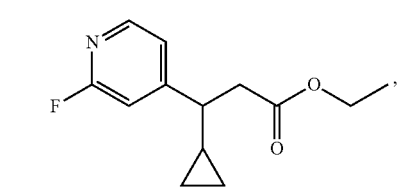

Compound 7a was prepared 2-fluoroisonicotinic acid according to the methods described in Example 3, Steps A-D. (LCMS, ESI pos.): Calcd. for C$_{13}$H$_{16}$FNO$_2$: 238.1 (M+H)$^+$; found: 237.9.

(B) 3-Cyclopropyl-3-(2-(((1r,4r)-4-(2-fluoro-5-methoxyphenyl)cyclohexyl)methoxy)pyridin-4-yl) propanoic acid, Cpd 4

Compound 4 was prepared from ((1r,4r)-4-(2-fluoro-5-methoxyphenyl)cyclohexyl)methanol, cpd 8a-1, and ethyl 3-cyclopropyl-3-(6-fluoropyridin-2-yl)propanoate, cpd 7a, according to the methods described in Example 3, Steps E and F. $^1$H NMR (400 MHz, DMSO-d$_6$) δ (ppm): 12.15 (brs, 1H), 8.03 (d, J=5.3 Hz, 1H), 7.03-7.07 (m, 1H), 6.91 (d, J=1.2 Hz, 1H), 6.84-6.90 (m, 1H), 6.74-6.78 (m, 1H), 6.71 (s, 1H), 4.09 (d, J=6.4 Hz, 2H), 3.72 (s, 3H), 2.71-2.81 (m, 1H), 2.68 (d, J=7.4 Hz, 2H), 2.22-2.24 (m, 1H), 1.88-1.99 (m, 2H), 1.79-1.82 (m, 3H), 1.47-1.61 (m, 2H), 1.20-1.24 (m, 2H), 0.93-1.04 (m, 1H), 0.46-0.55 (m, 1H), 0.26-0.35 (m, 2H), 0.16-0.19 (m, 1H). Mass Spectrum (LCMS, ESI pos.): Calcd. for C$_{25}$H$_{30}$FNO$_4$: 428.2 (M+H)$^+$, found 428.3.

Example 7

3-Cyclopropyl-3-(2-(((1r,4r)-4-(2-fluoro-5-methoxyphenyl)cyclohexyl)methoxy)pyridin-4-yl) propanoic acid Cpd 4

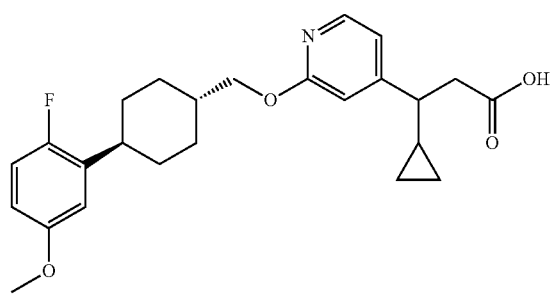 [SMILES: COc1ccc(F)c([C@H]2CC[C@H](COc3cc(C(CC(=O)O)C4CC4)ccn3)CC2)c1]

Example 8

3-Cyclopropyl-3-(2-(((1 s,4s)-4-(2-fluoro-5-methoxyphenyl)cyclohexyl)methoxy)pyridin-4-yl) propanoic acid, Cpd 5

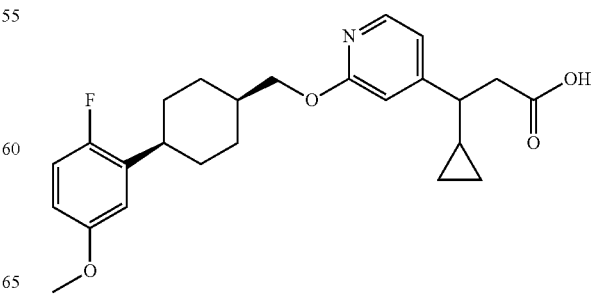

(A) ((1r,4r)-4-(2-Fluoro-5-methoxyphenyl)cyclo-hexyl)methanol (8a-1) and ((1s,4s)-4-(2-fluoro-5-methoxyphenyl)cyclohexyl)methanol (8a-2)

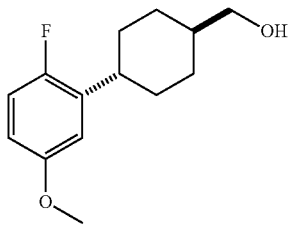

(8a-1)

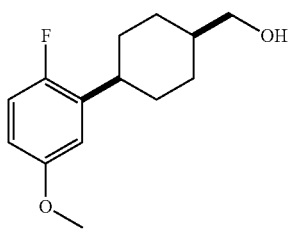

(8a-2)

(4-(2-Fluoro-5-methoxyphenyl)cyclohexyl)methanol, cpd 36c, (Example 36, Step C) was subjected to Supercritical Fluid Chromatography (SFC) on Chiralpak IA-SFC, 25 cm, column using $CO_2$/IPA (70/30 with 0.2 DEA) to give compounds 8a-1 and 8a-2.

Cpd 8a-1: $^1$H NMR (300 MHz, CDCl$_3$) δ (ppm): 6.86-6.92 (m, 1H), 6.70-6.74 (m, 1H), 6.60-6.65 (m, 1H), 3.75 (s, 3H), 3.49 (d, J=6.3 Hz, 2H), 2.73-2.79 (m, 1H), 1.88-1.92 (m, 4H), 1.40-1.61 (m, 4H), 1.05-1.18 (m, 1H).

Cpd 8a-2: $^1$H NMR (300 MHz, CDCl$_3$) δ (ppm): 6.86-6.92 (m, 1H), 6.71-6.73 (m, 1H), 6.61-6.64 (m, 1H), 3.70-3.75 (m, 5H), 2.82-2.86 (m, 1H), 1.45-1.89 (m, 9H).

(B) 3-Cyclopropyl-3-(2-(((1s,4s)-4-(2-fluoro-5-methoxyphenyl)cyclohexyl) methoxy)pyridin-4-yl) propanoic acid, Cpd 5

Compound 5 was prepared from ((1s,4s)-4-(2-fluoro-5-methoxyphenyl)cyclohexyl)methanol, cpd 8a-2, and ethyl 3-cyclopropyl-3-(6-fluoropyridin-2-yl)propanoate, cpd 7a, according to the methods described in Example 3, Steps E and F. $^1$H NMR (300 MHz, DMSO-d$_6$) δ (ppm): 8.04 (d, J=5.4 Hz, 1H), 7.00-7.06 (m, 1H), 6.86-6.96 (m, 2H), 6.71-6.79 (m, 2H), 4.37 (d, J=7.6 Hz, 2H), 3.73 (s, 3H), 2.80-2.83 (m, 1H), 2.69 (d, J=7.4 Hz, 2H), 2.14-2.29 (m, 2H), 1.83-1.85 (m, 2H), 1.52-1.75 (m, 6H), 0.92-1.08 (m, 1H), 0.45-0.52 (m, 1H), 0.20-0.35 (m, 2H), 0.11-0.19 (m, 1H). Mass Spectrum (LCMS, ESI pos.): Calcd. for $C_{25}H_{30}FNO_4$: 428.2 (M+H)$^+$, found 428.3.

Example 9

3-Cyclopropyl-3-(2-(((1r,4r)-4-(5-fluoro-2-methoxy-pyridin-4-yl)cyclohexyl)methoxy)pyridin-4-yl)pro-panoic acid, Cpd 8

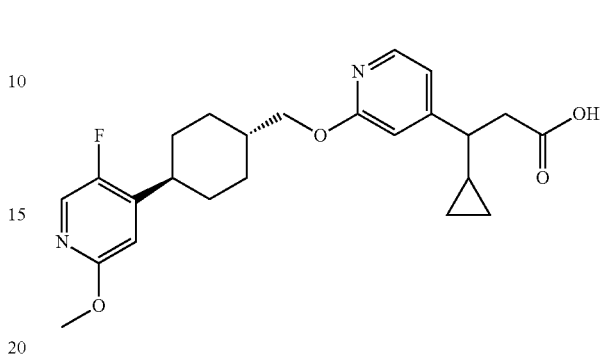

Compound 8 was prepared from ((1r,4r)-4-(5-fluoro-2-methoxypyridin-4-yl)cyclohexyl)methanol, cpd 1c-1 and ethyl 3-cyclopropyl-3-(2-fluoropyridin-4-yl)propanoate, cpd 7a, according to the methods described in Example 3, Steps E and F. $^1$H NMR (300 MHz, DMSO-d$_6$) δ (ppm): 7.98-8.06 (m, 2H), 6.87 (d, J=5.7 Hz, 1H), 6.76 (d, J=4.8 Hz, 1H), 6.68 (s, 1H), 4.08 (d, J=6.3 Hz, 2H), 3.81 (s, 3H), 2.71-2.80 (m, 1H), 2.50-2.57 (m, 2H), 2.18-2.29 (m, 1H), 1.90-1.94 (m, 2H), 1.80-1.82 (m, 3H), 1.50-1.52 (m, 2H), 1.18-1.31 (m, 2H), 0.90-1.01 (m, 1H), 0.41-0.51 (m, 1H), 0.20-0.40 (m, 2H), 0.04-0.11 (m, 1H). Mass Spectrum (LCMS, ESI pos.): Calcd. for $C_{24}H_{29}FN_2O_4$: 429.2 (M+H)$^+$, found 429.1.

Example 10

3-Cyclopropyl-3-(2-(((1s,4s)-4-(5-fluoro-2-methoxy-pyridin-4-yl)cyclohexyl)methoxy)pyridin-4-yl)pro-panoic acid, Cpd 7

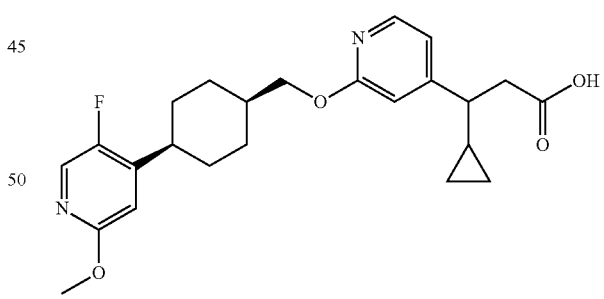

Compound 7 was prepared from ((1s,4s)-4-(5-fluoro-2-methoxypyridin-4-yl)cyclohexyl)methanol, cpd 1c-2, and ethyl 3-cyclopropyl-3-(2-fluoropyridin-4-yl)propanoate, cpd 7a according to the methods described in Example 3, Steps E and F. $^1$H NMR (300 MHz, CDCl$_3$) δ (ppm): 7.98-8.09 (m, 2H), 6.82-6.89 (m, 2H), 6.69 (s, 1H), 4.34 (d, J=7.6 Hz, 2H), 3.81 (s, 3H), 2.70-2.85 (m, 1H), 2.54-2.56 (m, 2H), 2.10-2.32 (m, 2H), 1.82-1.83 (m, 2H), 1.67-1.81 (m, 6H), 0.85-1.03 (m, 1H), 0.45-0.47 (m, 1H), 0.19-0.30 (m, 2H), 0.12-0.16 (m, 1H). Mass Spectrum (LCMS, ESI pos.): Calcd. for $C_{24}H_{29}FN_2O_4$: 429.2 (M+H)$^+$, found 429.1.

Example 11

3-Cyclopropyl-3-(5-(((1s,4s)-4-(5-fluoro-2-methoxy-pyridin-4-yl)cyclohexyl) methoxy)pyridin-3-yl)propanoic acid, Cpd 23

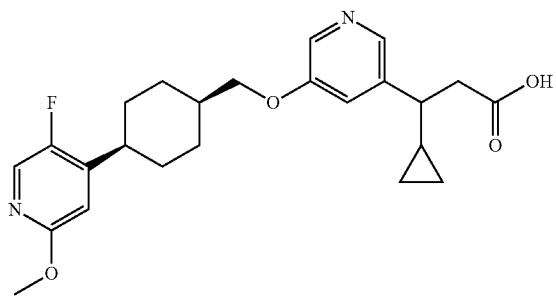 [SMILES: COc1cc([C@H]2CC[C@@H](COc3cncc(C(CC(=O)O)C4CC4)c3)CC2)c(F)cn1]

(A) Ethyl 5-(benzyloxy)nicotinate, 11a

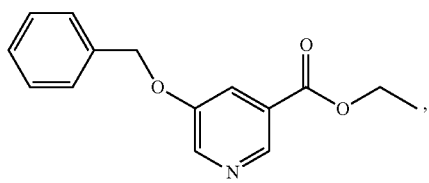

A solution of ethyl 5-hydroxynicotinate (31.0 g, 185 mmol), phenylmethanol (24.0 g, 223 mmol) and triphenylphosphine (97.3 g, 371 mmol) in THF (500 mL), was stirred for 20 min at 0° C. Diethyl azodicarboxylate (38.7 g, 222 mmol) in THF (40 mL) was then added drop-wise and the resulting solution was stirred overnight at RT. The reaction was then quenched by the addition of 200 mL of saturated aq. NH$_4$Cl solution. The resulting solution was extracted with ethyl acetate (3×500 mL). The organic layers were combined, dried over Na$_2$SO$_4$ and concentrated. The residue obtained was purified on silica gel with ethyl acetate/petroleum ether (0-15%) to give the compound 11a. Mass Spectrum (LCMS, ESI pos.): Calcd. for C$_{15}$H$_{15}$NO$_3$: 258.1 (M+H)$^+$, found 258.0.

(B) 5-(Benzyloxy)nicotinic acid, 11b

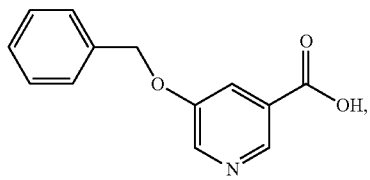

A mixture of ethyl 5-(benzyloxy)nicotinate 11a (23.0 g, 89.4 mmol), lithium hydroxide (15.0 g, 357 mmol) in THF (400 mL), ethanol (100 mL) and water (100 mL) was stirred overnight at 30° C. The pH of the solution was adjusted to 4 with 1 M aq. HCl. The resulting solution was extracted with ethyl acetate (3×500 mL). The organic layers were combined, dried over Na$_2$SO$_4$ and concentrated to give compound 11b. Mass Spectrum (LCMS, ESI pos.): Calcd. for C$_{13}$H$_{11}$NO$_3$: 230.1 (M+H)$^+$, found 230.0.

(C) 5-(Benzyloxy)-N-methoxy-N-methylnicotinamide, 11c

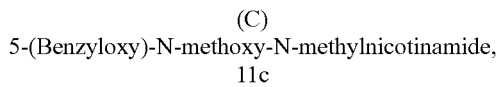
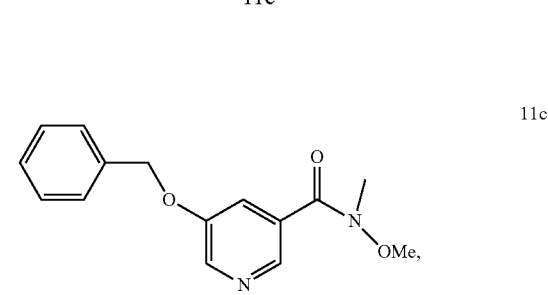

A mixture of 5-(benzyloxy)nicotinic acid, 11b (17.0 g, 74.1 mmol), N,O-dimethylhydroxylamine hydrochloride (8.68 g, 89.0 mmol), O-(7-azabenzotriazol-1-yl)-N,N,N,N-tetramethyluronium hexafluorophosphate (HATU) (42.3 g, 111 mmol) and triethylamine (30.9 mL, 222 mmol) in dichloromethane (300 mL) was stirred 24 h at RT. The reaction was then quenched by the addition of 100 mL of saturated aq. NH$_4$Cl. The resulting solution was extracted with dichloromethane (2×300 mL). The organic layers were combined, dried over Na$_2$SO$_4$ and concentrated. The residue obtained was purified on silica gel with ethyl acetate/petroleum ether (0-50%) to give compound 11c. Mass Spectrum (LCMS, ESI pos.): Calcd. for C$_{15}$H$_{16}$N$_2$O$_3$: 273.1 (M+H)$^+$, found 273.0.

(D) (5-(Benzyloxy)pyridin-3-yl)(cyclopropyl)methanone, 11d

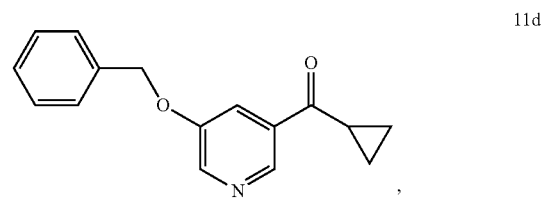 [SMILES: O=C(c1cncc(OCc2ccccc2)c1)C1CC1]

A solution of 5-(benzyloxy)-N-methoxy-N-methylnicotinamide, 11c (17.0 g, 62.4 mmol) in THF (300 mL) was cooled to 0° C. and treated with cyclopropylmagnesium bromide (125 mL, 125 mmol, 1M in THF) drop-wise. The resulting solution was stirred for 2 h at 0° C. and then treated with saturated aq. NH$_4$Cl (100 mL). The resulting mixture was extracted with ethyl acetate (3×500 mL). The separated organic layers were combined, dried over Na$_2$SO$_4$ and concentrated. The residue obtained was purified on silica gel to give compound 11d. Mass Spectrum (LCMS, ESI pos.): Calcd. for C$_{16}$H$_{15}$NO$_2$: 254.1 (M+H)$^+$, found 254.0.

(E) Ethyl 3-(5-(benzyloxy)pyridin-3-yl)-3-cyclopropylpropanoate, 11e

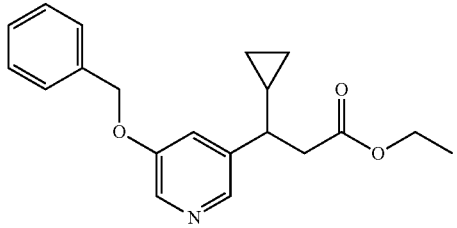

Compound 11e was prepared from (5-(benzyloxy)pyridin-3-yl)(cyclopropyl)methanone, 11d according to the methods described in the Example 3, Steps C and D. Mass Spectrum (LCMS, ESI pos.): Calcd. for $C_{20}H_{23}NO_3$: 326.2 (M+H)$^+$; found: 326.1.

(F) Ethyl 3-cyclopropyl-3-(5-hydroxypyridin-3-yl)propanoate, 11f

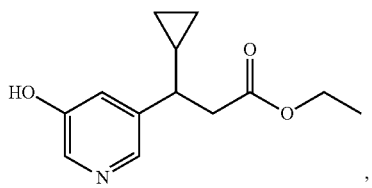

A mixture of ethyl 3-(5-(benzyloxy)pyridin-3-yl)-3-cyclopropylpropanoate, 11e (13 g, 40 mmol) and 10% Pd/C (425 mg) in ethanol (200 mL) was stirred overnight at 40° C. under a H$_2$ (3.5 atm) atmosphere. The reaction mixture was filtered and the filtrate was concentrated. The residue obtained was purified over silica with EtOAc/petroleum ether (20-90%) to give compound 11f. Mass Spectrum (LCMS, ESI pos.): Calcd. for $C_{13}H_{17}NO_3$: 236.1 (M+H)$^+$, found 236.0.

(G) 3-Cyclopropyl-3-(5-(((1s,4s)-4-(5-fluoro-2-methoxypyridin-4-yl)cyclohexyl) methoxy)pyridin-3-yl)propanoic acid, Cpd 23

Compound 23 was prepared from ((1 s,4s)-4-(5-fluoro-2-methoxypyridin-4-yl)cyclohexyl)methanol, cpd 1c-2 (Example 1, Step C) and ethyl 3-cyclopropyl-3-(5-hydroxypyridin-3-yl)propanoate 11f, according to the methods described in the Example 1, Steps D and E. $^1$H NMR (400 MHz, CD$_3$OD) δ (ppm): 8.11 (s, 1H), 8.04 (s, 1H), 7.87 (s, 1H), 7.41-7.42 (m, 1H), 6.75 (s, 1H), 4.17 (d, J=7.2 Hz, 2H), 3.85 (s, 3H), 2.73-2.93 (m, 3H), 2.26-2.37 (m, 2H), 1.91-1.99 (m, 2H), 1.72-1.79 (m, 6H), 1.11-1.13 (m, 1H), 0.64-0.66 (m, 1H), 0.35-0.46 (m, 2H), 0.16-0.20 (m, 1H). Mass Spectrum (LCMS, ESI pos.): Calcd. for $C_{24}H_{29}FN_2O_4$: 429.5 (M+H)$^+$; found: 429.2.

Example 12

3-Cyclopropyl-3-(5-(((1r,4r)-4-(5-fluoro-2-methoxypyridin-4-yl)cyclohexyl)methoxy)pyridin-3-yl)propanoic acid, Cpd 22

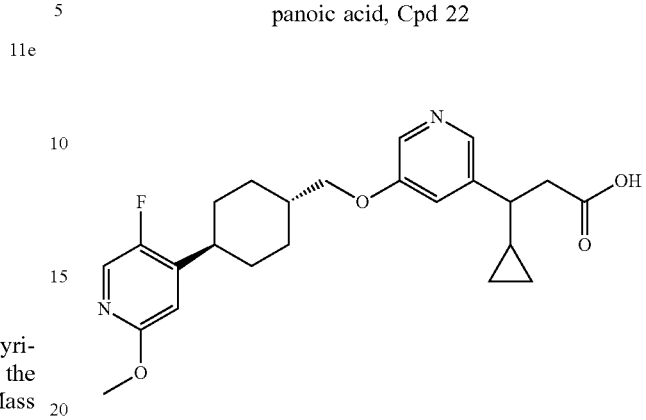

Compound 22 was prepared from ((1r,4r)-4-(5-fluoro-2-methoxypyridin-4-yl)cyclohexyl)methano, cpd 1c-1 (Example 1, Step C) and ethyl 3-cyclopropyl-3-(5-hydroxypyridin-3-yl)propanoate 11f, according to the methods described in Example 1 Steps D and E. $^1$H NMR (400 MHz, CD$_3$OD) δ (ppm): 8.06-8.11 (m, 2H), 7.91 (s, 1H), 7.40 (s, 1H), 6.72-6.74 (m, 1H), 3.96 (d, J=6.0 Hz, 2H), 3.88 (s, 3H), 2.75-2.91 (m, 3H), 2.35-2.42 (m, 1H), 2.08-2.11 (m, 2H), 1.91-1.99 (m, 3H), 1.57-1.65 (m, 2H), 1.31-1.41 (m, 2H), 1.04-1.17 (m, 1H), 0.64-0.69 (m, 1H), 0.36-0.50 (m, 2H), 0.18-0.23 (m, 1H). Mass Spectrum (LCMS, ESI pos.): Calcd. for $C_{24}H_{29}FN_2O_4$: 429.5 (M+H)$^+$; found: 429.2.

Example 13

3-Cyclopropyl-3-(5-(((1s,4s)-4-(2-fluoro-5-methoxyphenyl)cyclohexyl)methoxy)pyridin-3-yl)propanoic acid, Cpd 18

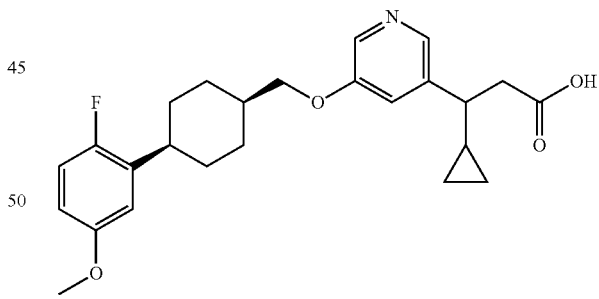

Compound 18 was prepared from ((1s,4s)-4-(2-fluoro-5-methoxyphenyl)cyclohexyl)methanol, cpd 8a-2 (Example 8, Step A) and ethyl 3-cyclopropyl-3-(5-hydroxypyridin-3-yl) propanoate 11f, according to the methods described in Example 1, Steps D and E. $^1$H NMR (400 MHz, CD$_3$OD) δ (ppm): 8.04-8.11 (m, 2H), 7.41 (s, 1H), 6.82-6.94 (m, 2H), 6.67-6.72 (m, 1H), 4.18 (d, J=7.5 Hz, 2H), 3.74 (s, 3H), 2.71-2.90 (m, 3H), 2.25-2.41 (m, 2H), 1.82-1.99 (m, 2H), 1.67-1.78 (m, 6H), 1.09-1.13 (m, 1H), 0.62-0.65 (m, 1H), 0.34-0.47 (m, 2H), 0.15-0.20 (m, 1H). Mass Spectrum (LCMS, ESI pos.): Calcd. for $C_{25}H_{30}FNO_4$: 428.2 (M+H)$^+$; found: 428.2.

Example 14

3-Cyclopropyl-3-(5-(((1r,4r)-4-(2-fluoro-5-methoxyphenyl)cyclohexyl)methoxy)pyridin-3-yl)propanoic acid, Cpd 21

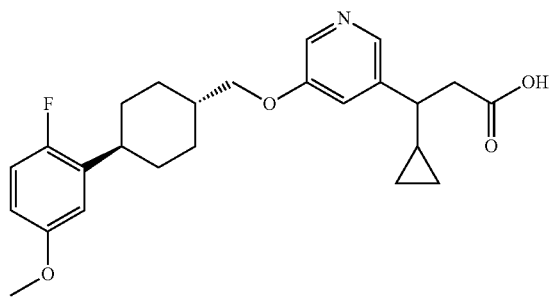 [SMILES: COc1ccc(F)c([C@H]2CC[C@H](COc3cncc(C(CC(=O)O)C4CC4)c3)CC2)c1]

Compound 21 was prepared from ((1r,4r)-4-(2-fluoro-5-methoxyphenyl)cyclohexyl)methanol, cpd 8a-1, and ethyl 3-cyclopropyl-3-(5-hydroxypyridin-3-yl)propanoate 11f, according to the methods described in the Example 1, Steps D and E. $^1$H NMR (400 MHz, CD$_3$OD) δ (ppm): 8.06-8.11 (m, 2H), 7.40 (s, 1H), 6.95 (t, J=9.4 Hz, 1H), 6.82-6.84 (m, 1H), 6.72-6.75 (m, 1H), 3.96 (d, J=6.4 Hz, 2H), 3.78 (s, 3H), 2.75-2.90 (m, 3H), 2.38-2.42 (m, 1H), 2.07-2.09 (m, 2H), 1.93-1.96 (m, 3H), 1.58-1.64 (m, 2H), 1.31-1.40 (m, 2H), 1.13-1.15 (m, 1H), 0.65-0.72 (m, 1H), 0.37-0.50 (m, 2H), 0.18-0.22 (m, 1H). Mass Spectrum (LCMS, ESI pos.): Calcd. for C$_{25}$H$_{30}$FNO$_4$: 428.2 (M+H)$^+$; found: 428.2.

Example 15

(S)-3-Cyclopropyl-3-(2-(((1r,4s)-4-(2-fluoro-5-methoxyphenyl)cyclohexyl)methoxy)pyridin-4-yl)propanoic acid (Cpd 27) and

(R)-3-cyclopropyl-3-(2-(((1r,4r)-4-(2-fluoro-5-methoxyphenyl)cyclohexyl)methoxy)pyridin-4-yl)propanoic acid (Cpd 26)

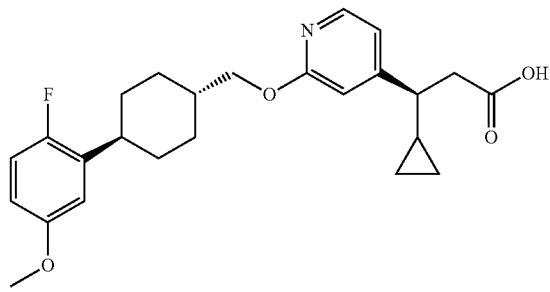

(Cpd 27)

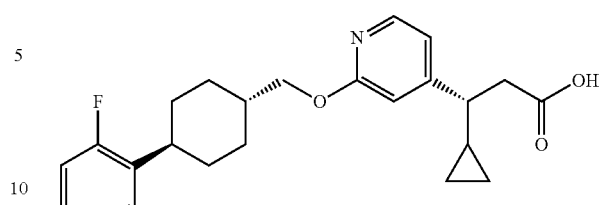

(Cpd 26)

3-Cyclopropyl-3-(2-(((1r,4r)-4-(2-fluoro-5-methoxyphenyl)cyclohexyl)methoxy)pyridin-4-yl)propanoic acid, cpd 4 (as prepared in Example 7) was subjected to preparative chriral HPLC on Chiralpak IC, 2×25 cm, 5 μm column with hexane (0.1% TFA)/EtOH to give compounds 27 and 26.

Cpd 27: $^1$H NMR (300 MHz, DMSO-d$_6$) δ (ppm): 8.01 (d, J=5.3 Hz, 1H), 7.03 (t, J=9.2 Hz, 1H), 6.91 (d, J=1.2 Hz, 1H), 6.81-6.90 (m, 1H), 6.71-6.76 (m, 2H), 4.07 (d, J=6.4 Hz, 2H), 3.70 (s, 3H), 2.66-2.78 (m, 3H), 2.20-2.22 (m, 1H), 1.90-1.93 (m, 2H), 1.77-1.80 (m, 3H), 1.51-1.53 (m, 2H), 1.18-1.24 (m, 2H), 0.96-0.99 (m, 1H), 0.46-0.55 (m, 1H), 0.26-0.35 (m, 2H), 0.16-0.19 (m, 1H). Mass Spectrum (LCMS, ESI pos.): Calcd. For C$_{25}$H$_{30}$FNO$_4$: 428.2 (M+H)$^+$; found: 428.1.

Cpd 26: $^1$H NMR (300 MHz, DMSO-d$_6$) δ (ppm): 8.01 (d, J=5.3 Hz, 1H), 7.03 (t, J=9.2 Hz, 1H), 6.90 (d, J=1.2 Hz, 1H), 6.81-6.90 (m, 1H), 6.71-6.76 (m, 2H), 4.07 (d, J=6.4 Hz, 2H), 3.71 (s, 3H), 2.66-2.75 (m, 3H), 2.20-2.49 (m, 1H), 1.90-1.93 (m, 2H), 1.77-1.80 (m, 3H), 1.50-1.54 (m, 2H), 1.18-1.88 (m, 2H), 0.97-0.98 (m, 1H), 0.46-0.55 (m, 1H), 0.26-0.35 (m, 2H), 0.16-0.19 (m, 1H). Mass Spectrum (LCMS, ESI pos.): Calcd. For C$_{25}$H$_{30}$FNO$_4$: 428.2 (M+H)$^+$; found: 428.1.

Example 16

3-Cyclopropyl-3-(4-(((1r,4r)-4-(2-fluoro-5-methoxyphenyl)cyclohexyl)methoxy)pyridin-2-yl)propanoic acid, Cpd 34, trifluoroacetic acid salt

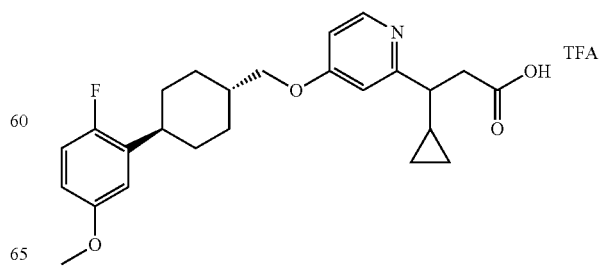

(A) Ethyl 3-(4-chloropyridin-2-yl)-3-cyclopropylacrylate, 16a

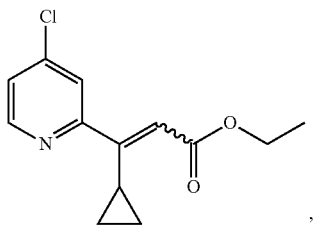
16a

Compound 16a was prepared from 4-chloropicolinic acid according to the methods described in Example 3, Steps A-C. Mass Spectrum (LCMS, ESI pos.): Calcd. For $C_{13}H_{14}ClNO_2$: 252.1 $(M+H)^+$; found: 251.9.

(B) Ethyl 3-(4-chloropyridin-2-yl)-3-cyclopropylpropanoate, 16b

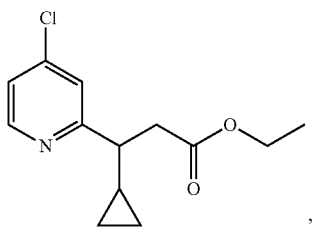
16b

To a mixture of compound 16a (4.0 g, 16 mmol) and $NiCl_2.6H_2O$ (1.7 g, 7.0 mmol) in ethanol (100 mL), $NaBH_4$ (1.3 g, 35 mmol) was added portion-wise. The resulting mixture was stirred overnight at RT. The reaction mixture was then treated with 100 mL saturated. aq. $NH_4Cl$. The resulting mixture was extracted with ethyl acetate (3×100 mL). The organic layers were combined and concentrated. The residue obtained was purified by flash chromatography (0-50% EtOAc/petroleum ether) on silica gel to give compound 16b. Mass Spectrum (LCMS, ESI pos.): Calcd. For $C_{13}H_{16}ClNO_2$: 254.1 $(M+H)^+$; found: 254.0.

(C) 3-Cyclopropyl-3-(4-(((1r,4r)-4-(2-fluoro-5-methoxyphenyl)cyclohexyl)methoxy)pyridin-2-yl) propanoic acid, Cpd 34

A mixture of compound 16b (100 mg, 0.39 mmol), ((1r,4r)-4-(2-fluoro-5-methoxyphenyl)cyclohexyl)methanol, Cpd 8a-1 (94 mg, 0.39 mmol), and 60% sodium hydride (32 mg, 0.79 mmol) in DMSO (1 mL) was stirred at 120° C. overnight. The reaction mixture was allowed to cool to RT and filtered. The filtrate was concentrated and the residue obtained was purified by Prep-HPLC on a Waters SunFire Prep C18 column (5 μm, 19×100 mm) using water (0.05% TFA) and $CH_3CN$ (0.05% TFA). After lyophilization, the trifluoroacetic acid salt of compound 34 was obtained as a white solid. $^1H$ NMR (300 MHz, DMSO-$d_6$) δ (ppm): 8.57 (d, J=6.9 Hz, 1H), 7.61 (d, J=2.6 Hz, 1H), 7.41-7.44 (m, 1H), 7.02-7.08 (m, 1H), 6.88-6.70 (m, 2H), 4.20 (d, J=5.8 Hz, 2H), 3.70-3.75 (m, 3H), 3.06-3.11 (m, 1H), 2.89-2.95 (m, 1H), 2.77-2.87 (m, 1H), 2.52-2.59 (m, 1H), 1.79-1.97 (m, 5H), 1.53-1.69 (m, 2H), 1.29 (m, 2H), 1.11-1.25 (m, 1H), 0.59-0.64 (m, 1H), 0.28-0.41 (m, 3H). Mass Spectrum (LCMS, ESI pos.): Calcd. For $C_{25}H_{30}FNO_4$: 428.2 $(M+H)^+$; found: 428.1.

Example 17

3-Cyclopropyl-3-(4-(((1s,4s)-4-(2-fluoro-5-methoxyphenyl)cyclohexyl)methoxy)pyridin-2-yl)propanoic acid, Cpd 35, trifluoroacetic acid salt

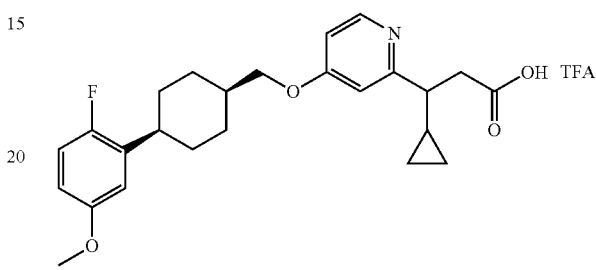

Compound 35 was prepared from ethyl 3-(4-chloropyridin-2-yl)-3-cyclopropylpropanoate, cpd 16b, and ((1s,4s)-4-(2-fluoro-5-methoxyphenyl)cyclohexyl)methanol, cpd 8a-2, according to the methods described in the Example 16. $^1H$ NMR (400 MHz, DMSO-$d_6$) δ (ppm): 8.53 (s, 1H), 7.60 (s, 1H), 7.44 (d, J=9.6 Hz, 1H), 6.98-7.03 (m, 1H), 6.85-6.87 (m, 1H), 6.71-6.75 (m, 1H), 4.41 (d, J=7.6 Hz, 2H), 3.68 (s, 3H), 3.03-3.10 (m, 1H), 2.80-2.92 (m, 2H), 2.52-2.54 (m, 1H), 2.15-2.25 (m, 1H), 1.81-1.84 (m, 2H), 1.54-1.68 (m, 6H), 1.07-1.08 (m, 1H), 0.58-0.60 (m, 1H), 0.34-0.37 (m, 2H), 0.25-0.26 (m, 1H). Mass Spectrum (LCMS, ESI pos.): Calcd. For $C_{25}H_{30}FNO_4$: 428.2 $(M+H)^+$; found: 428.1.

Example 18

3-Cyclopropyl-3-(4-(((1r,4r)-4-(5-fluoro-2-methoxypyridin-4-yl)cyclohexyl) methoxy)pyridin-2-yl)propanoic acid, Cpd 31

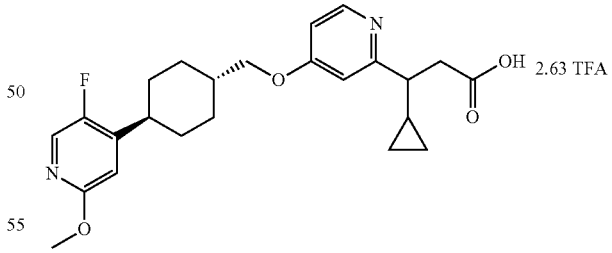

Compound 31 was prepared from ethyl 3-(4-chloropyridin-2-yl)-3-cyclopropylpropanoate, cpd 16b and ((1r,4r)-4-(5-fluoro-2-methoxypyridin-4-yl)cyclohexyl)methanol, cpd 1c-1, according to the methods described in Example 16. $^1H$ NMR (400 MHz, DMSO-$d_6$) δ (ppm): 8.61-8.62 (m, 1H), 8.02-8.03 (m, 1H), 7.62-7.63 (m, 1H), 7.41-7.43 (m, 1H), 6.75-6.76 (m, 1H), 4.18 (d, J=6.0 Hz, 2H), 3.79 (s, 3H), 3.06-3.13 (m, 1H), 2.86-2.91 (m, 1H), 2.76-2.81 (m, 1H), 2.52-2.59 (m, 1H), 1.51-1.95 (m, 7H), 1.24-1.30 (m, 2H), 1.07-1.10 (m, 1H), 0.58-0.60 (m, 1H), 0.35-0.38 (m, 2H), 027-0.29 (m, 1H). Mass Spectrum (LCMS, ESI pos.): Calcd. For $C_{24}H_{29}FN_2O_4$: 429.2 (M+H)$^+$; found: 429.2.

Example 19

3-Cyclopropyl-3-(4-(((1s,4s)-4-(5-fluoro-2-methoxy-pyridin-4-yl)cyclohexyl)methoxy)pyridine-2-yl)propanoic acid, Cpd 32 trifluoroacetic acid salt

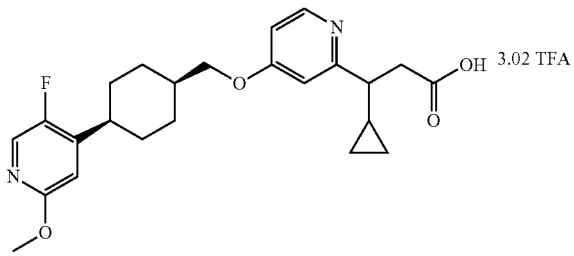 [SMILES: COc1cc([C@H]2CC[C@@H](COc3ccnc(C(CC(=O)O)C4CC4)c3)CC2)c(F)cn1]

Compound 32 was prepared from compound 16b and ((1s,4s)-4-(5-fluoro-2-methoxypyridin-4-yl)cyclohexyl) methanol, cpd 1c-2, according to the methods described in the Example 16, Step C. $^1$H NMR (400 MHz, DMSO-d$_6$) δ (ppm): 8.61-8.62 (m, 1H), 8.02-8.03 (m, 1H), 7.63-7.64 (m, 1H), 7.41-7.44 (m, 1H), 6.75-6.76 (m, 1H), 4.18 (d, J=6.0 Hz, 2H), 3.79 (s, 3H), 3.06-3.13 (m, 1H), 2.76-2.92 (m, 2H), 2.54-2.57 (m, 1H), 1.82-1.95 (m, 5H), 1.51-1.54 (m, 2H), 1.25-1.27 (m, 2H), 1.07-1.10 (m, 1H), 0.56-0.60 (m, 1H), 0.35-0.38 (m, 2H), 027-0.30 (m, 1H). Mass Spectrum (LCMS, ESI pos.): Calcd. For $C_{24}H_{29}FN_2O_4$: 429.2 (M+H)$^+$; found: 429.2.

Example 20

(3S)-3-Cyclopropyl-3-(3-((4-(5-fluoro-2-methoxy-pyridin-4-yl)-2-methylcyclohexyl) methoxy)phenyl) propanoic acid, Cpd 33

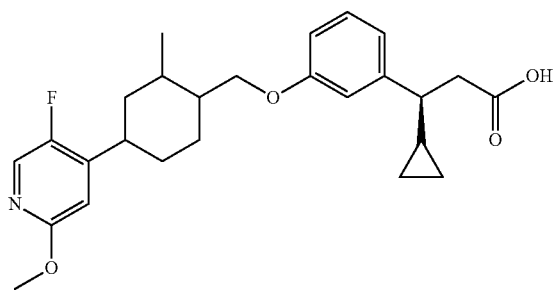 [SMILES: COc1cc(C2CCC(COc3cccc([C@@H](CC(=O)O)C4CC4)c3)C(C)C2)c(F)cn1]

(A) Ethyl 4-(5-fluoro-2-methoxypyridin-4-yl)-6-methylcyclohex-3-enecarboxylate, 20a

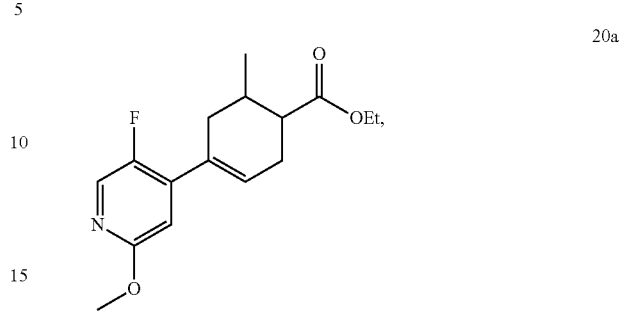

A solution of compound ethyl 2-methyl-4-oxocyclohexanecarboxylate (5.0 g, 27 mmol) in THF (70 mL) was treated with lithium bis(trimethylsilyl)amide (28 mL, 28 mmol, 1 M in THF) drop-wise under nitrogen at −70° C. The resulting solution was stirred for 30 min at −70° C. and a solution of trifluoro-N-phenyl-N-(trifluoromethylsulfonyl) methane sulfonamide (9.7 g, 27 mmol) in THF (10 mL) was added drop-wise with stirring. The reaction mixture was stirred for 2 h at −70° C. and treated with 100 mL of water. The resulting solution was extracted with ethyl acetate (3×100 mL). The organic layers were combined, dried over Na$_2$SO$_4$ and concentrated to give ethyl 6-methyl-4-(trifluoromethylsulfonyloxy)cyclohex-3-enecarboxylate as a light yellow oil, which was used in the next step without further purification.

A mixture of ethyl 6-methyl-4-(trifluoromethylsulfonyloxy)cyclohex-3-enecarboxylate (2 g, 6.0 mmol), 5-fluoro-2-methoxypyridin-4-ylboronic acid (1.7 g, 9.9 mmol), Pd(dppf)Cl$_2$.CH$_2$Cl$_2$ (258 mg, 0.316 mmol), dicesium carbonate (4.2 g, 13 mmol) in 1,4-dioxane (20 mL) and water (5 mL) was stirred for 2 h at 90° C. The reaction mixture was allowed to cool to RT and treated with 100 mL of water. The resulting solution was extracted with ethyl acetate (3×100 mL). The separated organic layers were combined, dried over Na$_2$SO$_4$ and concentrated under reduced pressure. The residue obtained was purified on silica gel with ethyl acetate/petroleum ether (0-10%) to give compound 20a as a light yellow oil. Mass Spectrum (LCMS, ESI pos.): Calcd. For $C_{16}H_{20}FNO_3$: 294.1 (M+H)$^+$; found: 294.0.

(B) (2'-Fluoro-5'-methoxy-3-methyl-2,3,4,5-tetrahydro-[1,1'-biphenyl]-4-yl)methanol, 20b

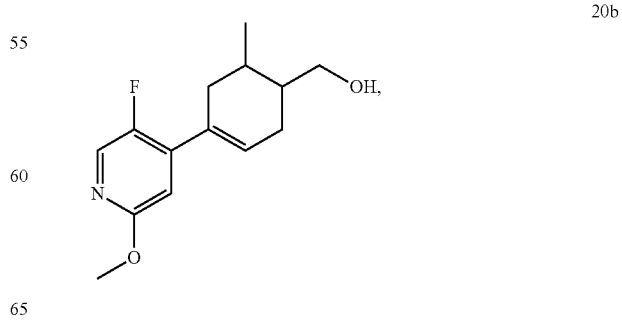

To a solution of compound 20a (1.0 g, 3.4 mmol) in THF (20 mL), LAH (260 mg, 6.8 mmol) was added at 0° C. The resulting solution was stirred for 30 min at 0° C. The reaction was then quenched by the addition of 2 g Na$_2$SO$_4$.10H$_2$O. The reaction mixture was filtered and the filtrate was concentrated. The residue obtained was purified on silica gel with ethyl acetate/petroleum ether (0-20%) to give compound 20b. Mass Spectrum (LCMS, ESI pos.): Calcd. For C$_{14}$H$_{18}$FNO$_2$: 252.1 (M+H)$^+$; found: 252.0.

(C) (4-(5-Fluoro-2-methoxypyridin-4-yl)-2-methyl-cyclohexyl)methanol, 20c

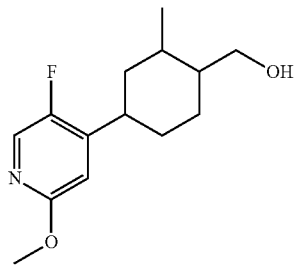

A mixture of (4-(5-fluoro-2-methoxypyridin-4-yl)-6-methylcyclohex-3-enyl)methanol, cpd 20b (600 mg, 2 mmol) and Pd/C (200 mg) in ethyl acetate (15 mL) and ethanol (15 mL) was stirred for 1 h at RT under a H$_2$ (3.5 atm) atmosphere. The solids were removed by filtration. The filtrate was concentrated under reduced pressure to give compound 20c. Mass Spectrum (LCMS, ESI pos.): Calcd. For C$_{14}$H$_{20}$FNO$_2$: 254.2 (M+H)$^+$; found: 254.2.

(D) (3S)-3-Cyclopropyl-3-(3-((4-(5-fluoro-2-methoxypyridin-4-yl)-2-methylcyclohexyl)methoxy)phenyl)propanoic acid, Cpd 33

Compound 33 was prepared from (S)-methyl 3-cyclopropyl-3-(3-hydroxyphenyl) propanoate and (4-(5-fluoro-2-methoxypyridin-4-yl)-2-methylcyclohexyl) methanol, 20c, according to the methods described in the Example 1, Steps D-E. $^1$H NMR (400 MHz, DMSO-d$_6$) δ (ppm): 8.02 (s, 1H), 7.16-7.21 (m, 1H), 6.75-6.85 (m, 4H), 4.04-4.10 (m, 2H), 3.80 (s, 3H), 2.81-2.91 (m, 1H), 2.62-2.66 (m, 2H), 2.22-2.27 (m, 1H), 2.08-2.11 (m, 2H), 1.91-1.93 (m, 1H), 1.40-1.56 (m, 5H), 0.95-1.01 (m, 4H), 0.47-0.50 (m, 1H), 0.21-0.33 (m, 2H), 0.09-0.14 (m, 1H). Mass Spectrum (LCMS, ESI pos.): Calcd. For C$_{26}$H$_{32}$FNO$_4$: 442.2 (M+H)$^+$; found: 442.2.

Example 21

(3S)-3-Cyclopropyl-3-(3-((4-(2-fluoro-5-methoxy-phenyl)-2-isobutylcyclohexyl) methoxy)phenyl) propanoic acid, Cpd 29

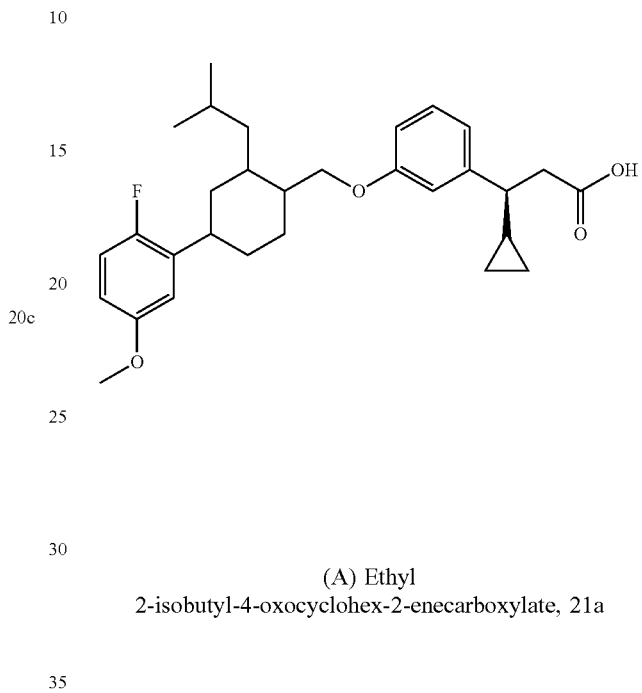

(A) Ethyl 2-isobutyl-4-oxocyclohex-2-enecarboxylate, 21a

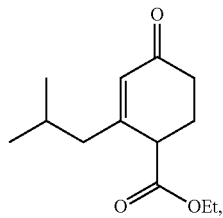

A solution of ethyl 5-methyl-3-oxohexanoate (5.00 g, 29.0 mmol), and sodium methylate (125 mg, 2.30 mmol) in methanol (10 mL) was treated with but-3-en-2-one (2.03 g, 29.0 mmol) drop-wise at 0° C. The resulting mixture was stirred for 1 h at RT and treated with HOAc (348 mg, 5.80 mmol), water (1 mL) and pyrrolidine (173 mg, 2.44 mmol). The resulting solution was stirred overnight at 80° C. The reaction mixture was allowed to cool to RT and treated with 20 mL of water. The resulting solution was extracted with ethyl acetate (3×40 mL). The separated organic layers were combined, dried over Na$_2$SO$_4$ and concentrated. The residue obtained was purified over silica gel with ethyl acetate: petroleum ether (15-50%) to give compound 21a as a brown oil. Mass Spectrum (LCMS, ESI pos.): Calcd. For C$_{13}$H$_{20}$O$_3$: 225.1 (M+H)$^+$; found: 225.1.

(B) Ethyl 2-isobutyl-4-oxocyclohexanecarboxylate, 21b

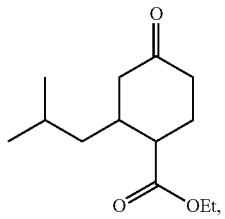

21b

A mixture of ethyl 2-isobutyl-4-oxocyclohex-2-enecarboxylate, cpd 21a (7.0 g, 31 mmol) and 10% Pd/C (332 mg), in ethanol (100 mL) was stirred overnight at RT under a hydrogen atmosphere (3.5 atm). The resulting mixture was filtered and the filtrate was concentrated to give compound 21b as a light brown oil. Mass Spectrum (LCMS, ESI pos.): Calcd. For $C_{13}H_{22}O_3$: 227.3 $(M+H)^+$; found: 227.0.

(C) (4-(2-Fluoro-5-methoxyphenyl)-2-isobutylcyclohexyl)methanol, 21c

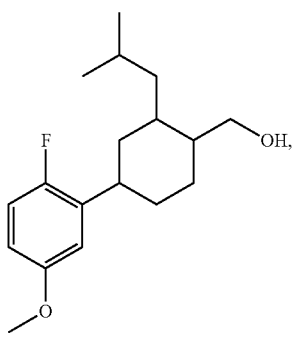

21c

Compound 21c was prepared from ethyl 2-isobutyl-4-oxocyclohexanecarboxylate, cpd 21b according to the methods described in Example 20, Steps A-C. Mass Spectrum (LCMS, ESI pos.): Calcd. For $C_{18}H_{27}FO_2$: 277.2 $[M-OH]^+$; found: 277.0.

(D) (3S)-3-Cyclopropyl-3-(3-((4-(2-fluoro-5-methoxyphenyl)-2-isobutylcyclohexyl) methoxy)phenyl)propanoic acid, Cpd 29

Compound 29 was prepared from (4-(2-fluoro-5-methoxyphenyl)-2-isobutylcyclohexyl)methanol 21c and (9-methyl 3-cyclopropyl-3-(3-hydroxyphenyl)propanoate according to the methods described in the Example 1, Steps D-E. $^1$H NMR (400 MHz, DMSO-$d_6$) δ (ppm): 12.0 (br m, 1H), 7.15-7.21 (m, 1H), 7.00-7.10 (m, 1H), 6.75-6.92 (m, 5H), 4.11-4.13 (m, 1H), 3.80-3.98 (m, 1H), 3.73 (s, 3H), 2.75-3.05 (m, 1H), 2.60-2.71 (m, 2H), 2.19-2.29 (m, 1H), 2.03-2.15 (m, 1H), 1.50-2.03 (m, 8H), 0.98-1.50 (m, 3H), 0.75-0.95 (m, 6H), 1.45-1.55 (m, 1H), 0.20-0.38 (m, 2H), 0.09-0.18 (m, 1H). Mass Spectrum (LCMS, ESI pos.): Calcd. For $C_{30}H_{39}FO_4$: 483.2 $[M+H]^+$; found: 483.3.

Example 22

(3S)-3-Cyclopropyl-3-(3-((4-(5-fluoro-2-methoxypyridin-4-yl)-2-isobutylcyclohexyl) methoxy)phenyl)propanoic acid, Cpd 30

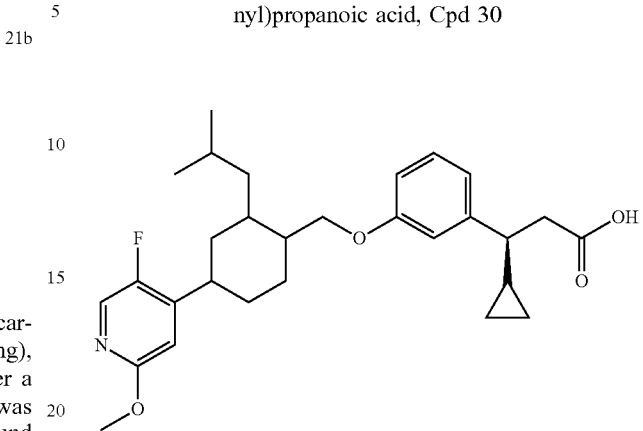

(A) (4-(5-Fluoro-2-methoxypyridin-4-yl)-2-isobutylcyclohexyl)methanol, 22a

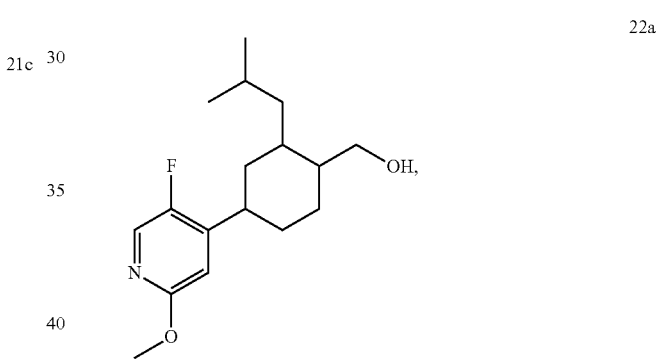

22a

Compound 22a was prepared from 5-fluoro-2-methoxypyridin-4-ylboronic acid and ethyl 2-isobutyl-4-oxocyclohex-2-enecarboxylate, cpd 21b, following the methods described in Example 20, Steps A-C. Mass Spectrum (LCMS, ESI pos.): Calcd. For $C_{17}H_{26}FNO_2$: 296.2 $[M+H]^+$; found: 296.2.

(B) (3S)-3-cyclopropyl-3-(3-((4-(5-fluoro-2-methoxypyridin-4-yl)-2-isobutylcyclohexyl) methoxy)phenyl)propanoic acid, Cpd 30

Compound 30 was prepared from (4-(5-fluoro-2-methoxypyridin-4-yl)-2-isobutylcyclohexyl)methanol, cpd 22a and (S)-methyl 3-cyclopropyl-3-(3-hydroxyphenyl)propanoate following the methods described in Example 1, Steps D-E. $^1$H NMR (400 MHz, DMSO-$d_6$) δ (ppm): 12.0 (brm, 1H), 8.04 (s, 1H), 7.15-7.25 (m, 1H), 6.75-6.86 (m, 4H), 4.10-4.16 (m, 1H), 3.95-4.02 (m, 1H), 3.81 (s, 3H), 2.80-3.05 (m, 1H), 2.62-2.70 (m, 2H), 2.20-2.29 (m, 1H), 2.02-2.19 (m, 1H), 1.80-1.92 (m, 1H), 1.28-1.78 (m, 7H), 0.98-1.28 (m, 3H), 1.75-1.95 (m, 6H), 0.45-0.52 (m, 1H), 0.20-0.37 (m, 2H), 0.05-0.15 (m, 1H). Mass Spectrum (LCMS, ESI pos.): Calcd. For $C_{29}H_{38}FNO_4$: 484.3 $[M+H]^+$; found: 484.2.

Example 23

3-(3-(((1s,4s)-4-(2-Fluoro-5-methoxyphenyl)cyclohexyl)methoxy)phenyl)hex-4-ynoic acid, Cpd 42

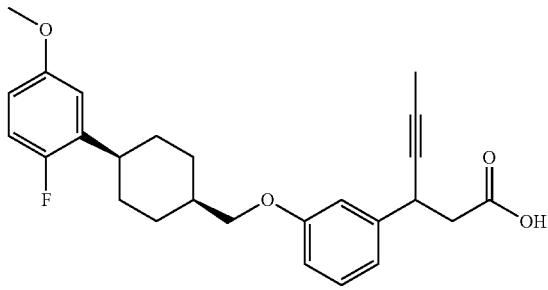 [SMILES: CC#CC(CC(=O)O)c1cccc(OC[C@H]2CC[C@@H](c3cc(OC)ccc3F)CC2)c1]

(A) 5-(3-Hydroxybenzylidene)-2,2-dimethyl-1,3-dioxane-4,6-dione, 23a

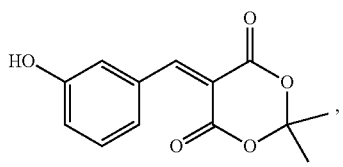

A mixture of 3-hydroxybenzaldehyde (30.0 g, 246 mmol) and 2,2-dimethyl-1,3-dioxane-4,6-dione (35.4 g, 246 mmol) in water (500 mL) was stirred for 2 h at 75° C. The resultant solids were collected by filtration and dried under reduced pressure to afford compound 23a. Mass Spectrum (LCMS, ESI pos.): Calcd. For $C_{13}H_{12}O_5$: 247.0 [M–H]$^+$; found: 247.1.

(B) 5-(1-(3-Hydroxyphenyl)but-2-yn-1-yl)-2,2-dimethyl-1,3-dioxane-4,6-dione, 23b

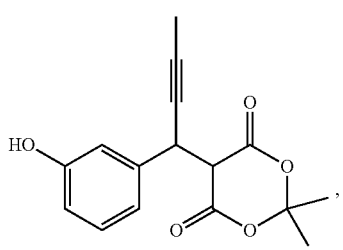

To a solution of prop-1-ynylmagnesium bromide (242 mL, 120 mmol, 0.5 M in THF), a solution of 5-(3-hydroxybenzylidene)-2,2-dimethyl-1,3-dioxane-4,6-dione, cpd 25a (10.0 g, 40.3 mmol) in THF (100 mL) was added drop-wise with stirring at 0° C. under $N_2$. The resulting solution was stirred for 2 h at RT. The reaction was then quenched by the addition of 100 mL of saturated, aq. $NH_4Cl$ and the pH value of the solution was adjusted to ~6 with 1 M HCl. The resulting solution was extracted with ethyl acetate (3×500 mL). The organic layers were combined, dried over anhydrous $Na_2SO_4$ and concentrated to give compound 23b. Mass Spectrum (LCMS, ESI pos.): Calcd. For $C_{16}H_{16}O_5$: 287.1 [M–H]$^+$; found: 287.1.

(C) 3-(3-Hydroxyphenyl)hex-4-ynoic acid, 23c

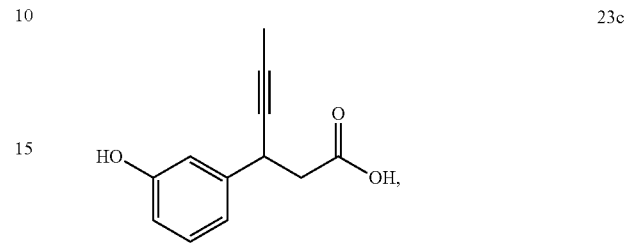

5-(1-(3-Hydroxyphenyl)but-2-ynyl)-2,2-dimethyl-1,3-dioxane-4,6-dione, cpd 23b (15 g, 38 mmol) in N,N-dimethylformamide (100 mL) and water (10 mL) was stirred overnight at 80° C. The reaction mixture was allowed to cool to RT, treated with 200 mL of water, and extracted with ethyl acetate (4×300 mL). The organic layers were combined, dried over anhydrous $Na_2SO_4$ and concentrated to give compound 23c. Mass Spectrum (LCMS, ESI pos.): Calcd. For $C_{12}H_{12}O_3$: 203.0 [M–H]$^+$; found: 203.1.

(D) Ethyl 3-(3-hydroxyphenyl)hex-4-ynoate, 23d

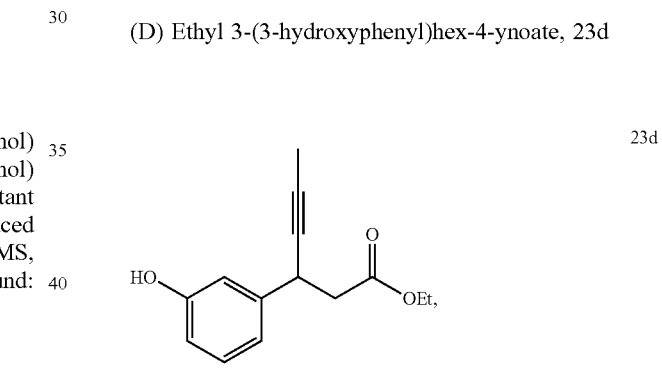

A solution of 3-(3-hydroxyphenyl)hex-4-ynoic acid, cpd 23c (10 g, 49 mmol) in ethanol (100 mL) and sulfuric acid (10 mL) was stirred overnight at 80° C. The reaction was allowed to cool to RT and then quenched by the addition of 200 mL of water. The resulting solution was extracted with ethyl acetate (4×300 mL). The organic layers were combined, dried over $Na_2SO_4$ and concentrated to give compound 23d. Mass Spectrum (LCMS, ESI pos.): Calcd. For $C_{14}H_{16}O_3$: 231.1 [M–H]$^+$; found: 231.1.

(E) 3-(3-(((1s,4s)-4-(2-fluoro-5-methoxyphenyl)cyclohexyl)methoxy)phenyl)hex-4-ynoic acid, Cpd 42

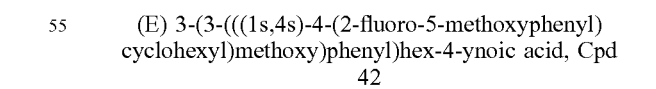

Compound 42 was prepared from 3-(3-hydroxyphenyl)hex-4-ynoate, cpd 23d (200 mg) and ((1s,4s)-4-(2-fluoro-5-methoxyphenyl)cyclohexyl)methanol, cpd 8a-2 (Example 8, Step A) following the methods described in Example 1, Steps D and E. $^1$H NMR (400 MHz, DMSO-d$_6$) δ (ppm): 12.26 (s, 1H), 7.19-7.28 (m, 1H), 7.00-7.09 (m, 1H), 6.82-6.98 (m, 4H), 6.70-6.79 (m, 1H), 4.09 (d, J=7.2 Hz, 2H), 3.91-3.99 (m, 1H), 3.73 (s, 3H), 2.80-2.85 (m, 1H), 2.61-2.70 (m, 2H), 2.15-2.20 (m, 1H), 1.82-1.91 (m, 2H), 1.79 (s, 3H), 1.50-1.73 (m, 6H). Mass Spectrum (LCMS, ESI pos.): Calcd. For $C_{26}H_{29}FO_4$: 425.5 [M+H]$^+$; found: 425.1.

Example 24

3-Ethoxy-3-(3-(((1s,4s)-4-(2-fluoro-5-methoxyphenyl)cyclohexyl) methoxy)phenyl) propanoic acid, trifluoroacetic acid salt Cpd 50

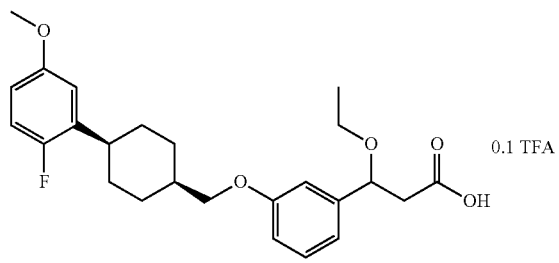 [SMILES: CCOC(CC(=O)O)c1cccc(OC[C@H]2CC[C@@H](c3cc(OC)ccc3F)CC2)c1]

(A) Ethyl 3-ethoxy-3-(3-hydroxyphenyl)propanoate, 24a

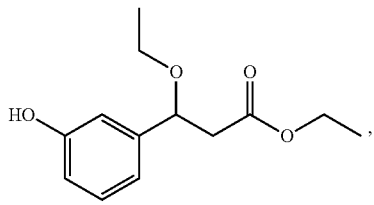

A mixture of (E)-ethyl 3-ethoxyacrylate (0.600 mL, 4.00 mmol), 3-hydroxyphenyl boronic acid (1.70 g, 12.0 mmol), Rh(COD)Cl$_2$ (102 mg, 0.207 mmol) and potassium hydroxide (234 mg, 4.17 mmol) in 1,4-dioxane (5 mL) and water (0.5 mL) was stirred for 2 h under a nitrogen atmosphere at 50° C. in a sealed tube. The reaction mixture was allowed to cool to RT and poured into 50 mL of saturated aq. NH$_4$Cl, followed by extraction with ethyl acetate (3×50 mL). The organic layers were combined, dried over Na$_2$SO$_4$ and concentrated. The residue obtained was purified on silica gel with ethyl acetate/petroleum ether (0-10%) to give compound 24a. Mass Spectrum (LCMS, ESI pos.): Calcd. For $C_{13}H_{18}O_4$: 237.1 [M–H]$^+$; found: 237.1.

(B) 3-Ethoxy-3-(3-(((1s,4s)-4-(2-fluoro-5-methoxyphenyl)cyclohexyl) methoxy)phenyl) propanoic acid, Cpd 50

Compound 50 was prepared from ((1s,4s)-4-(2-fluoro-5-methoxyphenyl)cyclohexyl) methanol, 8a-2 and ethyl 3-ethoxy-3-(3-hydroxy phenyl)propanoate 24a following the methods described in Example 1, Steps D and E. $^1$H NMR (400 MHz, DMSO-d$_6$) δ (ppm): 7.25-7.29 (m, 1H), 7.02-7.06 (m, 1H), 6.89-6.93 (m, 4H), 6.74-6.77 (m, 1H), 4.62-4.66 (m, 1H), 4.09 (t, J=7.6 Hz, 2H), 3.72 (s, 3H), 3.28-3.31 (m, 2H), 2.81-2.88 (m, 1H), 2.55-2.60 (m, 2H), 2.12-2.18 (m, 1H), 1.87-1.89 (m, 2H), 1.58-1.71 (m, 6H), 1.06 (t, J=6.8 Hz, 3H). Mass Spectrum (LCMS, ESI pos.): Calcd. For $C_{25}H_{31}FO_5$: 453.2 [M+Na]$^+$; found: 453.1.

Example 25

(S)-3-Cyclopropyl-3-(2-(((1r,4S)-4-(5-fluoro-2-methoxypyridin-4-yl)-4-methoxy cyclohexyl)methoxy)pyridin-4-yl)propanoic acid, Cpd 45 and (S)-3-cyclopropyl-3-(2-(((1s,4R)-4-(5-fluoro-2-methoxypyridin-4-yl)-4-methoxycyclohexyl)methoxy)pyridin-4-yl) propanoic acid, Cpd 44

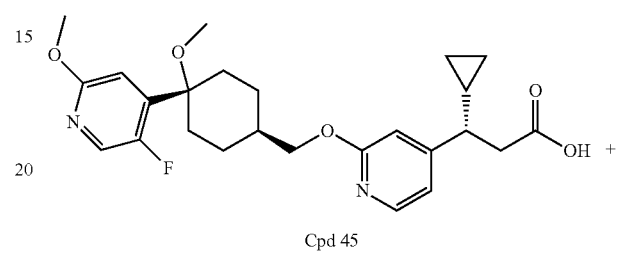

Cpd 45

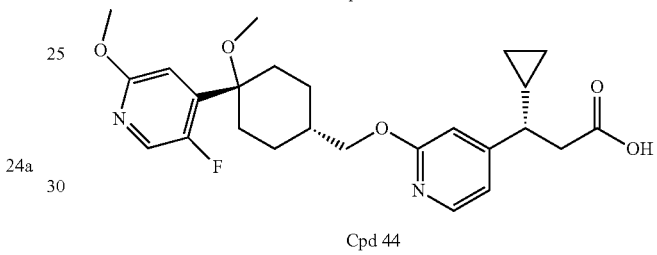

Cpd 44

(A) Ethyl 4-(5-fluoro-2-methoxypyridin-4-yl)-4-hydroxycyclohexanecarboxylate, 25a

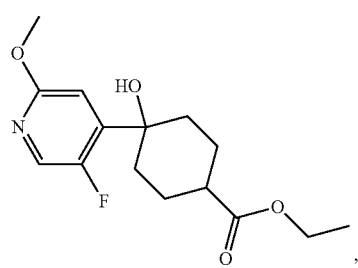

A solution of 4-bromo-5-fluoro-2-methoxypyridine (1.0 g, 4.8 mmol) in THF (15 mL) was cooled to −78° C. and n-butyllithium (2.2 mL, 5.5 mmol, 2.5 M in THF) was added drop-wise. The resulting mixture was stirred at −78° C. for 10 min and a solution of ethyl 4-oxocyclohexanecarboxylate (1.2 g, 7.3 mmol) in THF (5 mL) was added drop-wise with stirring. The resulting solution was stirred for 2 h at −78° C., poured into 100 mL of saturated, aq. NH$_4$Cl and extracted with ethyl acetate (3×100 mL). The separated organic layers were combined, dried over Na$_2$SO$_4$ and concentrated. The residue obtained was purified on silica gel with ethyl acetate/petroleum ether (0-20%) to give compound 25a. Mass Spectrum (LCMS, ESI pos.): Calcd. For $C_{15}H_{20}FNO_4$: 298.1 [M+H]$^+$; found: 297.9.

(B) Ethyl 4-(5-fluoro-2-methoxypyridin-4-yl)-4-methoxycyclohexanecarboxylate, 25b

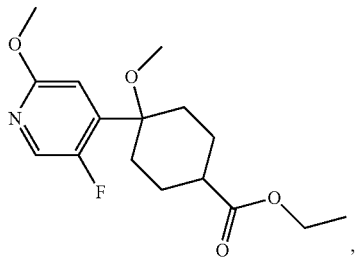

25b

To a solution of ethyl 4-(5-fluoro-2-methoxypyridin-4-yl)-4-hydroxycyclohexanecarboxylate, cpd 25a (500 mg, 1.7 mmol) in N,N-dimethylformamide (10 mL), 60% sodium hydride (80 mg, 2.0 mmol) was added. The resulting mixture was stirred for 10 min at 0° C. and treated with iodomethane (480 mg, 3.4 mmol). The resulting mixture was stirred for 2 h at 0° C. and poured into 100 mL of saturated aq. $NH_4C_1$. The resulting solution was extracted with ethyl acetate (3×100 mL). The separated organic layers were combined, dried over $Na_2SO_4$ and concentrated. The residue obtained was purified on silica gel with ethyl acetate/petroleum ether (0-20%) to give compound 25b. Mass Spectrum (LCMS, ESI pos.): Calcd. For $C_{16}H_{22}FNO_4$: 312.1 $[M+H]^+$; found: 312.1.

(C) (4-(5-Fluoro-2-methoxypyridin-4-yl)-4-methoxycyclohexyl)methanol, 25c

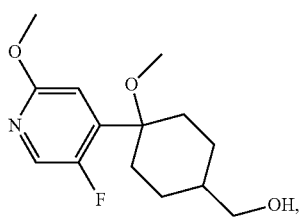

25c

To a solution of ethyl 4-(5-fluoro-2-methoxypyridin-4-yl)-4-methoxycyclohexanecarboxylate, cpd 25b (400 mg, 1.3 mmol) in THF (10 mL), diisobutylaluminium hydride (4 mL, 4 mmol, 1 M in hexane) was added drop-wise with stirring at −30° C. The resulting solution was stirred for 1 h at room temperature. The reaction was then quenched by the addition of saturated aq. seignette salt solution (50 mL). The resulting mixture was extracted with ethyl acetate (3×50 mL). The separated organic layers were combined, dried over $Na_2SO_4$ and concentrated. The residue obtained was purified on silica gel with ethyl acetate/petroleum ether (0-40%) to give compound 25c. Mass Spectrum (LCMS, ESI pos.): Calcd. For $C_{14}H_{20}FNO_3$: 270.1 $[M+H]^+$; found: 269.9.

(D) (S)-3-Cyclopropyl-3-(2-(((1r,4S)-4-(5-fluoro-2-methoxypyridin-4-yl)-4-methoxy cyclohexyl)methoxy)pyridin-4-yl)propanoic acid (Cpd 45) and (S)-3-cyclopropyl-3-(2-(((1s,4R)-4-(5-fluoro-2-methoxypyridin-4-yl)-4-methoxycyclohexyl)methoxy)pyridin-4-yl)propanoic acid (Cpd 44)

Compounds 45 and 44 were prepared from (4-(5-fluoro-2-methoxypyridin-4-yl)-4-methoxycyclohexyl)methanol, cpd 25c, and (S)-ethyl 3-cyclopropyl-3-(2-fluoropyridin-4-yl)propanoate, cpd 26d (Example 26, Step D), following the methods described in the Example 1, Steps D and E.

Cpd 45: $^1$H NMR (400 MHz, DMSO-d$_6$) δ (ppm): 8.09-8.10 (m, 1H), 8.02-8.03 (m, 1H), 6.92-6.93 (m, 1H), 6.79-6.80 (m, 1H), 6.72 (s, 1H), 4.19 (d, J=7.2 Hz, 2H), 3.84 (s, 3H), 2.98 (s, 3H), 2.69 (d, J=7.6 Hz, 2H), 2.21-2.23 (m, 3H), 2.01-2.09 (m, 1H), 1.83-1.89 (m, 2H), 1.74-1.77 (m, 2H), 1.33-1.34 (m, 2H), 0.97-1.01 (m, 1H), 0.51-0.52 (m, 1H), 0.22-0.31 (m, 2H), 0.11-0.19 (m, 1H). Mass Spectrum (LCMS, ESI pos.): Calcd. For $C_{25}H_{31}FN_2O_5$: 459.2 $[M+H]^+$; found: 459.1.

Cpd 44: $^1$H NMR (400 MHz, DMSO-d$_6$) δ (ppm): 8.05-8.07 (m, 2H), 6.94-6.95 (m, 1H), 6.73-6.77 (m, 2H), 4.10 (d, J=6.4 Hz, 2H), 3.83 (s, 3H), 3.01 (s, 3H), 2.70 (d, J=7.6 Hz, 2H), 2.21-2.27 (m, 1H), 2.12-2.15 (m, 2H), 1.67-1.84 (m, 5H), 1.41-1.51 (m, 2H), 0.99-1.02 (m, 1H), 0.49-0.54 (m, 1H), 0.26-0.36 (m, 2H), 0.16-0.20 (m, 1H). Mass Spectrum (LCMS, ESI pos.): Calcd. For $C_{25}H_{31}FN_2O_5$: 459.2 $[M+H]^+$; found: 459.2.

Example 26

(S)-3-Cyclopropyl-3-(2-((4-(6-methoxypyrazin-2-yl)cyclohexyl)methoxy)pyridin-4-yl)propanoic acid, Cpd 46

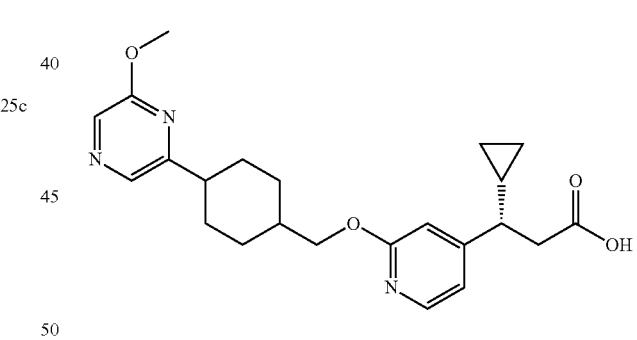

(A) Ethyl 4-(4,4,5,5-tetramethyl-1,3,2-dioxaborolan-2-yl)cyclohex-3-enecarboxylate, 26a

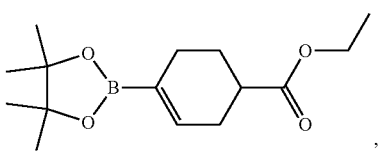

26a

A mixture of ethyl 4-(trifluoromethylsulfonyloxy)cyclohex-3-enecarboxylate, 29a (17 g, 56 mmol, Example 29, Step A), bis(pinacolato)diboron (21 g, 84 mmol), KOAc (16 g, 168 mmol) and Pd(dppf)Cl$_2$·CH$_2$Cl$_2$ (4.6 g, 5.6 mmol) in DMSO (100 mL) was stirred overnight at 80° C. The reaction mixture was allowed to cool to RT, treated with 100 mL of saturated, aq. NH$_4$Cl and extracted with ethyl acetate (3×300 mL). The combined organic layers were dried over Na$_2$SO$_4$ and concentrated. The residue obtained was purified on silica gel with ethyl acetate/petroleum ether (0-15%) to give compound 26a. Mass Spectrum (LCMS, ESI pos.): Calcd. For C$_{15}$H$_{25}$BO$_4$: 281.1 [M+H]$^+$; found: 281.0.

(B) Ethyl 4-(6-methoxypyrazin-2-yl)cyclohex-3-enecarboxylate, 26b

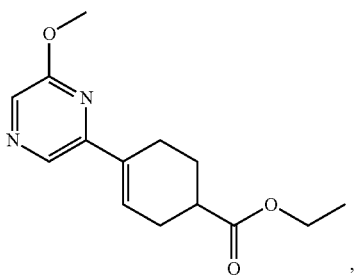

26b

A mixture of 2-bromo-6-methoxypyrazine (500 mg, 2.645 mmol), ethyl 4-(4,4,5,5-tetramethyl-1,3,2-dioxaborolan-2-yl)cyclohex-3-enecarboxylate, cpd 26a (1.48 g, 5.28 mmol), 1,1'-bis(diphenylphosphino)ferrocenepalladiumdichloride (107 mg, 0.131 mmol), cesium carbonate (2.15 g, 6.599 mmol) in 1,4-dioxane (6 mL) and water (1.5 mL) was stirred for 1 h at 80° C. The reaction mixture was allowed to cool to RT and treated with 10 mL of water. The resulting solution was extracted with ethyl acetate (3×10 mL). The organic layers were combined, dried over Na$_2$SO$_4$ and concentrated. The residue obtained was purified on silica gel with ethyl acetate/petroleum ether (0-20%) to give compound 26b. Mass Spectrum (LCMS, ESI pos.): Calcd. For C$_{14}$H$_{18}$N$_2$O$_3$: 263.1 [M+H]$^+$; found: 262.9.

(C) (4-(6-Methoxypyrazin-2-yl)cyclohexyl)methanol, 26c

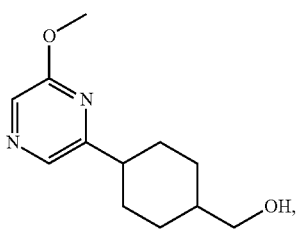

26c

Compound 26c was prepared from (ethyl 4-(6-methoxypyrazin-2-yl)cyclohex-3-enecarboxylate, 26b following the methods described in Example 20, Steps B and C. Mass Spectrum (LCMS, ESI pos.): Calcd. For C$_{12}$H$_{18}$N$_2$O$_2$: 223.1 [M+H]$^+$; found: 222.9.

(D) (S)-ethyl 3-cyclopropyl-3-(2-fluoropyridin-4-yl)propanoate, 26d

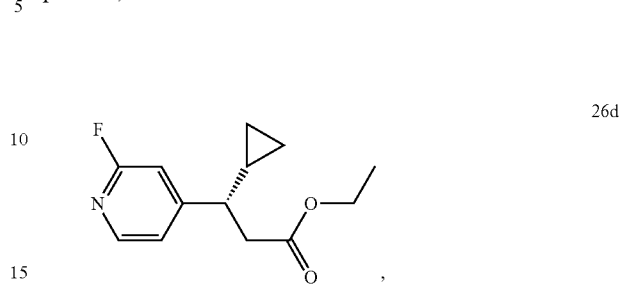

26d

Ethyl 3-cyclopropyl-3-(2-fluoropyridin-4-yl)propanoate, cpd 7a, was subjected preparative-HPLC on a Phenomenex™ Lux 5u Cellulose-45×25 cm, 5 um column using hexane (0.1% IPA): IPA=90:10 to give (S)-ethyl 3-cyclopropyl-3-(2-fluoropyridin-4-yl)propanoate, cpd 26d (retention time 10.8 min), and (R)-ethyl 3-cyclopropyl-3-(2-fluoropyridin-4-yl)propanoate (retention time 13.8 min).

(E) (S)-3-Cyclopropyl-3-(2-((4-(6-methoxypyrazin-2-yl)cyclohexyl)methoxy)pyridin-4-yl)propanoic acid, Cpd 46

Compound 46 was prepared from ((4-(6-methoxypyrazin-2-yl)cyclohexyl)methanol, cpd 26c and (S)-ethyl 3-cyclopropyl-3-(2-fluoropyridin-4-yl)propanoate, cpd 26d following the methods described in Example 3, Steps E and F. $^1$H NMR (400 MHz, DMSO-d$_6$) δ (ppm): 7.85-8.14 (m, 3H), 6.91-6.93 (m, 1H), 6.73-6.74 (m, 1H), 4.13 (dd, J=21.6, 6.6 Hz, 1H), 4.00 (d, J=6.3 Hz, 1H), 3.90 (d, J=4.2 Hz, 3H), 2.77-2.88 (m, 1H), 2.39-2.70 (m, 3H), 2.20-2.37 (m, 1H), 1.87-2.13 (m, 3H), 1.60-1.90 (m, 4H), 1.16-1.31 (m, 1H), 0.90-1.15 (m, 1H), 0.43-0.56 (m, 1H), 0.38-0.39 (m, 2H), 0.05-0.15 (m, 1H). Mass Spectrum (LCMS, ESI pos.): Calcd. For C$_{23}$H$_{29}$N$_3$O$_4$: 412.2 [M+H]$^+$; found: 412.1.

Example 27

(S)-3-Cyclopropyl-3-(2-((4-(4-methoxypyrimidin-2-yl)cyclohexyl)methoxy)pyridin-4-yl)propanoic acid, Cpd 49

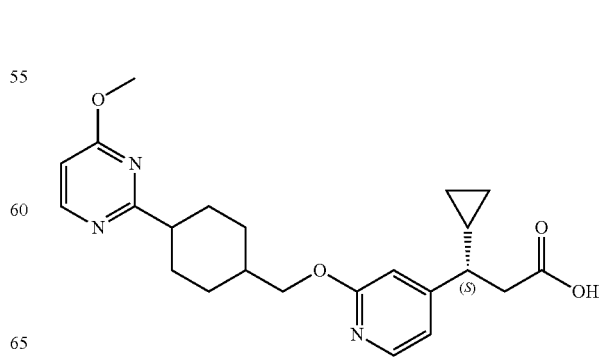

133

(A) (4-(4-Methoxypyrimidin-2-yl)cyclohexyl)methanol, 27a

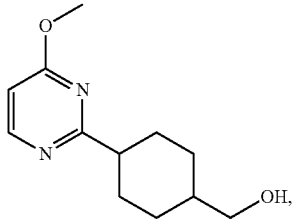

Compound 27a was prepared from 2-bromo-4-methoxypyrimidine and ethyl 4-(4,4,5,5-tetramethyl-1,3,2-dioxaborolan-2-yl)cyclohex-3-enecarboxylate, cpd 26a, according to the methods described in the Example 26, Steps B-C. Mass Spectrum (LCMS, ESI pos.): Calcd. For $C_{12}H_{18}N_2O_2$: 223.1 $[M+H]^+$; found: 223.1.

(B) (S)-3-cyclopropyl-3-(2-((4-(4-methoxypyrimidin-2-yl)cyclohexyl)methoxy)pyridin-4-yl)propanoic acid, Cpd 49

Compound 49 was prepared from (4-(4-methoxypyrimidin-2-yl)cyclohexyl)methanol, cpd 27a and (S)-ethyl 3-cyclopropyl-3-(2-fluoropyridin-4-yl)propanoate, cpd 26d following the methods described in the Example 3, Steps E and F. $^1$H NMR (400 MHz, $CD_3OD$) δ (ppm): 7.85-8.14 (m, 3H), 6.91-6.93 (m, 1H), 6.73-6.74 (m, 1H), 4.13 (dd, J=21.6, 6.6 Hz, 1H), 4.00 (d, J=6.3 Hz, 1H), 3.90 (d, J=4.2 Hz, 3H), 2.77-2.88 (m, 1H), 2.39-2.70 (m, 3H), 2.20-2.37 (m, 1H), 1.87-2.13 (m, 3H), 1.60-1.90 (m, 4H), 1.16-1.31 (m, 1H), 0.90-1.15 (m, 1H), 0.43-0.56 (m, 1H), 0.38-0.39 (m, 2H), 0.05-0.15 (m, 1H). Mass Spectrum (LCMS, ESI pos.): Calcd. For $C_{23}H_{29}N_3O_4$: 412.2 $[M+H]^+$; found: 412.1.

Example 28

(S)-3-Cyclopropyl-3-(3-(((1r,4 S)-4-(2-fluoro-5-methoxyphenyl)cyclohexyl) methoxy)phenyl) propanoic acid, Cpd 2

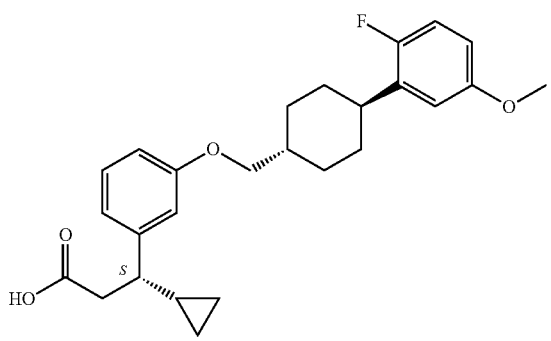

(A) Ethyl 4-(perfluorobutylsulfonyloxy)cyclohex-3-enecarboxylate, 28a

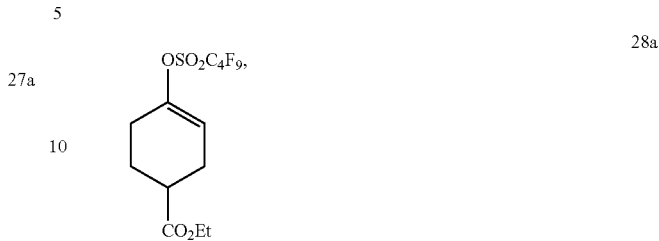

To a solution of ethyl 4-oxocyclohexanecarboxylate (615.0 g, 3.613 mol) in THF (1.2 L) at 15° C. under the atmosphere of nitrogen was added 1,1,2,2,3,3,4,4,4-nonafluorobutane-1-sulfonyl fluoride (1256 g, 4.158 mol), followed by addition of THF (1.3 L), a solution of DBU (617.0 g, 4.158 mol) in THF (1.25 L), and THF (1.25 L), sequentially. The reaction was kept at an internal temperature of 25° C. with mild heating overnight. Ice water (2.0 L) was added, followed by addition of water (3.0 L), sodium chloride (150 g) and ethyl acetate (5 L). The resulting mixture was stirred for 30 min. The organic layer was separated and washed with aqueous 4% NaCl (5.0 L). The organic layer was separated and dried over $Na_2SO_4$ (100 g), filtered, and concentrated under reduced pressure to give compound 28a which was used directly in the next step without further purification. $^1$H NMR (400 MHz, $CDCl_3$) δ (ppm): 5.81 (t, J=3.1 Hz, 1H), 4.18 (q, J=7.1 Hz, 2H), 2.62 (m, 1H), 2.45 (m, 4H), 2.16 (m, 1H), 2.11-1.87 (m, 1H), 1.28 (t, J=7.1 Hz, 3H).

(B) Ethyl 4-(2-fluoro-5-methoxyphenyl)cyclohex-3-enecarboxylate, 28b

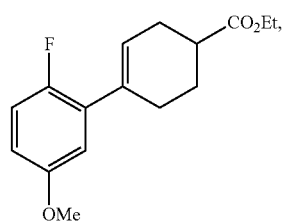

To a mixture of (2-fluoro-5-methoxyphenyl)boronic acid (200.0 g, 1.173 mol) in 1,4-dioxane (1.0 L) at 20° C., was added $K_3PO_4$ (918.6 g, 4.327 mol), followed by dioxane (4.0 L) and water (233.8 g, 13.0 mol) and the flask was evacuated and backfilled with nitrogen gas. Crude ethyl 4-(perfluorobutylsulfonyloxy)cyclohex-3-enecarboxylate, 28a (731.2 g, 1.620 mol) and 1,4-dioxane (1.0 L) were added. The flask was evacuated and backfilled with nitrogen gas. Pd(dppf)$Cl_2 \cdot CH_2Cl_2$ (72.0 g, 0.087 mol) was added, the flask was evacuated, and backfilled with nitrogen gas. The reaction was heated to 60° C. for 4 h under an inert atmosphere of nitrogen, after which time the reaction was judged completed by LCMS. The resulting solution was cooled to 25° C. and filtered. The filter cake was washed with ethyl acetate (1.0 L). To the filtrate was added ethyl acetate (4.0 L) and water (5.0 L) and the mixture was stirred for 30 min. The organic layer was separated, washed with water (5.0 L), dried over Na$_2$SO$_4$ and concentrated in vacuo. The residue was dissolved in ethyl acetate (5.0 L), petroleum ether (15.0 L) was added and stirred for 30 min. The precipitate was removed by filtration and washed with a mixture of petroleum ether and ethyl acetate (1.0 L, V:V=5:1). The filtrate was concentrated under reduced pressure to afford compound 28b. $^1$H NMR (400 MHz, CDCl$_3$) δ(ppm): 6.93 (t, J=3.1 Hz, 1H), 6.72 (m, 2H), 5.94 (m, 1H), 4.17 (q, J=7.1 Hz, 2H), 3.78 (s, 3H), 2.64 (m, 1H), 2.45 (m, 4H), 2.16 (m, 1H), 1.87 (m, 1H), 1.24 (t, J=7.1 Hz, 3H).

(C) (4-(2-Fluoro-5-methoxyphenyl)cyclohex-3-enyl) methanol, 28c

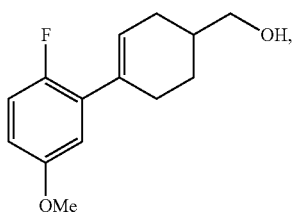

To a suspension of LiAlH$_4$ (55.1 g, 1.452 mol) in anhydrous THF (5.0 L), under a nitrogen atmosphere, cooled to 0-10° C. was added a solution of ethyl 4-(2-fluoro-5-methoxyphenyl)cyclohex-3-enecarboxylate, 28b (250. g, 0.899 mol) in anhydrous THF (2.5 L) over a period of 60 min. The reaction mixture was stirred at 0-10° C. for 2 h, after which time the reaction was judged complete by LCMS. The reaction was quenched by successive addition of water (55.1 mL), aqueous NaOH (15%, 55.1 mL) and water (165 mL) and the mixture was stirred for 30 min. The precipitate was removed by filtration and the organic phase was concentrated under reduced pressure. The residue obtained was purified by silica gel chromatography using a mixture of heptane and ethyl acetate (10:1 to 5:1 to 3:1) to give compound 28c. $^1$H NMR (300 MHz, acetone-d$_6$) δ (ppm): 6.95 (m, 1H), 6.75 (m, 2H), 5.90 (m, 1H), 3.74 (m, 3H), 3.65-3.38 (m, 3H), 2.52-2.15 (m, 3H), 2.00-1.67 (m, 3H), 1.47-1.22 (m, 1H).

(D) ((1r,4r)-4-(2-Fluoro-5-methoxyphenyl)cyclohexyl)methanol, 28d

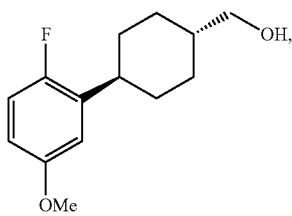

To a solution of compound 4-(2-fluoro-5-methoxyphenyl)cyclohex-3-enyl)methanol, 28c (50.0 g, 0.212 mol) in DCM (1.0 L), was added Ir(COD)(Py)(PCy$_3$)PF$_6$ (5.12 g, 6.36 mmol). The reaction was purged with hydrogen gas (3×) followed by pressurization under a hydrogen gas atmosphere (40 atm) and heating to 30° C. The reaction was judged complete (LCMS) after 5 h. The mixture was concentrated under reduced pressure. The residue was dissolved in THF (100 mL) and heated to 40° C. to give a clear solution. The solution was gradually cooled to 15° C., heptane (30 mL) was added and stirred for 2 h. A white solid precipitated from the mixture, then another portion of heptane (500 mL) was added over 30 min and the slurry was stirred for an additional 2 h. The mixture was cooled to 0-5° C. before it was filtered, washed with heptane (50 mL), dried under reduced pressure, to give compound 28d (trans:cis>99:1, purity 99.2% by HPLC) as a yellow solid. $^1$H NMR (400 MHz, CDCl$_3$) δ(ppm): 6.94 (m, 1H), 6.77 (m, 1H), 6.68 (m, 1H), 3.80 (s, 3H), 3.54 (m, 2H), 2.83 (m, 1H), 2.01-1.90 (m, 4H), 1.68-1.47 (m, 3H), 1.25-1.10 (m, 2H). Mass Spectrum (LCMS, ESI pos.): Calcd. For C$_{14}$H$_{19}$FO$_2$: 239.1 [M−H]$^+$; found: 239.4.

(E) (S)-methyl 3-cyclopropyl-3-(3-(((1r,4S)-4-(2-fluoro-5-methoxyphenyl)cyclohexyl) methoxy)phenyl)propanoate, 28e

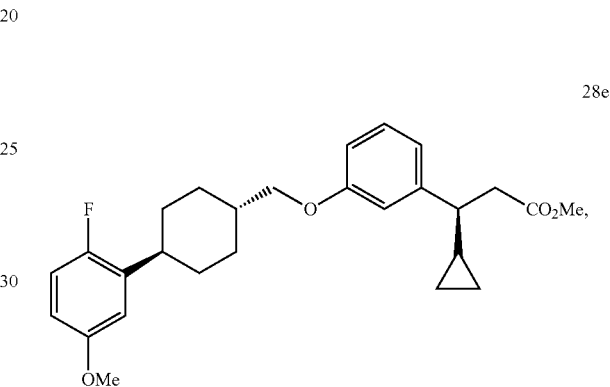

To a solution of ((1r,4,r)-4-(2-fluoro-5-methoxyphenyl)cyclohexyl)methanol, 28d (200.0 g, 0.840 mol) and (S)-methyl 3-cyclopropyl-3-(3-hydroxyphenyl)propanoate (203.0 g, 0.924 mol) in acetonitrile (1.5 L) was added tributylphosphine (255.0 g, 1.260 mol) under a nitrogen atmosphere. The solution was warmed to 80° C. and a solution of diethyl diazene-1,2-dicarboxylate (219.0 g, 1.260 mol) in acetonitrile (0.5 L) was added drop-wise over 1.5 h. The solution was stirred for 1 h and judged complete by LCMS. The mixture was concentrated to about 1.0 L under reduced pressure and ethyl acetate (3.0 L) was added. The organic layer was washed with saturated NaCl (3.0 L) and concentrated under reduced pressure. The residue was purified by chromatography on silica gel with heptane:ethyl acetate (20:1) to give compound 28e. $^1$H NMR (300 MHz, CDCl$_3$) δ (ppm); 7.26 (m, 1H), 6.96 (m, 1H), 6.83 (m, 4H), 6.70 (m, 1H), 3.86 (m, 1H), 3.83 (s, 3H), 3.65 (s, 3H), 2.88 (m, 1H), 2.78 (m, 2H), 2.37 (m, 1H), 2.04 (m, 5H), 1.59 (m, 2H), 1.45 (m, 1H), 1.30 (m, 3H), 0.99 (m, 3H), 0.59 (m, 1H), 0.47 (m, 1H), 0.29 (m, 1H), 0.19 (m, 1H). Mass Spectrum (LCMS, ESI pos.): Calcd. For C$_{27}$H$_{33}$FO$_4$: 441.2 [M−H]$^+$; found: 441.3.

(F) (S)-3-cyclopropyl-3-(3-(((1r,4S)-4-(2-fluoro-5-methoxyphenyl)cyclohexyl) methoxy)phenyl)propanoic acid, Cpd 2

To a solution of (S)-methyl 3-cyclopropyl-3-(3-(((1r,4S)-4-(2-fluoro-5-methoxyphenyl)cyclohexyl) methoxy)phenyl) propanoate, 28e (570.0 g, 1.295 mol) in THF (2.85 L) and methanol (2.85 L) was added a solution of NaOH (259.1 g, 6.478 mol) in water (2.85 L) at 20° C. over 30 min. The reaction mixture was stirred at 30° C. overnight. The mixture was cooled to 20° C. and the pH of the solution was adjusted to 4-5 with 4 N aq. HCl. Ethyl acetate (8.5 L) was added and the resulting mixture was stirred for 20 min. The separated organic layer was washed with 5% NaCl (5.7 L), dried over $Na_2SO_4$ and concentrated to about 2.8 L. Heptane (5.7 L) was then added and the resulting mixture was concentrated to about 5.7 L. This procedure was repeated twice. Heptane (2.85 L) was then added and the solution was cooled to 10-20° C. with stirring. The precipitate formed was collected by filtration, washed with heptane (2.0 L) and dried under reduced pressure to a constant weight to give compound 2. $^1$H NMR (400 MHz, $CDCl_3$): δ(ppm): 10.2 (brs, 1H), 7.25 (m, 1H), 6.94 (m, 1H), 6.82 (m, 4H), 6.68 (m, 1H), 3.82 (m, 2H), 3.80 (s, 3H), 2.85 (m, 3H), 2.37 (m, 1H), 2.05 (m, 2H), 1.99 (m, 2H), 1.96 (m, 1H), 1.54 (m, 2H), 1.31 (m, 2H), 1.06 (m, 1H), 0.61 (m, 1H), 0.47 (m, 1H), 0.33 (m, 1H), 0.21 (m, 1H). Mass Spectrum (LCMS, ESI neg.): Calcd. For $C_{26}H_{31}FO_4$: 425.3 [M–H]$^+$; found: 425.3.

Example 29

(S)-3-Cyclopropyl-3-(3-(((1s,4R)-4-(2-fluoro-5-methoxyphenyl)cyclohexyl) methoxy)phenyl) propanoic acid, Cpd 1

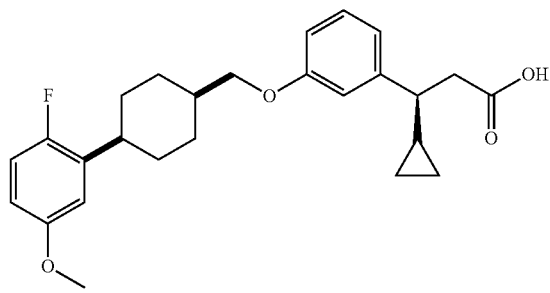

(A) Ethyl 4-(((trifluoromethyl)sulfonyl)oxy)cyclohex-3-enecarboxylate, 29a

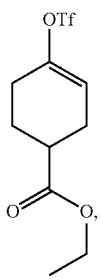

29a

To a solution of ethyl 4-oxocyclohexanecarboxylate (10.0 g, 58.7 mmol) in THF (50 mL), LiHMDS (61.7 mL, 61.7 mmol, 1 M in THF) was added drop-wise with stirring at −78° C. and the resulting solution was stirred for 1 h under a nitrogen atmosphere. At that time, trifluoro-N-phenyl-N-(trifluoromethylsulfonyl) methanesulfonamide (21.2 g, 59.3 mmol) in THF (50 mL) was added drop-wise. The resulting solution was stirred for 30 min at −78° C. and then at RT for 2 h. The reaction was then quenched by the addition of 150 mL of saturated $NH_4Cl$ solution. The resulting mixture was extracted with ethyl acetate (3×100 mL) and the organic layers were combined, dried over $Na_2SO_4$ and concentrated. The residue obtained was purified on silica gel with ethyl acetate/petroleum ether (0-5%) to give compound 29a, which was used without further purification.

(B) Ethyl 2'-fluoro-5'-methoxy-2,3,4,5-tetrahydro-[1,1'-biphenyl]-4-carboxylate, 29b

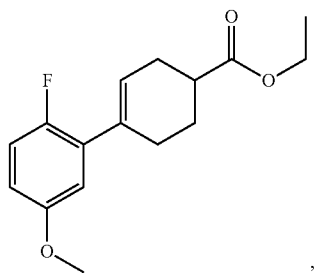

29b

A mixture of ethyl 4-(trifluoromethylsulfonyloxy)cyclohex-3-enecarboxylate, cpd 29a (7.5 g, 25 mmol), 2-fluoro-5-methoxyphenylboronic acid (6.3 g, 37 mmol), Pd(dppf) $Cl_2 \cdot CH_2Cl_2$ (1.0 g, 1.2 mmol) and $Cs_2CO_3$ (16 g, 50 mmol) in dioxane (80 mL) and water (20 mL) was stirred for 2 h at 80° C. under a nitrogen atmosphere. The reaction mixture was allowed to cool to RT and treated with 200 mL of water. The resulting solution was extracted with ethyl acetate (3×150 mL). The organic layers were combined, dried over $Na_2SO_4$ and concentrated. The residue obtained was purified on silica gel with ethyl acetate/petroleum ether (0-5%) to give compound 29b. Mass Spectrum (LCMS, ESI pos.): Calcd. For $C_{16}H_{19}FO_3$: 279.1 [M+H]$^+$; found: 279.2.

(C) (2'-Fluoro-5'-methoxy-2,3,4,5-tetrahydro-[1,1'-biphenyl]-4-yl)methanol, 29c

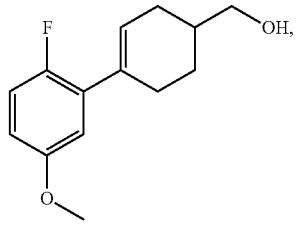

29c

To a solution of ethyl 4-(2-fluoro-5-methoxyphenyl)cyclohex-3-enecarboxylate, cpd 29b (5.5 g, 20 mmol) in THF (100 mL), $LiAlH_4$ (1.1 g, 29 mmol) was added in portions at 0° C. The resulting solution was stirred for 20 min at 0° C. The reaction was then quenched by the addition of 300 mL of saturated aq. potassium sodium tartrate solution and stirred for 30 min. The resulting solution was extracted with ethyl acetate (3×200 mL). The organic layers were combined, dried over anhydrous $Na_2SO_4$ and concentrated. The residue obtained was purified on silica gel with ethyl acetate/ petroleum ether (0-20%) to give compound 29c. Mass Spectrum (LCMS, ESI pos.): Calcd. For $C_{14}H_{17}FO_2$: 237.1 [M+H]$^+$; found: 237.2.

(D) (3S)-Methyl 3-cyclopropyl-3-(3-((2'-fluoro-5'-methoxy-2,3,4,5-tetrahydro-[1,1'-biphenyl]-4-yl)methoxy)phenyl)propanoate, 29d

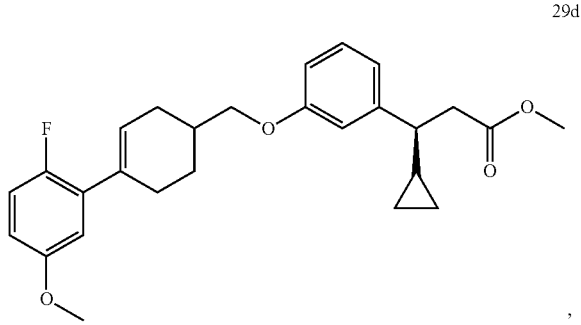 [SMILES: COC(=O)C[C@H](c1cccc(OCC2CC=C(c3cc(OC)ccc3F)CC2)c1)C1CC1]

29d

To a solution of (4-(2-fluoro-5-methoxyphenyl)cyclohex-3-enyl)methanol, cpd 29c (3.0 g, 13 mmol), (S)-methyl 3-cyclopropyl-3-(3-hydroxyphenyl)propanoate (2.9 g, 13 mmol) and (n-Bu)₃P (64 g, 32 mmol, 10% in hexane) in toluene (70 mL), a solution of ADDP (8.0 g, 32 mmol) in toluene (80 mL) was added drop-wise with stirring at 0° C. The resulting solution was stirred overnight at 60° C. The reaction was then allowed to cool to RT and quenched by the addition of 200 mL of water. The resulting solution was extracted with ethyl acetate (3×150 mL). The organic layers were combined and dried over Na₂SO₄ and concentrated. The residue was purified on silica gel with ethyl acetate/petroleum ether (0-5%) to give compound 29d. Mass Spectrum (LCMS, ESI pos.): Calcd. For $C_{27}H_{31}FO_4$: 461.2 [M+Na]⁺; found: 461.2.

(E) (S)-methyl 3-cyclopropyl-3-(3-(((1s,4R)-4-(2-fluoro-5-methoxyphenyl)cyclohexyl) methoxy)phenyl)propanoate, 29e

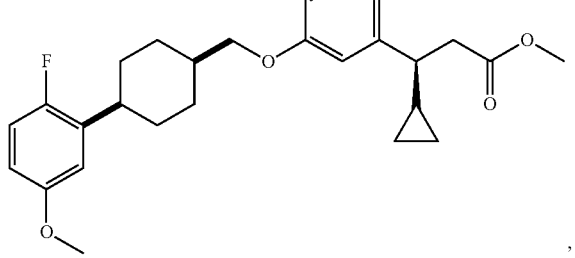

29e

A mixture of (3S)-methyl 3-cyclopropyl-3-(3-((4-(2-fluoro-5-methoxyphenyl)cyclohex-3-enyl)methoxy)phenyl)propanoate, cpd 29d (3.2 g, 7.3 mmol) and 10% Pd/C (0.50 mg) in methanol (100 mL) was stirred overnight at RT under a H₂ (3.5 atm) atmosphere. The reaction mixture was filtered and the filtrate was concentrated. The residue obtained was purified on silica gel with ethyl acetate/petroleum ether (0-5%) and then by Supercritical Fluid Chromatography (SFC) on Chiralpak AD-H SFC, 5×25 cm, column using CO₂/IPA (60/40 with 0.2 DEA). The compound that eluted at 4.64 min was collected to give compound 29e. ¹H NMR (400 MHz, CDCl₃) δ (ppm): 7.18-7.23 (m, 2H), 6.62-6.93 (m, 5H), 3.99 (d, J=7.5 Hz, 2H), 3.77 (s, 3H), 3.60 (s, 3H), 2.79-2.88 (m, 1H), 2.66-2.74 (m, 2H), 2.24-2.37 (m, 2H), 1.86-1.94 (m, 2H), 1.60-1.82 (m, 6H), 0.98-1.00 (m, 1H), 0.48-0.52 (m, 1H), 0.37-0.40 (m, 1H), 0.25-0.29 (m, 1H), 0.11-0.14 (m, 1H).

(F) (S)-3-cyclopropyl-3-(3-(((1s,4R)-4-(2-fluoro-5-methoxyphenyl)cyclohexyl) methoxy)phenyl) propanoic acid, Cpd 1

A mixture of (S)-methyl 3-cyclopropyl-3-(3-(((1r,4S)-4-(2-fluoro-5-methoxyphenyl)cyclohexyl)methoxy)phenyl) propanoate, cpd 29e (0.400 g, 0.908 mmol) and LiOH.H₂O (381 mg, 9.08 mmol) in THF (12 mL), methanol (3 mL) and water (3 mL) was stirred overnight at 30° C. The reaction mixture was allowed to cool to RT, concentrated and treated with 20 mL of water. The pH of the solution was adjusted to 6-7 with 2 M HCl. The resultant solids were collected by filtration and dried to give compound 1. ¹H NMR (300 MHz, CDCl₃) δ (ppm): 7.18 (t, J=8.1 Hz, 1H), 6.87-6.94 (m, 1H), 6.73-6.81 (m, 4H), 6.61-6.66 (m, 1H), 4.00 (d, J=7.5 Hz, 2H), 3.77 (s, 3H), 2.85-2.91 (m, 1H), 2.69-2.71 (m, 2H), 2.23-2.37 (m, 2H), 1.90-1.94 (m, 2H), 1.61-1.76 (m, 6H), 0.99-1.00 (m, 1H), 0.48-0.52 (m, 1H), 0.37-0.40 (m, 1H), 0.25-0.29 (m, 1H), 0.11-0.14 (m, 1H). Mass Spectrum (LCMS, ESI pos.): Calcd. For $C_{26}H_{31}FO_4$: 427.2 [M+H]⁺; found: 427.2.

Example 30

(S)-3-Cyclopropyl-3-(3-(((1s,4R)-4-(2-fluoro-5-methoxyphenyl)-4-hydroxycyclohexyl) methoxy)phenyl)propanoic acid, Cpd 3

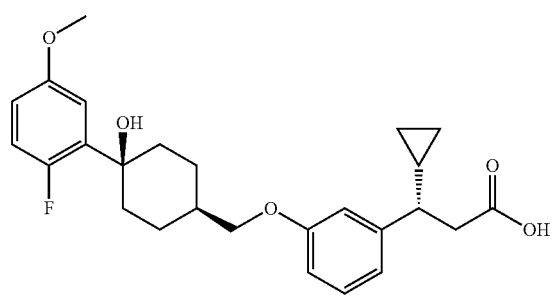 [SMILES: COc1ccc(F)c([C@]2(O)CC[C@@H](COc3cccc([C@@H](CC(=O)O)C4CC4)c3)CC2)c1]

(A) Ethyl (1s,4s)-4-(2-fluoro-5-methoxyphenyl)-4-hydroxycyclohexane-1-carboxylate (30a-1) and ethyl (1r,4r)-4-(2-fluoro-5-methoxyphenyl)-4-hydroxycyclohexane-1-carboxylate, (30a-2)

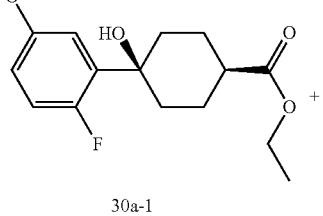

30a-1

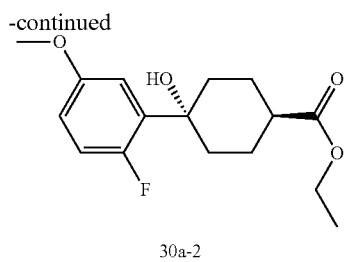

30a-2

To a solution of 2-bromo-1-fluoro-4-methoxybenzene (600 mg, 2.93 mmol) in THF (15 mL), cooled in a dry ice-acetone bath, was added n-BuLi (2.5 M in hexane, 2.34 mL, 5.85 mmol) drop-wise under an argon atmosphere. After 20 min at −78° C., a solution of ethyl 4-oxocyclohexane-1-carboxylate (1.17 mL, 7.32 mmol) in THF (15 mL) was added drop-wise. The mixture was stirred at −78° C. for 1 h, then was poured into saturated NH$_4$Cl (100 mL). The pH of the mixture was adjusted to ~7 using HCl (2 N) solution. The resulting mixture was extracted with ethyl acetate (2×50 mL). The combined organic layers were washed with brine, dried over Na$_2$SO$_4$, filtered and concentrated. The resulting residue was first purified by flash chromatography on silica gel with EtOAc/heptane (0-30%), then by preparative HPLC on a Phenomenex 5μ C18 column (30×100 mm) using an acetonitrile/water (0.1% TFA v/v) gradient (20-100%). The fractions containing the product were combined and made basic with saturated NaHCO$_3$ solution. The product was extracted with EtOAc, and the organic layer was washed with brine, dried over Na$_2$SO$_4$, filtered and concentrated to afford compounds 30a-1 and 30a-2.

Cpd 30a-1: $^1$H NMR (CDCl$_3$) δ (ppm): 7.14 (dd, J=6.6, 3.0 Hz, 1H), 6.93 (dd, J=11.6, 8.6 Hz, 1H), 6.72 (dt, J=9.1, 3.5 Hz, 1H), 4.15 (q, J=7.1 Hz, 2H), 3.77 (s, 3H), 2.39 (tt, J=11.8, 3.9 Hz, 1H), 2.30 (br s, 1H), 2.05-2.16 (m, 2H), 1.80-2.05 (m, 6H), 1.27 (t, J=7.3 Hz, 3H).

Cpd 30a-2: $^1$H NMR (CDCl$_3$) δ: 7.04 (dd, J=6.8, 3.3 Hz, 1H), 6.93 (dd, J=11.6, 9.1 Hz, 1H), 6.71 (dt, J=8.7, 3.5 Hz, 1H), 4.15 (q, J=7.1 Hz, 2H), 3.77 (s, 3H), 2.66 (t, J=4.3 Hz, 1H), 2.21-2.33 (m, 3H), 1.95-2.12 (m, 4H), 1.70 (br d, J=13.6 Hz, 2H), 1.27 (t, J=7.1 Hz, 3H).

(B) (1s,4s)-1-(2-Fluoro-5-methoxyphenyl)-4-(hydroxymethyl)cyclohexan-1-ol, 30b

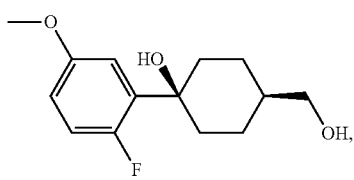

30b

To a solution of ethyl (1s,4s)-4-(2-fluoro-5-methoxyphenyl)-4-hydroxycyclohexane-1-carboxylate, cpd 30a-1 (63 mg, 0.21 mmol) cooled in an ice-water bath, was added LiAlH$_4$ (1 M in THF, 0.42 mL, 0.42 mmol) drop-wise under an argon atmosphere. The resulting mixture was stirred at 0° C. for 1 h before warming up to RT. The reaction was quenched with a saturated NH$_4$Cl solution. The mixture was extracted with EtOAc (2×20 mL). The combined organic layers were washed with brine, dried over Na$_2$SO$_4$, filtered and concentrated. The crude product was purified by flash chromatography on silica gel (0-70% EtOAc/heptane) to afford compound 30b as a white solid. Mass Spectrum (LCMS, ESI pos.): Calcd. For C$_{14}$H$_{19}$FO$_3$: 277.1 [M+Na]$^+$; found: 277.1.

(C) Methyl (S)-3-cyclopropyl-3-(3-(((1s,4R)-4-(2-fluoro-5-methoxyphenyl)-4-hydroxy cyclohexyl) methoxy)phenyl)propanoate, 30c

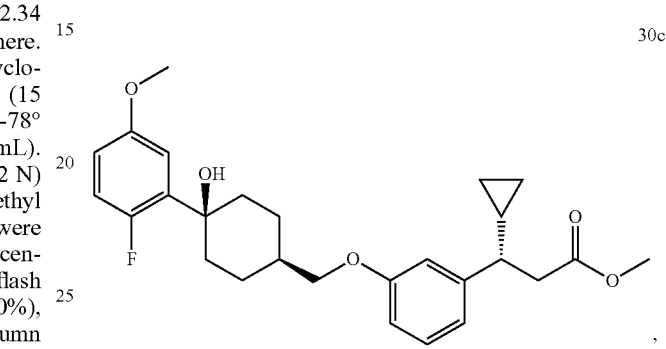

30c

To a solution of (1s,4s)-1-(2-fluoro-5-methoxyphenyl)-4-(hydroxymethyl)cyclohexan-1-ol, 30b (45 mg, 0.18 mmol) and (9-methyl 3-cyclopropyl-3-(3-hydroxyphenyl)propanoate (43 mg, 0.19 mmol) in THF (4 mL) was added PPh$_3$ (93 mg, 0.35 mmol) at RT followed by addition of a solution of di-tert-butyl azodicarboxylate (81 mg, 0.35 mmol) in THF (1 mL) drop-wise. The resulting mixture was stirred at RT for 2 days. The solvent was evaporated, and the residue was purified by flash chromatography on silica gel with EtOAc/heptane (0-30%) to afford compound 30c. Mass Spectrum (LCMS, ESI pos.): Calcd. For C$_{27}$H$_{33}$FO$_5$: 479.2 [M+Na]$^+$; found: 479.2.

(D) (S)-3-Cyclopropyl-3-(3-(((1s,4R)-4-(2-fluoro-5-methoxyphenyl)-4-hydroxycyclohexyl) methoxy) phenyl)propanoic acid, Cpd 3

To a solution of methyl (S)-3-cyclopropyl-3-(3-(((1s,4R)-4-(2-fluoro-5-methoxyphenyl)-4-hydroxycyclohexyl) methoxy)phenyl)propanoate, cpd 30c (50 mg, 0.11 mmol) in THF (2 mL) and MeOH (2 mL) was added 1N NaOH (2 mL, 2 mmol). The mixture was stirred at RT overnight. Water (10 mL) was added, and the pH of the mixture was adjusted to 4 using citric acid solution (2 M). Ethyl acetate (20 mL) was used to extract the mixture. The organic layer was washed with brine, dried over Na$_2$SO$_4$ and concentrated to give compound 3. $^1$H NMR (CDCl$_3$) δ (ppm): 7.21 (t, J=7.8 Hz, 1H), 7.12 (dd, J=6.6, 3.0 Hz, 1H), 6.95 (dd, J=11.6, 8.6 Hz, 1H), 6.75-6.84 (m, 3H), 6.73 (dt, J=8.7, 3.5 Hz, 1H), 3.83 (d, J=6.6 Hz, 2H), 3.78 (s, 3H), 2.69-2.85 (m, 2H), 2.29-2.39 (m, 1H), 2.13 (td, J=13.8, 4.3 Hz, 2H), 1.78-1.98 (m, 5H), 1.55-1.69 (m, 2H), 0.97-1.10 (m, 1H), 0.57 (td, J=8.7, 3.8 Hz, 1H), 0.38-0.48 (m, 1H), 0.29 (dq, J=9.6, 4.9 Hz, 1H), 0.17 (dt, J=9.7, 5.0 Hz, 1H). Mass Spectrum (LCMS, ESI pos.): Calcd. For C$_{26}$H$_{31}$FO$_5$: 465.2 [M+Na]$^+$; found: 465.1.

Example 31

(S)-3-Cyclopropyl-3-(3-(((1r,4S)-4-(2-fluoro-5-methoxyphenyl)-4-hydroxycyclohexyl) methoxy)phenyl)propanoic acid, Cpd 6

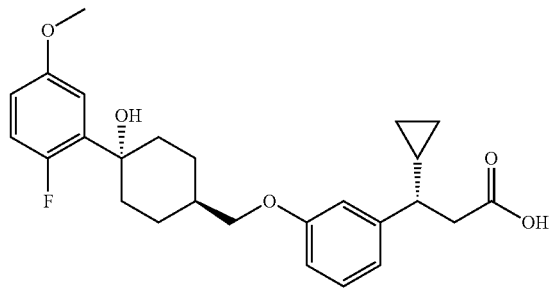 [SMILES: COc1ccc(F)c([C@]2(O)CC[C@H](COc3cccc([C@@H](CC(=O)O)C4CC4)c3)CC2)c1]

(A) (1r,4r)-1-(2-Fluoro-5-methoxyphenyl)-4-(hydroxymethyl)cyclohexan-1-ol, 31a

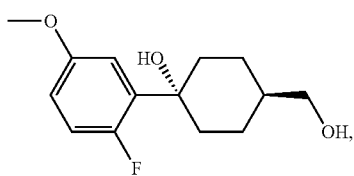

(1r,4r)-1-(2-Fluoro-5-methoxyphenyl)-4-(hydroxymethyl)cyclohexan-1-ol was prepared from ethyl (1r,4r)-4-(2-fluoro-5-methoxyphenyl)-4-hydroxycyclohexane-1-carboxylate 30a-2 (Example 30, Step A) using the method described in Example 30, Step B. Mass Spectrum (LCMS, ESI pos.): Calcd. For $C_{14}H_{19}FO_3$: 277.1 [M+Na]$^+$; found: 277.1.

(B) Methyl (S)-3-cyclopropyl-3-(3-(((1r,4S)-4-(2-fluoro-5-methoxyphenyl)-4-hydroxy cyclohexyl)methoxy)phenyl)propanoate, 31b

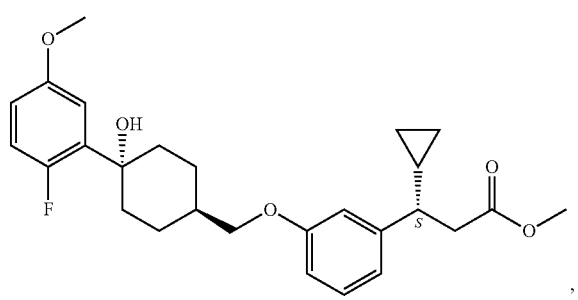

Compound 31b was prepared from (1r,4r)-1-(2-fluoro-5-methoxyphenyl)-4-(hydroxymethyl)cyclohexan-1-ol, cpd 31a, and (9-methyl 3-cyclopropyl-3-(3-hydroxyphenyl)propanoate using the method described in Example 30, Step C.

Mass Spectrum (LCMS, ESI pos.): Calcd. For $C_{27}H_{33}FO_5$: 479.2 [M+Na]$^+$; found: 479.2.

(C) (S)-3-Cyclopropyl-3-(3-(((1r,4S)-4-(2-fluoro-5-methoxyphenyl)-4-hydroxycyclohexyl) methoxy)phenyl)propanoic acid, Cpd 6

Compound 6 was prepared from methyl (S)-3-cyclopropyl-3-(3-(((1r,4S)-4-(2-fluoro-5-methoxyphenyl)-4-hydroxycyclohexyl)methoxy)phenyl)propanoate, cpd 31b, using the method described in Example 30, Step D. $^1$H NMR (CDCl$_3$) δ (ppm): 7.21 (t, J=7.8 Hz, 1H), 7.07 (dd, J=6.8, 3.3 Hz, 1H), 6.95 (dd, J=12.1, 9.1 Hz, 1H), 6.69-6.84 (m, 4H), 3.94 (d, J=7.1 Hz, 2H), 3.78 (s, 3H), 2.71-2.84 (m, 2H), 2.30-2.44 (m, 3H), 2.11-2.21 (m, 1H), 1.97-2.07 (m, 2H), 1.62-1.74 (m, 2H), 1.49-1.60 (m, 2H), 0.96-1.09 (m, 1H), 0.53-0.63 (m, 1H), 0.37-0.47 (m, 1H), 0.29 (dq, J=9.5, 4.7 Hz, 1H), 0.12-0.21 (m, 1H). Mass Spectrum (LCMS, ESI pos.): Calcd. For $C_{26}H_{31}FO_5$: 465.2 [M+Na]$^+$; found: 465.1.

Example 32

(S)-3-Cyclopropyl-3-(3-(((1s,4R)-4-(2-fluoro-5-methoxyphenyl)-4-methoxycyclohexyl) methoxy)phenyl)propanoic acid, Cpd 11

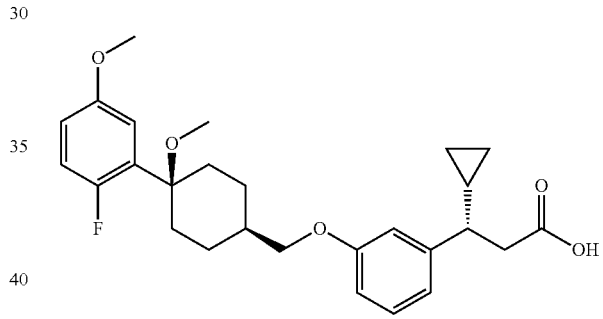

(A) Ethyl 4-(2-fluoro-5-methoxyphenyl)-4-hydroxycyclohexane-1-carboxylate, 32a

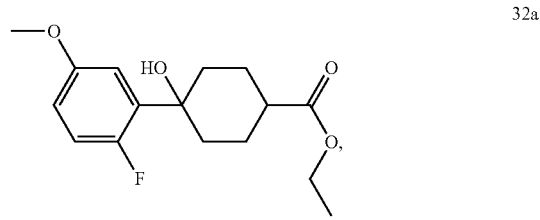 [SMILES: CCOC(=O)C1CCC(O)(c2cc(OC)ccc2F)CC1]

Ethyl 4-(2-fluoro-5-methoxyphenyl)-4-hydroxycyclohexane-1-carboxylate, cpd 32a was prepared from 2-bromo-1-fluoro-4-methoxybenzene and ethyl 4-oxocyclohexane-1-carboxylate using the method described in Example 30, Step A. Purification by flash chromatography afforded a mixture of cis- and trans-isomers, used directly in the following step. Mass Spectrum (LCMS, ESI pos.): Calcd. For $C_{16}H_{21}FO_4$: 279.1 [M-OH]$^+$; found: 279.1.

(B) 1-(2-Fluoro-5-methoxyphenyl)-4-(hydroxymethyl)cyclohexan-1-ol, 32b

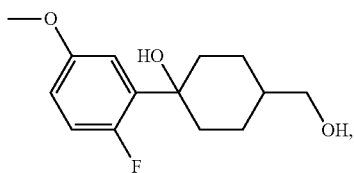

32b

Compound 32b was prepared from ethyl 4-(2-fluoro-5-methoxyphenyl)-4-hydroxycyclohexane-1-carboxylate, cpd 32a, using the method described in Example 30, Step B. Purification via flash chromatography afforded a mixture of cis- and trans-isomers, used directly in the following step. Mass Spectrum (LCMS, ESI pos.): Calcd. For $C_{14}H_{19}FO_3$: 237.1 [M-OH]$^+$; found: 237.1.

(C) Methyl (S)-3-cyclopropyl-3-(3-((4-(2-fluoro-5-methoxyphenyl)-4-hydroxycyclohexyl) methoxy) phenyl)propanoate, 32c

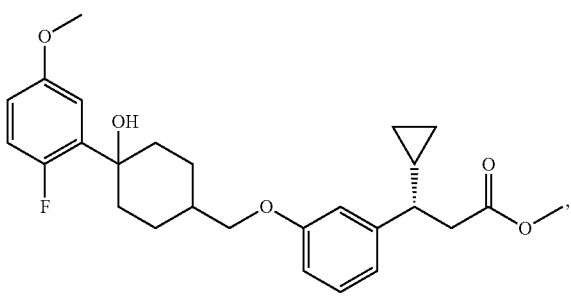

32c

Compound 32c was prepared from 1-(2-fluoro-5-methoxyphenyl)-4-(hydroxymethyl)cyclohexan-1-ol, cpd 32b and (9-methyl 3-cyclopropyl-3-(3-hydroxy phenyl)propanoate using the method described in Example 30, Step C. Purification via flash column chromatography afforded a mixture of cis- and trans-isomers, used directly in the following step.

(D) Methyl (S)-3-cyclopropyl-3-(3-(((1s,4R)-4-(2-fluoro-5-methoxyphenyl)-4-methoxycyclohexyl)methoxy)phenyl)propanoate, (32d-1), and methyl (S)-3-cyclopropyl-3-(3-(((1r,4S)-4-(2-fluoro-5-methoxyphenyl)-4-methoxycyclohexyl)methoxy)phenyl)propanoate, (32d-2)

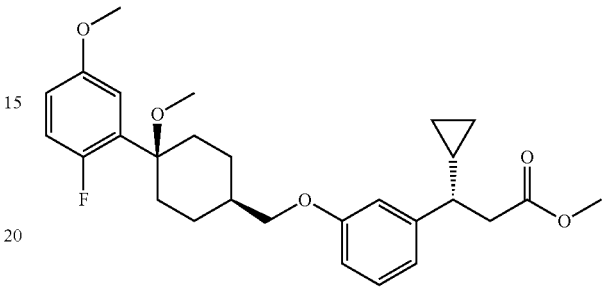

32d-1

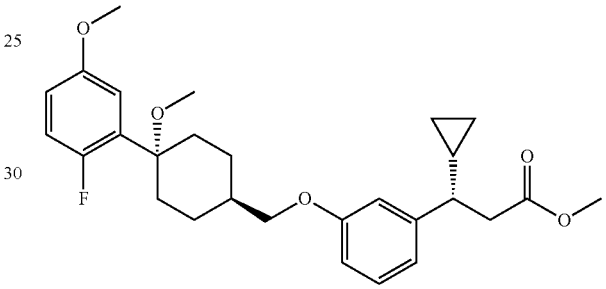

32d-2

To a solution of methyl (S)-3-cyclopropyl-3-(3-(((4-(2-fluoro-5-methoxyphenyl)-4-hydroxycyclohexyl)methoxy)phenyl)propanoate, cpd 32c (54 mg, 0.12 mmol) in DMF (1 mL) cooled in an ice-water bath was added NaH (60% in mineral oil, 5.7 mg, 0.14 mmol). The mixture was stirred at 0° C. for 10 min, then CH$_3$I (15 µL, 0.24 mmol) was added drop-wise under an argon atmosphere. After 2 h at 0° C., the reaction was warmed up to RT. Ethyl acetate (20 mL) was added, and the organic layer was washed sequentially with water and brine, dried over Na$_2$SO$_4$, filtered, and concentrated, to afford a crude material. The crude material was purified by preparative-HPLC on a Phenomenex 5µ C18 column (30×100 mm) using an acetonitrile/water (0.1% TFA v/v) gradient (20-80%) to afford compounds 32d-1 and 32d-2.

Cpd 32d-1: $^1$H NMR (CDCl$_3$) δ (ppm): 7.18-7.24 (m, 1H), 6.89-7.00 (m, 2H), 6.70-6.84 (m, 4H), 3.82 (d, J=6.6 Hz, 2H), 3.79 (s, 3H), 3.62 (s, 3H), 3.12 (s, 3H), 2.68-2.81 (m, 2H), 2.29-2.38 (m, 1H), 2.22 (d, J=12.6 Hz, 2H), 1.76-1.96 (m, 5H), 1.46-1.62 (m, 2H), 0.96-1.10 (m, 1H), 0.52-0.64 (m, 1H), 0.38-0.48 (m, 1H), 0.26 (dq, J=9.5, 4.7 Hz, 1H), 0.11-0.20 (m, 1H).

Cpd 32d-2: $^1$H NMR (CDCl$_3$) δ (ppm): 7.19 (t, J=7.8 Hz, 1H), 6.90-7.01 (m, 2H), 6.77 (td, J=12.4, 8.1 Hz, 4H), 3.85 (d, J=7.1 Hz, 2H), 3.80 (s, 3H), 3.61 (s, 3H), 3.08 (s, 3H), 2.67-2.79 (m, 2H), 2.36-2.47 (m, 2H), 2.28-2.36 (m, 1H), 2.04-2.15 (m, 1H), 1.94-2.04 (m, 2H), 1.82 (ddd, J=13.3, 9.0, 4.0 Hz, 2H), 1.34-1.45 (m, 2H), 0.95-1.07 (m, 1H), 0.52-0.62 (m, 1H), 0.37-0.47 (m, 1H), 0.25 (dq, J=9.6, 4.9 Hz, 1H), 0.10-0.19 (m, 1H).

(E) (S)-3-Cyclopropyl-3-(3-(((1s,4R)-4-(2-fluoro-5-methoxyphenyl)-4-methoxycyclohexyl) methoxy)phenyl)propanoic acid, Cpd 11

Compound 11 was prepared from methyl (S)-3-cyclopropyl-3-(3-(((1s,4R)-4-(2-fluoro-5-methoxyphenyl)-4-methoxycyclohexyl)methoxy)phenyl)propanoate, cpd 32d-1 using the method described in Example 30, Step D. $^1$H NMR (CDCl$_3$) δ (ppm): 7.18-7.24 (m, 1H), 6.89-6.99 (m, 2H), 6.72-6.84 (m, 4H), 3.81 (d, J=6.6 Hz, 2H), 3.79 (s, 3H), 3.12 (s, 3H), 2.71-2.84 (m, 2H), 2.30-2.39 (m, 1H), 2.22 (d, J=12.6 Hz, 2H), 1.76-1.95 (m, 5H), 1.46-1.61 (m, 2H), 0.95-1.09 (m, 1H), 0.53-0.64 (m, 1H), 0.43 (tt, J=8.9, 4.7 Hz, 1H), 0.29 (dq, J=9.5, 4.7 Hz, 1H), 0.17 (dt, J=10.0, 4.9 Hz, 1H). Mass Spectrum (LCMS, ESI pos.): Calcd. For C$_{27}$H$_{33}$FO$_5$: 479.2 [M+Na]$^+$; found: 479.2.

Example 33

(S)-3-Cyclopropyl-3-(3-(((1r,4S)-4-(2-fluoro-5-methoxyphenyl)-4-methoxycyclohexyl) methoxy)phenyl)propanoic acid, Cpd 12

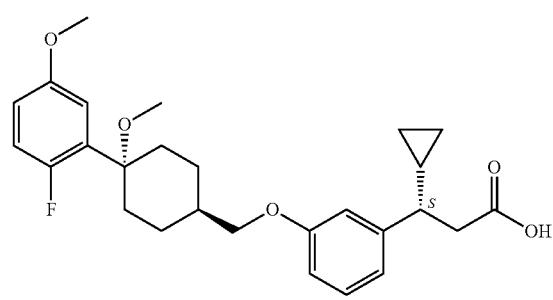

Compound 12 was prepared from methyl (S)-3-cyclopropyl-3-(3-(((1r,4S)-4-(2-fluoro-5-methoxyphenyl)-4-methoxycyclohexyl)methoxy)phenyl)propanoate, 32d-2 (Example 32, Step D) using the method described in Example 30, Step D. $^1$H NMR (CDCl$_3$) δ (ppm): 7.20 (t, J=7.8 Hz, 1H), 6.89-7.00 (m, 2H), 6.70-6.84 (m, 4H), 3.85 (d, J=7.1 Hz, 2H), 3.79 (s, 3H), 3.08 (s, 3H), 2.74-2.81 (m, 2H), 2.37-2.47 (m, 2H), 2.28-2.37 (m, 1H), 2.04-2.15 (m, 1H), 1.93-2.04 (m, 2H), 1.82 (ddd, J=13.4, 9.1, 3.8 Hz, 2H), 1.34-1.45 (m, 2H), 0.96-1.08 (m, 1H), 0.53-0.63 (m, 1H), 0.37-0.48 (m, 1H), 0.29 (dq, J=9.5, 4.7 Hz, 1H), 0.11-0.22 (m, 1H). Mass Spectrum (LCMS, ESI pos.): Calcd. For C$_{27}$H$_{33}$FO$_5$: 479.2 [M+Na]$^+$; found: 479.2.

Example 34

(S)-3-Cyclopropyl-3-(3-(((1r,4S)-4-fluoro-4-(2-fluoro-5-methoxyphenyl)cyclohexyl)methoxy)phenyl)propanoic acid, Cpd 19

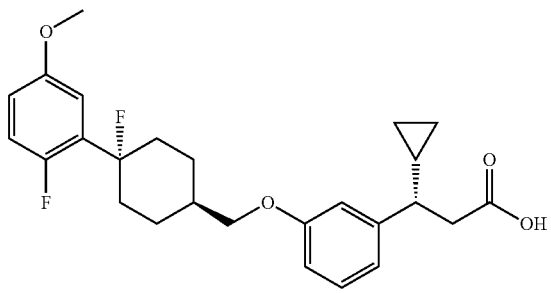 [SMILES: COc1ccc(F)c([C@]2(F)CC[C@H](COc3cccc([C@@H](CC(=O)O)C4CC4)c3)CC2)c1]

(A) Methyl (S)-3-cyclopropyl-3-(3-(((1r,4S)-4-fluoro-4-(2-fluoro-5-methoxyphenyl)cyclohexyl)methoxy)phenyl)propanoate, (34a-1) and methyl (S)-3-cyclopropyl-3-(3-(((1s,4R)-4-fluoro-4-(2-fluoro-5-methoxyphenyl)cyclohexyl)methoxy)phenyl) propanoate (34a-2)

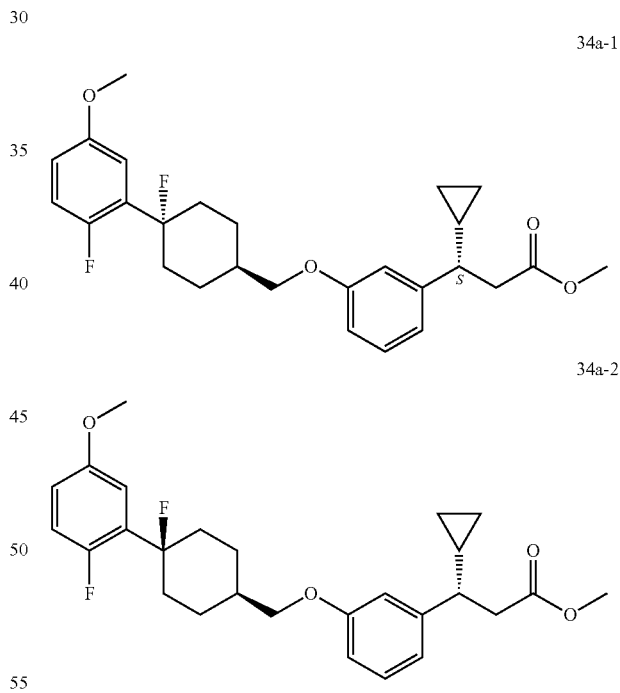

To a solution of methyl (S)-3-cyclopropyl-3-(3-(((4-(2-fluoro-5-methoxyphenyl)-4-hydroxycyclohexyl)methoxy)phenyl)propanoate, cpd 32c (109 mg, 0.239 mmol) in DCM (5 mL) in a plastic bottle was added bis(2-methoxyethyl)aminosulfur trifluoride (132 µL, 0.716 mmol) at 0° C. The mixture was warmed to RT overnight. The solvent was evaporated, and the crude material was first purified by flash chromatography on silica gel with EtOAc/heptane (0-20%) and then by preparative HPLC on an Agilent 5µ C18 column (30×100 mm) using an acetonitrile/water (0.1% TFA, v/v) gradient (20-100%) to afford compounds 34a-1 and 34a-2.

Cpd 34a-1: ¹H NMR (CDCl₃) δ (ppm): 7.19-7.25 (m, 1H), 7.05 (dd, J=6.3, 3.3 Hz, 1H), 6.91-6.98 (m, 1H), 6.71-6.86 (m, 4H), 4.06 (d, J=7.6 Hz, 2H), 3.79 (s, 3H), 3.62 (s, 3H), 2.69-2.82 (m, 2H), 2.19-2.41 (m, 4H), 1.99-2.12 (m, 2H), 1.72-1.90 (m, 4H), 0.97-1.11 (m, 1H), 0.53-0.63 (m, 1H), 0.39-0.49 (m, 1H), 0.27 (dq, J=9.5, 4.7 Hz, 1H), 0.12-0.21 (m, 1H).

Cpd 34a-2: ¹H NMR (CDCl₃) δ (ppm): 7.19-7.25 (m, 1H), 7.07 (dd, J=6.3, 3.3 Hz, 1H), 6.90-7.00 (m, 1H), 6.73-6.86 (m, 4H), 3.83 (d, J=6.1 Hz, 2H), 3.80 (s, 3H), 3.62 (s, 3H), 2.68-2.82 (m, 2H), 2.30-2.38 (m, 1H), 2.19-2.30 (m, 1H), 2.09-2.19 (m, 1H), 1.94-2.09 (m, 3H), 1.89 (d, J=13.1 Hz, 2H), 1.52-1.66 (m, 2H), 0.96-1.11 (m, 1H), 0.53-0.64 (m, 1H), 0.38-0.48 (m, 1H), 0.26 (dq, J=9.6, 4.9 Hz, 1H), 0.12-0.19 (m, 1H).

(B) (S)-3-Cyclopropyl-3-(3-(((1r,4S)-4-fluoro-4-(2-fluoro-5-methoxyphenyl)cyclohexyl) methoxy)phenyl)propanoic acid, Cpd 19

Compound 19 was prepared from methyl (S)-3-cyclopropyl-3-(3-(((1r,4S)-4-fluoro-4-(2-fluoro-5-methoxyphenyl)cyclohexyl)methoxy)phenyl) propanoate, cpd 34a-1, using the method described in Example 30, Step D. ¹H NMR (CDCl₃) δ (ppm): 7.19-7.25 (m, 1H), 7.05 (dd, J=6.3, 3.3 Hz, 1H), 6.90-6.98 (m, 1H), 6.78-6.85 (m, 3H), 6.75 (dt, J=9.0, 3.3 Hz, 1H), 4.06 (d, J=7.1 Hz, 2H), 3.79 (s, 3H), 2.72-2.85 (m, 2H), 2.19-2.41 (m, 4H), 2.00-2.12 (m, 2H), 1.72-1.89 (m, 4H), 0.98-1.09 (m, 1H), 0.53-0.64 (m, 1H), 0.38-0.49 (m, 1H), 0.30 (dq, J=9.5, 4.9 Hz, 1H), 0.18 (dq, J=9.9, 5.0 Hz, 1H). Mass Spectrum (LCMS, ESI pos.): Calcd. For $C_{26}H_{30}F_2O_4$: 467.2 [M+Na]⁺; found: 467.3.

Example 35

(S)-3-Cyclopropyl-3-(3-(((1s,4R)-4-fluoro-4-(2-fluoro-5-methoxyphenyl)cyclohexyl)methoxy)phenyl)propanoic acid, Cpd 20

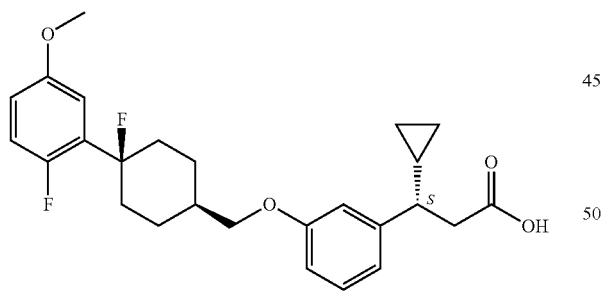

Compound 20 was prepared from methyl (S)-3-cyclopropyl-3-(3-(((1s,4R)-4-fluoro-4-(2-fluoro-5-methoxyphenyl)cyclohexyl)methoxy)phenyl)propanoate, cpd 34a-2, using the method described in Example 30, Step D. ¹H NMR (CDCl₃) δ (ppm): 7.19-7.25 (m, 1H), 7.07 (dd, J=6.6, 3.0 Hz, 1H), 6.91-6.99 (m, 1H), 6.72-6.85 (m, 4H), 3.83 (d, J=6.1 Hz, 2H), 3.80 (s, 3H), 2.71-2.87 (m, 2H), 2.30-2.39 (m, 1H), 2.08-2.30 (m, 2H), 1.94-2.08 (m, 3H), 1.84-1.94 (m, 2H), 1.59 (q, J=12.0 Hz, 2H), 0.96-1.11 (m, 1H), 0.52-0.66 (m, 1H), 0.38-0.50 (m, 1H), 0.30 (dq, J=9.5, 4.9 Hz, 1H), 0.13-0.24 (m, 1H). Mass Spectrum (LCMS, ESI pos.): Calcd. For $C_{26}H_{30}F_2O_4$: 467.2 [M+Na]⁺; found: 467.3.

Example 36

(R)-3-Cyclopropyl-3-(3-(((1s,4S)-4-(2-fluoro-5-methoxyphenyl)cyclohexyl)methoxy)phenyl)propanoic acid, Cpd 37 and (R)-3-cyclopropyl-3-(3-(((1r,4R)-4-(2-fluoro-5-methoxyphenyl)cyclohexyl)methoxy)phenyl)propanoic acid, Cpd 38

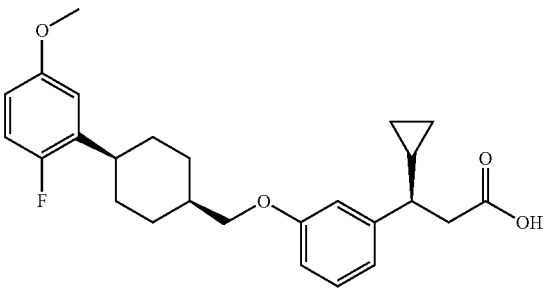

Cpd 37

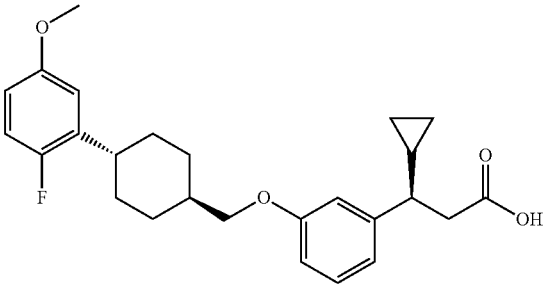

Cpd 38

(A) Ethyl 2'-fluoro-5'-methoxy-2,3,4,5-tetrahydro-[1,1'-biphenyl]-4-carboxylate, 36a

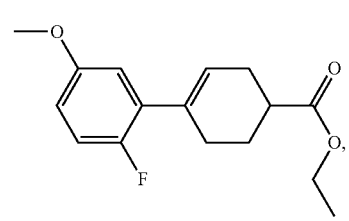

36a

To a solution of ethyl 4-(2-fluoro-5-methoxyphenyl)-4-hydroxycyclohexane-1-carboxylate, 32a (444 mg, 1.50 mmol) in benzene (10 mL) was added p-toluenesulfonic acid monohydrate (285 mg, 1.50 mmol). The mixture was stirred at 85° C. for 2 h. The solvent was evaporated, and the residue was dissolved in a mixture of EtOAc/water (100 mL/100 mL). The organic layer was washed with saturated, aq. NaHCO₃ and brine, dried over Na₂SO₄ and concentrated to give compound 36a. Mass Spectrum (LCMS, ESI pos.): Calcd. For $C_{16}H_{19}FO_3$: 279.1 [M+H]⁺; found: 279.1.

(B) (2'-Fluoro-5'-methoxy-2,3,4,5-tetrahydro-[1,1'-biphenyl]-4-yl)methanol, 36b

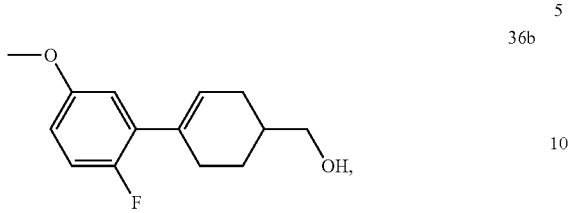

36b

Compound 36b was prepared from ethyl 2'-fluoro-5'-methoxy-2,3,4,5-tetrahydro-[1,1'-biphenyl]-4-carboxylate, cpd 36a using the method described in Example 30, Step B. $^1$H NMR (CDCl$_3$) δ (ppm): 6.88-6.98 (m, 1H), 6.66-6.79 (m, 2H), 5.94 (br. s., 1H), 3.78 (s, 3H), 3.56-3.65 (m, 2H), 2.26-2.54 (m, 3H), 1.82-2.01 (m, 3H), 1.59 (br. s., 1H), 1.37-1.51 (m, 1H).

(C) (4-(2-Fluoro-5-methoxyphenyl)cyclohexyl)methanol, 36c

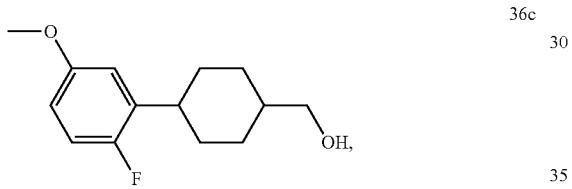

36c

A mixture of (2'-fluoro-5'-methoxy-2,3,4,5-tetrahydro-[1,1'-biphenyl]-4-yl)methanol, cpd 36b (300 mg, 1.27 mmol) and 10% Pd/C (167.6 mg) in MeOH (20 mL) and EtOAc (20 mL) was stirred under a hydrogen (60 psi) atmosphere at RT in a Parr-shaker overnight. The mixture was filtered through a pad of diatomaceous earth and the filtrate was concentrated. The crude product was purified by flash chromatography on silica gel with EtOAc/heptane (0-50%) to afford compound 36c, which was used as a mixture of cis- and trans-isomers in the next step without further purification.

(D) Ethyl (E)-3-cyclopropylacrylate, 36d

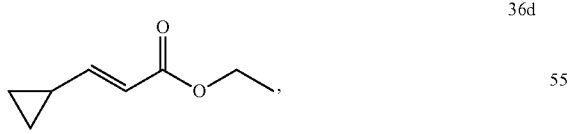

36d

To a solution of cyclopropanecarbaldehyde (20.4 g, 285 mmol) in THF (30 mL) at 0° C. was added ethyl 2-(triphenylphosphoranylidene)acetate (107 g, 292 mmol) portionwise under a nitrogen atmosphere. The mixture was then stirred at RT for 16 h. The solvent was evaporated, and the crude solid was triturated with heptane to remove triphenylphosphine oxide. The filtrate was concentrated and the resulting residue was purified by vacuum distillation (head 80° C., oil bath 120° C., vacuum 20 torr) to afford compound 36d. $^1$H NMR (CDCl$_3$) δ (ppm): 6.42 (dd, J=15.7, 10.1 Hz, 1H), 5.89 (d, J=15.7 Hz, 1H), 4.17 (q, J=7.1 Hz, 2H), 1.51-1.67 (m, 1H), 1.29 (t, J=7.1 Hz, 3H), 0.90-1.02 (m, 2H), 0.59-0.72 (m, 2H).

(E) Ethyl (S)-3-cyclopropyl-3-(3-hydroxyphenyl)propanoate, (36e-1) and ethyl (R)-3-cyclopropyl-3-(3-hydroxyphenyl)propanoate, (36e-2)

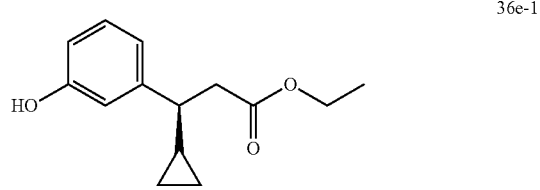

36e-1

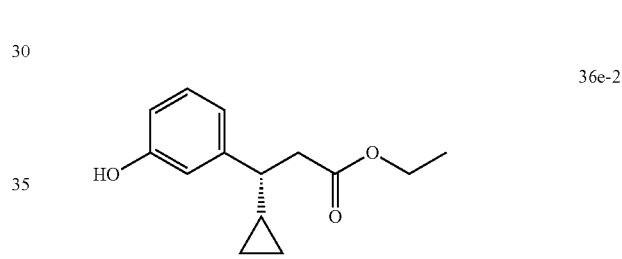

36e-2

To a solution of chloro(1,5-cyclooctadiene)rhodium (I) dimer (2.46 g, 4.99 mmol) in 1,4-dioxane (50 mL) was added NaOH (aq. 1N, 150 mL, 150 mmol) at RT under a nitrogen atmosphere. (3-Hydroxyphenyl)boronic acid (27.6 g, 200 mmol) was added, followed by the addition of ethyl (E)-3-cyclopropylacrylate, cpd 36d (14 g, 100 mmol) in 1,4-dioxane (50 mL). The mixture was stirred at 50° C. for 16 h. The mixture was poured into ethyl acetate/water and acidified with 2N HCl to pH-4. The aqueous layer was extracted with ethyl acetate (2×). The combined organic layers were dried (Na$_2$SO$_4$), filtered and concentrated. The resulting residue was first purified by flash chromatography on silica gel with EtOAc/heptane (0-30%) to give a yellow oil, which was further purified by chiral SFC on a Chiralcel OD-H 5 μm column (250×30 mm) using 93% CO$_2$, 7% 1-PrOH to afford compounds 36e-1 ([α]$_D^{20}$=+35.7) and 36e-2.

Cpd 36e-2: $^1$H NMR (CDCl$_3$) δ (ppm): 7.17 (t, J=7.8 Hz, 1H), 6.81 (d, J=7.6 Hz, 1H), 6.72 (t, J=2.0 Hz, 1H), 6.67-6.71 (m, 1H), 4.98 (s, 1H), 4.07 (qd, J=7.1, 3.5 Hz, 2H), 2.66-2.79 (m, 2H), 2.32 (dt, J=9.6, 7.6 Hz, 1H), 1.18 (t, J=7.3 Hz, 3H), 0.95-1.06 (m, 1H), 0.54-0.62 (m, 1H), 0.39-0.48 (m, 1H), 0.27 (dq, J=9.5, 4.7 Hz, 1H), 0.12-0.19 (m, 1H).

(F) Ethyl (R)-3-cyclopropyl-3-(3-((4-(2-fluoro-5-methoxyphenyl)cyclohexyl)methoxy)phenyl) propanoate, 36f

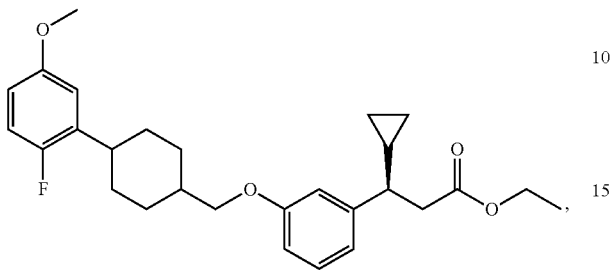

36f

To a solution of (4-(2-fluoro-5-methoxyphenyl)cyclohexyl)methanol, cpd 36c (226 mg, 0.948 mmol), ethyl (R)-3-cyclopropyl-3-(3-hydroxyphenyl)propanoate, cpd 36e-2 (444 mg, 1.90 mmol) and tri-n-butyl phosphine (468 µL, 1.90 mmol) in toluene (15 mL) was added a solution of 1,1'-(azodicarbonyl)dipiperidine (431 mg, 1.71 mmol) in toluene (5 mL) at 0° C. drop-wise under an argon atmosphere. The mixture was stirred at 60° C. for 16 h. The solvent was evaporated, and the residue was purified by flash chromatography on silica gel (0-15% EtOAc/heptane) to afford compound 36f as a colorless oil. Mass Spectrum (LCMS, ESI pos.): Calcd. For $C_{24}H_{35}FO_4$: 455.3 $[M+1]^+$; found: 455.3.

(G) (R)-3-Cyclopropyl-3-(3-(((1s,4S)-4-(2-fluoro-5-methoxyphenyl)cyclohexyl)methoxy)phenyl)propanoic acid (Cpd 37) and (R)-3-cyclopropyl-3-(3-(((1r,4R)-4-(2-fluoro-5-methoxyphenyl)cyclohexyl)

(H) methoxy)phenyl)propanoic acid (Cpd 38)

To a solution of ethyl (R)-3-cyclopropyl-3-(3-((4-(2-fluoro-5-methoxyphenyl)cyclohexyl)methoxy)phenyl)propanoate, 36f (130 mg, 0.286 mmol) in THF (5 mL) and EtOH (5 mL) was added NaOH (1N, 5 mL, 5 mmol). The mixture was stirred at RT for 18 h. Water (10 mL) was added, and the mixture was acidified to pH-4 using 2 M citric acid solution and then extracted with EtOAc (100 mL). The organic layer was washed with brine, dried over $Na_2SO_4$, filtered and concentrated. The resulting crude material was purified by chiral SFC (stationary phase: Chiralcel OD-H 5 µm 250×20 mm), mobile phase: 80% $CO_2$, 20% MeOH) to afford compounds 37 and 38.

Cpd 37: $^1H$ NMR (CDCl$_3$) δ (ppm): 7.21 (t, J=8.1 Hz, 1H), 6.88-6.95 (m, 1H), 6.81 (dd, J=4.8, 3.3 Hz, 2H), 6.74-6.79 (m, 2H), 6.65 (dt, 3.5 Hz, 1H), 4.02 (d, J=7.1 Hz, 2H), 3.76 (s, 3H), 2.89 (br s, 1H), 2.76 (br s, 2H), 2.29-2.39 (m, 1H), 2.20-2.29 (m, 1H), 1.89-2.00 (m, 2H), 1.59-1.80 (m, 6H), 0.98-1.08 (m, 1H), 0.51-0.62 (m, 1H), 0.43 (tt, J=8.7, 4.7 Hz, 1H), 0.24-0.34 (m, 1H), 0.12-0.21 (m, 1H). Mass Spectrum (LCMS, ESI pos.): Calcd. For $C_{26}H_{31}FO_4$: 427.2 $[M+H]^+$; found: 427.2.

Cpd 38: $^1H$ NMR (CDCl$_3$) δ (ppm): 7.23 (t, J=7.8 Hz, 1H), 6.94 (t, J=9.3 Hz, 1H), 6.75-6.85 (m, 4H), 6.67 (dt, J=9.1, 3.5 Hz, 1H), 3.81 (d, J=6.6 Hz, 2H), 3.79 (s, 3H), 2.81-2.91 (m, 1H), 2.75-2.81 (m, 2H), 2.30-2.41 (m, 1H), 2.01-2.10 (m, 2H), 1.96 (br d, J=10.6 Hz, 1H), 1.82-1.92 (m, 1H), 1.54 (qd, J=12.7, 2.8 Hz, 2H), 1.28 (qd, J=12.6, 3.0 Hz, 2H), 0.99-1.10 (m, 1H), 0.55-0.64 (m, 1H), 0.45 (tt, J=8.7, 4.7 Hz, 1H), 0.31 (dq, J=9.5, 4.9 Hz, 1H), 0.19 (dt, J=9.6, 4.8 Hz, 1H). Mass Spectrum (LCMS, ESI pos.): Calcd. For $C_{26}H_{31}FO_4$: 449.2 $[M+Na]^+$; found: 449.2.

Example 37

(R)-3-Cyclopropyl-3-(3-(((1s,4S)-4-(2-fluoro-5-methoxyphenyl)cyclohexyl)methoxy)phenyl)propanoic acid, Cpd 28

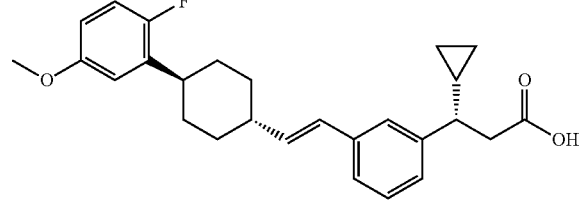

(A) (S)-methyl 3-cyclopropyl-3-(3-(((trifluoromethyl)sulfonyl)oxy)phenyl)propanoate, 37a

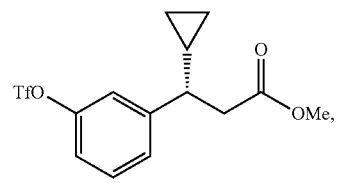

37a

A solution of (9-methyl 3-cyclopropyl-3-(3-hydroxyphenyl)propanoate (2.0 g, 9.0 mmol) and trimethylamine (3.0 g, 30 mmol) in DCM (30 mL) was cooled to 0° C. and treated with trifluoromethanesulfonic anhydride (3.0 g, 10 mmol) drop-wise. The resulting mixture was stirred for 3 h at RT and poured into 20 g of crushed ice. The pH of the mixture was adjusted to pH 6-7 with NaHCO$_3$. The resulting solution was extracted with ethyl acetate (3×200 mL). The organic layers were combined, washed with brine (100 mL), dried and concentrated to give compound 37a. Mass Spectrum (LCMS, ESI pos.): Calcd. For $C_{14}H_{15}F_3O_5S$: 353.0 $[M+H]^+$; found: 353.1.

(B) (S)-methyl 3-cyclopropyl-3-(3-(hydroxymethyl)phenyl)propanoate, 37b

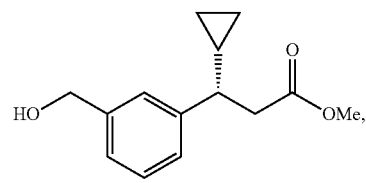

37b

A mixture of (S)-methyl 3-cyclopropyl-3-(3-(trifluoromethylsulfonyloxy)phenyl) propanoate, cpd 37a (2.0 g, 5.6 mmol), potassium acetoxymethyltrifluoroborate (3.0 g, 16 mmol), tris(dibenzylideneacetone)dipalladium (600 mg, 0.65 mmol), Na₂CO₃ (4.0 g, 37 mmol) and 2-dicyclohexylphosphino-2',6'-diisopropoxy-1,1'-biphenyl (300 mg, 0.6 mmol) in water (10 mL) and dioxane (100 mL) was stirred under an argon atmosphere at 80° C. for 10 h. The reaction mixture was cooled to RT and filtered through a pad of silica gel. The filter cake was washed with ethyl acetate (2×50 mL). The combined organic layers were washed with brine (3×50 mL), dried over Na₂SO₄ and concentrated. The residue obtained was purified on silica gel with EtOAc/heptane (1:8) to give compound 37b. Mass Spectrum (LCMS, ESI pos.): Calcd. For $C_{14}H_{18}O_3$: 217.1 [M-OH]⁺; found: 217.2.

(C) (S)-methyl 3-cyclopropyl-3-(3-((dimethoxyphosphoryl)methyl)phenyl)propanoate, 37c

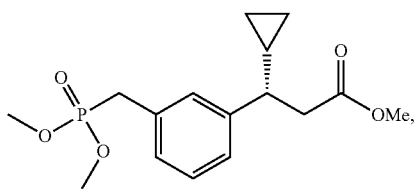

37c

To a mixture of ((S)-methyl 3-cyclopropyl-3-(3-(hydroxymethyl)phenyl)propanoate, cpd 37b (1.0 g, 4.2 mmol) and ZnI₂ (135 mg, 0.420 mmol), trimethyl phosphite (2.0 g, 16 mmol) in toluene (10 mL) was added under a nitrogen atmosphere. The resulting mixture was heated at refluxing temperature overnight. The reaction mixture was allowed to cool to RT and poured into 5 g of crushed ice. The pH of the solution was then adjusted to 6~7 with saturated aq. NaHCO₃. The resulting solution was extracted with ethyl acetate (3×100 mL). The organic layers were combined, washed with brine (100 mL), dried and concentrated to give compound 37c. Mass Spectrum (LCMS, ESI pos.): Calcd. For $C_{27}H_{31}FO_3$: 327.2 [M+H]⁺; found: 327.2.

(D) (1r,4r)-4-(2-Fluoro-5-methoxyphenyl)cyclohexanecarbaldehyde, 37d

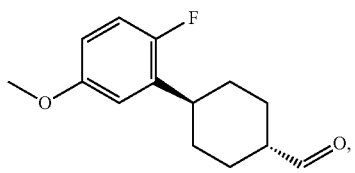

37d

To a solution of ((1r,4r)-4-(2-fluoro-5-methoxyphenyl)cyclohexyl)methanol, cpd 8a-1 (1.0 g, 4.2 mmol) in dichloromethane (10 mL) was added pyridinium chlorochromate (2.0 g, 9.2 mmol) at 0° C. under a nitrogen atmosphere. The resulting solution was stirred for 10 h at 30° C. and concentrated. The residue was purified on silica gel with EtOAc/heptane (1:10) to give compound 37d. Mass Spectrum (LCMS, ESI pos.): Calcd. For $C_{14}H_{17}FO_2$: 237.1 [M+H]⁺; found: 236.9.

(E) (S)-methyl 3-cyclopropyl-3-(3-((E)-2-((1r,4S)-4-(2-fluoro-5-methoxyphenyl)cyclohexyl) vinyl)phenyl)propanoate, 37e

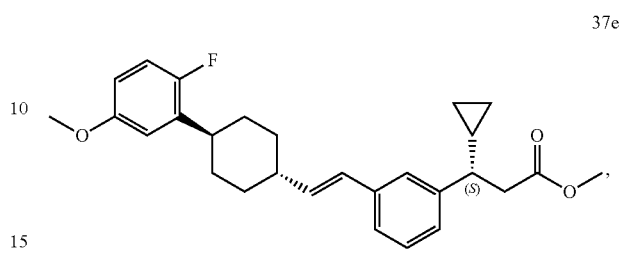

37e

To a solution of (S)-methyl 3-cyclopropyl-3-(3-((dimethoxyphosphoryl)methyl)phenyl) propanoate, cpd 37c (326 mg, 1.0 mmol) and ((1r,4r)-4-(2-fluoro-5-methoxyphenyl) cyclohexanecarbaldehyde, cpd 37d (236 mg, 1.0) in THF (5 mL) was added 15-crown-5 (220 mg, 1.0 mmol) and NaH (100 mg, 2.5 mmol) at 0° C. under a nitrogen atmosphere. The resulting solution was stirred for 10 h at 30° C. and concentrated. The residue was purified over silica gel EtOAc/heptane (1:10) to give compound 37e. Mass Spectrum (LCMS, ESI pos.): Calcd. for $C_{28}H_{33}FO_3$: 437.2 [M+H]⁺; found: 437.3.

(F) (S)-3-cyclopropyl-3-(3-((E)-2-((1r,4S)-4-(2-fluoro-5-methoxyphenyl)cyclohexyl) vinyl)phenyl) propanoic acid, Cpd 28

To a solution of (S)-methyl 3-cyclopropyl-3-(3-((E)-2-((1r,4S)-4-(2-fluoro-5-methoxyphenyl)cyclohexyl)vinyl) phenyl)propanoate, cpd 37e (150 mg, 0.34 mmol) in THF (5 mL) and water (5 mL) was added LiOH.H₂O (50 mg, 1.2 mmol). The reaction mixture was stirred at 30° C. for 24 h and treated with ethyl acetate (50 mL). The pH of the mixture was adjusted to 6-7 with 3N HCl. The resulting mixture was washed with brine, dried over MgSO₄, and concentrated. The crude product obtained was re-crystallized from ethyl acetate/n-hexanes to give compound 28. ¹H NMR (300 MHz, CDCl₃) δ (ppm): 7.21-7.25 (m, 3H), 7.08-7.20 (m, 1H), 6.93-6.96 (m, 1H), 6.75-6.90 (m, 1H), 6.65-6.69 (m, 1H), 6.36-6.41 (m, 1H), 6.18-6.20 (m, 1H), 3.75-3.78 (m, 3H), 2.79-2.82 (m, 3H), 2.35-2.38 (m, 1H), 2.10-2.30 (m, 1H), 1.94-2.01 (m, 4H), 1.37-1.57 (m, 4H), 1.00-1.05 (m, 1H), 0.58-0.61 (m, 1H), 0.42-0.45 (m, 1H), 0.28-0.33 (m, 1H), 0.16-0.19 (m, 1H). Mass Spectrum (LCMS, ESI pos.): Calcd. for $C_{27}H_{31}FO_3$: 421.2 [M–H]⁺; found: 421.2.

Example 38

(S)-3-Cyclopropyl-3-(3-(2-((1r,4R)-4-(2-fluoro-5-methoxyphenyl)cyclohexyl)ethyl)phenyl) propanoic acid, Cpd 36

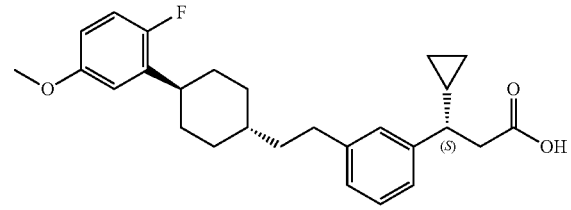

(A) (S)-methyl 3-cyclopropyl-3-(3-(2-((1r,4R)-4-(2-fluoro-5-methoxyphenyl) cyclohexyl)ethyl)phenyl) propanoate, 38a

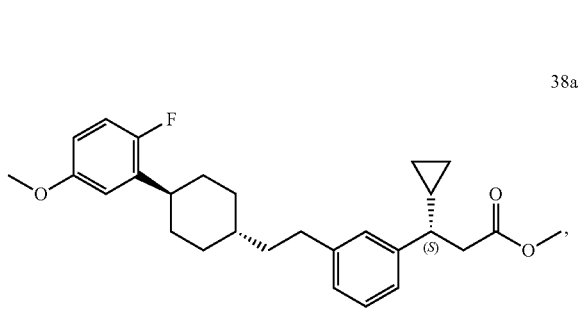

38a

A mixture of (S)-methyl 3-cyclopropyl-3-(3-((E)-2-((1r,4S)-4-(2-fluoro-5-methoxyphenyl)cyclohexyl)vinyl)phenyl)propanoate, cpd 37e (160 mg, 0.37 mmol) and 10% Pd/C (4 mg) in ethanol (20 mL) was stirred overnight at 40° C. under a hydrogen (3.5 atm) atmosphere. The resulting mixture was concentrated and the residue obtained was purified over silica with EtOAc/petroleum ether (15-50%) to give compound 38a. Mass Spectrum (LCMS, ESI pos.): Calcd. for $C_{28}H_{35}FO_3$: 439.2 [M+H]$^+$; found: 439.3.

(B) (S)-3-cyclopropyl-3-(3-(2-((1r,4R)-4-(2-fluoro-5-methoxyphenyl)cyclohexyl)ethyl)phenyl) propanoic acid, Cpd 36

Compound 36 was prepared from (S)-methyl 3-cyclopropyl-3-(3-(2-((1r,4R)-4-(2-fluoro-5-methoxyphenyl)cyclohexyl)ethyl)phenyl)propanoate cpd 38a following the methods described in Example 37, Step F. $^1$H NMR (300 MHz, DMSO-d$_6$) δ (ppm): 11.95 (brs, 1H), 7.18-7.22 (m, 1H), 7.02-7.08 (m, 4H), 6.74-6.83 (m, 2H), 3.73 (s, 3H), 2.51-2.74 (m, 5H), 2.26-2.29 (m, 1H), 1.89-2.00 (m, 2H), 1.76-1.79 (m, 2H), 1.47-1.56 (m, 4H), 1.25-1.39 (m, 1H), 0.99-1.19 (m, 3H), 0.49-0.52 (m, 1H), 0.23-0.40 (m, 2H), 0.11-0.14 (m, 1H). Mass Spectrum (LCMS, ESI pos.): Calcd. for $C_{27}H_{33}FO_3$: 425.2 [M+H]$^+$; found: 425.1.

Example 39

(S)-3-Cyclopropyl-3-(3-((((1r,4 S)-4-(2-fluoro-5-methoxyphenyl)cyclohexyl)methyl)amino)phenyl) propanoic acid, Cpd 40

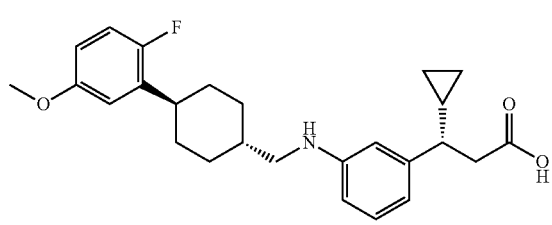 [SMILES: COc1ccc(F)c([C@H]2CC[C@H](CNc3cccc([C@@H](CC(=O)O)C4CC4)c3)CC2)c1]

(A) (S)-Methyl 3-cyclopropyl-3-(3-((diphenylmethylene)amino)phenyl)propanoate, 39a

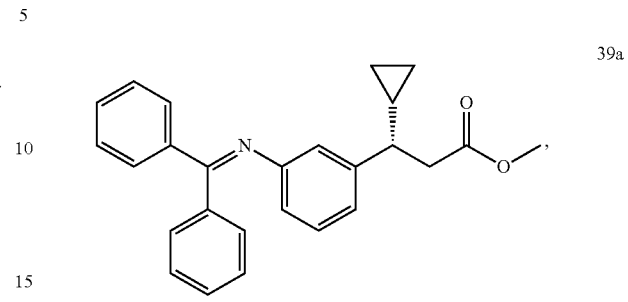

39a

A mixture of (S)-3-(1-cyclopropyl-2-methoxyethyl)phenyl trifluoromethanesulfonate, cpd 37a (1.0 g, 2.8 mmol), benzophenone imine (0.62 g, 3.4 mmol), Pd$_2$(dba)$_3$.CHCl$_3$ (88 mg, 0.08 mmol), K$_3$PO$_4$ (1.5 g, 7.1 mmol) and t-BuXphos (0.11 g, 0.25 mmol) in ethylene glycol dimethyl ether (6 mL) was stirred overnight at 80° C. under a nitrogen atmosphere. The reaction mixture was allowed to cool to RT, treated with 20 mL of saturated aq. NH$_4$Cl and extracted with ethyl acetate (3×15 mL). The organic layers were combined, dried over Na$_2$SO$_4$ and concentrated. The residue obtained was purified on silica gel with EtOAc/petroleum ether (0-15%) to give compound 39a. Mass Spectrum (LCMS, ESI pos.): Calcd. for $C_{26}H_{25}NO_2$: 384.2 [M+H]$^+$; found: 384.1.

(B) (S)-Methyl 3-(3-aminophenyl)-3-cyclopropylpropanoate, 39b

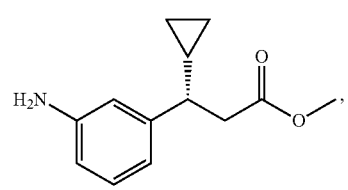

39b

To a solution of (S)-methyl 3-cyclopropyl-3-(3-(diphenylmethyleneamino)phenyl) propanoate, cpd 39a (0.50 g, 1.3 mmol) in THF (15 mL), conc. HCl (2 mL) was added. The resulting solution was stirred for 1 h at RT and neutralized with saturated aq. NaHCO$_3$. The resulting solution was extracted with ethyl acetate (3×15 mL). The organic layers were combined and dried Na$_2$SO$_4$ and concentrated. The residue obtained was purified on silica gel with EtOAc/petroleum ether (0-30%) to give compound 39b. Mass Spectrum (LCMS, ESI pos.): Calcd. for $C_{13}H_{17}NO_2$: 220.1 [M+H]$^+$; found: 219.9.

(C) (S)-Methyl 3-cyclopropyl-3-(3-((((1r,4S)-4-(2-fluoro-5-methoxyphenyl)cyclohexyl)methyl)amino)phenyl)propanoate, 39c

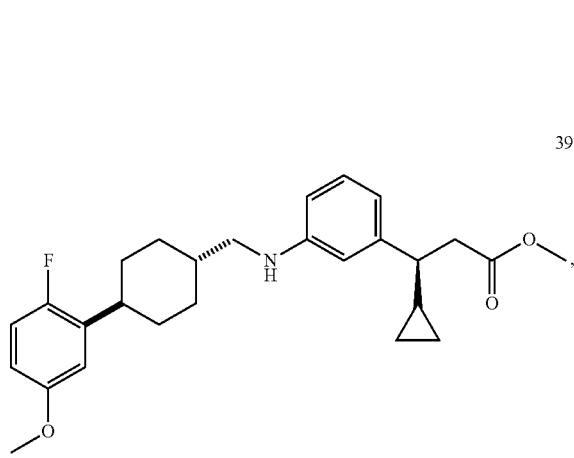

To a solution of (1r,4r)-4-(2-fluoro-5-methoxyphenyl)cyclohexanecarbaldehyde, cpd 37d (70 mg, 0.30 mmol) and (S)-methyl 3-(3-aminophenyl)-3-cyclopropylpropanoate, cpd 39b (65 mg, 0.30 mmol) in dichloromethane (5 mL), NaCNBH$_3$ (37 mg, 0.59 mmol) was added. The resulting solution was stirred for 2 h at RT, treated with 10 mL of saturated aq. NH$_4$Cl and extracted with dichloromethane (3×10 mL). The organic layers were combined, dried over Na$_2$SO$_4$ and concentrated. The residue obtained was purified on silica gel with ethyl acetate/petroleum ether (0-10%) to give compound 39c. Mass Spectrum (LCMS, ESI pos.): Calcd. for C$_{27}$H$_{34}$FNO$_3$: 440.3 [M+H]$^+$; found: 440.2.

(D) (S)-3-Cyclopropyl-3-(3-((((1r,4S)-4-(2-fluoro-5-methoxyphenyl)cyclohexyl)methyl)amino) phenyl)propanoic acid, Cpd 40

Compound 40 was prepared from (S)-methyl 3-cyclopropyl-3-(3-(((1r,4S)-4-(2-fluoro-5-methoxyphenyl)cyclohexyl)methylamino)phenyl)propanoate, cpd 39c, following the methods described in Example 37, Step F. $^1$H NMR (300 MHz, CDCl$_3$) δ (ppm): 7.09-7.15 (m, 1H), 6.89-6.95 (m, 1H), 6.73-6.76 (m, 1H), 6.63-6.68 (m, 1H), 6.52-6.59 (m, 1H), 6.45-6.51 (m, 2H), 3.77 (s, 3H), 3.01 (d, J=6.6 Hz, 2H), 2.76-2.82 (m, 3H), 2.28-2.31 (m, 1H), 1.91-2.01 (m, 4H), 1.42-1.51 (m, 2H), 1.17-1.28 (m, 3H), 1.01-1.04 (m, 1H), 0.55-0.58 (m, 1H), 0.43-0.46 (m, 1H), 0.26-0.29 (m, 1H), 0.17-0.20 (m, 1H). Mass Spectrum (LCMS, ESI pos.): Calcd. for C$_{26}$H$_{32}$FNO$_3$: 424.2 [M−H]$^+$; found: 424.1.

Example 40

(S)-3-cyclopropyl-3-(3-((((1s,4R)-4-(2-fluoro-5-methoxyphenyl)cyclohexyl)methyl)amino)phenyl)propanoic acid, Cpd 47

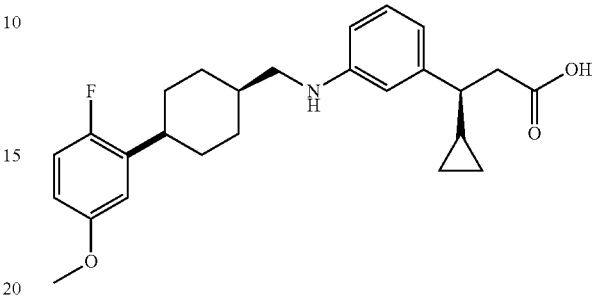

(A) (1s,4s)-4-(2-fluoro-5-methoxyphenyl)cyclohexanecarbaldehyde, 40a

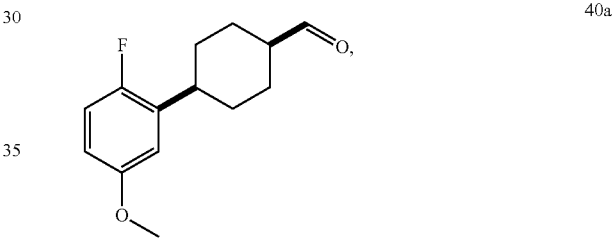

Compound 40a was prepared from ((1s,4s)-4-(2-fluoro-5-methoxyphenyl)cyclohexyl)methanol, cpd 8a-2 (Example 8, Step A) following the methods described in Example 37, Step D.

(B) (S)-3-cyclopropyl-3-(3-((((1s,4R)-4-(2-fluoro-5-methoxyphenyl)cyclohexyl) methyl)amino)phenyl)propanoic acid, Cpd 47

Compound 47 was prepared from (1s,4s)-4-(2-fluoro-5-methoxyphenyl)cyclohexane carbaldehyde, cpd 40a and (S)-methyl 3-(3-aminophenyl)-3-cyclopropylpropanoate, cpd 39b (Example 39) following the methods described in Example 39, Steps C and D. $^1$H NMR (300 MHz, CDCl$_3$) δ (ppm): 7.09-7.15 (m, 1H), 6.89-6.95 (m, 1H), 6.75-6.79 (m, 1H), 6.64-6.68 (m, 1H), 6.57-6.59 (m, 1H), 6.47-6.51 (m, 2H), 3.77 (s, 3H), 3.21 (d, J=7.5 Hz, 2H), 3.01 (d, J=6.6 Hz, 1H), 2.75-2.86 (m, 1H), 2.77 (d, J=7.5 Hz, 2H), 2.28-2.31 (m, 1H), 1.95-2.01 (m, 2H), 1.82-1.85 (m, 1H), 1.63-1.72 (m, 3H), 1.35-1.43 (m, 1H), 1.21-1.25 (m, 1H), 1.01-1.03 (m, 1H), 0.55-0.58 (m, 1H), 0.41-0.44 (m, 1H), 0.26-0.29 (m, 1H), 0.17-0.20 (m, 1H). Mass Spectrum (LCMS, ESI pos.): Calcd. for C$_{26}$H$_{32}$FNO$_3$: 426.2 [M+H]$^+$; found: 426.2.

Example 41

5-((S)-2-Cyclopropyl-2-(3-(((1r,4S)-4-(2-fluoro-5-methoxyphenyl)cyclohexyl)methoxy)phenyl)ethyl)-1H-tetrazole, Cpd 17

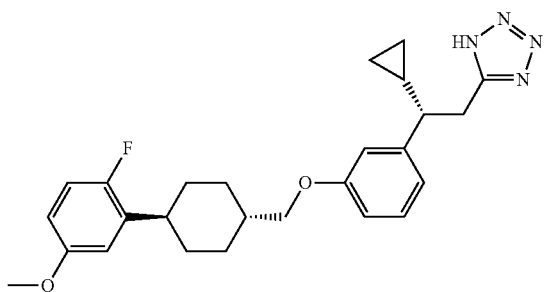 [SMILES: COc1ccc(F)c([C@H]2CC[C@H](COc3cccc([C@@H](Cc4nnn[nH]4)C4CC4)c3)CC2)c1]

(A) (S)-Methyl 3-(3-(benzyloxy)phenyl)-3-cyclopropylpropanoate, 41a

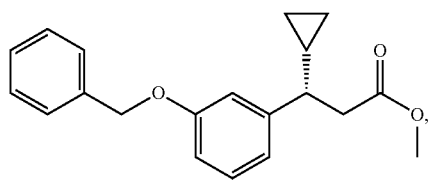

A mixture of (S)-methyl 3-cyclopropyl-3-(3-hydroxyphenyl)propanoate (500 mg, 2.270 mmol), (bromomethyl)benzene (388 mg, 2.269 mmol) and potassium carbonate (627 mg, 4.537 mmol) in acetonitrile (100 mL) was stirred overnight at 25° C. The reaction mixture was treated with 200 mL of water and extracted with ethyl acetate (3×100 mL). The organic layers were combined and concentrated. The residue obtained was purified on silica gel with ethyl acetate/petroleum ether (0-10%) to obtain compound 41a as colorless oil. $^1$H NMR (300 MHz (CDCl$_3$) δ(ppm): 7.27-7.45 (m, 5H), 7.18 (d, J=7.7 Hz, 1H), 6.76-6.89 (m, 3H), 5.03 (s, 2H), 3.58 (s, 3H), 2.65-2.78 (m, 2H), 2.32 (dd, J$_1$=9.7 Hz, J$_2$=7.5 Hz, 1H), 0.91-1.03 (m, 1H), 0.46-0.60 (m, 1H), 0.30-0.39 (m, 1H), 0.18-0.23 (m, 1H), 0.09-0.11 (m, 1H).

(B) (S)-3-(3-(Benzyloxy)phenyl)-3-cyclopropylpropanoic acid, 41b

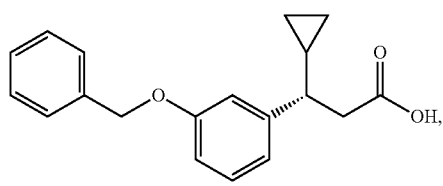

A mixture of (S)-methyl 3-(3-(benzyloxy)phenyl)-3-cyclopropylpropanoate, cpd 41a (320 mg, 1.836 mmol) and LiOH.H$_2$O (400 mg, 9.532 mmol) in water (10 mL), methanol (2 mL) and tetrahydrofuran (20 mL) was stirred overnight at room temperature. The mixture was concentrated and then diluted with 50 mL of water. The pH of the solution was adjusted to 4~5 with 1M HCl solution. The resultant solids were collected by filtration to obtain compound 41b as a white solid. Mass Spectrum (LCMS, ESI pos.): Calcd. for C$_{19}$H$_{20}$O$_3$: 297.1 [M+H]$^+$; found: 297.1.

(C) (S)-3-(3-(Benzyloxy)phenyl)-3-cyclopropylpropanamide, 41c

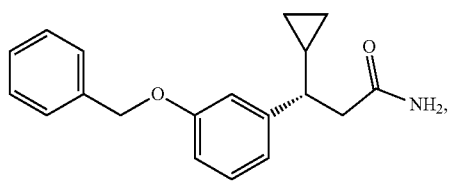

A mixture of ammonium chloride (359 mg, 6.71 mmol) and trimethylamine (1.02 g, 10.1 mmol) in dichloromethane (20 mL) was stirred for 5 min at RT and treated with 3-(3-(benzyloxy)phenyl)-3-cyclopropylpropanoic acid, cpd 41b (956 mg, 3.23 mmol) and O-(7-azabenzotriazol-1-yl)-N,N,N,N-tetramethyluronium hexafluorophosphate (2.57 g, 6.76 mmol). The resulting mixture was stirred overnight at RT and treated with 20 mL of saturated aq. NaHCO$_3$ solution. The resulting solution was extracted with ethyl acetate (3×100 mL). The organic phases were combined, dried over Na$_2$SO$_4$ and concentrated. The residue obtained was purified on silica gel with ethyl acetate/petroleum ether (0-80%) to give compound 41c. Mass Spectrum (LCMS, ESI pos.): Calcd. for C$_{19}$H$_{21}$NO$_2$: 296.4 [M+H]$^+$; found: 296.2.

(D) (S)-3-(3-(Benzyloxy)phenyl)-3-cyclopropylpropanenitrile, 41d

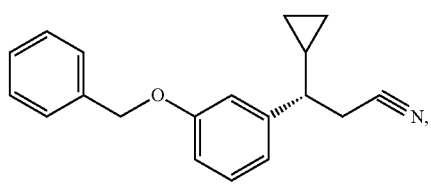

To a mixture of (S)-3-(3-(benzyloxy)phenyl)-3-cyclopropylpropanamide, cpd 41c (0.10 mg, 0.34 mmol) and triethylamine (86 mg, 0.85 mmol) in dichloromethane (10 mL) 2,2,2-trifluoroacetic anhydride (0.11 mg, 0.51 mmol) was added drop-wise with stirring at 0° C. The resulting solution was stirred for 10 min at 0° C. and treated with 5 mL of water. The resulting solution was extracted with ethyl acetate (3×10 mL). The organic layers were combined and concentrated to give compound 41d. $^1$H NMR (300 MHz, CDCl$_3$) δ (ppm): 7.51-7.23 (m, 5H), 6.96-6.83 (m, 1H), 5.08 (s, 3H), 2.74 (d, J=6.8 Hz, 2H), 2.10-2.20 (m, 1H), 1.10-1.20 (m, 1H), 0.70-0.80 (m, 1H), 0.32-0.42 (m, 1H), 0.52-0.62 (m, 1H), 0.10-0.20 (m, 1H).

(E) (S)-3-Cyclopropyl-3-(3-hydroxyphenyl)propanenitrile, 41e

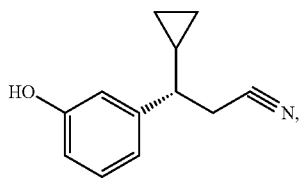

A mixture of (S)-3-(3-(benzyloxy)phenyl)-3-cyclopropylpropanenitrile, cpd 41d (2 g, 7 mmol) and 10% Pd/C (1.0 g) in MeOH (200 mL) was stirred overnight at RT. The reaction mixture was filtered and the filtrate was concentrated to give compound 41e. Mass Spectrum (LCMS, ESI pos.): Calcd. for $C_{12}H_{13}NO$: 188.1 $[M+H]^+$; found: 188.0.

(F) (S)-3-cyclopropyl-3-(3-(((1r,4S)-4-(2-fluoro-5-methoxyphenyl)cyclohexyl) methoxy)phenyl)propanenitrile, 41f

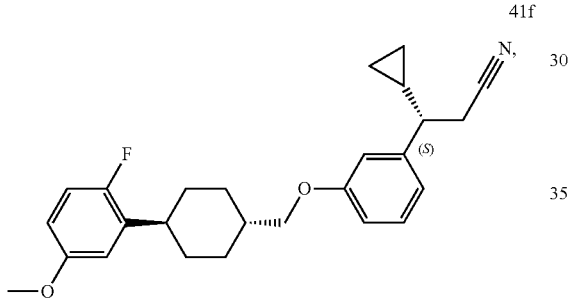

To a solution of ((1r,4r)-4-(2-fluoro-5-methoxyphenyl)cyclohexyl)methanol, cpd 8a-1 (150 mg, 0.63 mmol, Example 8, Step A), (S)-3-cyclopropyl-3-(3-hydroxyphenyl) propanenitrile, cpd 41e (140 mg, 0.75 mmol), Ph$_3$P (330 mg, 1.2 mmol) in tetrahydrofuran (10 mL) was added (E)-di-tert-butyl diazene-1,2-dicarboxylate (173 mg, 0.751 mmol) in THF at 0° C. The resulting mixture was stirred 0.5 h at RT and overnight at 60° C. The reaction mixture was allowed to cool to RT and treated with 10 mL of water. The resulting solution was extracted with ethyl acetate (3×10 mL). The organic layers were combined, dried over Na$_2$SO$_4$ and concentrated. The residue obtained was then purified on silica gel with ethyl acetate/petroleum ether (0-10%) to give compound 41f. Mass Spectrum (LCMS, ESI pos.): Calcd. for $C_{26}H_{30}FNO_2$: 408.2 $[M+H]^+$; found: 408.2.

(G) 5-((S)-2-cyclopropyl-2-(3-(((1r,4S)-4-(2-fluoro-5-methoxyphenyl)cyclohexyl) methoxy)phenyl) ethyl)-1H-tetrazole, Cpd 17

A mixture of (S)-3-cyclopropyl-3-(3-(((1r,4S)-4-(2-fluoro-5-methoxyphenyl)cyclohexyl)methoxy)phenyl)propanenitrile, cpd 41f (233 mg, 0.572 mmol), azidotrimethylsilane (328 mg, 2.84 mmol) and bis(tri-n-butyltin) oxide (136 mg, 0.228 mmol) in toluene (2 mL) was stirred overnight at 110° C. under a nitrogen atmosphere. The reaction mixture was allowed to cool to RT and treated with 5 mL of water. The resulting solution was extracted with ethyl acetate (3×5 mL). The organic phases were combined, dried over Na$_2$SO$_4$ and concentrated. This residue obtained was purified by reverse phase flash chromatography using Flash Spherical C18 column (120 g, 20-35 μm, 100 Å) eluting with CH$_3$CN:H$_2$O (0.05% TFA) to give compound 17. $^1$H NMR (400 MHz, CD$_3$OD) δ (ppm): 7.14-7.16 (m, 1H), 6.90-6.95 (m, 1H), 6.80-6.82 (m, 1H), 6.69-6.76 (m, 4H), 3.76-3.78 (m, 5H), 3.31-3.39 (m, 2H), 2.83-3.30 (m, 1H), 2.27-2.30 (m, 1H), 2.00-2.04 (m, 2H), 1.88-1.91 (m, 3H), 1.57-1.60 (m, 2H), 1.26-1.30 (m, 2H), 1.10-1.20 (m, 1H), 0.56-0.57 (m, 1H), 0.43-0.44 (m, 1H), 0.08-0.14 (m, 2H). Mass Spectrum (LCMS, ESI pos.): Calcd. for $C_{26}H_{31}FN_4O_2$: 451.2 $[M+H]^+$; found: 451.1.

Example 42

5-((S)-2-Cyclopropyl-2-(3-(((1s,4R)-4-(2-fluoro-5-methoxyphenyl)cyclohexyl)methoxy)phenyl)ethyl)-1H-tetrazole, Cpd 39

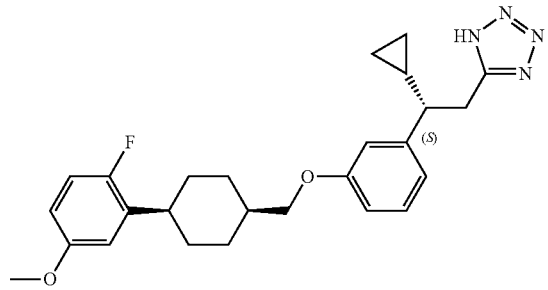

(A) (S)-3-Cyclopropyl-3-(3-(((1s,4R)-4-(2-fluoro-5-methoxyphenyl)cyclohexyl) methoxy)phenyl)propanamide, 42a

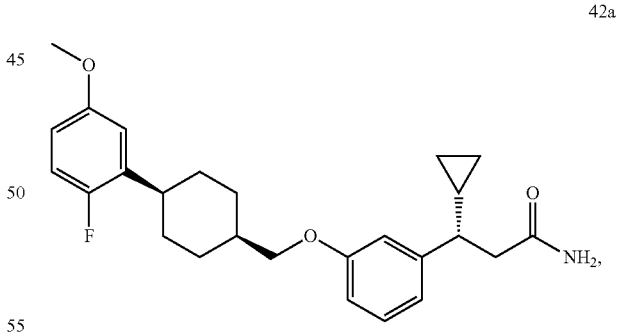

A mixture of ammonium chloride (363 mg, 6.78 mmol) and trimethylamine (206 mg, 2.04 mmol) in dichloromethane (10 mL) was stirred for 5 min at RT. (S)-3-cyclopropyl-3-(3-(((1s,4R)-4-(2-fluoro-5-methoxyphenyl)cyclohexyl) methoxy) phenyl)propanoic acid (289 mg, 0.678 mmol, Example 29) and O-(7-azabenzotriazol-1-yl)-N,N,N,N-tetramethyluronium hexafluorophosphate (387 mg, 1.02 mmol) were then added and the resulting mixture was stirred overnight at RT. The reaction was then quenched by the addition of 10 mL of water and extracted with ethyl acetate (3×30 mL). The organic layers were combined and concentrated. The residue obtained was purified on silica gel with ethyl acetate/petroleum ether (0-50%) to give compound 42a. Mass Spectrum (LCMS, ESI pos.): Calcd. for $C_{26}H_{32}FNO_3$: 426.5 [M+H]$^+$; found: 426.2.

(B) (S)-3-Cyclopropyl-3-(3-(((1s,4r)-4-(2-fluoro-5-methoxyphenyl)cyclohexyl) methoxy)phenyl)propanenitrile, 42b

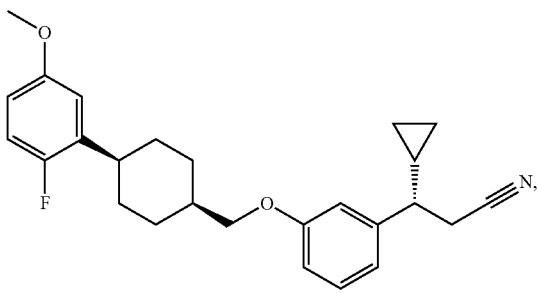

To a solution of 5-methoxyphenyl)cyclohexyl)methoxy) phenyl)propanamide, cpd 42a (200 mg, 0.470 mmol) and triethylamine (166 mg, 1.64 mmol) in DCM (10 mL), trifluoroacetic anhydride (197 mg, 0.938 mmol) was added drop-wise with stirring at 0° C. The resulting solution was stirred for 0.5 h at 0° C. and treated with 50 mL of saturated aq. NaHCO$_3$ solution. The resulting solution was extracted with ethyl acetate (3×50 mL). The organic layers were combined, dried over Na$_2$SO$_4$ and concentrated. The residue obtained was purified over silica with ethyl acetate/petroleum ether (1:5) to give compound 42b. Mass Spectrum (LCMS, ESI pos.): Calcd. for $C_{26}H_{30}FNO_2$: 408.2 [M+H]$^+$; found: 408.2.

(C) 5-((S)-2-cyclopropyl-2-(3-(((1s,4R)-4-(2-fluoro-5-methoxyphenyl)cyclohexyl) methoxy)phenyl) ethyl)-1H-tetrazole, Cpd 39

A mixture of (S)-3-cyclopropyl-3-(3-(((1s,4R)-4-(2-fluoro-5-methoxyphenyl)cyclohexyl) methoxy)phenyl)propanenitrile, cpd 42b (0.140 g, 0.344 mmol), azidotrimethylsilane (118 mg, 1.02 mmol) and bis(tri-n-butyltin) oxide (41.0 mg, 0.069 mmol) in toluene (2 mL) was stirred overnight at 110° C. in a sealed tube. The reaction mixture was allowed to cool to RT and treated with 10 mL of water. The resulting solution was extracted with ethyl acetate (3×10 mL). The organic phase was combined, dried over Na$_2$SO$_4$ and concentrated. The residue obtained was purified on silica gel with ethyl acetate/petroleum ether (1:1) to give compound 39. $^1$H NMR (300 MHz, DMSO-d$_6$) δ (ppm): 7.12-7.20 (m, 1H), 7.04 (dd, J$_1$=10.1 Hz, J$_2$=8.9 Hz, 1H), 6.92 (dd, J$_1$=6.2 Hz, J$_2$=3.1 Hz, 1H), 6.70-6.84 (m, 4H), 4.04 (d, J=7.5 Hz, 2H), 3.73 (s, 3H), 3.30-3.33 (m, 2H), 2.80-2.85 (m, 1H), 2.31 (q, J=8.0 Hz, 1H), 2.05-2.20 (m, 1H), 1.80-1.98 (m, 2H), 1.53-1.76 (m, 6H), 1.09-1.24 (m, 1H), 0.26-0.59 (m, 2H), 0.01-0.14 (m, 2H). Mass Spectrum (LCMS, ESI pos.): Calcd. for $C_{26}H_{31}FN_4O_2$: 451.2 [M+H]$^+$; found: 451.3.

Example 43

(S)-3-cyclopropyl-3-(2-(((1s,4R)-4-(2-ethoxy-5-fluoropyridin-4-yl)cyclohexyl)methoxy)pyridin-4-yl) propanoic acid, Cpd 48

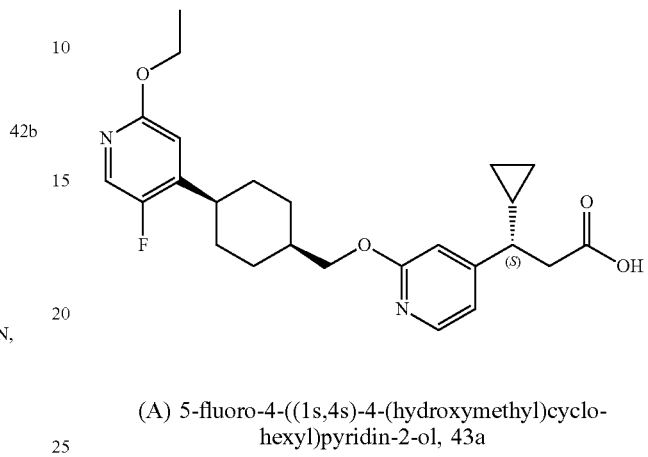

(A) 5-fluoro-4-((1s,4s)-4-(hydroxymethyl)cyclohexyl)pyridin-2-ol, 43a

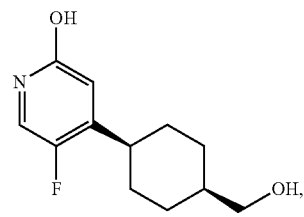

A mixture of ((1 s,4s)-4-(5-fluoro-2-methoxypyridin-4-yl)cyclohexyl)methanol (0.30 g, 1.2 mmol, Example 1, Step C) and conc. HCl (3 mL) in 1,4-dioxane (3 mL) was stirred overnight at 100° C. The mixture was concentrated and then diluted with 10 mL of water. The pH of the solution was adjusted to 7 with saturated aq. NaHCO$_3$. The resultant solids were collected to give compound 43a. Mass Spectrum (LCMS, ESI pos.): Calcd. for $C_{12}H_{16}FNO_2$: 226.1 [M+H]$^+$; found: 225.8.

(B) ((1 s,4s)-4-(2-ethoxy-5-fluoropyridin-4-yl)cyclohexyl)methanol, 43b

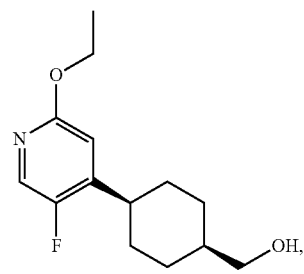

A mixture of 5-fluoro-4-((1s,4s)-4-(hydroxymethyl)cyclohexyl)pyridin-2-ol, cpd 43a (0.27 g, 1.2 mmol), iodoethane (0.28 mg, 1.8 mmol), and silvercarbonate (0.43 mg, 1.5 mmol) in toluene (5 mL) was stirred for 5 h at 60° C. The solution was filtered and concentrated. The residue obtained was purified on silica gel with ethyl acetate/petroleum ether (0-30%) to give compound 43b. Mass Spectrum (LCMS, ESI pos.): Calcd. for $C_{14}H_{20}FNO_2$: 254.1 $[M+H]^+$; found: 253.9.

(C) (S)-methyl 3-cyclopropyl-3-(2-(((1s,4R)-4-(2-ethoxy-5-fluoropyridin-4-yl)cyclohexyl) methoxy) pyridin-4-yl)propanoate, 43c

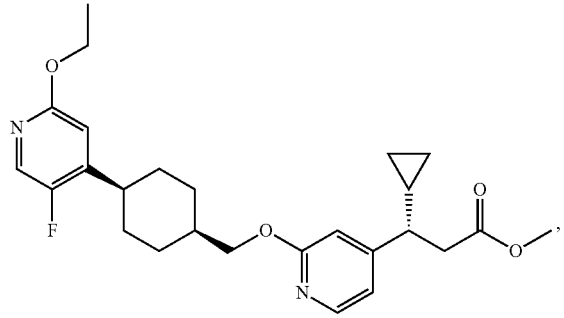

A solution of ((1s,4s)-4-(2-ethoxy-5-fluoropyridin-4-yl) cyclohexyl)methanol, cpd 43b (99 mg, 0.392 mmol) and (S)-methyl 3-(2-chloropyridin-4-yl)-3-cyclopropylpropanoate (47 mg, 0.196 mmol), in tetrahydrofuran (1.5 mL) was stirred for 10 min at 70° C. Potassium tert-butoxide (0.392 mL, 0.392 mmol, 1M in THF) was then added at 70° C. and stirring was continued for 6 h at 70° C. The reaction mixture was allowed to cool to RT and treated with 2 mL of water. The resulting solution was extracted with ethyl acetate (3×2 mL). The organic phases were combined, dried over $Na_2SO_4$ and concentrated to give compound 43c. Mass Spectrum (LCMS, ESI pos.): Calcd. for $C_{26}H_{33}FN_2O_4$: 457.2 $[M+H]^+$; found: 457.2.

(D) (S)-3-cyclopropyl-3-(2-(((1s,4R)-4-(2-ethoxy-5-fluoropyridin-4-yl)cyclohexyl) methoxy)pyridin-4-yl)propanoic acid, Cpd 48

Compound 48 was prepared from (S)-methyl 3-cyclopropyl-3-(2-(((1s,4R)-4-(2-ethoxy-5-fluoropyridin-4-yl)cyclohexyl) methoxy)pyridin-4-yl)propanoate, cpd 43c, according to the method described in Example 1, Step E. $^1$H NMR (300 MHz, DMSO-$d_6$) δ (ppm): 11.48 (br, 1H), 8.00-8.04 (m, 2H), 6.90 (d, J=5.3 Hz, 1H), 6.67-6.84 (m, 2H), 4.17-4.39 (m, 3H), 4.08 (d, J=6.3 Hz, 1H), 2.62-2.84 (m, 3H), 2.18-2.27 (m, 1H), 1.77-1.98 (m, 4H), 1.41-1.75 (m, 4H), 1.12-1.35 (m, 4H), 0.97-0.99 (m, 1H), 0.47-0.52 (m, 1H), 0.09-0.41 (m, 3H). Mass Spectrum (LCMS, ESI pos.): Calcd. for $C_{25}H_{31}FN_2O_4$: 443.2 $[M+H]^+$; found: 443.1.

Example 44

(R)-3-Cyclopropyl-3-(2-(((1r,4R)-4-(5-fluoro-2-methoxypyridin-4-yl)cyclohexyl) methoxy)pyridin-4-yl)propanoic acid, Cpd 24 and (S)-3-Cyclopropyl-3-(2-(((1r,4S)-4-(5-fluoro-2-methoxypyridin-4-yl)cyclohexyl) methoxy)pyridin-4-yl)propanoic acid, Cpd 25

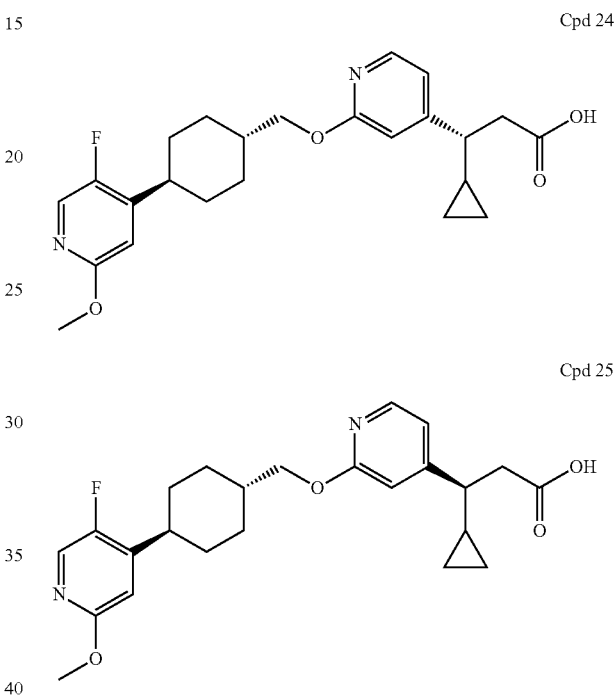

3-Cyclopropyl-3-(2-(((1r,4r)-4-(5-fluoro-2-methoxypyridin-4-yl)cyclohexyl)methoxy)pyridin-4-yl)propanoic acid, cpd 8 (Example 9) was subjected to preparative SFC using Chiralpak IA 4.6×150 mm, 5 μm column with a gradient $CO_2$/IPA 60/40 to give compounds 24 and 25.

Cpd 24: $^1$H NMR (400 MHz, DMSO-$d_6$) δ (ppm): 12.10 (br, 1H), 8.00-8.02 (m, 2H), 6.88 (d, J=5.2 Hz, 1H), 6.75 (d, J=5.2 Hz, 1H), 6.68 (s, 1H), 4.06 (d, J=6.4 Hz, 2H), 3.79 (s, 3H), 2.78 (t, J=12.4 Hz, 1H), 2.65 (d, J=7.6 Hz, 2H), 2.20-2.24 (m, 1H), 1.90-1.93 (m, 2H), 1.79-1.82 (m, 3H), 1.51 (dd, $J_1$=12.4 Hz, $J_2$=23.2 Hz, 2H), 1.19-1.24 (m, 2H), 0.95-0.98 (m, 1H), 0.46-0.50 (m, 1H), 0.23-0.34 (m, 2H), 0.13-0.16 (m, 1H). Mass Spectrum (LCMS, ESI pos.): Calcd. for $C_{24}H_{29}FN_2O_4$: 429.2 $(M+H)^+$, found 429.1.

Cpd 25: $^1$H NMR (400 MHz, DMSO-$d_6$) δ (ppm): 12.10 (br, 1H), 8.00-8.02 (m, 2H), 6.87-6.89 (m, 1H), 6.75 (d, J=5.2 Hz, 1H), 6.68 (s, 1H), 4.06 (d, J=6.4 Hz, 2H), 3.79 (s, 3H), 2.78 (t, J=12.4 Hz, 1H), 2.65 (d, J=7.6 Hz, 2H), 2.20-2.22 (m, 1H), 1.90-1.93 (m, 2H), 1.79-1.82 (m, 3H), 1.51 (dd, $J_1$=12.4, $J_2$=23.2 Hz, 2H), 1.20 (dd, $J_1$=10.4 Hz, $J_2$=22.4 Hz, 2H), 0.96-0.98 (m, 1H), 0.48-0.50 (m, 1H), 0.23-0.36 (m, 2H), 0.13-0.16 (m, 1H). Mass Spectrum (LCMS, ESI pos.): Calcd. for $C_{24}H_{29}FN_2O_4$: 429.2 $(M+H)^+$, found 429.1.

Example 45

4-((1S,4r)-4-(((4-((S)-1-Cyclopropyl-2-(1H-tetrazol-5-yl)ethyl)pyridin-2-yl)oxy)methyl)cyclohexyl)-5-fluoro-2-methoxypyridine, Cpd 43

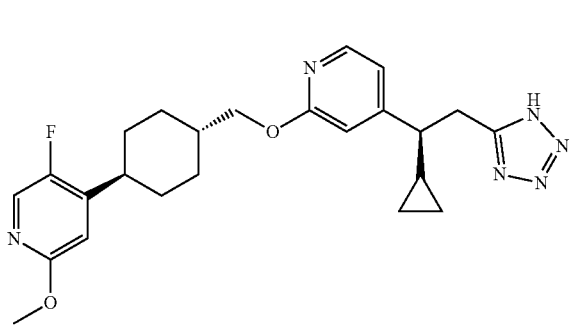 [SMILES: COc1cc([C@H]2CC[C@H](COc3cc([C@@H](Cc4nnn[nH]4)C4CC4)ccn3)CC2)c(F)cn1]

(A) (S)-3-Cyclopropyl-3-(2-(((1r,4S)-4-(5-fluoro-2-methoxypyridin-4-yl)cyclohexyl) methoxy)pyridin-4-yl)propanamide, 45a

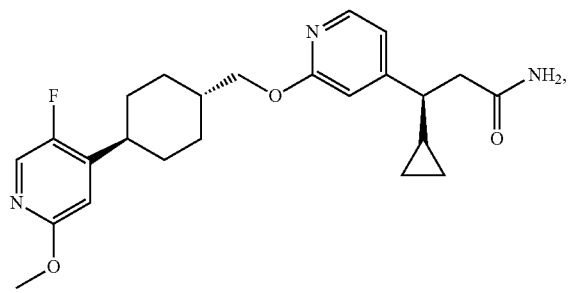

45a

A mixture of NH$_4$Cl (222 mg, 4.15 mmol) and N-ethyl-N-isopropylpropan-2-amine (162 mg, 1.25 mmol) in N,N-dimethylformamide (2 mL) was stirred for 5 min at RT. (S)-3-cyclopropyl-3-(2-(((1r,4S)-4-(5-fluoro-2-methoxypyridin-4-yl)cyclohexyl)methoxy)pyridin-4-yl)propanoic acid, compound 25 (0.180 g, 0.420 mmol, Example 44) and O-(7-azabenzotriazol-1-yl)-N,N,N,N-tetramethyluronium hexafluorophosphate (239 mg, 0.629 mmol) were then added. The resulting solution was stirred overnight at RT and treated with 20 mL of saturated aq. NaHCO$_3$ solution. The resulting solution was extracted with ethyl acetate (3×10 mL). The organic phases were combined, dried over Na$_2$SO$_4$ and concentrated. The residue obtained was purified on silica gel with ethyl acetate/petroleum ether (0-70%) to give compound 45a. Mass Spectrum (LCMS, ESI pos.): Calcd. for C$_{24}$H$_{30}$FN$_3$O$_3$: 428.5 (M+H)$^+$, found 428.2.

(B) (S)-3-Cyclopropyl-3-(2-(((1r,4S)-4-(5-fluoro-2-methoxypyridin-4-yl)cyclohexyl) methoxy)pyridin-4-yl)propanenitrile, 45b

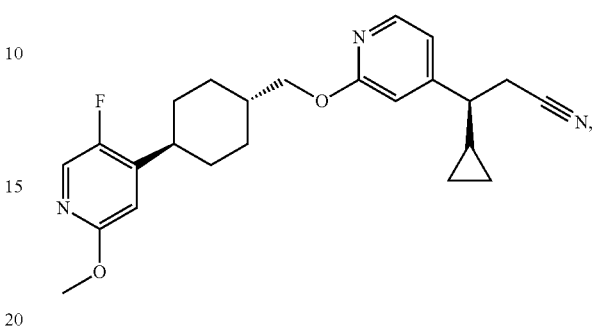

45b

A solution of (S)-3-cyclopropyl-3-(2-(((1r,4S)-4-(5-fluoro-2-methoxypyridin-4-yl)cyclohexyl)methoxy)pyridin-4-yl)propanamide, cpd 45a (0.150 mg, 0.351 mmol) and triethylamine (124 mg, 1.23 mmol) in dichloromethane (10 mL) was stirred for 5 min at 0° C. and treated with trifluoroacetic anhydride (147 mg, 0.702 mmol). After addition, the resulting solution was stirred for 10 min at 0° C. The reaction was then quenched by the addition of 10 mL of water. The resulting solution was extracted with dichloromethane (3×10 mL). The organic phases were combined, dried over Na$_2$SO$_4$ and concentrated. The residue obtained was purified on silica gel with ethyl acetate/petroleum ether (0-20%) to give compound 45b. Mass Spectrum (LCMS, ESI pos.): Calcd. for C$_{24}$H$_{28}$FN$_3$O$_2$: 410.2 (M+H)$^+$, found 410.0.

(C) 4-((1S,4r)-4-(((4-((S)-1-cyclopropyl-2-(1H-tetrazol-5-yl)ethyl)pyridin-2-yl)oxy)methyl)cyclohexyl)-5-fluoro-2-methoxypyridine, Cpd 43

A mixture of (S)-3-cyclopropyl-3-(2-(((1r,4S)-4-(5-fluoro-2-methoxypyridin-4-yl)cyclohexyl)methoxy)pyridin-4-yl)propanenitrile, 45b (88 mg, 0.215 mmol), azidotrimethylsilane (74.2 mg, 0.645 mmol) and bis(tri-n-butyltin) oxide (25.6 mg, 0.043 mmol) in toluene (2 mL) was stirred overnight at 110° C. under a nitrogen atmosphere in a sealed tube. The reaction was allowed to cool to RT and quenched with 5 mL of water. The resulting solution was extracted with ethyl acetate (3×5 mL). The organic phases were combined, dried over Na$_2$SO$_4$ and concentrated. The solid obtained was purified by reverse-phase flash chromatography on a Flash Spherical C18 column (120 g, 20-35 μm, 100 Å, Agela Technologies) with acetonitrile/water (0.5% TFA) gradient (20-50%) to give compound 43. $^1$H NMR (400 MHz, DMSO-d$_6$) δ (ppm): 7.99-8.06 (m, 2H), 6.85 (dd, J=5.3, 1.4 Hz, 1H), 6.76 (d, J=5.0 Hz, 1H), 6.68 (d, J=1.4 Hz, 1H), 4.06 (d, J=6.4 Hz, 2H), 3.80 (s, 3H), 3.31-3.35 (m, 2H), 2.70-2.81 (m, 1H), 2.30-2.34 (m, 1H), 1.91 (dd, J=13.2, 3.5 Hz, 2H), 1.80-1.84 (m, 3H), 1.44-1.58 (m, 2H), 1.05-1.28 (m, 3H), 0.45-0.49 (m, 1H), 0.35-0.38 (m, 1H), 0.05-0.15 (m, 2H). Mass Spectrum (LCMS, ESI pos.): Calcd. for C$_{24}$H$_{29}$FN$_6$O$_2$: 453.2 (M+H)$^+$, found 453.2.

Example 46

(2R,3R)-3-Cyclopropyl-3-(3-(((1r,4R)-4-(2-fluoro-5-methoxyphenyl)cyclohexyl) methoxy)phenyl)-2-methylpropanoic acid, Cpd 51, trifluoroacetic acid salt and (2S,3R)-3-Cyclopropyl-3-(3-(((1r,4R)-4-(2-fluoro-5-methoxyphenyl)cyclohexyl)methoxy)phenyl)-2-methylpropanoic acid Cpd 52, trifluoroacetic acid salt

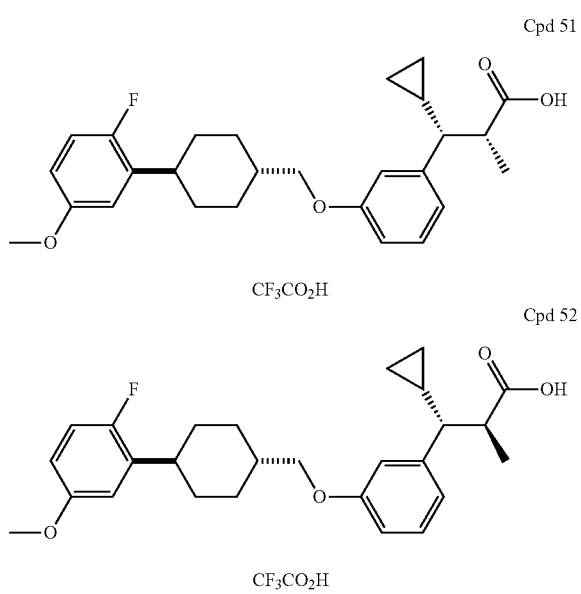

(A) (S)-Methyl 3-(3-((tert-butyldimethylsilyl)oxy)phenyl)-3-cyclopropylpropanoate, 46a

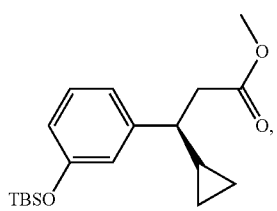

To a solution of (S)-methyl 3-cyclopropyl-3-(3-hydroxyphenyl)propanoate (2.00 g, 9.08 mmol) in dichloromethane (70 mL) was added imidazole (1.24 g, 18.2 mmol) and TBSCl (1.76 g, 11.7 mmol) at 0° C. The reaction mixture was stirred for 4 h at rt and was diluted with water (100 mL). The resulting mixture was extracted with ethyl acetate (3×100 mL). The organic layers were combined, dried over $Na_2SO_4$, filtered and concentrated. The residue obtained was purified over silica gel with ethyl acetate/petroleum ether (0-30%) to afford compound 46a. Mass Spectrum (LCMS, ESI pos.): Calcd. for $C_{19}H_{30}O_3Si$: 335.2 (M+H)$^+$, found 335.2.

(B) ((3R)-methyl 3-(3-((tert-butyldimethylsilyl)oxy)phenyl)-3-cyclopropyl-2-methylpropanoate, 46b

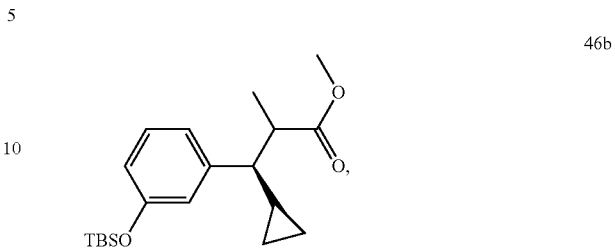

To a solution of (S)-methyl 3-(3-(tert-butyldimethylsilyloxy)phenyl)-3-cyclopropylpropanoate, 46a (1.0 g, 3.0 mmol) in THF (20 mL) was added lithium diisopropylamide (2.3 mL, 4.6 mmol) drop-wise with stirring at −78° C. under a nitrogen atmosphere. After 30 min, iodomethane (510 mg, 3.6 mmol) was added at −78° C., and the reaction mixture was warmed slowly to room temperature and stirred for 1 h. The reaction was then quenched with water (20 mL). The resulting solution was extracted with ethyl acetate (3×30 mL). The organic layers were combined, dried over anhydrous sodium sulfate, filtered and concentrated. The residue obtained was purified over silica gel with EtOAc/petroleum ether (0-5%) to give compound 46b. Mass Spectrum (LCMS, ESI pos.): Calcd. for $C_{20}H_{32}O_3Si$: 349.2 (M+H)$^+$, found 349.2.

(C) (3R)-Methyl 3-cyclopropyl-3-(3-hydroxyphenyl)-2-methylpropanoate, 46c

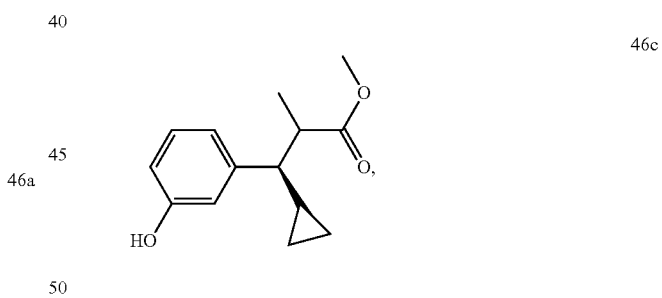

To a solution of (3R)-methyl 3-(3-(tert-butyldimethylsilyloxy)phenyl)-3-cyclopropyl-2-methylpropanoate, 46b (700 mg, 2 mmol) in THF (10 mL) was added tetrabutylammonium fluoride (3 mL, 3 mmol). The resulting solution was stirred at room temperature for 2 h and concentrated. The reaction was then quenched with water (15 mL). The resulting mixture was extracted with ethyl acetate (3×20 mL). The organic layers were combined, dried over anhydrous sodium sulfate, filtered and concentrated. The residue obtained was purified over silica gel with EtOAc/petroleum ether (0-10%) to give compound 46c. Mass Spectrum (LCMS, ESI pos.): Calcd. for $C_{14}H_{18}O_3$: 235.0 (M+H)$^+$, found 235.0.

(D) (3R)-Methyl 3-cyclopropyl-3-(3-(((1r,4R)-4-(2-fluoro-5-methoxyphenyl)cyclohexyl)methoxy)phenyl)-2-methylpropanoate, 46d

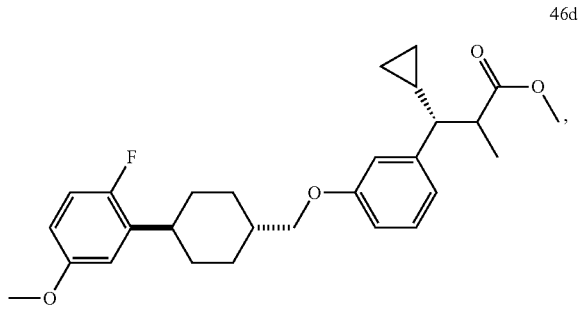

46d

To a solution of (3R)-methyl 3-cyclopropyl-3-(3-hydroxyphenyl)-2-methylpropanoate, 46c (310 mg, 1.3 mmol) in toluene (2 mL) was added ((1r,4r)-4-(2-fluoro-5-methoxyphenyl)cyclohexyl)methanol (0.38 g, 1.6 mmol), tributylphosphine (670 mg, 3.3 mmol) and a solution of 1,1'-(azodicarbonyl)-dipiperidine (0.84 mg, 3.3 mmol) in toluene (10 mL) drop-wise with stirring at 0° C. The resulting mixture was stirred at 60° C. for 2 h under a nitrogen atmosphere. Upon cooling to RT, the reaction was quenched with water (20 mL). The resulting mixture was extracted with ethyl acetate (3×20 mL). The organic layers were combined, dried over $Na_2SO_4$, filtered and concentrated. The residue obtained was purified over silica gel with EtOAc/petroleum ether (0-30%) to give compound 46d. Mass Spectrum (LCMS, ESI pos.): Calcd. for $C_{28}H_{35}FO_4$: 455.3 $(M+H)^+$, found 455.3.

(E) (2R,3R)-3-cyclopropyl-3-(3-(((1r,4R)-4-(2-fluoro-5-methoxyphenyl)cyclohexyl) methoxy)phenyl)-2-methylpropanoic acid, Cpd 51, and

(2S,3R)-3-cyclopropyl-3-(3-(((1r,4R)-4-(2-fluoro-5-methoxyphenyl)cyclohexyl)methoxy)phenyl)-2-methylpropanoic, Cpd 52

To a solution of (3R)-methyl 3-cyclopropyl-3-(3-(((1r, 4R)-4-(2-fluoro-5-methoxyphenyl)cyclohexyl)methoxy) phenyl)-2-methylpropanoate, 46d (290 mg, 0.638 mmol) in THF (20 mL) was added lithium hydroxide (153 mg, 6.38 mmol), water (10 mL) and methanol (2 mL). The resulting solution was stirred overnight at RT. The mixture was concentrated under reduced pressure and then diluted with 10 mL of water. The pH value of the solution was adjusted to 4-5 with 1N HCl solution. The solids formed were collected by filtration and purified by preparative chiral HPLC on a Chiralpak IA2, 25 cm, 5 μm chiral column using EtOH: hexane (0.1% TFA) over 10.5 min to give compounds.

Cpd 51: Retention time (Peak 1) 5.87 min., (2R*, 3R)-3-cyclopropyl-3-(3-(((1r, 4R)-4-(2-fluoro-5-methoxyphenyl)cyclohexyl)methoxy)phenyl)-2-methylpropanoic acid: $^1$H NMR (300 MHz, DMSO-$d_6$) δ (ppm): 7.20 (t, J=7.8 Hz, 1H), 7.05 (dd, $J_1$=10.1 Hz, $J_2$=8.9 Hz, 1H), 6.72-6.87 (m, 5H), 3.81 (d, J=6.2 Hz, 2H), 3.72 (s, 3H), 2.65-2.84 (m, 2H), 1.74-2.02 (m, 6H), 1.50-1.55 (m, 2H), 1.02-1.33 (m, 3H), 0.82 (d, J=6.9 Hz, 3H), 0.46-0.57 (m, 1H), 0.19-0.35 (m, 2H), −0.07-0.00 (m, 1H). Mass Spectrum (LCMS, ESI pos.): Calcd. for $C_{27}H_{33}FO_4$: 441.2 $(M+H)^+$; found: 441.2.

Cpd 52: Retention time (Peak 2) 8.01 min., (2S*, 3R)-3-cyclopropyl-3-(3-(((1r, 4R)-4-(2-fluoro-5-methoxyphenyl)cyclohexyl)methoxy)phenyl)-2-methylpropanoic acid: $^1$H-NMR (300 MHz, DMSO-$d_6$) δ (ppm): 7.16 (t, J=7.9 Hz, 1H), 7.05 (dd, dd, $J_1$=10.1 Hz, $J_2$=8.8 Hz, 1H), 6.71-6.87 (m, 5H), 3.79 (d, J=6.2 Hz, 2H), 3.72 (s, 3H), 2.69-2.88 (m, 2H), 1.89-2.08 (m, 3H), 1.73-1.91 (m, 3H), 1.44-1.64 (m, 2H), 1.21 (t, J=8.0 Hz, 5H), 0.96-1.02 (m, 1H), 0.60-0.65 (m, 1H), 0.25-0.30 (m, 2H), −0.13--0.05 (m, 1H). Mass Spectrum (LCMS, ESI pos.): Calcd. for $C_{27}H_{33}FO_4$: 441.2 $(M+H)^+$; found: 441.2.

Example 47

(2S,3R)-3-cyclopropyl-3-(3-(((1r,4R)-4-(2-fluoro-5-methoxyphenyl)cyclohexyl)methoxy)phenyl)-2-methylpropanoic acid, Cpd 52

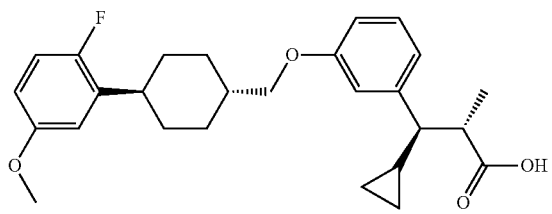 [SMILES: COc1ccc(F)c([C@H]2CC[C@H](COc3cccc([C@H](C4CC4)[C@H](C)C(=O)O)c3)CC2)c1]

(A) (2S,3R)-methyl 3-cyclopropyl-3-(3-hydroxyphenyl)-2-methylpropanoate, 47a and (2R,3R)-methyl 3-cyclopropyl-3-(3-hydroxyphenyl)-2-methylpropanoate, 47a-1

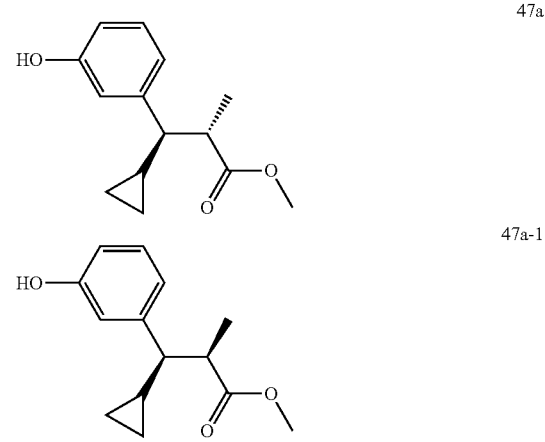

47a 47a-1

(3R)-Methyl 3-cyclopropyl-3-(3-hydroxyphenyl)-2-methylpropanoate, compound 46c, was subjected SFC separation on a CHIRALPAK-IC-SFC-025 cm×25 cm(5 μm) column using 20% IPA (0.1% $NH_3$ in MeOH)/$CO_2$ for 10 min. to give compounds 49a and 49a-1.

Cpd 47a: Retention time (Peak 1) 3.98 min., (2S,3R)-methyl 3-cyclopropyl-3-(3-hydroxyphenyl)-2-methylpropanoate. $^1$H NMR (300 MHz, CDCl$_3$) δ (ppm): 7.17 (t, J=7.8 Hz, 1H), 6.65-6.73 (m, 3H), 5.35 (brs, 1H), 3.74 (s, 3H), 2.81 (dd, $J_1$=6.9 Hz, $J_2$=9.9 Hz, 1H), 1.88 (t, J=9.6 Hz, 1H), 0.99-1.05 (m, 1H), 0.95 (d, J=6.9 Hz, 3H), 0.52-0.58 (m, 1H), 0.21-0.35 (m, 2H), −0.03-0.04 (m, 1H). Mass Spectrum (LCMS, ESI pos.): Calcd. for $C_{14}H_{18}O_3$: 235.1 (M+H)⁺; found: 235.1.

Cpd 47a-1: Retention time (Peak 2) 5.06 min., (2R,3R)-methyl 3-cyclopropyl-3-(3-hydroxyphenyl)-2-methylpropanoate. ¹H NMR (300 MHz, CDCl₃) δ (ppm): 7.16 (t, J=7.8 Hz, 1H), 6.68-6.79 (m, 3H), 5.30-5.50 (br.m, 1H), 3.55 (s, 3H), 2.89 (dd, J₁=7.2 Hz, J₂=8.1 Hz, 1H), 2.15 (t, J=9.6 Hz, 1H), 1.30 (d, J=6.9 Hz, 3H), 1.02-1.10 (m, 1H), 0.67-0.75 (m, 1H), 0.29-0.50 (m, 2H), −0.03-0.05 (m, 1H). Mass Spectrum (LCMS, ESI pos.): Calcd. for $C_{14}H_{18}O_3$: 235.13 (M+H)⁺; found: 235.10.

(B) (2S,3R)-Methyl 3-cyclopropyl-3-(3-(((1r,4R)-4-(2-fluoro-5-methoxyphenyl)cyclohexyl)methoxy)phenyl)-2-methylpropanoate, 47b

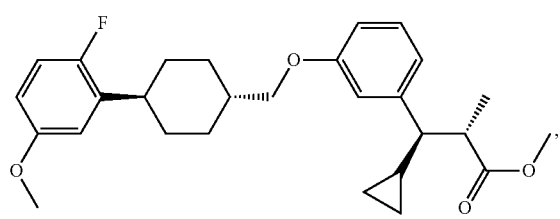

47b

Compound 47b was prepared from ((1r,4r)-4-(2-fluoro-5-methoxyphenyl)cyclohexyl)methanol and (2S,3R)-methyl 3-cyclopropyl-3-(3-hydroxyphenyl)-2-methylpropanoate, compound 47a, according to the methods described in Example 46, Step D. Mass Spectrum (LCMS, ESI pos.): Calcd. for $C_{28}H_{35}FO_4$: 455.3 (M+H)⁺, found 455.3.

(C) (2S,3R)-3-cyclopropyl-3-(3-(((1r,4R)-4-(2-fluoro-5-methoxyphenyl)cyclohexyl) methoxy)phenyl)-2-methylpropanoic acid, Cpd 52

To a solution of (2S,3R)-methyl 3-cyclopropyl-3-(3-(((1r,4R)-4-(2-fluoro-5-methoxyphenyl)cyclohexyl)methoxy) phenyl)-2-methylpropanoate, cpd 47b (160 mg, 0.35 mmol) in THF (8 mL) was added water (2 mL), methanol (2 mL) and lithium hydroxide (59 mg, 1.4 mmol). The resulting solution was stirred overnight at RT. The mixture was concentrated and then diluted with 5 mL of water. The pH of the solution was adjusted to 4-5 with 1N HCl solution. The solids formed were collected by filtration to afford compound 52. ¹H NMR (400 MHz, DMSO-d₆) δ (ppm): 12.15-12.35 (br s, 1H), 7.15-7.25 (m, 1H), 7.02-7.08 (m, 1H), 6.83-6.89 (m, 1H), 6.70-6.80 (m, 4H), 3.81 (d, J=6.4 Hfz, 2H), 3.73 (s, 3H), 2.65-2.80 (m, 2H), 1.87-1.98 (m, 3H), 1.76-1.86 (m, 3H), 1.46-1.58 (m, 2H), 1.18-1.28 (m, 2H), 1.05-1.15 (m, 1H), 0.81 (d, J=7.2 Hz, 3H), 0.45-0.55 (m, 1H), 0.18-0.30 (m, 2H), −0.04-−0.10 (m, 1H). Mass Spectrum (LCMS, ESI pos.): Calcd. for $C_{27}H_{33}FO_4$: 441.2 (M+H)⁺; found: 441.2.

Example 48

(2S,3R)-3-cyclopropyl-3-(3-(((1s,4S)-4-(2-fluoro-5-methoxyphenyl)cyclohexyl) methoxy)phenyl)-2-methylpropanoic acid, Cpd 53

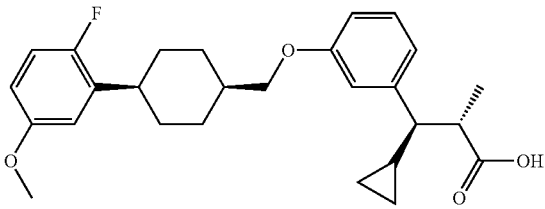 [SMILES: COc1ccc(F)c([C@H]2CC[C@@H](COc3cccc([C@H](C4CC4)[C@H](C)C(=O)O)c3)CC2)c1]

Compound was prepared from methyl and (2S,3R)-methyl 3-cyclopropyl-3-(3-hydroxyphenyl)-2-methylpropanoate, compound 47a and ((1r,4r)-4-(2-fluoro-5-methoxyphenyl)cyclohexyl)methanol, compound 8a-1, according to the methods described in Example 46. ¹H NMR (300 MHz, DMSO-d₆) δ (ppm): 7.21 (t, J=7.8 Hz, 1H), 7.00-7.05 (m, 1H), 6.65-6.95 (m, 5H), 4.08 (d, J=7.5 Hz, 2H), 3.72 (s, 3H), 2.65-2.85 (m, 2H), 2.08-2.18 (m, 1H), 1.75-1.95 (m, 3H), 1.48-1.72 (m, 6H), 1.05-1.15 (m, 1H), 0.82 (d, J=6.9 Hz, 3H), 0.45-0.55 (m, 1H), 0.15-0.30 (m, 2H), −0.02-−0.12 (m, 1H). Mass Spectrum (LCMS, ESI pos.): Calcd. for $C_{27}H_{33}FO_4$: 441.2 (M+H)⁺; found: 441.2.

Example 49

(3S)-3-Cyclopropyl-2-fluoro-3-(3-(((1r,4S)-4-(2-fluoro-5-methoxyphenyl)cyclohexyl) methoxy)phenyl)propanoic acid, Cpd 54

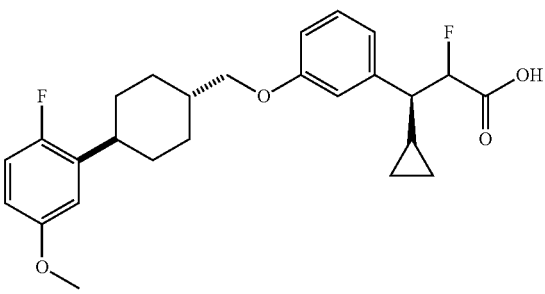

(A) (3S)-Methyl 3-(3-(tert-butyldimethylsilyloxy) phenyl)-3-cyclopropyl-2-fluoropropanoate, 49a

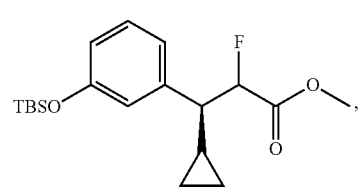

49a

To a solution of (S)-methyl 3-(3-(tert-butyldimethylsilyloxy)phenyl)-3-cyclopropylpropanoate, 46a (335 mg, 1.00 mmol) in THF (5 mL) maintained under a nitrogen atmosphere, was added lithium diisopropylamide (0.751 mL, 1.50 mmol) dropwise with stirring at −78° C. After 30 min, N-fluoro-N-(phenylsulfonyl) benzenesulfonamide (379 mg, 1.20 mmol) in THF (3 mL) was added and the mixture was warmed slowly to RT. The reaction was then quenched with water (10 mL). The resulting solution was extracted with ethyl acetate (3×15 mL). The organic layers were combined, dried over anhydrous sodium sulfate, filtered and concentrated. The residue obtained was purified by silica gel with EtOAc/petroleum ether (0-5%) to give compound 49a. Mass Spectrum (LCMS, ESI pos.): Calcd. for $C_{19}H_{29}FO_3Si$: 352.2 (M+H)$^+$; found: 352.2.

(B) (3S)-methyl 3-cyclopropyl-2-fluoro-3-(3-hydroxyphenyl)propanoate, 49b

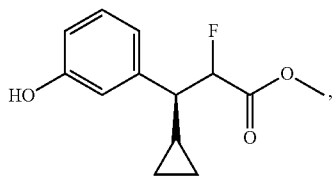

49b

To a solution of (3S)-methyl 3-(3-(tert-butyldimethylsilyloxy)phenyl)-3-cyclopropyl-2-fluoropropanoate, 49a (0.30 g, 0.90 mmol) in THF (10 mL) was added tetrabutylammonium fluoride (1.2 mL, 1.2 mmol). The resulting solution was stirred at RT for 2 h. The resulting mixture was concentrated and then treated with water (15 mL). The resulting solution was extracted with ethyl acetate (3×15 mL). The organic layers were combined, dried over anhydrous sodium sulfate, filtered and concentrated. The residue obtained was purified over silica gel with EtOAc/petroleum ether (0-10%) to give compound 49b. Mass Spectrum (LCMS, ESI pos.): Calcd. for $C_{13}H_{15}FO_3$: 239.2 (M+H)$^+$; found: 239.1.

(C) (3S)-Methyl 3-cyclopropyl-2-fluoro-3-(3-(((1r, 4S)-4-(2-fluoro-5-methoxyphenyl)cyclohexyl) methoxy)phenyl)propanoate, 49c

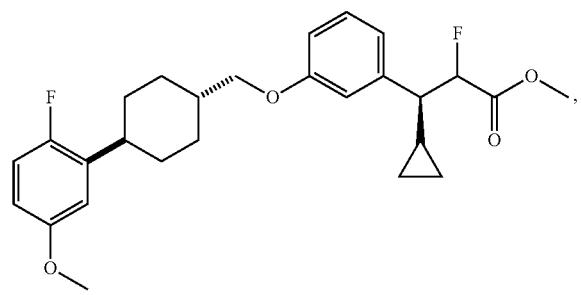

49c

Compound 49c was prepared from ((1r,4r)-4-(2-fluoro-5-methoxyphenyl)cyclohexyl) methanol and (3S)-methyl 3-cyclopropyl-2-fluoro-3-(3-hydroxyphenyl) propanoate, cpd 49b, according to the methods described in Example 46, Step D. Mass Spectrum (LCMS, ESI pos.): Calcd. for $C_{27}H_{32}F_2O_4$: 481.2 (M+Na)$^+$, found 481.2.

(D) (3S)-3-cyclopropyl-2-fluoro-3-(3-(((1r,4 S)-4-(2-fluoro-5-methoxyphenyl)cyclohexyl) methoxy) phenyl)propanoic acid, Cpd 54

To a solution of (3S)-methyl 3-cyclopropyl-2-fluoro-3-(3-(((1r,4S)-4-(2-fluoro-5-methoxyphenyl)cyclohexyl) methoxy)phenyl)propanoate, 49c (250 mg, 0.54 mmol) in THF (8 mL), methanol (2 mL) and water (2 mL), was added lithium hydroxide (229 mg, 5.45 mmol). The resulting mixture was stirred at 30° C. overnight. The resulting mixture was concentrated under reduced pressure. The reaction mixture was then diluted with 20 mL of water. The pH value of the solution was adjusted to 5-6 with 2N HCl. The resulting precipitate was collected by filtration to give compound 54. $^1$H NMR (400 MHz, DMSO-d$_6$) δ (ppm): 7.03-7.21 (m, 2H), 6.82-6.90 (m, 3H), 6.74-6.78 (m, 2H), 4.50-4.63 (m, 1H), 3.77-3.82 (m, 2H), 3.73 (s, 3H), 2.70-2.90 (m, 1H), 2.25-2.45 (m, 1H), 1.95-1.98 (m, 2H), 1.79-1.82 (m, 3H), 1.54-1.57 (m, 2H), 1.18-1.28 (m, 3H), 0.32-0.53 (m, 3H), −0.13-0.05 (m, 1H). Mass Spectrum (LCMS, ESI pos.): Calcd. for $C_{26}H_{30}F_2O_4$: 443.5 (M−H)$^-$; found: 443.1.

Example 50

3-Cyclopropyl-3-(3-(((1 s,4 s)-4-(2-fluoro-5-methoxyphenyl)cyclohexyl)methoxy)phenyl)propanoic acid, Cpd 55

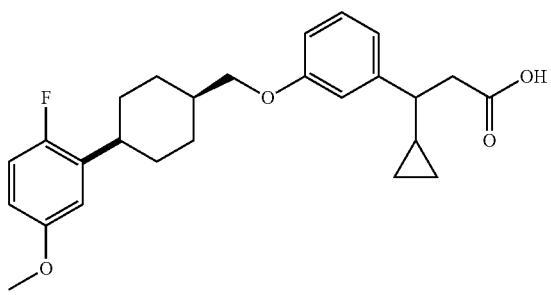

Compound 55 was prepared from methyl 3-cyclopropyl-3-(3-hydroxyphenyl) propanoate and ((1r,4r)-4-(2-fluoro-5-methoxyphenyl)cyclohexyl)methanol, cpd 8a-1 (Example 8, Step A), according to the methods described in Example 28, Steps E-F. $^1$H NMR (300 MHz, DMSO-d$_6$) δ (ppm): 7.17-7.22 (m, 1H), 7.00-7.07 (m, 1H), 6.70-6.91 (m, 5H), 4.07 (d, J=7.5 Hz, 2H), 3.72 (s, 3H), 2.75-2.88 (m, 1H), 2.62-2.68 (m, 2H), 2.10-2.23 (m, 2H), 1.80-1.90 (m, 2H), 1.52-1.73 (m, 6H), 0.95-1.05 (m, 1H), 0.45-0.55 (m, 1H), 0.18-0.35 (m, 2H), 0.07-0.17 (m, 1H). Mass Spectrum (LCMS, ESI pos.): Calcd. for $C_{26}H_{31}FO_4$: 444.1 [M+NH$_4$]$^+$; found: 443.1.

Example 51

3-Cyclopropyl-3-(3-(((1r,4r)-4-(2-fluoro-5-methoxyphenyl)cyclohexyl)methoxy)phenyl) propanoic acid, Cpd 56

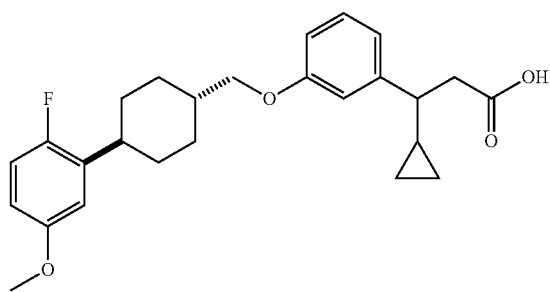

Compound 56 was prepared from methyl 3-cyclopropyl-3-(3-hydroxyphenyl) propanoate and ((1r,4r)-4-(2-fluoro-5-methoxyphenyl)cyclohexyl)methanol according to the methods described in Example 28, Steps E-F. $^1$H NMR (300 MHz, DMSO-d$_6$) δ (ppm): 7.18 (t, J=8.1 Hz, 1H), 7.05 (t, J=9.6 Hz, 1H), 6.70-6.88 (m, 5H), 3.81 (d, J=6.3 Hz, 2H), 3.73 (s, 3H), 2.70-2.80 (m, 1H), 2.58-2.66 (m, 2H), 2.18-2.26 (m, 1H), 1.90-2.00 (m, 2H), 1.75-1.85 (m, 3H), 1.48-1.60 (m, 2H), 1.16-1.30 (m, 2H), 0.95-1.05 (m, 1H), 0.45-0.54 (m, 1H), 0.18-0.38 (m, 2H), 0.05-0.15 (m, 1H). Mass Spectrum (LCMS, ESI pos.): Calcd. for C$_{26}$H$_{31}$FO$_4$: 444.1 [M+NH$_4$]$^+$; found: 443.1.

Example 52

(2S,3R)-3-cyclopropyl-3-(3-(((1r,4R)-4-(5-ethyl-2-fluorophenyl)cyclohexyl)methoxy)phenyl)-2-methylpropanoic acid, Cpd 57

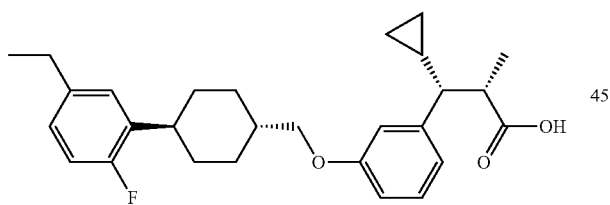

(A) 1-(3-Bromo-4-fluorophenyl)ethanol, 52a

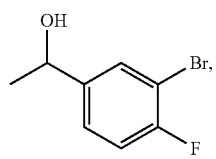

To a solution of 1-(3-bromo-4-fluorophenyl)ethanone (400 mg, 1.84 mmol) in methanol (20 mL) was added sodium borohydride (141 mg, 3.73 mmol). The resulting mixture was stirred at rt for 2 h. The reaction was quenched with water (30 mL). The resulting mixture was extracted with ethyl acetate (3×30 mL). The organic layers were combined, dried over Na$_2$SO$_4$, filtered and concentrated. The residue obtained was purified by flash column chromatography on silica gel (0-20% EtOAc/petroleum ether) to afford compound 52a as a yellow oil. Mass Spectrum (LCMS, ESI pos.): Calcd. for C$_8$H$_8$BrFO: 202.8 (M-OH)$^+$; found: 202.8.

(B) 2-Bromo-4-ethyl-1-fluorobenzene, 52b

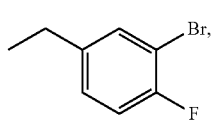

To a solution of 1-(3-bromo-4-fluorophenyl)ethanol, cpd 52a (350.0 mg, 1.598 mmol) in 2,2,2-trifluoroacetic acid (5 mL) was added triethylsilane (372.0 mg, 3.199 mmol). The resulting mixture was stirred at 60° C. for 5 h. After cooling to rt, the reaction was quenched with water (30 mL). The resulting mixture was extracted with ethyl acetate (3×30 mL). The organic layers were combined, dried over Na$_2$SO$_4$, filtered and concentrated. The residue obtained was purified by flash column chromatography on silica gel (0-20% EtOAc/petroleum ether) to afford compound 52b as a yellow oil. $^1$H NMR (400 MHz, CDCl$_3$) δ (ppm) 7.35-7.41 (m, 1H), 6.93-7.20 (m, 2H), 2.63 (q, J=7.6 Hz, 2H), 1.24 (td, J=7.6, 1.3 Hz, 3H).

(C) Ethyl 5'-ethyl-2'-fluoro-2,3,4,5-tetrahydro-[1,1'-biphenyl]-4-carboxylate, 52c

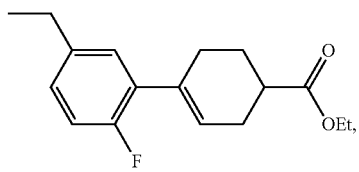

To a solution of 2-bromo-4-ethyl-1-fluorobenzene, 52b (260.0 mg, 1.280 mmol) in 1,4-dioxane (8 mL) and water (2 mL) was added ethyl 4-(4,4,5,5-tetramethyl-1,3,2-dioxaborolan-2-yl)cyclohex-3-enecarboxylate (430.0 mg, 1.688 mmol), PdCl$_2$(dppf)CH$_2$C$_{12}$ (52.0 mg, 0.064 mmol), and potassium carbonate (442.0 mg, 3.198 mmol). The resulting mixture was maintained under a nitrogen atmosphere and stirred at 90° C. for 2 h. After cooling to rt, the reaction was quenched with water (30 mL). The resulting mixture was extracted with ethyl acetate (3×30 mL). The organic layers were combined, dried over Na$_2$SO$_4$, filtered and concentrated. The residue obtained was purified by flash column chromatography on silica gel (0-13% EtOAc/petroleum ether) to afford compound 52c. Mass Spectrum (LCMS, ESI pos.): Calcd. for C$_{17}$H$_{21}$FO$_2$: 277.0 [M+H]$^+$; found: 277.0.

(D) (4-(5-Ethyl-2-fluorophenyl)cyclohex-3-enyl)methanol, 52d

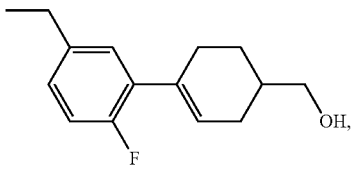

To a solution of ethyl 4-(5-ethyl-2-fluorophenyl)cyclohex-3-enecarboxylate, cpd 52c (280 mg, 1.0 mmol) in THF (10 mL) was added diisobutylaluminium hydride (4 mL, 4.0 mmol, 1 M in THF) at −30° C. The resulting mixture was maintained under a nitrogen atmosphere and stirred at −30° C. to 0° C. The reaction was quenched with saturated aq. potassium sodium tartrate (30 mL). The resulting mixture was extracted with EtOAc (3×30 mL). The organic layers were combined, dried over $Na_2SO_4$, filtered and concentrated. The residue obtained was purified by flash column chromatography on silica gel (0-18% EtOAc/petroleum ether) to give compound 52d. Mass Spectrum (LCMS, ESI pos.): Calcd. for $C_{15}H_{19}FO$: 217.1 (M-OH)$^+$; found: 217.0.

(E) ((1r,4r)-4-(5-Ethyl-2-fluorophenyl)cyclohexyl)methanol, 52e

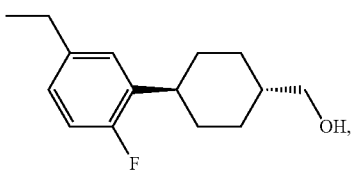

To a solution of (4-(5-ethyl-2-fluorophenyl)cyclohex-3-enyl)methanol, 52d (180 mg, 0.768 mmol) in dichloromethane (5 mL) was added Ir(COD)(Py)(PCy$_3$)PF$_6$ (50 mg, 0.062 mmol). The resulting mixture was maintained under a H$_2$ atmosphere (60 atm) at 40° C. with stirring for 32 h. After cooling to rt, the reaction was quenched with water (30 mL). The resulting mixture was extracted with ethyl acetate (3×30 mL). The organic layers were combined, filtered and concentrated. The residue obtained was purified by flash column chromatography on silica gel (0-25% EtOAc/petroleum ether) to afford compound 52e as a yellow oil (130 mg, 71.6% yield). Mass Spectrum (LCMS, ESI pos.): Calcd. for $C_{15}H_{21}FO$: 219.0 [M-OH]$^+$; found: 219.0 [M-OH]$^+$.

(F) (2S,3R)-methyl 3-cyclopropyl-3-(3-(((1r,4R)-4-(5-ethyl-2-fluorophenyl)cyclohexyl) methoxy)phenyl)-2-methylpropanoate, 52f

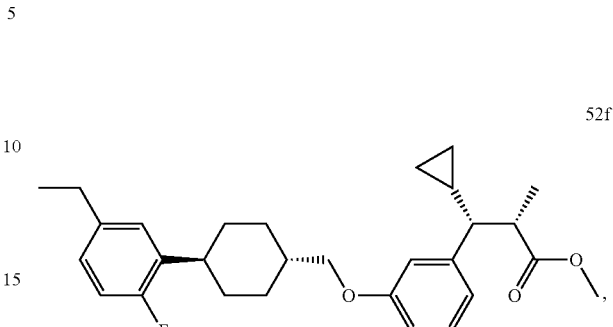

To a solution of ((1r,4r)-4-(5-ethyl-2-fluorophenyl)cyclohexyl)methanol, 52e (130 mg, 0.550 mmol) in toluene (5 mL) was added (2S,3R)-methyl 3-cyclopropyl-3-(3-hydroxyphenyl)-2-methylpropanoate, cpd 47a (154 mg, 0.657 mmol), 1,1'-(azodicarbonyl)-dipiperidine (278 mg, 1.102 mmol) and tributylphosphane (223 mg, 1.102 mmol). The resulting mixture was maintained under a nitrogen atmosphere and stirred at 60° C. for 2 h. After cooling to rt, the reaction was quenched with water (30 mL). The resulting mixture was extracted with ethyl acetate (3×30 mL). The organic layers were combined, dried over $Na_2SO_4$, filtered and concentrated. The residue obtained was purified by silica gel chromatography (0-10% EtOAc/petroleum ether) to afford compound 52f as a yellow oil. Mass Spectrum (LCMS, ESI pos.): Calcd. For $C_{29}H_{37}FO_3$: 453.3 [M+H]$^+$; found: 453.2 [M+H]$^+$.

(G) (2S,3R)-3-cyclopropyl-3-(3-(((1r,4R)-4-(5-ethyl-2-fluorophenyl)cyclohexyl) methoxy)phenyl)-2-methylpropanoic acid, Cpd 57

To a solution of (2S,3R)-methyl 3-cyclopropyl-3-(3-(((1r,4R)-4-(5-ethyl-2-fluorophenyl)cyclohexyl)methoxy)phenyl)-2-methylpropanoate, 52f (140 mg, 0.309 mmol) in tetrahydrofuran (4 mL), water (1 mL) and methanol (1 mL) was added lithium hydroxide (130 mg, 3.094 mmol). The resulting solution was stirred overnight at 60° C. The mixture was concentrated under reduced pressure and then diluted with water (5 mL). The pH of the solution was adjusted to 4-5 with 1M HCl solution. The resulting solution was extracted with ethyl acetate (3×15 mL) and the organic phases were combined, dried over $Na_2SO_4$, filtered and concentrated. The residue obtained was purified by reverse-phase flash chromatography on an Agela Flash Spherical C18(2) Column, 20-35 μm, 100 Å, using CH$_3$CN:H$_2$O (0.05% TFA) to afford compound 57. $^1$H NMR (300 MHz, DMSO-d$_6$) δ (ppm): 12.20 (s, 1H), 7.14-7.22 (m, 2H), 7.01-7.05 (m, 2H), 6.76-6.80 (m, 3H), 3.80 (d, J=6.2 Hz, 2H), 2.67-2.90 (m, 2H), 2.50-2.60 (m, 2H), 1.75-2.02 (m, 6H), 1.47-1.69 (m, 2H), 1.00-1.39 (m, 6H), 0.89 (d, J=6.9 Hz, 3H), 0.45-0.67 (m, 1H), 0.21-0.40 (m, 2H), (−0.10)-(−0.02) (m, 1H). Mass Spectrum (LCMS, ESI pos.): Calcd. For $C_{28}H_{35}FO_3$: 456.1 [M+NH$_4^+$]$^+$; found: 456.1.

Example 53

(R)-3-Cyclopropyl-3-(2-(((1s,4S)-4-(2-fluoro-5-methoxyphenyl)cyclohexyl)methoxy)pyridin-4-yl)propanoic acid, Cpd 41

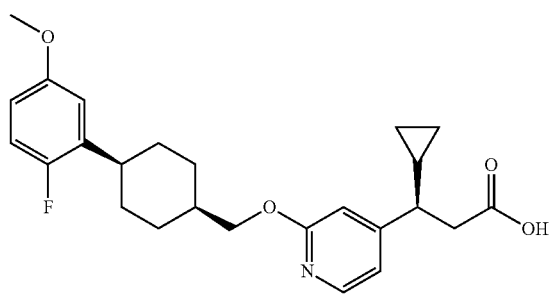 [SMILES: COc1ccc(F)c([C@H]2CC[C@@H](COc3cc([C@H](CC(=O)O)C4CC4)ccn3)CC2)c1]

(A) (R)-Ethyl 3-cyclopropyl-3-(2-fluoropyridin-4-yl)propanoate, 53a and (S)-ethyl 3-cyclopropyl-3-(2-fluoropyridin-4-yl)propanoate, 53a-1

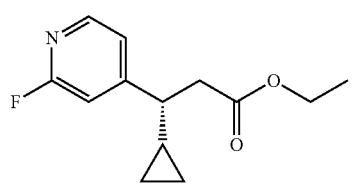

(53a)

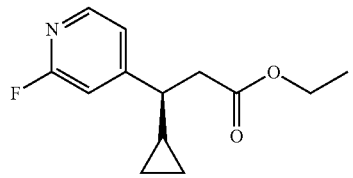

(53a-1)

Ethyl 3-cyclopropyl-3-(2-fluoropyridin-4-yl)propanoate, 7a was subjected to preparative HPLC on a Lux Cellulose column (0.46×15 cm) using hexane (0.1% IPA):IPA=90:10 to give cpd 53a and cpd 53a-1.

Cpd 53a: $^1$H-NMR (400 MHz, DMSO-$d_6$) δ (ppm) 8.14 (d, J=5.2 Hz, 1H), 7.30-7.31 (m, 1H), 7.15 (s, 1H), 3.91-4.01 (m, 2H), 2.71-2.91 (m, 2H), 2.33-2.39 (m, 1H), 0.95-1.15 (m, 4H), 0.50-0.57 (m, 1H), 0.25-0.38 (m, 2H), 0.16-0.22 (m, 1H).

Cpd 53a-1: $^1$H-NMR (400 MHz, DMSO-$d_6$) δ (ppm) 8.13-8.17 (m, 1H), 7.27-7.35 (m, 1H), 7.15 (s, 1H), 3.89-4.04 (m, 2H), 2.75-2.88 (m, 2H), 2.33-2.39 (m, 1H), 0.99-1.09 (m, 4H), 0.50-0.56 (m, 1H), 0.25-0.40 (m, 2H), 0.11-0.24 (m, 1H).

(B) (R)-3-Cyclopropyl-3-(2-(((1s,4S)-4-(2-fluoro-5-methoxyphenyl)cyclohexyl)methoxy)pyridin-4-yl)propanoic acid, Cpd 41

Compound 41 was prepared from ((1s,4s)-4-(2-fluoro-5-methoxyphenyl)cyclohexyl)methanol, cpd 8a-2, and (R)-ethyl 3-cyclopropyl-3-(2-fluoropyridin-4-yl)propanoate, cpd 53a, according to the methods described in Example 3, Steps E and F. $^1$H NMR (400 MHz, DMSO-$d_6$) δ (ppm) 12.06 (brs, 1H), 8.04 (d, J=5.3 Hz, 1H), 7.04 (dd, $J_1$=10.2 Hz, $J_2$=8.9 Hz, 1H), 6.85-6.93 (m, 2H), 6.69-6.77 (m, 2H), 4.36 (d, J=7.7 Hz, 2H), 3.72 (s, 3H), 2.80 (d, J=9.4 Hz, 1H), 2.68 (d, J=7.4 Hz, 2H), 2.10-2.28 (m, 2H), 1.85 (d, J=10.0 Hz, 2H), 1.54-1.72 (m, 6H), 0.91-1.01 (m, 1H), 0.41-0.52 (m, 1H), 0.22-0.39 (m, 2H), 0.11-0.22 (m, 1H). (LCMS, ESI pos.): Calcd. for $C_{25}H_{30}FNO_4$: 428.2 (M+H)$^+$; found: 428.2.

Example 54

(3S)-3-Cyclopropyl-2-fluoro-3-(3-(((1r,4S)-4-(2-fluoro-5-methoxyphenyl)cyclohexyl)methoxy)phenyl)-2-methylpropanoic acid Cpd 58

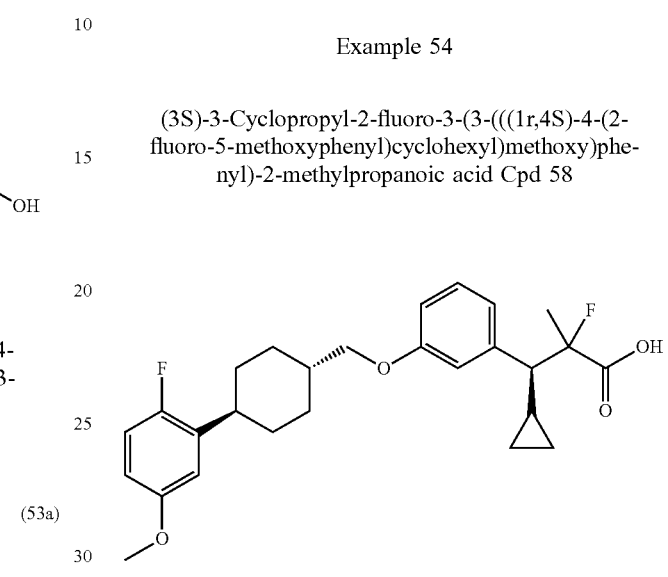

(G) Ethyl 4-(((trifluoromethyl)sulfonyl)oxy)cyclohex-3-ene-1-carboxylate, 54a

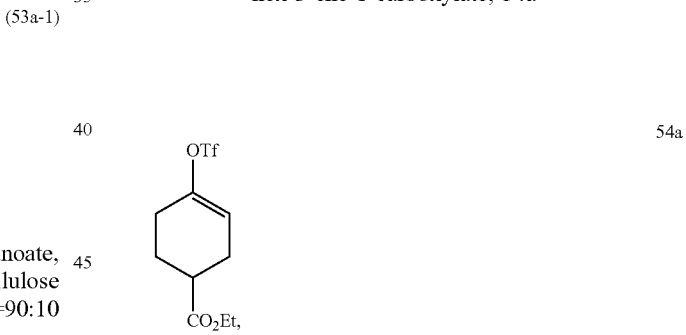

54a

To a solution of ethyl 4-oxocyclohexanecarboxylate (5 g, 29.38 mmol) in THF (100 mL) was added LiHMDS (32.3 mL, 32.3 mmol, 1 M in hexane) dropwise at −78° C. under nitrogen. After 30 min, trifluoro-N-phenyl-N-(trifluoromethylsulfonyl)methanesulfonamide (11 g, 30.79 mmol) was added at −78° C. The resulting mixture was stirred for 2 h at −78° C. The reaction was then quenched by the addition of NH$_4$Cl solution (satd., aq., 100 mL). The resulting mixture was extracted with EtOAc (3×100 mL). The organic layers were combined, dried over Na$_2$SO$_4$, filtered and the filtrate concentrated under reduced pressure to give compound 54a, which was used directly in the next step without further purification. $^1$H NMR (400 MHz, CDCl$_3$) δ (ppm): 5.81 (t, J=3.1 Hz, 1H), 4.18 (q, J=7.1 Hz, 2H), 2.62 (m, 1H), 2.45 (m, 4H), 2.16 (m, 1H), 2.11-1.87 (m, 1H), 1.28 (t, J=7.1 Hz, 3H).

(H) Ethyl 4-(2-fluoro-5-methoxyphenyl)cyclohex-3-enecarboxylate, 54b

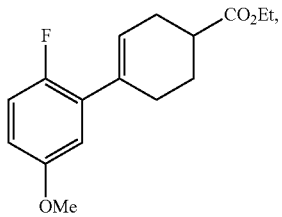

54b

To the mixture of ethyl 4-(((trifluoromethyl)sulfonyl)oxy)cyclohex-3-ene-1-carboxylate, 54a (7.5 g, 24.81 mmol), 2-fluoro-5-methoxyphenylboronic acid (6.3 g, 37.07 mmol), Pd(dppf)Cl$_2$.CH$_2$Cl$_2$ (1 g, 1.23 mmol), and Cs$_2$CO$_3$ (16.2 g, 49.72 mmol) was added dioxane (80 mL) and water (20 mL) under nitrogen. The reaction mixture was stirred for 2 h at 80° C. After cooling down, the reaction was quenched by the addition of water (200 mL). The resulting mixture was extracted with EtOAc (3×150 mL). The organic layers were combined, dried over anhydrous sodium sulfate and concentrated under reduced pressure. The residue was purified by flash chromatography on silica gel (0-5% EtOAc/petroleum ether) to afford compound 54b as a light yellow oil (5.5 g, 79.6% yield). $^1$H NMR (400 MHz, CDCl$_3$) δ (ppm): 6.93 (t, J=3.1 Hz, 1H), 6.72 (m, 2H), 5.94 (m, 1H), 4.17 (q, J=7.1 Hz, 2H), 3.78 (s, 3H), 2.64 (m, 1H), 2.45 (m, 4H), 2.16 (m, 1H), 1.87 (m, 1H), 1.24 (t, J=7.1 Hz, 3H).

(I) (4-(2-Fluoro-5-methoxyphenyl)cyclohex-3-enyl)methanol, 54c

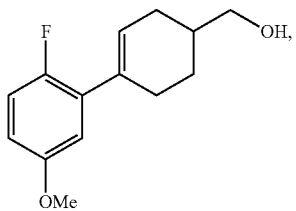

54c

To a solution of ethyl 4-(2-fluoro-5-methoxyphenyl)cyclohex-3-enecarboxylate, 54b (5.5 g, 19.76 mmol) in THF (100 mL) was added LiAlH$_4$ (1.1 g, 28.98 mmol) in portions under nitrogen at 0° C. The resulting solution was stirred for 20 min at 0° C. The reaction was then quenched by the addition of tartrate potassium sodium solution (satd., aq., 300 mL) and the reaction stirred for 30 min. The resulting mixture was extracted with EtOAc (3×200 mL). The organic layers were combined and dried over anhydrous sodium sulfate, filtered, and the filtrate concentrated under reduced pressure. The residue was purified by flash chromatography on silica gel (0-20% EtOAc/petroleum ether) to afford compound 54c as a colorless oil (3.8 g, 81.3% yield). $^1$H NMR (300 MHz, acetone-d$_6$) δ (ppm): 6.95 (m, 1H), 6.75 (m, 2H), 5.90 (m, 1H), 3.74 (s, 3H), 3.65-3.38 (m, 3H), 2.52-2.15 (m, 3H), 2.00-1.67 (m, 3H), 1.47-1.22 (m, 1H).

(J) ((1r,4r)-4-(2-Fluoro-5-methoxyphenyl)cyclohexyl)methanol, 54d

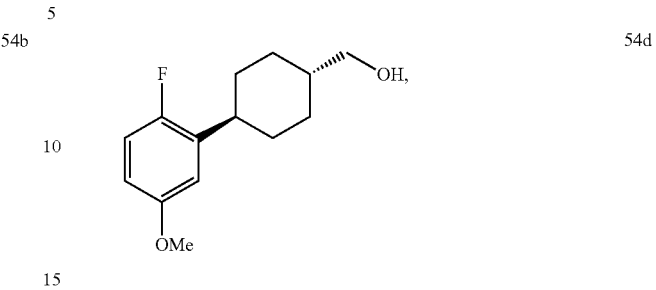

54d

To a solution of 4-(2-fluoro-5-methoxyphenyl)cyclohex-3-enyl)methanol, 54c (50.0 g, 0.212 mol) in DCM (1.0 L), was added Ir(COD)(Py)(PCy$_3$)PF$_6$ (5.12 g, 6.36 mmol). The reaction was purged with hydrogen gas (3×) followed by pressurization under a hydrogen gas atmosphere (40 atm) and heating to 30° C. The reaction was judged complete (LCMS) after 5 h. The mixture was concentrated under reduced pressure. The residue was dissolved in THF (100 mL) and heated to 40° C. to give a clear solution. The solution was gradually cooled to 15° C., heptane (30 mL) was added and the reaction stirred for 2 h. A white solid precipitated from the mixture, then another portion of heptane (500 mL) was added over 30 min and the slurry was stirred for an additional 2 h. The mixture was cooled to 0-5° C. before it was filtered, washed with heptane (50 mL), and dried under reduced pressure, to give compound 54d (trans:cis>99:1, purity 99.2% by HPLC) as a yellow solid. $^1$H NMR (400 MHz, CDCl$_3$) δ(ppm): 6.94 (m, 1H), 6.77 (m, 1H), 6.68 (m, 1H), 3.80 (s, 3H), 3.54 (m, 2H), 2.83 (m, 1H), 2.01-1.90 (m, 4H), 1.68-1.47 (m, 3H), 1.25-1.10 (m, 2H). Mass Spectrum (LCMS, ESI pos.): Calcd. For C$_{14}$H$_{19}$FO$_2$: 239.1 [M−H]$^+$; found: 239.4.

(K) Methyl (2S,3R)-3-(3-((tert-butyldimethylsilyl)oxy)phenyl)-3-cyclopropyl-2-methylpropanoate, 54e

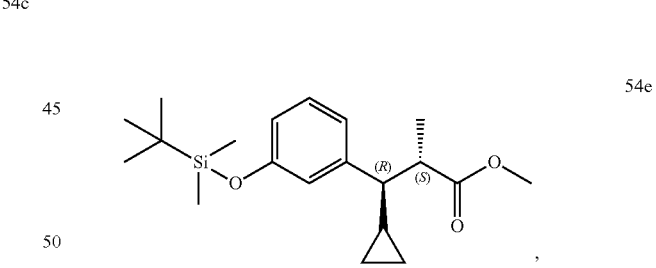

54e

To a solution of (2S,3R)-methyl 3-cyclopropyl-3-(3-hydroxyphenyl)-2-methylpropanoate (3 g, 12.81 mmol) in DCM (25 mL) was added 1H-imidazole (1.05 g, 15.37 mmol). The resulting solution was cooled to 0° C. in a water/ice bath, then tert-butylchlorodimethylsilane (2.12 g, 14.09 mmol) was added with stirring at 0° C. The resulting solution was stirred at rt for 3 h. The reaction was then quenched with brine (300 mL). The resulting mixture was extracted with DCM (3×300 mL). The combined organic layers were dried over Na$_2$SO$_4$, filtered and the filtrate concentrated. The crude residue was purified by column chromatography on silica gel (0-30% EtOAc/petroleum ether) to afford compound 54e as a yellow oil (3.8 g, 55.4% yield). Mass Spectrum (LCMS, ESI pos.): Calcd. For C$_{20}$H$_{32}$O$_3$Si 348.21 [M−H]$^+$; found: 371.15 [M+Na]$^+$.

(L) Methyl (3S)-3-(3-((tert-butyldimethylsilyl)oxy)phenyl)-3-cyclopropyl-2-fluoro-2-methylpropanoate, 54f

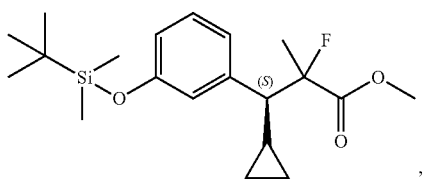

To a solution of (2S,3R)-methyl 3-(3-(tert-butyldimethylsilyloxy)phenyl)-3-cyclopropyl-2-methylpropanoate, 54e (4 g, 11.48 mmol) in THF (50 mL) was added LDA (2.0 M in THF, 11.5 mL, 22.95 mmol) at −78° C. dropwise for 30 min. The resulting solution was stirred at 0° C. for 30 min and cooled to −78° C. again before dropwise addition of N-fluorobenzenesulfonimide (7.24 g, 22.95 mmol). The resulting solution was stirred at rt for 2 h, then was quenched with water (400 mL). The resulting mixture was extracted with DCM (3×400 mL). The combined organic layers were dried over $Na_2SO_4$, filtered and the filtrate concentrated. The crude material was purified by column chromatography over silica gel (0-10% EtOAc/petroleum ether) to afford compound 54f as a yellow oil (3.8 g, 44.0% yield). Mass Spectrum (LCMS, ESI pos.): Calcd. For $C_{20}H_{31}FO_3Si$: 366.20, found: 367.3 $[M+H]^+$.

(M) Methyl (3S)-3-cyclopropyl-2-fluoro-3-(3-hydroxyphenyl)-2-methylpropanoate, 54g

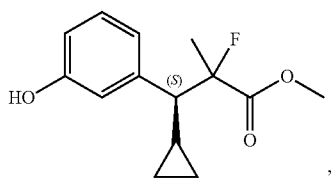

To a solution of (3S)-methyl 3-(3-(tert-butyldimethylsilyloxy)phenyl)-3-cyclopropyl-2-fluoro-2-methylpropanoate, 54f (3 g, 8.19 mmol) in THF (30 mL) was added tetrabutylammonium fluoride (1 M in THF, 16 mL) at 0° C. The resulting solution was stirring at rt for 2 h. The reaction was then quenched with water (300 mL). The resulting mixture was extracted with EtOAc (3×300 mL), and the combined organic layers were dried over $Na_2SO_4$, filtered and the filtrate concentrated. The crude material was purified by column chromatography over silica gel (0-60% EtOAc/petroleum ether) to afford compound 54g as a yellow oil (2 g, 89.5% yield). Mass Spectrum (LCMS, ESI pos.): Calcd. For $C_{14}H_{17}FO_3$: 252.12, found: 253.1 $[M+H]^+$.

(N) Methyl (3S)-3-cyclopropyl-2-fluoro-3-(3-(((1r,4S)-4-(2-fluoro-5-methoxyphenyl)cyclohexyl)methoxy)phenyl)-2-methylpropanoate, 54h

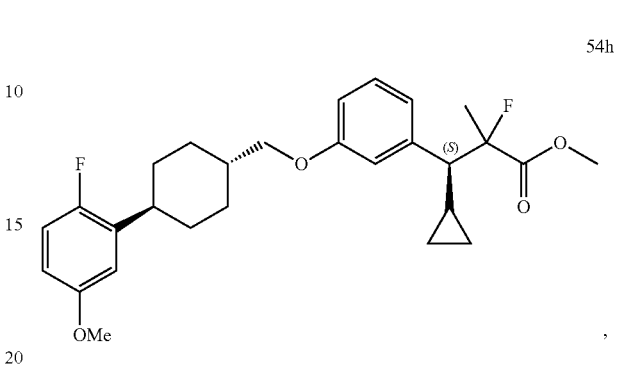

To a solution of (3S)-methyl 3-cyclopropyl-2-fluoro-3-(3-hydroxyphenyl)-2-methylpropanoate, 54g (500 mg, 1.98 mmol) in toluene (25 ml) was added ((1r,4r)-4-(2-fluoro-5-methoxyphenyl)cyclohexyl)methanol, 54d (614 mg, 2.58 mmol) and tributylphosphane (1.002 g, 4.955 mmol) under nitrogen at 0° C. This was followed by the addition of 1,1'-(azodicarbonyl)-dipiperidine (1.25 g, 4.96 mmol) in toluene (25 mL). The reaction mixture was stirred overnight at 60° C. before it was quenched with water (300 mL). The resulting mixture was extracted with EtOAc (3×300 mL). The organic layers were combined, dried over $Na_2SO_4$, filtered and the filtrate concentrated. The resultant residue was purified by column chromatography over silica gel (0-20% EtOAc/petroleum ether) to afford compound 54h (600 mg, 57.9% yield) as a yellow oil. Mass Spectrum (LCMS, ESI pos.): Calcd. for $C_{28}H_{34}F_2O_4$: 472.24, found: 495.3 $[M+Na]^+$.

(O) (3S)-3-Cyclopropyl-2-fluoro-3-(3-(((1r,4S)-4-(2-fluoro-5-methoxyphenyl)cyclohexyl)methoxy)phenyl)-2-methylpropanoic acid Cpd 58

To a solution of (3S)-methyl 3-cyclopropyl-2-fluoro-3-(3-(((1r,4S)-4-(2-fluoro-5-methoxyphenyl)cyclohexyl)methoxy)phenyl)-2-methylpropanoate, 54h (600 mg, 1.27 mmol) in THF (16 mL), water (8 mL) and methanol (4 mL) was added LiOH (304 mg, 12.70 mmol). The resulting solution was stirred overnight at rt. The mixture was concentrated under reduced pressure and then diluted with water (100 mL). The pH value of the solution was adjusted to 4-5 with HCl solution (1N, aq.). The precipitates were collected by filtration. The resultant crude material was purified by reverse-phase flash chromatography (C18 Column: Agela Technologies, Cat. #: SO230120-2, 120g, 20-35 μm, 100 Å; Mobile phase: A-$CH_3CN$, B-$H_2O$, 0.05% $NH_4HCO_3$ (v/v) as the modifier; Gradient: 15% A to 85% A within 30 min). The fractions were collected, combined and lyophilized to afford Cpd 58 as a white solid (500 mg, 85.2% yield). Compound 58 was found to be a mixture of Cpd 59 and Cpd 60. Mass Spectrum (LCMS, ESI pos.): Calcd. for $C_{27}H_{32}F_2O_4$: 458.23, found: 476.2 $[M+NH_4]^+$.

Example 55

(2R,3S)-3-Cyclopropyl-2-fluoro-3-(3-(((1r,4S)-4-(2-fluoro-5-methoxyphenyl)cyclohexyl)methoxy)phenyl)-2-methylpropanoic acid Cpd 59 and (2S,3S)-3-Cyclopropyl-2-fluoro-3-(3-(((1r,4S)-4-(2-fluoro-5-methoxyphenyl)cyclohexyl)methoxy)phenyl)-2-methylpropanoic acid Cpd 60

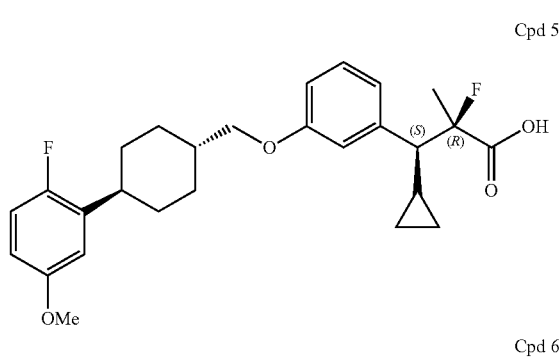

Cpd 59

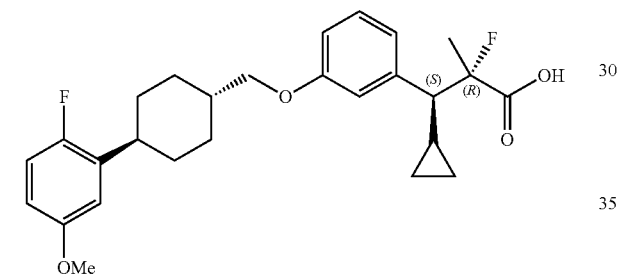

Cpd 60

(3S)-3-Cyclopropyl-2-fluoro-3-(3-(((1r,4S)-4-(2-fluoro-5-methoxyphenyl) cyclohexyl)methoxy)phenyl)-2-methylpropanoic acid, Cpd 58 (as prepared in Example 54) was subjected to preparative chiral HPLC separation on a Chiralpak IC, 2×25 cm, 5 µm column with hexane (0.1% TFA): EtOH=70:30 (v/v) to give Cpd 59 and Cpd 60 as white solids upon lyophilization.

Cpd 59: $^1$H NMR (400 MHz, DMSO-d$_6$) δ (ppm): 7.16-7.32 (m, 1H), 7.00-7.10 (m, 1H), 6.80-6.95 (m, 4H), 6.70-6.80 (m, 1H), 3.80-3.90 (m, 2H), 3.50-3.70 (s, 3H), 2.70-2.90 (m, 1H), 2.10-2.30 (m, 1H), 1.90-2.05 (m, 2H), 1.72-1.89 (m, 3H), 1.42-1.65 (m, 2H), 1.11-1.38 (m, 6H), 0.50-0.65 (m, 1H), 0.20-0.40 (m, 2H), −0.16--0.05 (m, 1H). $^{19}$F NMR (376 MHz, DMSO-d$_6$) δ −130.28, −162.38. Further NMR studies using COSY, HSQC, HMBC and NOESY spectra concluded that the chiral center a to the carboxylate is of R configuration. Mass Spectrum (LCMS, ESI pos.): Calcd. For $C_{27}H_{32}F_2O_4$: 458.23, found: 481.2 [M+Na]$^+$.

Cpd 60: $^1$H NMR (300 MHz, DMSO-d$_6$) δ (ppm): 7.11-7.25 (m, 1H), 7.00-7.12 (m, 1H), 6.67-6.91 (m, 5H), 3.79 (d, J=6.2 Hz, 2H), 3.73 (s, 3H), 2.70-2.90 (m, 1H), 2.20-2.40 (m, 1H), 1.89-2.05 (m, 2H), 1.74-1.89 (m, 3H), 1.69 (s, 2H), 1.40-1.70 (m, 3H), 1.10-1.38 (m, 3H), 0.65-0.85 (m, 1H), 0.40-0.60 (m, 1H), 0.20-0.38 (m, 1H), −0.20--0.05 (m, 1H). Mass Spectrum (LCMS, ESI pos.): Calcd. For $C_{27}H_{32}F_2O_4$: 458.23, found: 459.2 [M+H]$^+$.

Example 56

(2R,3S)-3-Cyclopropyl-2-fluoro-3-(3-(((1r,4S)-4-(2-fluoro-5-methoxyphenyl)cyclohexyl)methoxy)phenyl)-2-methylpropanoic acid Cpd 59

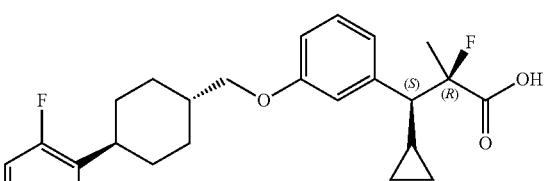

(A) Methyl (S)-3-cyclopropyl-3-(3-(((1r,4S)-4-(2-fluoro-5-methoxyphenyl)cyclohexyl) methoxy)phenyl)propanoate, 56a

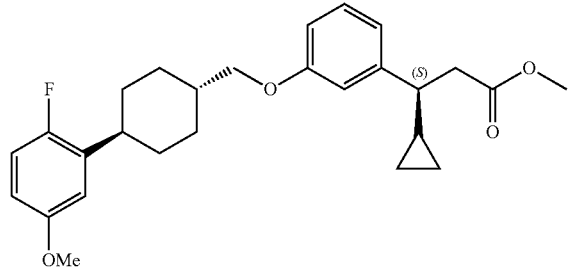

56a

To a solution of ((1r,4r)-4-(2-fluoro-5-methoxyphenyl) cyclohexyl)methanol, 54d (200 g, 0.84 mol) and (9-methyl 3-cyclopropyl-3-(3-hydroxyphenyl)propanoate (203 g, 0.92 mol) in acetonitrile (1.5 L) was added tributylphosphine (255.0 g, 1.260 mol) under a nitrogen atmosphere. The solution was warmed to 80° C. and a solution of diethyl diazene-1,2-dicarboxylate (219 g, 1.26 mol) in acetonitrile (0.5 L) was added dropwise over 1.5 h. The solution was stirred for 1 h and judged complete by LCMS. The mixture was concentrated to about 1.0 L under reduced pressure and ethyl acetate (3.0 L) was added. The organic layer was washed with saturated NaCl (3.0 L) and concentrated under reduced pressure. The residue was purified by chromatography on silica gel (heptane:ethyl acetate, 20:1) to give compound 56a. $^1$H NMR (300 MHz, CDCl$_3$) δ (ppm): 7.26 (m, 1H), 6.96 (m, 1H), 6.83 (m, 4H), 6.70 (m, 1H), 3.86 (m, 1H), 3.83 (s, 3H), 3.65 (s, 3H), 2.88 (m, 1H), 2.78 (m, 2H), 2.37 (m, 1H), 2.04 (m, 5H), 1.59 (m, 2H), 1.45 (m, 1H), 1.30 (m, 3H), 0.99 (m, 3H), 0.59 (m, 1H), 0.47 (m, 1H), 0.29 (m, 1H), 0.19 (m, 1H). Mass Spectrum (LCMS, ESI pos.): Calcd. For $C_{27}H_{33}FO_4$: 440.24; found: 441.3 [M+H]$^+$.

(B) (S)-3-Cyclopropyl-3-(3-(((1r,4S)-4-(2-fluoro-5-methoxyphenyl)cyclohexyl) methoxy)phenyl)propanoic acid, 56b

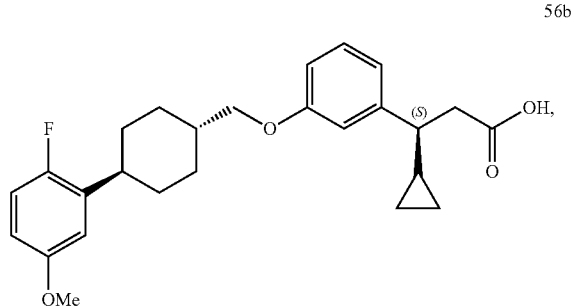

56b

To a solution of (S)-methyl 3-cyclopropyl-3-(3-(((1r,4S)-4-(2-fluoro-5-methoxyphenyl)cyclohexyl)methoxy)phenyl) propanoate, 56a (570 g, 1.30 mol) in THF (2.85 L) and methanol (2.85 L) was added a solution of NaOH (259 g, 6.48 mol) in water (2.85 L) at 20° C. over 30 min. The reaction mixture was stirred at 30° C. overnight. The mixture was cooled to 20° C. and the pH of the solution was adjusted to 4-5 with HCl (aq., 4 N). Ethyl acetate (8.5 L) was added and the resulting mixture was stirred for 20 min. The separated organic layer was washed with 5% NaCl (5.7 L), dried over Na$_2$SO$_4$, filtered, and the filtrate concentrated to about 2.8 L. Heptane (5.7 L) was then added and the resulting mixture was concentrated to about 5.7 L. This procedure was repeated twice. Heptane (2.85 L) was then added and the solution was cooled to 10-20° C. with stirring. The precipitate formed was collected by filtration, washed with heptane (2.0 L) and dried under reduced pressure to a constant weight to give compound 56b. $^1$H NMR (400 MHz, CDCl$_3$): δ(ppm): 10.2 (brs, 1H), 7.25 (m, 1H), 6.94 (m, 1H), 6.82 (m, 4H), 6.68 (m, 1H), 3.82 (m, 2H), 3.80 (s, 3H), 2.85 (m, 3H), 2.37 (m, 1H), 2.05 (m, 2H), 1.99 (m, 2H), 1.96 (m, 1H), 1.54 (m, 2H), 1.31 (m, 2H), 1.06 (m, 1H), 0.61 (m, 1H), 0.47 (m, 1H), 0.33 (m, 1H), 0.21 (m, 1H). Mass Spectrum (LCMS, ESI neg.): Calcd. For C$_{26}$H$_{31}$FO$_4$: 426.53; found: 425.3 [M−H]$^+$.

(C) (S)-3-((S)-3-Cyclopropyl-3-(3-(((1r,4S)-4-(2-fluoro-5-methoxyphenyl)cyclohexyl)methoxy)phenyl)propanoyl)-4-isopropyl-5,5-dimethyloxazolidin-2-one, 56c

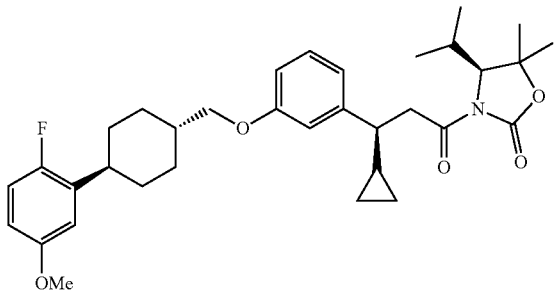

56c

To a solution of (5)-methyl 3-cyclopropyl-3-(3-(((1r,4S)-4-(2-fluoro-5-methoxyphenyl)cyclohexyl)methoxy)phenyl) propanoic acid, 56b (8.0 g, 18.76 mmol) in DCM (100 mL) cooled in an ice-water bath was added DMF (100 μL) and oxalyl chloride (2.62 mL, 30.95 mmol) in a drop-wise fashion under argon. The mixture was stirred at 0° C. for 10 min and at rt for 1 h. Solvent was removed under reduced pressure and the residue was dried under high vacuum overnight to afford (S)-3-cyclopropyl-3-(3-(((1r,4S)-4-(2-fluoro-5-methoxyphenyl)cyclohexyl)methoxy)phenyl)propanoyl chloride, which was directly used in the next step.

To a solution of (S)-4-isopropyl-5,5-dimethyloxazolidin-2-one (3.23 g, 20.52 mmol; prepared according to the methods described by J. Alvarado, et al. *J. Org. Chem.*, 2014, 79, 6206-6220) in THF (70 mL) was added n-BuLi dropwise at −78° C. under an argon atmosphere. After stirring at −78° C. for 30 min, a solution of (S)-3-cyclopropyl-3-(3-(((1r,4S)-4-(2-fluoro-5-methoxyphenyl)cyclohexyl)methoxy)phenyl)propanoyl chloride (8.3 g, 18.65 mmol) in THF (30 mL) was added dropwise. The mixture was stirred at −78° C. for 2 h, then at rt for another 1 h. NH$_4$Cl solution (satd., 100 mL) was added to quench the reaction. EtOAc (2×200 mL) was used to extract the mixture. The combined organic layers were washed with brine, dried over Na$_2$SO$_4$, filtered and the filtrate concentrated. The resultant residue was purified by flash chromatography (0-30% EtOAc/heptane) to afford compound 56c as a colorless oil (9.8 g, 92.9% yield). Mass Spectrum (LCMS, ESI pos.): Calcd. For C$_{34}$H$_{44}$FNO$_5$: 565.73; found: 566.4 [M+H]$^+$.

(D) (4S)-3-((3S)-3-Cyclopropyl-2-fluoro-3-(3-(((1r,4S)-4-(2-fluoro-5-methoxyphenyl)cyclohexyl)methoxy)phenyl)propanoyl)-4-isopropyl-5,5-dimethyloxazolidin-2-one, 56d

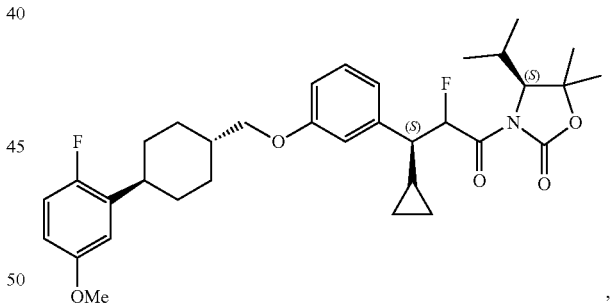

56d

To a solution of (S)-3-((S)-3-cyclopropyl-3-(3-(((1r,4S)-4-(2-fluoro-5-methoxyphenyl)cyclohexyl)methoxy)phenyl) propanoyl)-4-isopropyl-5,5-dimethyloxazolidin-2-one, 56c (8.4 g, 14.85 mmol) in THF (60 mL) was added LiHMDS (1.0 M in THF, 29.70 mL, 29.70 mmol) dropwise at −78° C. under an argon atmosphere. After 1 h at −78° C., the mixture was stirred at −15° C. for 40 min. The mixture was cooled to −78° C. again and a solution of N-fluorobenzenesulfonimide (9.37 g, 29.70 mmol) in THF (20 mL) was added dropwise under argon. The reaction was allowed to slowly warm to rt, followed by stirring overnight. The reaction mixture was quenched with NH$_4$C$_1$ (satd., 200 mL). The mixture was extracted with EtOAc (2×100 mL), and the organic layers were combined, washed with brine, and dried over Na$_2$SO$_4$. After filtration and concentration, the residue was washed with ether. The insoluble white solid was removed by filtration and washed with DCM. The filtrate was concentrated and purified by flash chromatography (dry pack, 0-30% EtOAc/heptane) to give compound 56d as a pale yellow solid (7.95 g, 91.7% yield). Mass Spectrum (LCMS, ESI pos.): Calcd. For $C_{34}H_{43}F_2NO_5$: 583.72; found: 584.4 [M+H]$^+$.

(E) (S)-3-((2R,3S)-3-Cyclopropyl-2-fluoro-3-(3-(((1r,4S)-4-(2-fluoro-5-methoxyphenyl)cyclohexyl)methoxy)phenyl)-2-methylpropanoyl)-4-isopropyl-5,5-dimethyloxazolidin-2-one, 56e

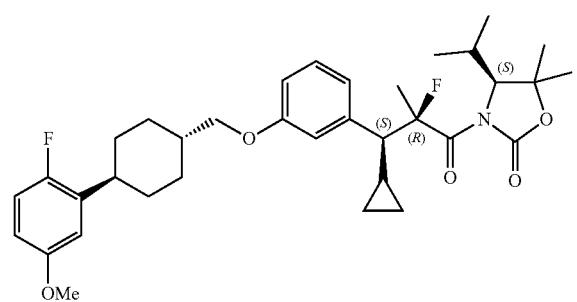

To a solution of (4S)-3-((3S)-3-cyclopropyl-2-fluoro-3-(3-(((1r,4S)-4-(2-fluoro-5-methoxyphenyl)cyclohexyl)methoxy)phenyl)propanoyl)-4-isopropyl-5,5-dimethyloxazolidin-2-one, 56d (6.9 g, 11.82 mmol) in THF (80 mL) was added LiHMDS (1.0 M in THF, 35.46 mL, 35.46 mmol) dropwise at −78° C. under argon. After 30 min at −78° C., the mixture was stirred at 0° C. for 80 min before cooling again to −78° C. Iodomethane (4.42 mL, 70.93 mmol) was added dropwise, under argon, to the reaction mixture. The reaction was allowed to gradually warm to rt, followed by stirring for 2 d. The mixture was quenched with NH$_4$Cl (satd.), extracted with EtOAc (2×100 mL), and the organic layers were combined, washed with brine, and dried over Na$_2$SO$_4$. After filtration and concentration, the resultant residue was treated with hot EtOAc. Upon cooling, a white solid (compound 56d, 3.2 g) precipitated and was collected by filtration. The filtrate was concentrated and purified by flash column chromatography (dry pack, 0-25% EtOAc/heptane) to afford another 2 g of compound 56d as a white solid (total 5.2 g, 72.4% yield). Mass Spectrum (LCMS, ESI pos.): Calcd. For $C_{35}H_{45}F_2NO_5$: 597.74; found: 598.4 [M+H]$^+$.

(F) (2R,3S)-3-Cyclopropyl-2-fluoro-3-(3-(((1r,4S)-4-(2-fluoro-5-methoxyphenyl)cyclohexyl)methoxy)phenyl)-2-methylpropanoic acid, Cpd 59

To a solution of (S)-3-((2R,3S)-3-cyclopropyl-2-fluoro-3-(3-(((1r,4S)-4-(2-fluoro-5-methoxyphenyl)cyclohexyl)methoxy)phenyl)-2-methylpropanoyl)-4-isopropyl-5,5-dimethyloxazolidin-2-one, 3e (5.66 g, 9.47 mmol) in THF (80 mL) was added LiOH (0.91 g, 37.88 mmol) and H$_2$O$_2$ (30% in water, 7.74 mL, 75.75 mmol) at 0° C. The mixture was stirred at rt for 4 d. EtOAc (200 mL) was added, and the organic layer was washed sequentially with NaOH (1 N, 50 mL), HCl (1 N, 50 mL) and brine, then dried over Na$_2$SO$_4$. The mixture was filtered and the filtrate was concentrated and purified by flash column chromatography (0-100% EtOAc/heptane). Certain fractions contained pure Cpd 59, while some fractions contained a mixture of Cpd 59 and the oxazolidone. The mixed fractions were pooled and solvent was removed under reduced pressure. The resultant residue was treated with NaOH (1 N, 50 mL), and the mixture was extracted with ether (2×30 mL). The aqueous layer was acidified with HCl (2 N) and extracted with EtOAc (50 mL). The organic layer was washed with brine and dried over Na$_2$SO$_4$. Once filtered and concentrated, an oxazolidone impurity remained. The material was further purified by recrystallization from EtOAc/heptane (1:20 v/v). Cpd 59 was obtained as a white solid (4.1 g, 94.4% yield). $^1$H NMR (400 MHz, DMSO-d$_6$) δ (ppm): 13.28 (s, 1H), 7.18-7.25 (m, 1H), 7.05 (dd, J=10.1, 9.1 Hz, 1H), 6.84 (br d, J=6.1 Hz, 4H), 6.76 (dt, 3.5 Hz, 1H), 3.81 (d, J=6.1 Hz, 2H), 3.73 (s, 3H), 2.71-2.83 (m, 1H), 2.19-2.31 (m, 1H), 1.96 (br d, J=10.6 Hz, 2H), 1.76-1.88 (m, 3H), 1.48-1.62 (m, 2H), 1.17-1.37 (m, 6H), 0.50-0.61 (m, 1H), 0.28-0.42 (m, 2H), −0.12--0.03 (m, 1H). Mass Spectrum (LCMS, ESI pos.): Calcd. For $C_{27}H_{32}F_2O_4$: 458.54; found: 481.3 [M+Na]$^+$.

Example 57

(3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid Cpd 61

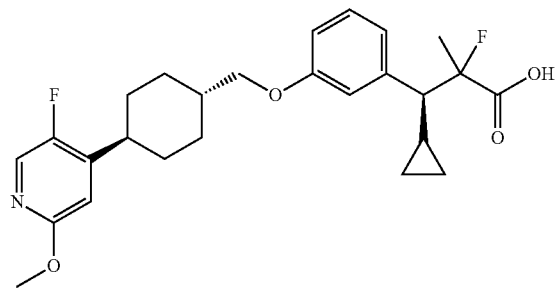 [SMILES: COc1cc([C@H]2CC[C@H](COc3cccc([C@H](C4CC4)C(C)(F)C(=O)O)c3)CC2)c(F)cn1]

(F) Ethyl 4-(5-fluoro-2-methoxypyridin-4-yl)cyclohex-3-enecarboxylate, 57a

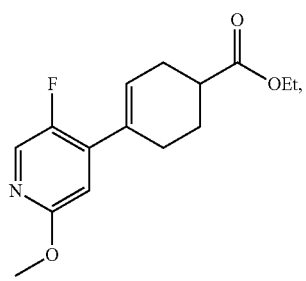

A mixture of ethyl 4-(trifluoromethylsulfonyloxy)cyclohex-3-enecarboxylate, 54a (34.0 g, 112 mmol), 5-fluoro-2-methoxypyridin-4-ylboronic acid (28.8 g, 168 mmol), Pd(dppf)Cl$_2$.CH$_2$Cl$_2$ (2.00 g, 2.45 mmol), and triethylamine (34.1 g, 337 mmol) in ethanol (300 mL) was stirred for 2 h at 90° C. The reaction was cooled to rt and treated with water (300 mL). The resulting mixture was extracted with EtOAc (3×300 mL). The organic layers were combined, dried over $Na_2SO_4$, filtered, and the filtrate concentrated. The resultant residue was purified by flash chromatography (0-5% EtOAc/petroleum ether) to afford compound 57a. Mass Spectrum (LCMS, ESI pos.): Calcd. for $C_{15}H_{18}FNO_3$: 279.1; found: 280.0 [M+H]$^+$.

(G) (4-(5-Fluoro-2-methoxypyridin-4-yl)cyclohex-3-en-1-yl)methanol, 57b

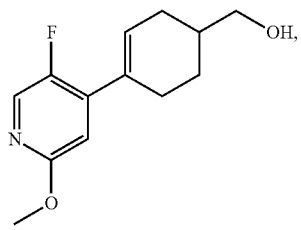

57b

To a solution of ethyl 3-(5-fluoro-2-methoxypyridin-4-yl)cyclohex-3-enecarboxylate, 57a, (15.0 g, 53.7 mmol) in THF (150 mL) was added DIBAL (163 mL, 163 mmol, 1 M in hexane) at −20° C. The resulting solution was stirred for 0.5 h at −20° C., allowed to warm to rt and stirred for 1 h. The reaction was then quenched by potassium sodium tartrate solution (satd., 100 mL). The resulting solution was extracted with EtOAc (3×150 mL). The organic layers were combined, dried over $Na_2SO_4$ and concentrated. The residue obtained was purified by flash chromatography (0-40% EtOAc/petroleum ether) to give compound 57b as a yellow oil. Mass Spectrum (LCMS, ESI pos.): Calcd. for $C_{13}H_{16}FNO_2$: 237.1; found: 237.9 [M+H]$^+$.

(H) ((1r,4r)-4-(5-Fluoro-2-methoxypyridin-4-yl)cyclohexyl)methanol, 57c-1 and

((1s,4s)-4-(5-Fluoro-2-methoxypyridin-4-yl)cyclohexyl)methanol, 57c-2

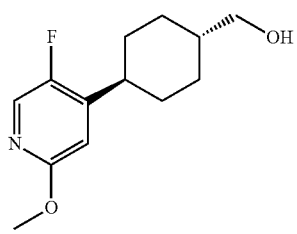

57c-1

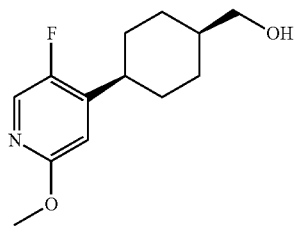

57c-2

A mixture of (3-(5-fluoro-2-methoxypyridin-4-yl)cyclohex-3-enyl)methanol, 57b (6.8 g, 29 mmol) and Pd on carbon (10%, 3.4 g) in MeOH (50 mL) was stirred for 1 h at rt under a hydrogen (3.5 atm) atmosphere. The reaction mixture was filtered and the filtrate was concentrated. The resulting residue was purified by preparative chiral HPLC on a Chiralpak IC-2×25 cm, 5 μm chiral column (hexane:EtOH; 0.1% TFA, v/v) with gradient (20-90% over 40 min) to give compounds 57c-1 and 57c-2.

Cpd 57c-1: $^1$H NMR (400 MHz, CDCl$_3$) δ (ppm): 7.89 (s, 1H), 6.59 (d, J=5.1 Hz, 1H), 3.89 (s, 3H), 3.51 (d, J=6.3 Hz, 2H), 2.77 (t, J=12.0 Hz, 1H), 1.92-1.96 (m, 4H), 1.39-1.79 (m, 4H), 1.09-1.26 (m, 2H).

Cpd 57c-2: $^1$H NMR (400 MHz, CDCl$_3$) δ (ppm): 7.88 (s, 1H), 6.59 (d, J=4.8 Hz, 1H), 3.89 (s, 3H), 3.70 (d, J=7.2 Hz, 2H), 2.82-2.90 (m, 1H), 1.91-1.95 (m, 1H), 1.80-1.89 (m, 2H), 1.61-1.79 (m, 7H).

(I) (3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid, Cpd 61

Compound 61 was prepared from ((1r,4r)-4-(5-fluoro-2-methoxypyridin-4-yl)cyclohexyl)methanol, 57c-1 and (3S)-methyl 3-cyclopropyl-2-fluoro-3-(3-hydroxyphenyl)-2-methylpropanoate, 54g according to the methods described in Example 54, Steps H and I. $^1$H NMR (300 MHz, DMSO-d$_6$) δ (ppm): 8.02 (d, J=1.9 Hz, 1H), 7.20 (dd, J$_1$=9.0 Hz, J$_2$=7.5 Hz, 1H), 6.72-6.86 (m, 4H), 3.80 (d, J=3.3 Hz, 5H), 2.70-2.83 (m, 1H), 2.16-2.33 (m, 1H), 1.95 (d, J=13.0 Hz, 2H), 1.82 (d, J=12.3 Hz, 3H), 1.43-1.61 (m, 2H), 1.10-1.33 (m, 6H), 0.45-0.60 (m, 1H), 0.25-0.40 (m, 2H), −0.19−−0.09 (m, 1H). Mass Spectrum (LCMS, ESI pos.): Calcd. for $C_{26}H_{31}F_2NO_4$: 459.2; found: 460.2 [M+H]$^+$.

Example 58

(2R,3S)-3-Cyclopropyl-2-fluoro-3-(3-((1r,4S)-4-(2-fluoro-5-methoxypyridin-4-yl)cyclohexyl)methoxy)phenyl)-2-methylpropanoic acid Cpd 62 and

(2S,3S)-3-Cyclopropyl-2-fluoro-3-(3-(((1r,4S)-4-(2-fluoro-5-methoxypyridin-4-yl)cyclohexyl)methoxy)phenyl)-2-methylpropanoic acid Cpd 63

Cpd 62

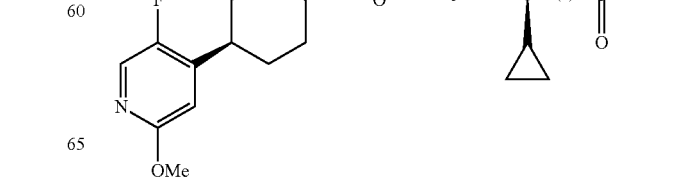

Cpd 63

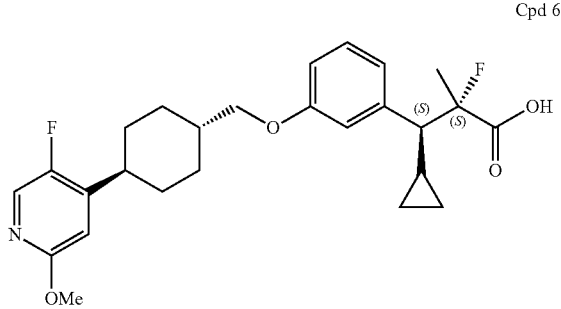

Cpd 62 and Cpd 63 were prepared from (3S)-3-cyclopropyl-2-fluoro-3-(3-(((1r,4S)-4-(2-fluoro-5-methoxypyridin-4-yl)cyclohexyl)methoxy)phenyl)-2-methylpropanoic acid, Cpd 61 using the method described in Example 55.

Cpd 62: $^1$H NMR (400 MHz, DMSO-d$_6$) δ (ppm): 7.98-8.17 (m, 1H), 7.18-7.26 (m, 1H), 6.70-6.86 (m, 4H), 3.80 (d, J=4.1 Hz, 5H), 2.73-2.78 (m, 1H), 2.24 (dd, J$_1$=29.4 Hz, J$_2$=10.5 Hz, 1H), 1.95 (dd, J$_1$=13.5 Hz, J$_2$=3.6 Hz, 2H), 1.77-1.88 (m, 3H), 1.44-1.59 (m, 2H), 1.16-1.34 (m, 6H), 0.50-0.60 (m, 1H), 0.25-0.40 (m, 2H), −0.20-−0.10 (m, 1H). Mass Spectrum (LCMS, ESI pos.): Calcd. For C$_{26}$H$_{31}$F$_2$NO$_4$: 459.2; found: 460.4 [M+H]$^+$.

Cpd 63: $^1$H NMR (400 MHz, DMSO-d$_6$) δ (ppm): 7.99-8.24 (m, 1H), 7.10-7.20 (m, 1H), 6.70-6.82 (m, 4H), 3.72-3.83 (m, 5H), 2.75 (dd, J, =13.8 Hz, J$_2$=10.5 Hz, 1H), 2.24-2.39 (m, 1H), 1.94 (dd, J$_1$=12.7 Hz, J$_2$=3.6 Hz, 2H), 1.81 (d, J=11.8 Hz, 3H), 1.57 (d, J=21.6 Hz, 3H), 1.48-1.52 (m, 1H), 1.09-1.29 (m, 4H), 0.70-0.80 (m, 1H), 0.40-0.50 (m, 1H), 0.25-0.35 (m, 1H), −0.20-−0.10 (m, 1H). Mass Spectrum (LCMS, ESI pos.): Calcd. For C$_{26}$H$_{31}$F$_2$NO$_4$: 459.2; found: 460.3 [M+H]$^+$.

Example 59

(2R,3S)-3-(3-((4-(2-Chloro-5-methoxyphenyl)cyclohexyl)methoxy)phenyl)-3-cyclopropyl-2-fluoro-2-methylpropanoic acid, Cpd 64

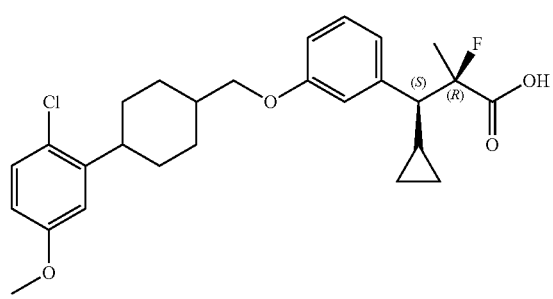

(F) Ethyl 4-(4,4,5,5-tetramethyl-1,3,2-dioxaborolan-2-yl)cyclohex-3-enecarboxylate, 59a

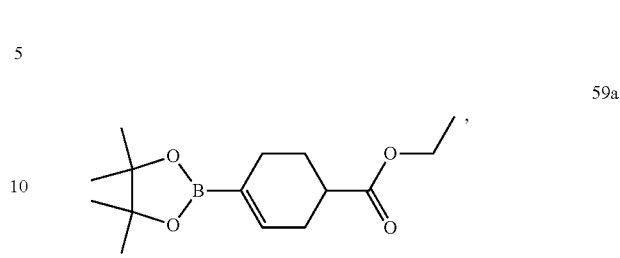

A mixture of ethyl 4-(trifluoromethylsulfonyloxy)cyclohex-3-enecarboxylate, 54a (17 g, 56 mmol), bis(pinacolato)diboron (21 g, 84 mmol), KOAc (16 g, 168 mmol) and Pd(dppf)Cl$_2$·CH$_2$Cl$_2$ (4.6 g, 5.6 mmol) in DMSO (100 mL) was stirred overnight at 80° C. The reaction mixture was allowed to cool to RT, treated with NH$_4$Cl (100 mL, satd., aq.) and extracted with EtOAc (3×300 mL). The combined organic layers were dried over Na$_2$SO$_4$, filtered, and the filtrate concentrated. The residue obtained was purified by flash chromatography on silica gel with EtOAc/petroleum ether (0-15%) to give compound 6a. Mass Spectrum (LCMS, ESI pos.): Calcd. For C$_{15}$H$_{25}$BO$_4$: 280.1; found: 281.0 [M+H]$^+$.

(G) Ethyl 2'-chloro-5'-methoxy-2,3,4,5-tetrahydro-[1,1'-biphenyl]-4-carboxylate, 59b

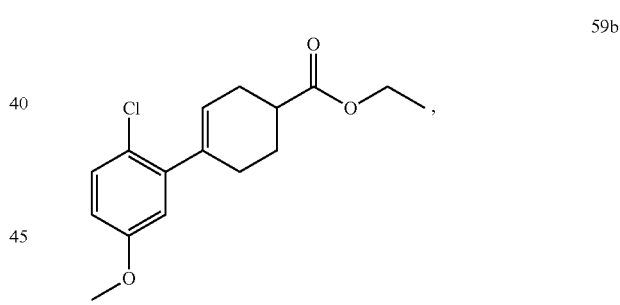

To a solution of 2-bromo-1-chloro-4-methoxybenzene (1 g, 4.52 mmol) and ethyl 4-(4,4,5,5-tetramethyl-1,3,2-dioxaborolan-2-yl)cyclohex-3-enecarboxylate, 59a (1.52 g, 5.42 mmol) in 1,4-dioxane (25 mL) and water (5 mL) was added Pd(dppf)Cl$_2$·CH$_2$Cl$_2$ (184.5 mg, 0.23 mmol) and cesium carbonate (2.94 g, 9.03 mmol) under nitrogen. The resulting mixture was stirred at 80° C. for 2 h. After cooling to rt, the reaction was quenched with water (20 mL). The resulting mixture was extracted with EtOAc (3×20 mL). The organic layers were combined, dried over Na$_2$SO$_4$, filtered and the filtrate concentrated. The residue obtained was purified by flash chromatography on silica gel (0-5% EtOAc/petroleum ether) to afford compound 59b as a yellow oil (1.2 g, 90.1% yield). Mass Spectrum (LCMS, ESI pos.): calcd for C$_{16}$H$_{19}$ClO$_3$: 294.1, found: 295.3 [M+H]$^+$.

(H) (2'-Chloro-5'-methoxy-2,3,4,5-tetrahydro-[1,1'-biphenyl]-4-yl)methanol, 59c

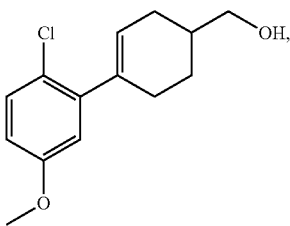

Compound 6c was prepared from ethyl 2'-chloro-5'-methoxy-2,3,4,5-tetrahydro-[1,1'-biphenyl]-4-carboxylate, 6b, according to the method described in Example 4, Step B. Mass Spectrum (LCMS, ESI pos.): calcd for $C_{14}H_{17}ClO_2$: 252.1, found: 253.1 $[M+H]^+$.

(I) (4-(2-Chloro-5-methoxyphenyl)cyclohexyl)methanol, 59d

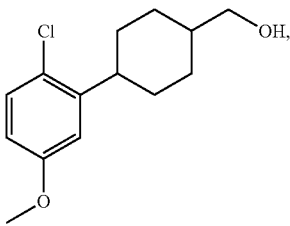

A mixture of (4-(2-chloro-5-methoxyphenyl)cyclohex-3-enyl)methanol, 59c (250 mg, 0.99 mmol) and Ir(COD)(Py)(PCy$_3$)PF$_6$ (80 mg, 0.099 mmol) in DCM (5 mL) was stirred at 30° C. for 12 h under a H$_2$ (g, 40 atm) atmosphere. The mixture was concentrated to remove solvent and the residue obtained was purified by flash chromatography on silica gel (0-20% EtOAc/petroleum ether) to afford compound 59d as a mixture of trans- and cis-isomers (trans:cis=83:17). Mass Spectrum (LCMS, ESI pos.): calcd. for $C_{14}H_{19}ClO_2$: 254.11, found: 237.2 $[M-OH]^+$.

(J) Methyl (2R,3S)-3-cyclopropyl-2-fluoro-3-(3-hydroxyphenyl)-2-methylpropanoate, 59e

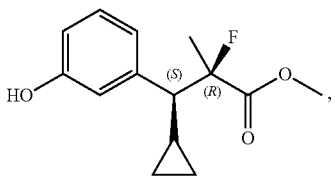

Compound 59e was prepared from the racemic mixture of (3S)-methyl 3-cyclopropyl-2-fluoro-3-(3-hydroxyphenyl)-2-methylpropanoate, 54g, through chiral Prep-HPLC with the following conditions: Column name: Lux 5μ Celluloes-3, AXIA Packed 2.12×25 cm, 5 μm 00G-4493-P0-AX742027-1, Mobile Phase A: CO$_2$: 85%; Mobile Phase B: isopropyl alcohol:15%; Flow rate: 40 g/min; Detector: 220 nm. $^1$H NMR (400 MHz, DMSO-d$_6$) δ (ppm): 9.32 (s, 1H), 7.10 (t, J=7.6 Hz, 1H), 6.65-6.68 (m, 3H), 3.75 (s, 3H), 2.14 (dd, J$_1$=10.8 Hz, J$_2$=30 Hz, 1H), 1.22-1.28 (m, 3H), 1.04 (d, J=6 Hz, 1H), 0.49-0.56 (m, 1H), 0.30-0.37 (m, 1H), 0.16-0.22 (m, 1H), −0.12-−0.06 (m, 1H).

(K) (3S)-3-(3-(((4-(2-Chloro-5-methoxyphenyl)cyclohexyl)methoxy)phenyl)-3-cyclopropyl-2-fluoro-2-methylpropanoic acid, Cpd 64

Compound 64 was prepared from (4-(2-chloro-5-methoxyphenyl)cyclohexyl)methanol, 59d and methyl (2R,3S)-3-cyclopropyl-2-fluoro-3-(3-hydroxyphenyl)-2-methylpropanoate, 59e according to the methods described in Example 54, Steps H and I. $^1$H NMR (300 MHz, DMSO-d$_6$) δ (ppm): 7.30 (dd, J$_1$=8.7 Hz, J$_2$=3.5 Hz, 1H), 7.14-7.23 (m, 1H), 6.75-6.97 (m, 5H), 3.75-3.78 (m, 5H), 2.80-2.95 (m, 1H), 2.22-2.42 (m, 1H), 1.40-2.05 (m, 7H), 1.15-1.32 (m, 3H), 1.05 (d, J=21.0 Hz, 3H), 0.37-0.54 (m, 2H), 0.21 (m, 1H), −0.26-−0.13 (m, 1H). Mass Spectrum (LCMS, ESI pos.): Calcd. for $C_{27}H_{32}ClFO_4$: 474.2; found: 492.2 $[M+NH_4]^+$.

Example 60

(3S)-3-(3-((4-(2-Chloro-5-ethylphenyl)cyclohexyl)methoxy)phenyl)-3-cyclopropyl-2-fluoro-2-methylpropanoic acid, Cpd 65

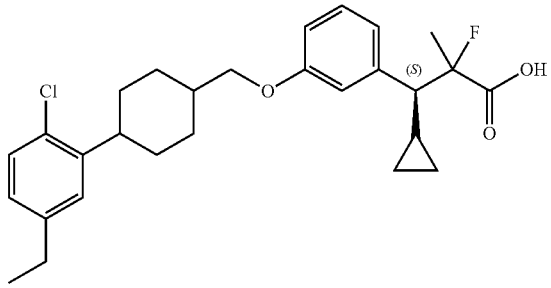

(A) (4-(2-Chloro-5-ethylphenyl)cyclohexyl)methanol, 60a

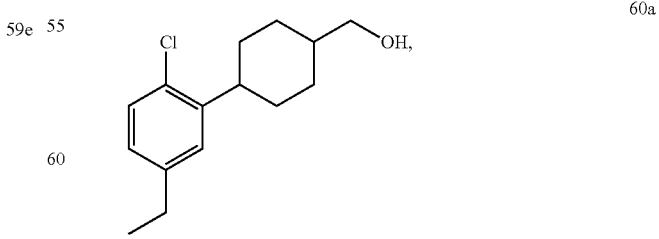

Compound 60a was prepared using the method described in Example 59, Steps A-D. Mass Spectrum (LCMS, ESI pos.): calcd. for $C_{15}H_{21}ClO$: 250.11, found: 251.1 $[M+H]^+$.

(B) (3S)-3-(3-((4-(2-Chloro-5-ethylphenyl)cyclohexyl)methoxy)phenyl)-3-cyclopropyl-2-fluoro-2-methylpropanoic acid, Cpd 65

Compound 65 was prepared from (4-(2-chloro-5-ethylphenyl)cyclohexyl)methanol, 60a and (3S)-methyl 3-cyclopropyl-2-fluoro-3-(3-hydroxyphenyl)-2-methylpropanoate, 54g according to the methods described in Example 54, Steps H and I. $^1$H NMR (300 MHz, DMSO-d$_6$) δ (ppm): 7.29 (t, J=6.8 Hz, 1H), 7.12-7.25 (m, 2H), 7.03-7.12 (m, 1H), 6.78-6.92 (m, 3H), 3.81 (d, J=6.2 Hz, 2H), 2.84-2.98 (m, 1H), 2.58 (q, J=7.7 Hz, 2H), 2.25-2.41 (m, 1H), 1.94-2.04 (m, 2H), 1.77-1.89 (m, 2H), 1.42-1.69 (m, 3H), 1.03-1.34 (m, 9H), 0.37-0.59 (m, 2H), 0.12-0.26 (m, 1H), −0.10-−0.30 (m, 1H). Mass Spectrum (LCMS, ESI pos.): Calcd. for $C_{28}H_{34}ClFO_3$: 472.2; found: 490.5 [M+NH$_4$]$^+$.

Example 61

(3S)-3-Cyclopropyl-2-fluoro-3-(3-((4-(3-methoxyphenyl)cyclohexyl)methoxy)phenyl)-2-methylpropanoic acid, Cpd 66

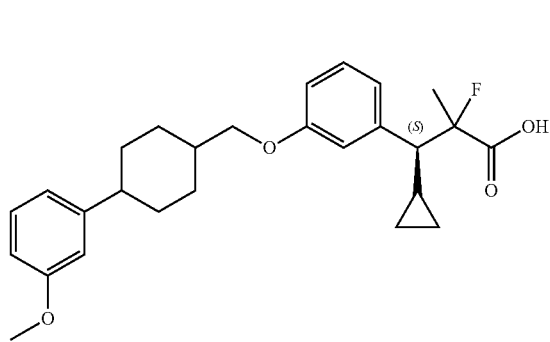

(A) (4-(3-Methoxyphenyl)cyclohexyl)methanol, 61a

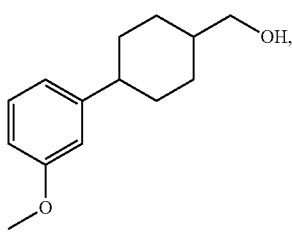

61a

To a solution of (4-(3-methoxyphenyl)cyclohex-3-enyl)methanol (prepared using the methods described in Example 6, Steps A-C (200 mg, 0.92 mmol) in methanol (6 mL) and ethyl acetate (6 mL) was added Pd/C (100 mg, 10% wt). The resulting solution was stirred at rt for 4 h under a H$_2$ ((g), 3.5 atm) atmosphere. The mixture was filtered through a pad of diatomaceous earth. The filtrate was concentrated under reduced pressure to afford compound 61a as a yellow oil (160 mg, 21.7% yield). Mass Spectrum (LCMS, ESI pos.): calcd. for $C_{14}H_{20}O_2$: 220.15, found: 221.0 [M+H]$^+$.

(B) (3S)-3-Cyclopropyl-2-fluoro-3-(3-((4-(3-methoxyphenyl)cyclohexyl)methoxy)phenyl)-2-methylpropanoic acid, Cpd 66

Compound 66 was prepared from (4-(3-methoxyphenyl)cyclohexyl)methanol, 61 and (3S)-methyl 3-cyclopropyl-2-fluoro-3-(3-hydroxyphenyl)-2-methylpropanoate, 54g according to the methods described in Example 54, Steps H and I. $^1$H NMR (300 MHz, DMSO-d$_6$) δ (ppm): 7.07-7.34 (m, 2H), 6.62-6.98 (m, 6H), 3.76-4.10 (m, 2H), 3.60-3.76 (m, 3H), 2.40-2.50 (m, 1H), 2.15-2.37 (m, 1H), 1.90-2.05 (m, 2H), 1.74-1.90 (m, 3H), 1.40-1.74 (m, 3H), 1.10-1.40 (m, 5H), 0.45-0.60 (m, 1H), 0.20-0.42 (m, 2H), −0.17-−0.03 (m, 1H). Mass Spectrum (LCMS, ESI pos.): Calcd. for $C_{27}H_{33}FO_4$: 440.24, found: 458.3 [M+NH$_4$]$^+$.

Example 62

(3S)-3-Cyclopropyl-3-(3-((4-(2,5-difluoropyridin-4-yl)cyclohexyl)methoxy)phenyl)-2-fluoro-2-methylpropanoic acid, Cpd 67

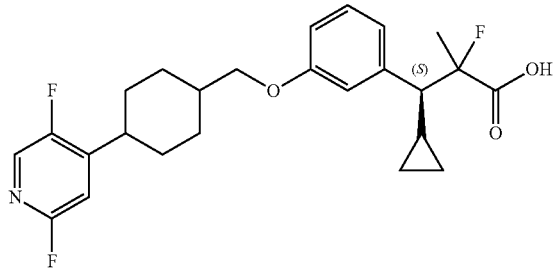

Compound 67 was prepared using the methods described in Example 61, Steps A and B. $^1$H NMR (300 MHz, CD$_3$OD) δ (ppm): 7.82-8.01 (m, 1H), 7.15-7.22 (m, 1H), 6.99-7.15 (m, 1H), 6.73-6.92 (m, 3H), 3.80-4.09 (m, 2H), 2.95 (t, J=12.5 Hz, 1H), 2.19-2.41 (m, 1H), 1.90-2.10 (m, 4H), 1.77 (d, J=6.7 Hz, 1H), 1.51-1.72 (m, 2H), 1.07-1.47 (m, 6H), 0.44-0.68 (m, 2H), 0.28-0.40 (m, 1H), −0.16-−0.01 (m, 1H). Mass Spectrum (LCMS, ESI pos.): Calcd. for $C_{25}H_{28}F_3NO_3$: 447.2, found: 448.2 [M+H]$^+$.

Example 63

(3S)-3-Cyclopropyl-3-(3-(((1r,4S)-4-(5-ethyl-2-fluorophenyl)cyclohexyl)methoxy)phenyl)-2-fluoro-2-methylpropanoic acid, Cpd 68

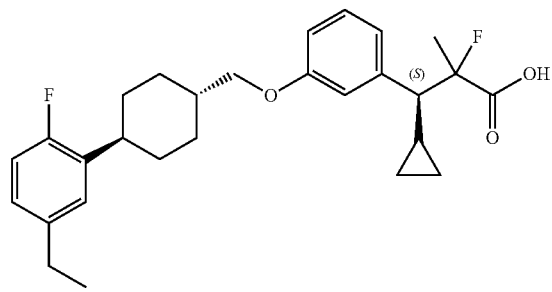

(A) 1-(3-Bromo-4-fluorophenyl)ethan-1-ol, 63a

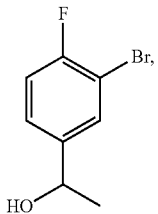

63a

To a solution of 1-(3-bromo-4-fluorophenyl)ethanone (868 mg, 4.00 mmol) in methanol (20 mL) was added sodium borohydride (303 mg, 8.01 mmol). The resulting mixture was stirred at rt for 2h. The reaction was quenched with water (30 mL). The resulting mixture was extracted with EtOAc (3×30 mL). The organic layers were combined, dried over anhydrous $Na_2SO_4$, filtered and the filtrate concentrated. The residue obtained was purified by flash chromatography on silica gel (0-15% EtOAc/petroleum ether) to afford compound 63a as a yellow oil (600 mg, 68.4% yield). Mass Spectrum (LCMS, ESI pos.): Calcd. for $C_8H_8BrFO$: 218.0, found: 201.1 $[M-OH]^+$.

(B) 2-Bromo-4-ethyl-1-fluorobenzene, 63b

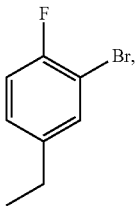

63b

To a solution of 2-bromo-4-ethyl-1-fluorobenzene, 63a (600 mg, 2.74 mmol) in TFA (3 mL) was added triethylsilane (637 mg, 5.48 mmol). The resulting mixture was stirred for 5 h at 60° C. The reaction was quenched with NaHCO3 solution (satd., 20 mL). The resulting mixture was extracted with EtOAc (3×30 mL). The organic layers were combined, dried over $Na_2SO_4$, filtered and the filtrate concentrated. The residue obtained was purified by flash chromatography on silica gel (0-15% EtOAc/petroleum ether) to afford compound 63b as a yellow oil (360 mg, 64.7% yield). Mass Spectrum (LCMS, ESI pos.): Calcd. for $C_8H_8BrF$: 202.0, found: 203.0 $[M+H]^+$.

(C) (5'-Ethyl-2'-fluoro-2,3,4,5-tetrahydro-[1,1'-biphenyl]-4-yl)methanol, 63c

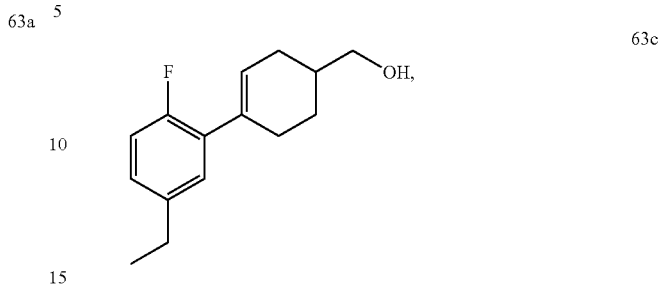

63c

Compound 63c was prepared from 2-bromo-4-ethyl-1-fluorobenzene, 63b using the methods described in Example 6, Steps B and C. Mass Spectrum (LCMS, ESI pos.): Calcd. for $C_{15}H_{19}FO$: 234.1, found: 235.3 $[M+H]^+$.

(D) ((1r,4r)-4-(5-Ethyl-2-fluorophenyl)cyclohexyl)methanol, 63d

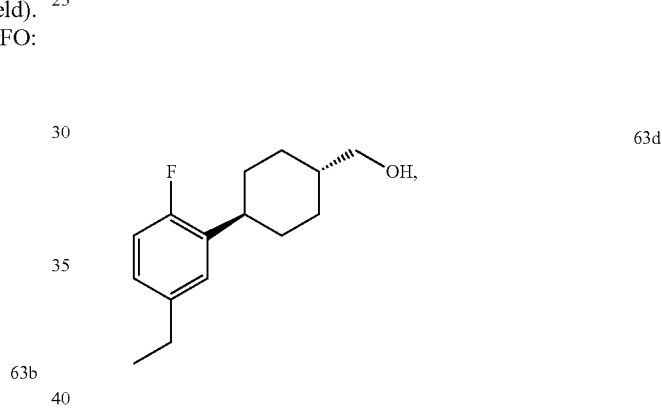

63d

Compound 63d was prepared from (5'-ethyl-2'-fluoro-2,3,4,5-tetrahydro-[1,1'-biphenyl]-4-yl)methanol, 63c using the method described in Example 54, Step D. Mass Spectrum (LCMS, ESI pos.): Calcd. for $C_{15}H_{21}FO$: 236.2, found: 219.3 $[M-OH]^+$.

(E) (3S)-3-Cyclopropyl-3-(3-(((1r,4S)-4-(5-ethyl-2-fluorophenyl)cyclohexyl)methoxy)phenyl)-2-fluoro-2-methylpropanoic acid, Cpd 68

Compound 68 was prepared from ((1r,4r)-4-(5-ethyl-2-fluorophenyl)cyclohexyl) methanol, 63d and (3S)-methyl 3-cyclopropyl-2-fluoro-3-(3-hydroxyphenyl)-2-methylpropanoate, 54g using the methods described in Example 54, Steps H and I. $^1$H NMR (300 MHz, $CD_3OD$) δ (ppm): 7.17-7.26 (m, 2H), 7.01-7.08 (m, 1H), 6.85-6.98 (m, 4H), 3.90-3.92 (m, 2H), 2.86-2.93 (m, 1H), 2.65-2.73 (m, 2H), 2.32-2.46 (m, 1H), 2.11-2.16 (m, 2H), 1.97-2.01 (m, 3H), 1.67-1.72 (m, 2H), 1.23-1.45 (m, 9H), 0.61-0.65 (m, 2H), 0.35-0.42 (m, 1H), −0.05-0.05 (m, 1H). Mass Spectrum (LCMS, ESI pos.): Calcd. for $C_{28}H_{34}F_2O_3$: 456.3, found: 457.5 $[M+H]^+$.

Example 64

(3S)-3-Cyclopropyl-2-fluoro-3-(3-((4-(2-methoxy-pyridin-4-yl)cyclohexyl)methoxy)phenyl)-2-methyl-propanoic acid, Cpd 69

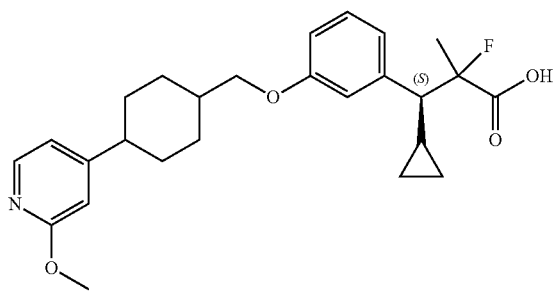

(A) (4-(2-Methoxypyridin-4-yl)cyclohex-3-en-1-yl)methanol, 64a

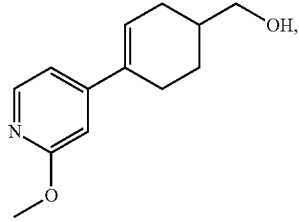

Compound 64a was prepared from (2-methoxypyridin-4-yl)boronic acid using the methods described in Example 54, Step A-C. Mass Spectrum (LCMS, ESI pos.): Calcd. for $C_{13}H_{17}NO_2$: 219.2, found: 220.1 [M+H]$^+$.

(B) (4-(2-Methoxypyridin-4-yl)cyclohexyl)methanol, 64b

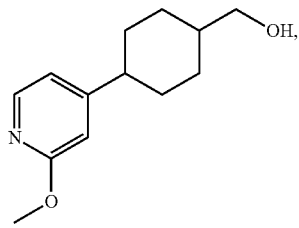

Compound 64b was prepared from (4-(2-methoxypyridin-4-yl)cyclohex-3-en-1-yl)methanol, 64a using the methods described in Example 61, Step A. Mass Spectrum (LCMS, ESI pos.): Calcd. for $C_{13}H_{19}NO_2$: 221.3, found: 222.1 [M+H]$^+$.

(C) (3S)-3-Cyclopropyl-2-fluoro-3-(3-((4-(2-methoxypyridin-4-yl)cyclohexyl)methoxy)phenyl)-2-methylpropanoic acid, Cpd 69

Compound 69 was prepared from (4-(2-methoxypyridin-4-yl)cyclohexyl)methanol, 64b and (3S)-methyl 3-cyclopropyl-2-fluoro-3-(3-hydroxyphenyl)-2-methylpropanoate, 54g using the methods described in Example 54, Steps H and I. $^1$H NMR (300 MHz, CD$_3$OD) δ (ppm): 7.98 (s, 1H), 7.18-7.24 (m, 1H), 6.83-6.91 (m, 4H), 6.67-6.70 (m, 1H), 4.03 (d, J=6 Hz, 1H), 3.87 (s, 3H), 3.84 (d, J=6 Hz, 1H), 2.45-2.70 (m, 1H), 2.17-2.31 (m, 1H), 1.68-1.92 (m, 8H), 1.38-1.41 (m, 1H), 1.25-1.32 (m, 4H), 0.37-0.63 (m, 3H), −0.05-0.01 (m, 1H). Mass Spectrum (LCMS, ESI pos.): Calcd. for $C_{26}H_{32}FNO_4$: 441.5, found: 442.2 [M+H]$^+$.

Example 65

(3S)-3-Cyclopropyl-2-fluoro-3-(3-((4-(5-methoxy-2-methylphenyl)cyclohexyl)methoxy)phenyl)-2-methylpropanoic acid, Cpd 70

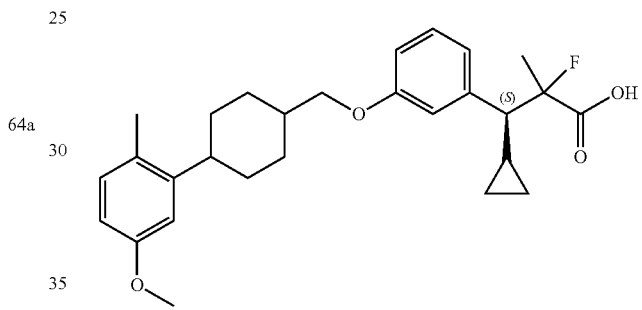

Compound 70 was prepared using the same methods described in Example 64. $^1$H NMR (300 MHz, CD$_3$OD) δ (ppm): 7.17-7.19 (m, 1H), 7.00-7.03 (m, 1H), 6.76-6.88 (m, 4H), 6.60-6.63 (m, 1H), 4.57-4.63 (brs, 1H), 4.10-4.12 (m, 1H), 3.82-3.84 (m, 1H), 3.73-3.75 (m, 3H), 2.68-2.76 (m, 1H), 2.25-2.36 (m, 4H), 2.04-2.07 (m, 2H), 1.71-1.92 (m, 3H), 1.45-1.68 (m, 3H), 1.29-1.30 (m, 2H), 1.20-1.21 (m, 1H), 1.14-1.15 (m, 1H), 0.28-0.61 (m, 3H), −0.09-−0.01 (m, 1H). Mass Spectrum (LCMS, ESI neg.): Calcd. for $C_{28}H_{35}FO_4$: 454.3, found: 453.2 [M−H]$^−$.

Example 66

(3S)-3-Cyclopropyl-2-fluoro-3-(3-((4-(5-methoxy-2-(pyridin-2-ylcarbamoyl)phenyl)cyclohexyl)methoxy)phenyl)-2-methylpropanoic acid, Cpd 71

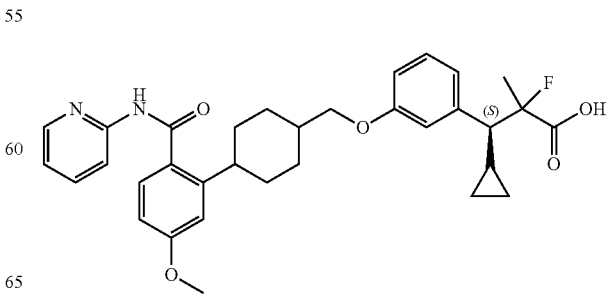

(A) tert-Butyl 2-(4-(hydroxymethyl)cyclohexyl)-4-methoxybenzoate, 66a

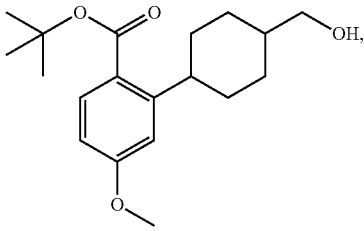

66a

Compound 66a was prepared from tert-butyl 2-bromo-4-methoxybenzoate using the methods described in Example 59, Step A-C, and Example 61, Step A. Mass Spectrum (LCMS, ESI pos.): Calcd. for $C_{19}H_{28}O_4$: 320.2, found: 343.1 [M+Na]$^+$.

(B) tert-Butyl 2-(4-(((3-((1S)-1-cyclopropyl-2-fluoro-3-methoxy-2-methyl-3-oxopropyl)phenoxy)methyl)cyclohexyl)-4-methoxybenzoate, 66b

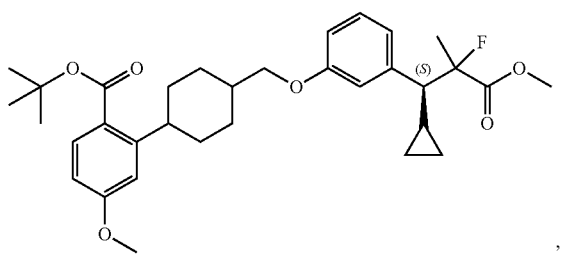

66b

Compound 66b was prepared from tert-butyl 2-(4-(hydroxymethyl)cyclohexyl)-4-methoxybenzoate, 663a using the same method described in Example 54, Step H. Mass Spectrum (LCMS, ESI pos.): Calcd. for $C_{33}H_{43}FO_6$: 554.3, found: 577.3 [M+Na]$^+$.

(C) 2-(4-(((3-((1S)-1-Cyclopropyl-2-fluoro-3-methoxy-2-methyl-3-oxopropyl)phenoxy)methyl)cyclohexyl)-4-methoxybenzoic acid, 66c

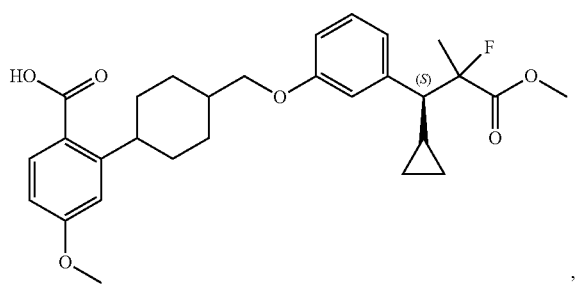

66c

To a solution of tert-butyl 2-(4-(((3-((1S)-1-cyclopropyl-2-fluoro-3-methoxy-2-methyl-3-oxopropyl)phenoxy)methyl)cyclohexyl)-4-methoxybenzoate, 66b (250 mg, 0.45 mmol) in DCM (6 mL) was added TFA (1 mL) at 0° C. The resulting solution was stirring at rt for 2 h. The solvent was removed under reduced pressure and water was added. The pH value of the mixture was adjusted to 4-5 with NaHCO$_3$ solution (aq., 1 N). The resulting mixture was extracted with EtOAc (2×30 mL). The organic layers were combined, dried over Na$_2$SO$_4$, filtered and the filtrate concentrated to afford compound 66c as a red oil. Mass Spectrum (LCMS, ESI pos.): Calcd. for $C_{29}H_{35}FO_6$: 498.2, found: 521.0 [M+Na]$^+$.

(D) Methyl (3S)-3-cyclopropyl-2-fluoro-3-(3-((4-(5-methoxy-2-(pyridin-2-ylcarbamoyl)phenyl)cyclohexyl)methoxy)phenyl)-2-methylpropanoate, 66d

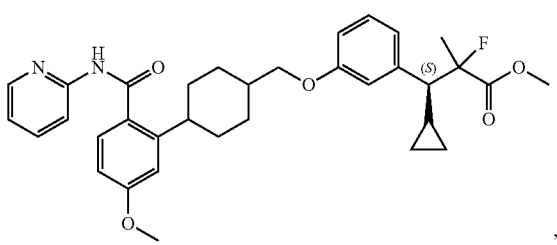

66d

To a solution of 2-(4-((3-((1S)-1-cyclopropyl-2-fluoro-3-methoxy-2-methyl-3-oxopropyl)phenoxy)methyl)cyclohexyl)-4-methoxybenzoic acid, 66c (200 mg, 0.40 mmol) in THF (2 ml) was added 1-chloro-N,N,2-trimethylprop-1-en-1-amine (48.2 mg, 0.36 mmol) at rt, and the mixture was stirred at 50° C. for 1 h. The reaction mixture was cooled to rt, then 2-aminopyridine (49.1 mg, 0.52 mmol) and triethylamine (60.9 mg, 0.60 mmol) were added. The mixture was stirred at 60° C. for 3 h, then was quenched with brine (50 mL). The resulting mixture was extracted with EtOAc (3×50 mL). The organic layers were combined, dried over Na$_2$SO$_4$, filtered and concentrated. The residue obtained was purified by flash chromatography on silica gel (0-60% EtOAc/petroleum ether) to afford compound 66d as yellow oil (110 mg, 33.0% yield). Mass Spectrum (LCMS, ESI pos.): Calcd. for $C_{34}H_{39}FN_2O_5$: 574.3, found: 575.0 [M+H]$^+$.

(E) (3S)-3-Cyclopropyl-2-fluoro-3-(3-((4-(5-methoxy-2-(pyridin-2-ylcarbamoyl)phenyl)cyclohexyl)methoxy)phenyl)-2-methylpropanoic acid, Cpd 71

To a solution of methyl (3S)-3-cyclopropyl-2-fluoro-3-(3-((4-(5-methoxy-2-(pyridin-2-ylcarbamoyl)phenyl)cyclohexyl)methoxy)phenyl)-2-methylpropanoate (110 mg, 0.19 mmol) in THF (4 mL), water (2 mL) and methanol (1 mL) was added LiOH (45.8 mg, 1.91 mmol). The resulting solution was stirred overnight at rt. The mixture was concentrated under reduced pressure and then diluted with water (40 mL). The pH value of the solution was adjusted to 4-5 with HCl solution (aq., 1 N). The resulting mixture was extracted with EtOAc (3×20 mL). The organic layers were combined, dried over Na$_2$SO$_4$, filtered and the filtrate concentrated. The residue obtained was purified by reverse-phase flash chromatography (C18 column, 120g, 20-35 μm, 100 Å, 15-75% CH$_3$CN/H$_2$O (0.05% TFA) in 30 min) to afford compound 71 as a white solid (40.0 mg, 32.0% yield). $^1$H-NMR (400 MHz, DMSO-d$_6$) δ (ppm): 8.30-8.50 (m, 1H), 7.90-8.09 (m, 2H), 7.40-7.60 (m, 1H), 7.13-7.32 (m, 2H), 6.95-7.05 (m, 1H), 6.70-6.91 (m, 4H), 4.02-4.20 (m, 1H), 3.70-3.90 (m, 4H), 2.95-3.15 (m, 1H), 1.99-2.34 (m, 2H), 1.75-1.97 (m, 3H), 1.39-1.75 (m, 5H), 1.00-1.34 (m, 4H), 0.43-0.64 (m, 1H), 0.20-0.40 (m, 2H), −0.19-0.00 (m, 1H); Mass Spectrum (LCMS, ESI pos.): Calcd. for $C_{33}H_{37}FN_2O_5$: 560.27, found: 561.2 [M+H]$^+$.

Example 67

(3S)-3-Cyclopropyl-2-fluoro-3-(3-((E)-2-((1r,4S)-4-(2-fluoro-5-methoxyphenyl)cyclohexyl)vinyl)phenyl)-2-methylpropanoic acid, Cpd 72

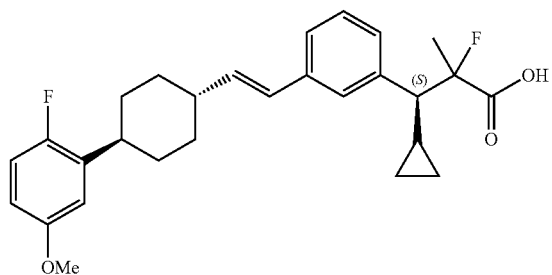

(A) Methyl (3S)-3-cyclopropyl-2-fluoro-2-methyl-3-(3-(((trifluoromethyl)sulfonyl)oxy)phenyl)propanoate, 67a

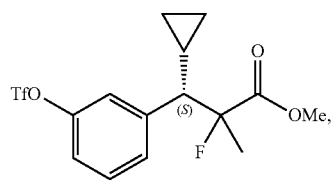

To a solution of methyl (3S)-3-cyclopropyl-2-fluoro-3-(3-hydroxyphenyl)-2-methylpropanoate, 54g (2.5 g, 9.91 mmol) in DCM (30 mL) was added 2,6-dimethylpyridine (1.38 g, 12.88 mmol) and trifluoromethanesulfonic anhydride (3.36 g, 11.89 mmol) at 0° C. The resulting solution was stirred at rt for 2 h before it was quenched by water (300 mL). The mixture was extracted with EtOAc (3×300 mL), and the organic layers were combined, dried over $Na_2SO_4$, filtered and the filtrate concentrated. The residue obtained was purified by flash chromatography on silica gel (0-60% EtOAc/petroleum ether) to afford compound 67a as a yellow oil. Mass Spectrum (LCMS, ESI pos.): Calcd. For $C_{15}H_{16}F_4O_5S$: 384.1; found: 385.0 [M+H]$^+$.

(B) Methyl (3S)-3-cyclopropyl-2-fluoro-3-(3-(hydroxymethyl)phenyl)-2-methylpropanoate, 67b

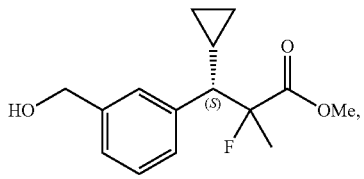

To a solution of methyl (3S)-3-cyclopropyl-2-fluoro-2-methyl-3-(3-(((trifluoromethyl)sulfonyl)oxy)phenyl)propanoate, 67a (500 mg, 1.30 mmol) in 1,4-dioxane (10 mL) and water (1 mL) was added potassium acetoxymethyltrifluoroborate (471 mg, 2.60 mmol), sodium carbonate (281 mg, 2.60 mmol), tris(dibenzylideneacetone)dipalladium(0) (119 mg, 0.13 mmol) and RuPhos (152 mg, 0.33 mmol). The resulting mixture was maintained under nitrogen and stirred at 100° C. for 2 h. After cooling to rt, the reaction was quenched with water (20 mL). The resulting mixture was extracted with EtOAc (3×30 mL). The organic layers were combined, dried over $Na_2SO_4$, filtered, and the filtrate concentrated. The residue obtained was purified by flash chromatography on silica gel (0-10% EtOAc/petroleum ether) to afford compound 67b as a yellow oil (260 mg, 75.0% yield). Mass Spectrum (LCMS, ESI pos.): Calcd. For $C_{15}H_{19}FO_3$: 266.1; found: 289.2 [M+Na]$^+$.

(G) Methyl (3S)-3-(3-(bromomethyl)phenyl)-3-cyclopropyl-2-fluoro-2-methylpropanoate, 67c

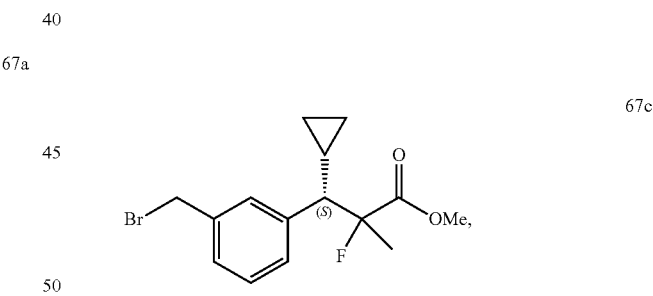

To a solution of methyl (3S)-3-cyclopropyl-2-fluoro-3-(3-(hydroxymethyl)phenyl)-2-methylpropanoate, 67b (260 mg, 0.97 mmol) in DCM (10 mL) was added DMF (0.2 mL) and phosphorus(V) tribromide oxide (420 mg, 1.47 mmol) at 0° C. The resulting mixture was stirred at rt for 2 h. The reaction was quenched with water (20 mL) and extracted with DCM (3×30 mL). The organic layers were combined, dried over $Na_2SO_4$, filtered and the filtrate concentrated to provide compound 67c as a yellow oil. Mass Spectrum (LCMS, ESI pos.): Calcd. For $C_{15}H_{18}BrFO_2$: 328.0, found: 329.1 [M+H]$^+$.

(H) Methyl (3S)-3-cyclopropyl-3-(3-((dimethoxyphosphoryl)methyl)phenyl)-2-fluoro-2-methylpropanoate, 67d

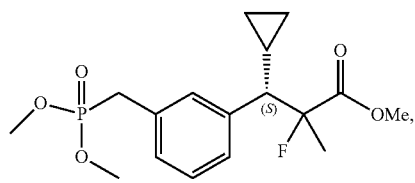

A solution of methyl (3S)-3-(3-(bromomethyl)phenyl)-3-cyclopropyl-2-fluoro-2-methylpropanoate, 67c (180 mg, 0.55 mmol) in trimethylphosphite (3 mL) was stirred at 110° C. for 2 h. After cooling down to rt, the reaction was quenched with water (20 mL). The resulting mixture was extracted with EtOAc (3×30 mL). The organic layers were combined, dried over anhydrous sodium sulfate, filtered and concentrated. The residue obtained was purified by flash chromatography on silica gel (0-60% EtOAc/petroleum ether) to afford compound 67d as yellow oil (120 mg, 61.2% yield). Mass Spectrum (LCMS, ESI pos.): Calcd. for $C_{17}H_{24}FO_5P$: 358.1, found: 359.2 [M+H]$^+$.

(I) (1r,4r)-4-(2-Fluoro-5-methoxyphenyl)cyclohexane-1-carbaldehyde, 67e

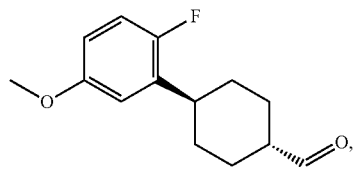

To a solution of ((1r,4r)-4-(2-fluoro-5-methoxyphenyl)cyclohexyl)methanol, 54d (1.0 g, 4.2 mmol) in DCM (10 mL) was added pyridinium chlorochromate (2.0 g, 9.2 mmol) at 0° C. under nitrogen. The resulting solution was stirred at 30° C. for 10 h and the solvent was evaporated. The residue obtained was purified by flash chromatography on silica gel (0-10% EtOAc/heptane) to afford compound 67e. Mass Spectrum (LCMS, ESI pos.): Calcd. For $C_{14}H_{17}FO_2$: 236.1; found: 236.9 [M+H]$^+$.

(J) Methyl (3S)-3-cyclopropyl-2-fluoro-3-(3-((E)-2-((1r,4S)-4-(2-fluoro-5-methoxyphenyl)cyclohexyl)vinyl)phenyl)-2-methylpropanoate, 67f

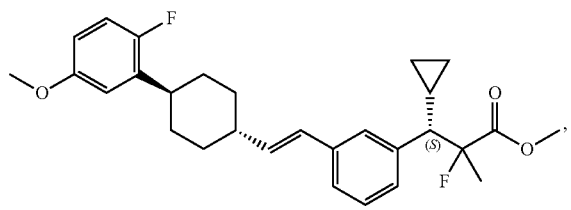

To a solution of methyl (3S)-3-cyclopropyl-3-(3-((dimethoxyphosphoryl)methyl)phenyl)-2-fluoro-2-methylpropanoate, 67d (120 mg, 0.34 mmol) in THF (5 mL) was added NaH (48 mg, 2.00 mmol) at 0° C. under nitrogen. The resulting mixture was stirred at 0° C. for 0.5 h, then (1r,4r)-4-(2-fluoro-5-methoxyphenyl)cyclohexanecarbaldehyde, 67e (79 mg, 0.34 mmol) was added at 0° C. The resulting mixture was stirred at rt for 2 h. The reaction was quenched with ammonium chloride (satd., 20 mL). The resulting mixture was extracted with EtOAc (3×30 mL). The organic layers were combined, dried over Na$_2$SO$_4$, filtered and the filtrate concentrated. The resultant residue was purified by flash chromatography on silica gel (0-30% EtOAc/petroleum ether) to afford compound 67f as a yellow oil (80 mg, 50.9% yield). Mass Spectrum (LCMS, ESI pos.): Calcd. for $C_{29}H_{34}F_2O_3$: 468.2, found: 491.2 [M+Na]$^+$.

(K) (3S)-3-Cyclopropyl-2-fluoro-3-(3-((E)-2-((1r,4S)-4-(2-fluoro-5-methoxyphenyl)cyclohexyl)vinyl)phenyl)-2-methylpropanoic acid, Cpd 72

To a solution of methyl (3S)-3-cyclopropyl-2-fluoro-3-(3-((E)-2-((1r,4S)-4-(2-fluoro-5-methoxyphenyl)cyclohexyl)vinyl)phenyl)-2-methylpropanoate, 67f (20 mg, 0.043 mmol) in THF (3 mL) and water (3 mL) was added LiOH (10 mg, 0.42 mmol). The resulting mixture was stirred overnight at rt. The mixture was concentrated under a vacuum and then diluted with water (5 mL). The pH value of the solution was adjusted to 4-5 with HCl solution (aq., 1 N). The solids formed were collected by filtration and dried in an oven under reduced pressure to afford compound 72 as a yellow solid. $^1$H NMR (300 MHz, CD$_3$OD) δ (ppm): 7.23-7.26 (m, 3H), 7.13-7.14 (m, 1H), 6.89-6.92 (m, 1H), 6.79-6.82 (m, 1H), 6.69-6.73 (m, 1H), 6.39-6.45 (m, 1H), 6.25-6.28 (m, 1H), 3.73-3.76 (m, 3H), 2.78-2.85 (m, 1H), 2.19-2.30 (m, 2H), 1.89-2.00 (m, 4H), 1.60-1.65 (m, 2H), 1.40-1.44 (m, 3H), 1.24-1.37 (m, 3H), 0.55-0.62 (m, 1H), 0.35-0.43 (m, 2H), −0.04-0.00 (m, 1H). Mass Spectrum (LCMS, ESI neg.): Calcd. for $C_{28}H_{32}F_2O_3$: 454.23, found: 453.10 [M−H]$^−$.

Example 68

(3S)-3-Cyclopropyl-2-fluoro-3-(3-(2-((1r,4R)-4-(2-fluoro-5-methoxyphenyl)cyclohexyl)ethyl)phenyl)-2-methylpropanoic acid, Cpd 73

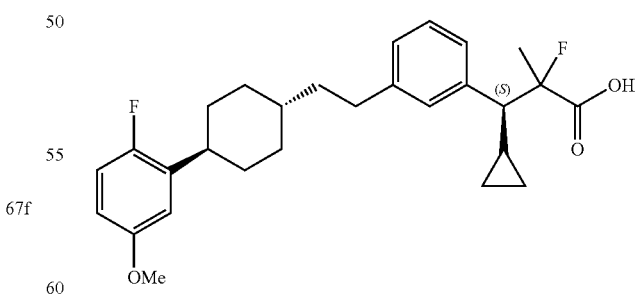

To a solution of (3S)-3-cyclopropyl-2-fluoro-3-(3-((E)-2-((1r,4S)-4-(2-fluoro-5-methoxyphenyl)cyclohexyl)vinyl)phenyl)-2-methylpropanoic acid, Cpd 71 (60 mg, 0.13 mmol) in methanol (5 mL) was added Pd/C (10% wt, 70 mg, 0.066 mmol). Then the reaction was maintained under H$_2$ ((g), 3.5 atm) and stirred overnight at rt. The reaction mixture was filtered and concentrated under reduced pressure, then diluted with water (5 mL). The pH value of the solution was adjusted to 4-5 with HCl solution (aq., 1 N). The resultant solids were collected by filtration and dried in an oven under reduced pressure to afford compound 73 as a white solid. ¹H NMR (300 MHz, CD₃OD) δ (ppm): 7.02-7.17 (m, 4H), 6.84-6.90 (m, 1H), 6.63-6.73 (m, 2H), 3.71 (s, 3H), 2.74-2.80 (m, 1H), 2.60-2.66 (m, 2H), 2.20-2.34 (m, 1H), 1.78-1.93 (m, 4H), 1.21-1.58 (m, 6H), 1.09-1.17 (m, 5H), 0.46-0.57 (m, 2H), 0.22-0.30 (m, 1H), −0.12-0.08 (m, 1H). Mass Spectrum (LCMS, ESI neg.): Calcd. for $C_{28}H_{34}F_2O_3$: 456.25, found: 455.15 [M−H]⁻.

Example 69

(2R,3S)-3-Cyclopropyl-2-fluoro-3-(3-(((1r,4S)-4-(2-fluoro-5-(trifluoromethoxy)phenyl)cyclohexyl)methoxy)phenyl)-2-methylpropanoic acid, Cpd 74

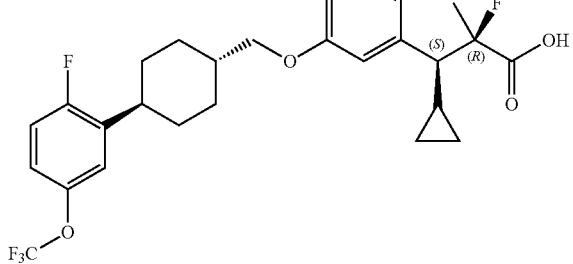

(A) ((1r,4r)-4-(2-Fluoro-5-(trifluoromethoxy)phenyl)cyclohexyl)methanol, 69a

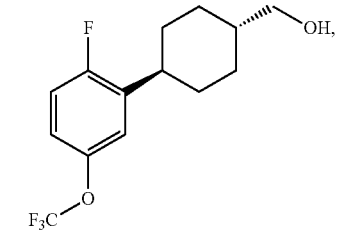

69a

Compound 69a was prepared using the methods described in Example 1, Steps A-D. Mass Spectrum (LCMS, ESI pos.): calcd. for $C_{14}H_{16}F_4O_2$: 292.1, found: 275.1 [M-OH]⁺.

(B) (2R,3S)-3-Cyclopropyl-2-fluoro-3-(3-(((1r,4S)-4-(2-fluoro-5-(trifluoromethoxy)phenyl)cyclohexyl)methoxy)phenyl)-2-methylpropanoic acid, Cpd 74

Compound 74 was prepared from ((1r,4r)-4-(2-fluoro-5-(trifluoromethoxy)phenyl)cyclohexyl)methanol, 69a and methyl (2R,3S)-3-cyclopropyl-2-fluoro-3-(3-hydroxyphenyl)-2-methylpropanoate, 59e according to the methods described in Example 54, Steps H and I. ¹H NMR (300 MHz, DMSO-d₆) δ (ppm): 13.26 (s, 1H), 7.15-7.40 (m, 4H), 6.80-6.93 (m, 3H), 3.83 (d, J=6.2 Hz, 2H), 2.73-2.94 (m, 1H), 2.15-2.42 (m, 1H), 1.73-2.06 (m, 5H), 1.45-1.67 (m, 2H), 1.19-1.38 (m, 6H), 0.49-0.68 (m, 1H), 0.25-0.42 (m, 2H), −0.07-−0.18 (m, 1H). Mass Spectrum (LCMS, ESI neg.): Calcd. for $C_{27}H_{29}F_5O_4$: 512.2, found: 511.4 [M−H]⁻.

Example 70

(2R,3S)-3-Cyclopropyl-3-(3-((4-(2,5-difluorophenyl)cyclohexyl)methoxy)phenyl)-2-fluoro-2-methylpropanoic acid, Cpd 75

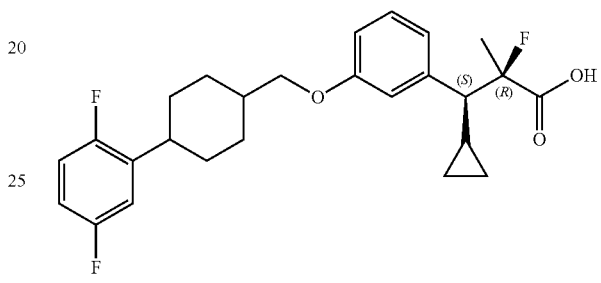

(A) Methyl (S)-3-(3-(benzyloxy)phenyl)-3-cyclopropylpropanoate, 70a

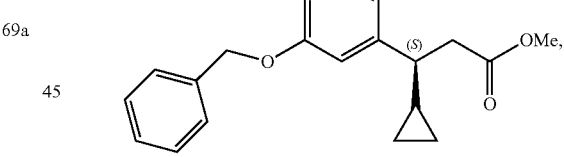

70a

To a solution of (S)-methyl 3-cyclopropyl-3-(3-hydroxyphenyl)propanoate (2 g, 9.08 mmol), $Cs_2CO_3$ (7.4 g, 22.7 mmol) in acetonitrile (30 mL) was added benzyl bromide (2.02 g, 11.80 mmol) dropwise with stirring at rt for 10 min. The reaction was then stirred at 50° C. for 4 h. Upon cooling to rt, the reaction was quenched by water (500 mL). The resulting mixture was extracted with EtOAc (3×500 mL), and the organic layers were combined and dried over $Na_2SO_4$, filtered, and the filtrate concentrated under reduced pressure. The residue was purified by flash chromatography on silica gel (0-10% EtOAc/petroleum ether) to afford compound 70a as a light yellow oil (2.2 g, 65.3%). Mass Spectrum (LCMS, ESI pos.): calcd. for $C_{20}H_{22}O_3$: 310.2, found: 311.0 [M+H]⁺.

(B) (S)-3-((S)-3-(3-(Benzyloxy)phenyl)-3-cyclopropylpropanoyl)-4-isopropyl-5,5-dimethyloxazolidin-2-one, 70b

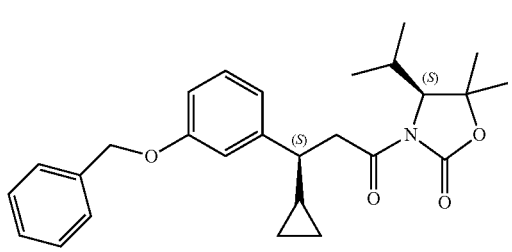

Compound 70b was prepared from methyl (S)-3-(3-(benzyloxy)phenyl)-3-cyclopropylpropanoate, 70a using the methods described in Example 56, Steps A-C. Mass Spectrum (LCMS, ESI pos.): calcd. for $C_{27}H_{33}NO_4$: 435.2, found: 458.0 $[M+Na]^+$.

(C) (4S)-3-((3S)-3-(3-(Benzyloxy)phenyl)-3-cyclopropyl-2-fluoropropanoyl)-4-isopropyl-5,5-dimethyloxazolidin-2-one, 70c

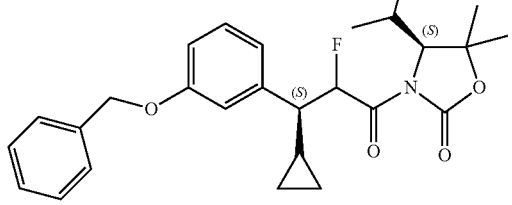

To a solution of (S)-3-((S)-3-(3-(benzyloxy)phenyl)-3-cyclopropylpropanoyl)-4-isopropyl-5,5-dimethyloxazolidin-2-one, 70b (2.3 g, 5.28 mmol) in THF (60 mL) was added LDA (2.0 M in THF/heptane/ethylbenzene, 5.28 mL, 10.56 mmol) dropwise at −78° C. under nitrogen. The resulting solution was stirred at 0° C. for 1 h, then it was cooled at −78° C. and N-fluoro-N-(phenylsulfonyl)benzenesulfonamide (3.33 g, 10.56 mmol) was added. The reaction mixture was warmed to rt and stirred for 2 h. The reaction was quenched with ammonium chloride (aq., satd., 100 mL). The resulting mixture was extracted with EtOAc (3×50 mL). The organic layers were combined, dried over $Na_2SO_4$, filtered and the filtrate concentrated. The residue obtained was purified by flash chromatography on silica gel (5-20% EtOAc/petroleum ether) to afford compound 70c as a colorless oil (2.3 g, 88.1% yield). Mass Spectrum (LCMS, ESI pos.): calcd. for $C_{27}H_{32}FNO_4$: 453.2, found: 454.0 $[M+H]^+$.

(D) (S)-3-((2R,3S)-3-(3-(Benzyloxy)phenyl)-3-cyclopropyl-2-fluoro-2-methylpropanoyl)-4-isopropyl-5,5-dimethyloxazolidin-2-one, 70d

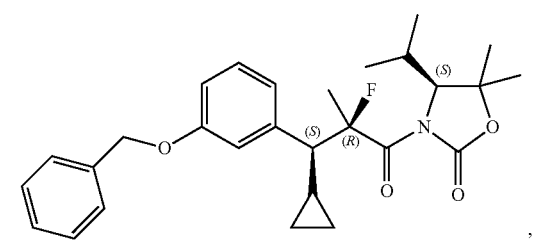

Compound 70d was prepared from (4S)-3-((3S)-3-(3-(benzyloxy)phenyl)-3-cyclopropyl-2-fluoropropanoyl)-4-isopropyl-5,5-dimethyloxazolidin-2-one, 17c using the method described in Example 3, Step E. Mass Spectrum (LCMS, ESI pos.): calcd. for $C_{28}H_{34}FNO_4$: 467.2, found: 490.0 $[M+Na]^+$.

(E) (S)-3-((2R,3S)-3-Cyclopropyl-2-fluoro-3-(3-hydroxyphenyl)-2-methylpropanoyl)-4-isopropyl-5,5-dimethyloxazolidin-2-one, 70e

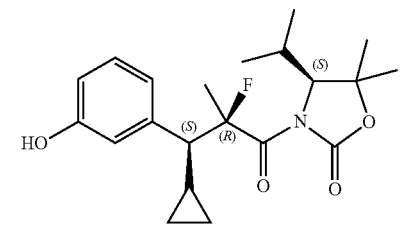

To a solution of (S)-3-((2R,3S)-3-(3-(benzyloxy)phenyl)-3-cyclopropyl-2-fluoro-2-methylpropanoyl)-4-isopropyl-5,5-dimethyloxazolidin-2-one, 70d (900 mg, 1.92 mmol) in methanol (10 mL) and ethyl acetate (10 mL) was added Pd/C (10%, 900 mg). The flask was evacuated and flushed with nitrogen three times, then hydrogen was introduced. The reaction was stirred at rt overnight. The catalyst was removed by filtration, and the filtrate was concentrated under reduced pressure to afford compound 70e as a white solid (690 mg, 88.5% yield). Mass Spectrum (LCMS, ESI pos.): calcd. for $C_{21}H_{28}FNO_4$: 377.2, found: 378.0 $[M+H]^+$.

(F) (4-(2,5-Difluorophenyl)cyclohexyl)methanol, 70f

Compound 70f was prepared using the methods described in Example 61, Step A. Mass Spectrum (LCMS, ESI pos.): calcd. for $C_{13}H_{16}F_2O$: 226.1, found: 209.3 [M-OH]⁺.

(G) (S)-3-((2R,3S)-3-Cyclopropyl-3-(3-((4-(2,5-difluorophenyl)cyclohexyl)methoxy)phenyl)-2-fluoro-2-methylpropanoyl)-4-isopropyl-5,5-dimethyloxazolidin-2-one, 70g

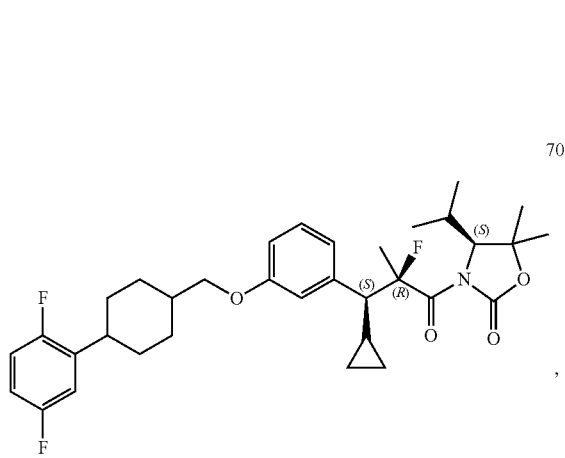

Compound 70g was prepared from (4-(2,5-difluorophenyl)cyclohexyl)methanol, 70f and (S)-3-((2R,3S)-3-cyclopropyl-2-fluoro-3-(3-hydroxyphenyl)-2-methylpropanoyl)-4-isopropyl-5,5-dimethyloxazolidin-2-one, 17e using the method described in Example 1, Step H. Mass Spectrum (LCMS, ESI pos.): calcd. for $C_{34}H_{42}F_3NO_4$: 585.3, found: 586.3 [M+H]⁺.

(H) (2R,3S)-3-Cyclopropyl-3-(3-((4-(2,5-difluorophenyl)cyclohexyl)methoxy)phenyl)-2-fluoro-2-methylpropanoic acid, Cpd 75

To a solution of (S)-3-((2R,3S)-3-cyclopropyl-3-(3-((4-(2,5-difluorophenyl)cyclohexyl)methoxy)phenyl)-2-fluoro-2-methylpropanoyl)-4-isopropyl-5,5-dimethyloxazolidin-2-one, 70g (70 mg, 0.12 mmol) in THF (1.5 mL) was added $H_2O_2$ (30% in water, 0.5 mL) and LiOH (7.2 mg, 0.17 mmol). The reaction mixture was stirred overnight at 30° C. The mixture was concentrated under reduced pressure. Water was added and the pH value of the solution was adjusted to 4-5 with 1 N HCl solution. The resultant precipitates were collected by filtration and purified by Prep-HPLC with the following conditions (1#-Waters-1): Column: Xbridge C18, 30×150 mm; mobile phase: water (0.05% TFA) and $CH_3CN$ (60% $CH_3CN$ to 88% in 7 min, hold 95% in 7 min). The fractions were pooled and lyophilized to afford compound 75 as a white solid (17.6 mg, 32.5% yield). ¹H NMR (300 MHz, DMSO-$d_6$) δ (ppm): 7.12-7.30 (m, 3H), 6.98-7.09 (m, 1H), 6.79-6.94 (m, 3H), 4.07 (d, J=7.4 Hz, 1H), 3.80 (d, J=6.2 Hz, 1H), 2.68-2.95 (m, 1H), 2.13-2.35 (m, 1H), 1.74-2.01 (m, 4H), 1.40-1.70 (m, 4H), 1.13-1.40 (m, 5H), 0.48-0.63 (m, 1H), 0.25-0.40 (m, 2H), −0.05-−0.15 (m, 1H). Mass Spectrum (LCMS, ESI neg.): Calcd. for $C_{26}H_{29}F_3O_3$: 446.2, found: 445.4 [M−H]⁻.

Example 71

(2R,3S)-3-Cyclopropyl-2-fluoro-3-(3-((2'-fluoro-5'-methoxy-2,3,4,5-tetrahydro-[1,1'-biphenyl]-4-yl)methoxy)phenyl)-2-methylpropanoic acid, Cpd 76

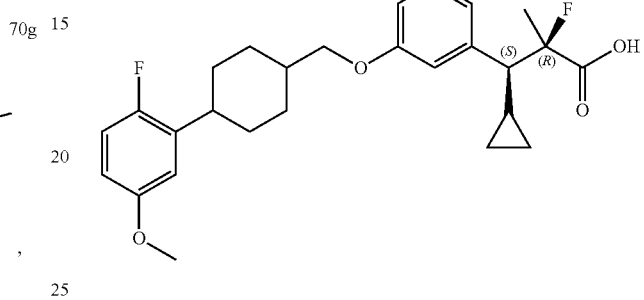

Compound 76 was prepared from (4-(2-fluoro-5-methoxyphenyl)cyclohex-3-enyl)methanol, 54c and (S)-3-((2R,3S)-3-cyclopropyl-2-fluoro-3-(3-hydroxyphenyl)-2-methylpropanoyl)-4-isopropyl-5,5-dimethyloxazolidin-2-one, 70e using the method described in Example 70, Steps H and G. ¹H-NMR (400 MHz, CD$_3$OD) δ (ppm): 7.19-7.23 (m, 1H), 6.91-6.95 (m, 1H), 6.84-6.91 (m, 3H), 6.75-6.83 (m, 2H), 5.93 (s, 1H), 3.91 (d, J=6.0 Hz, 2H), 3.75 (s, 3H), 2.42-2.45 (m, 3H), 2.04-2.19 (m, 4H), 1.58 (m, 1H), 1.38-1.41 (m, 1H), 1.31 (d, J=21.6 Hz, 3H), 0.59-0.63 (m, 1H), 0.38-0.45 (m, 2H), 0.00-0.03 (m, 1H). Mass Spectrum (LCMS, ESI pos.): calcd. for $C_{27}H_{30}F_2O_4$: 456.2, found: 457.3 [M+H]⁺.

Example 72

(3S)-3-Cyclopropyl-2-fluoro-3-(3-((((1r,4S)-4-(2-fluoro-5-methoxyphenyl)cyclohexyl)methyl)amino)phenyl)-2-methylpropanoic acid, Cpd 77

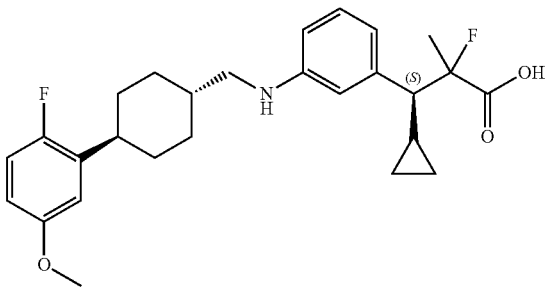

(A) Methyl (3S)-3-cyclopropyl-3-(3-((diphenylmethylene)amino)phenyl)-2-fluoro-2-methylpropanoate, 72a

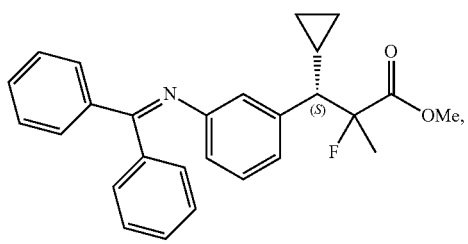

To a solution of (3S)-methyl 3-cyclopropyl-2-fluoro-2-methyl-3-(3-(trifluoromethylsulfonyloxy)phenyl)propanoate, 67a (400 mg, 1.04 mmol) in toluene (10 mL) was added diphenylmethanimine (207 mg, 1.14 mmol), cesium carbonate (1.02 g, 3.12 mmol), tris(dibenzylideneacetone)dipalladium(0) (95 mg, 0.10 mmol) and XPhos (198 mg, 0.42 mmol). The resulting mixture was maintained under nitrogen and stirred at 110° C. for 3 h. After cooling to rt, the reaction was quenched with water (20 mL). The resulting mixture was extracted with EtOAc (3×30 mL). The organic layers were combined, dried over $Na_2SO_4$, filtered and the filtrates concentrated. The resultant residue was purified by flash chromatography on silica gel (0-10% EtOAc/petroleum ether) to afford compound 72a as a yellow oil (300 mg, 69.3% yield). Mass Spectrum (LCMS, ESI pos.): mass calcd. for $C_{27}H_{26}FNO_2$: 415.2, found: 416.2 $[M+H]^+$.

(B) Methyl (3S)-3-(3-aminophenyl)-3-cyclopropyl-2-fluoro-2-methylpropanoate, 72b

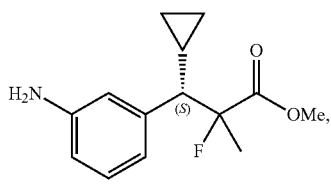

To a solution of (3S)-methyl 3-cyclopropyl-3-(3-(diphenylmethyleneamino)phenyl)-2-fluoro-2-methylpropanoate, 72a (300 mg, 0.72 mmol) in THF (10 mL) was added HCl solution (2 M in water, 2 mL). The resulting solution was stirred for 2 h at rt. The reaction was then quenched with $NaHCO_3$ (aq., satd., 20 mL). The resulting solution was extracted with DCM (3×20 mL), and the organic layers were combined and dried over $Na_2SO_4$, filtered, and the filtrate concentrated under reduced pressure. The residue was purified by flash chromatography on silica gel (0-30% EtOAc/petroleum ether) to afford compound 72b (150 mg, 82.6% yield). Mass Spectrum (LCMS, ESI pos.): mass calcd. for $C_{14}H_{18}FNO_2$: 251.1, found: 252.2 $[M+H]^+$.

(C) Methyl (3S)-3-cyclopropyl-2-fluoro-3-(3-((((1r,4S)-4-(2-fluoro-5-methoxyphenyl)cyclohexyl)methyl)amino)phenyl)-2-methylpropanoate, 72c To a solution of (3S)-methyl 3-(3-aminophenyl)-3-cyclopropyl-2-fluoro-2-methylpropanoate, 72b (150 mg, 0.60 mmol) in methanol (10 mL) was added (1r,4r)-4-(2-fluoro-5-methoxyphenyl)cyclohexanecarbaldehyde, 67e (141 mg, 0.60 mmol) and acetic acid (2 mL). The resulting mixture was stirred for 1 h at rt. Sodium cyanotrihydroborate (113 mg, 1.80 mmol) was added. The resulting mixture was stirred overnight at rt. The reaction was then quenched with $NaHCO_3$ solution (aq., satd., 20 mL). The resulting solution was extracted with DCM (3×20 mL), and the organic layers were combined and dried over $Na_2SO_4$, filtered, and the filtrate concentrated under reduced pressure. The residue was purified by flash chromatography on silica gel (0-70% EtOAc/petroleum ether) to afford compound 72c as a yellow oil (80 mg, 28.4% yield). Mass Spectrum (LCMS, ESI pos.): mass calcd. for $C_{28}H_{35}F_2NO_3$: 471.3, found: 472.2 $[M+H]^+$.

(D) (3S)-3-Cyclopropyl-2-fluoro-3-(3-((((1r,4S)-4-(2-fluoro-5-methoxyphenyl)cyclohexyl)methyl)amino)phenyl)-2-methylpropanoic acid, Cpd 77

To a solution of (3S)-methyl 3-cyclopropyl-2-fluoro-3-(3-(((1r,4S)-4-(2-fluoro-5-methoxyphenyl)cyclohexyl)methylamino)phenyl)-2-methylpropanoate, 72c (80 mg, 0.17 mmol) in THF (6 mL) and water (6 mL) was added LiOH (41 mg, 1.71 mmol). The resulting mixture was stirred overnight at rt. The mixture was concentrated under reduced pressure and then diluted with water (15 mL). The pH value of the solution was adjusted to 4-5 with 1M HCl solution. The resultant solids were collected by filtration and dried in an oven under reduced pressure to afford compound 77 as a yellow solid. $^1$H-NMR (300 MHz, $CD_3OD$) δ (ppm): 7.37-7.40 (m, 1H), 7.14-7.20 (m, 3H), 6.90-6.97 (m, 1H), 6.70-6.78 (m, 2H), 3.74-3.76 (m, 3H), 3.21-3.24 (m, 2H), 2.66-2.83 (m, 1H), 2.28-2.42 (m, 1H), 1.89-2.03 (m, 4H), 1.72-1.82 (m, 1H), 1.44-1.58 (m, 3H), 1.26-1.36 (m, 5H), 0.66-0.70 (m, 1H), 0.42-0.48 (m, 2H), −0.01-0.01 (m, 1H). Mass Spectrum (LCMS, ESI pos.): mass calcd. for $C_{27}H_{33}F_2NO_3$: 457.24, found: 458.50 $[M+H]^+$.

Example 73

(3S)-3-Cyclopropyl-2-fluoro-3-(3-(((4-(2-fluoro-5-methoxyphenyl)cyclohexyl)oxy)methyl)phenyl)-2-methylpropanoic acid, Cpd 78

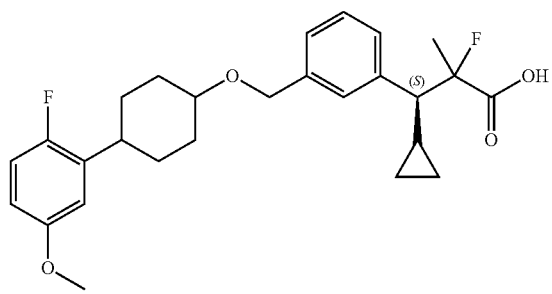

(A) 8-(2-Fluoro-5-methoxyphenyl)-1,4-dioxaspiro[4.5]dec-7-ene, 73a

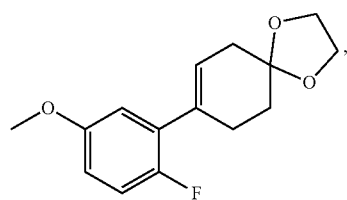

To a solution of 2-bromo-1-fluoro-4-methoxybenzene (1 g, 4.88 mmol) in 1,4-dioxane (40 mL) was added 2-{1,4-dioxaspiro[4.5]dec-7-en-8-yl}-4,4,5,5-tetramethyl-1,3,2-dioxaborolane (0.75 g, 2.82 mmol), Pd(dppf)C$_{12}$.CH$_2$C$_{12}$ (0.2 g, 0.24 mmol), cesium carbonate (4 g, 12.277 mmol) and water (10 mL). The resulting solution was stirred overnight at 80° C. under nitrogen. After cooling to rt, water was added. The resulting mixture was extracted with EtOAc (3×100 mL), and the organic layers were combined and dried over Na$_2$SO$_4$, filtered, and the filtrate concentrated under reduced pressure. The residue was purified by flash chromatography on silica gel (0-10% EtOAc/petroleum ether) to afford compound 73a as a light yellow oil (600 mg, 46.5% yield). Mass Spectrum (LCMS, ESI pos.): mass calcd. For C$_{15}$H$_{17}$FO$_3$ 264.12: found: 265.2 [M+H]$^+$.

(B) 2'-Fluoro-5'-methoxy-2,5-dihydro-[1,1'-biphenyl]-4(3H)-one, 73b

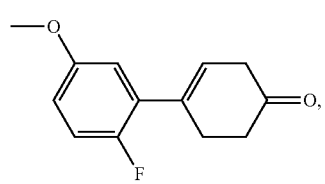

To a solution of 8-(2-fluoro-5-methoxyphenyl)-1,4-dioxaspiro[4.5]dec-7-ene, 73a (520 mg, 1.97 mmol) in THF (5 mL) was added 2 M HCl (aq., 5 mL). The reaction was stirred overnight at rt. The reaction was quenched with NaHCO$_3$ solution (aq., satd., 50 mL). The resulting mixture was extracted with EtOAc (3×100 mL), and the organic layers were combined, dried over Na$_2$SO$_4$, filtered, and the filtrate concentrated under reduced pressure to afford compound 73b as a light yellow oil (350 mg, 48.5% yield). Mass Spectrum (LCMS, ESI pos.): mass calcd. For C$_{13}$H$_{13}$FO$_2$: 220.09, found 221.0 [M+H]$^+$.

(C) 2'-Fluoro-5'-methoxy-2,3,4,5-tetrahydro-[1,1'-biphenyl]-4-ol, 73c

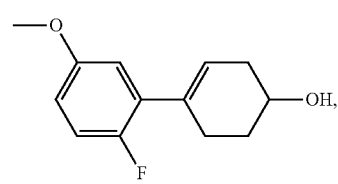

To a solution of 2'-fluoro-5'-methoxy-2,5-dihydro-[1,1'-biphenyl]-4(3H)-one, 73b (300 mg, 1.36 mmol) in THF (10 mL) was added NaBH$_4$ (103 mg, 2.72 mmol). The reaction was stirred overnight at rt. The reaction was then quenched with NH$_4$Cl solution (aq., satd., 50 mL). The resulting mixture was extracted with EtOAc (3×50 mL), and the organic layers were combined, dried over Na$_2$SO$_4$, filtered, and the filtrate concentrated under reduced pressure to afford compound 73c as a light yellow oil (230 mg, 71.0% yield). Mass Spectrum (LCMS, ESI pos.): mass calcd. For C$_{13}$H$_{13}$FO$_2$: 222.11 found: 205.0 [M-OH]$^+$.

(D) 4-(2-Fluoro-5-methoxyphenyl)cyclohexan-1-ol, 73d

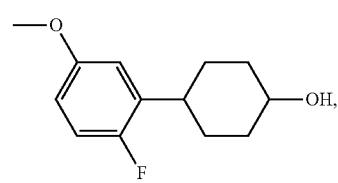

To a solution of 2'-fluoro-5'-methoxy-2,3,4,5-tetrahydro-[1,1'-biphenyl]-4-ol, 73c (230 mg, 1.04 mmol) in methanol (10 mL) was added Pd/C (115 mg, 10% wt) under nitrogen. The mixture was stirred overnight at rt under a H$_2$ ((g), 3.5 atm) atmosphere. The catalyst was removed by filtration. The filtrate was concentrated under reduced pressure to afford compound 73d as a light yellow oil (200 mg, 54.3% yield). Mass Spectrum (LCMS, ESI pos.): mass calcd. For C$_{13}$H$_{17}$FO$_2$: 224.12 found: 207.1 [M-OH]$^+$.

(E) (3S)-3-Cyclopropyl-2-fluoro-3-(3-(((4-(2-fluoro-5-methoxyphenyl)cyclohexyl)oxy)methyl)phenyl)-2-methylpropanoic acid, Cpd 78

To a solution of 4-(2-fluoro-5-methoxyphenyl)cyclohexan-1-ol, 73d (150 mg, 0.18 mmol) in DMF (2 mL) was added NaH (60% in mineral oil, 53.5 mg, 1.34 mmol) at rt under nitrogen. The reaction mixture was stirred for 30 min, then a solution of methyl (3S)-3-(3-(bromomethyl)phenyl)-3-cyclopropyl-2-fluoro-2-methylpropanoate, 67c (242.2 mg, 0.74 mmol) in DMF (1 mL) was added at rt. The resulting mixture was stirred overnight at 50° C. After cooling to rt, the reaction was quenched with water (150 mL). The pH value of the solution was adjusted to 4-5 with 1 M HCl solution. The resulting mixture was extracted with EtOAc (3×150 mL). The organic layers were combined, dried over Na$_2$SO$_4$, filtered, and the filtrate concentrated under reduced pressure. The crude product was purified by reverse-phase flash chromatography with the following conditions: column: Cat. No.: SO230120-2, C18, 120g, 20-35 μm, 100 Å; mobile phase: 15-70% CH$_3$CN/H$_2$O (0.05% TFA) in 30 min. The fractions were pooled and lyophilized to afford compound 78 as a white solid (25.8 mg, 7.4% yield). $^1$H NMR (300 MHz, DMSO-d$_6$) δ 7.13-7.36 (m, 4H), 6.95-7.10 (m, 1H), 6.67-6.86 (m, 2H), 4.40-4.63 (m, 2H), 3.65-3.85 (m, 3H), 3.40-3.46 (m, 1H), 2.66-2.89 (m, 1H), 2.20-2.40 (m, 1H), 2.05-2.18 (m, 1H), 1.90-2.03 (m, 1H), 1.66-1.87 (m, 2H), 1.44-1.66 (m, 3H), 1.29-1.44 (m, 2H), 1.11-1.28 (m, 3H), 0.50-0.70 (m, 1H), 0.20-0.43 (m, 2H), −0.19−−0.04 (m, 1H). Mass Spectrum (LCMS, ESI pos.): mass calcd. for C$_{27}$H$_{32}$F$_2$O$_4$: 458.23, found: 476.2 [M+NH$_4$]$^+$.

Example 74

(3S)-3-Cyclopropyl-2-fluoro-3-(2-(((1r,4S)-4-(2-fluoro-5-methoxyphenyl)cyclohexyl)methoxy)pyridin-4-yl)-2-methylpropanoic acid, Cpd 79

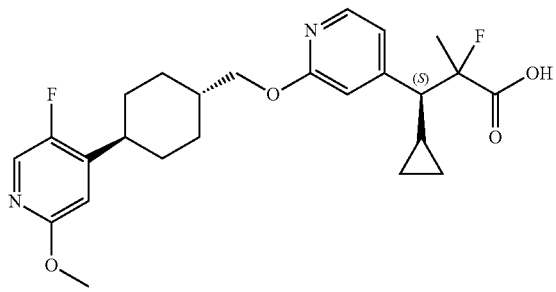

(A) Methyl (3R)-3-(2-chloropyridin-4-yl)-3-cyclopropyl-2-methylpropanoate, 74a

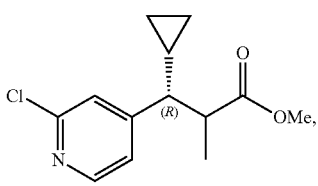

To a solution of (S)-methyl 3-(2-chloropyridin-4-yl)-3-cyclopropylpropanoate (2 g, 8.34 mmol) in THF (20 ml) was added lithium diisopropylamide (2M in THF, 6.3 mL, 12.6 mmol) dropwise with stirring at −78° C. After 30 min, a solution of iodomethane (3.55 g, 25.01 mmol) in THF (20 ml) was added dropwise at −78° C. The resulting solution was stirred for another 2h at −78° C. before it was quenched by the addition of NH$_4$Cl (satd., aq., 100 mL). The resulting solution was extracted with EtOAc (3×200 mL). The organic layers were combined, and dried over anhydrous sodium sulfate and concentrated under vacuum. The residue was purified by flash chromatography on silica gel (0-10% EtOAc/petroleum ether) to afford compound 74a as light yellow oil (2 g, 91.9% yield). Mass Spectrum (LCMS, ESI pos.): mass calcd. for C$_{13}$H$_{16}$C$_1$NO$_2$: 253.1, found: 254.1 [M+H]$^+$.

(B) Methyl (3S)-3-(2-chloropyridin-4-yl)-3-cyclopropyl-2-fluoro-2-methylpropanoate, 74b

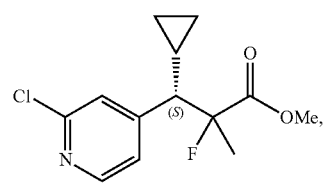

To a solution of methyl (3R)-3-(2-chloropyridin-4-yl)-3-cyclopropyl-2-methylpropanoate, 74a (2.1 g, 8.28 mmol) in THF (50 ml) was added lithium diisopropylamide (2M in THF, 8.3 ml, 16.6 mmol) with stirring at −78° C. After 30 min, a solution of N-fluorobenzenesulfonimide (5.2 g, 16.49 mmol) in THF (10 ml) was added dropwise with stirring at −78° C. The resulting solution was stirred for another 2h at −78° C. before it was quenched by the addition of NH$_4$Cl (satd., aq., 100 mL). The resulting solution was extracted with EtOAc (3×100 mL). The organic layers were combined, and dried over anhydrous sodium sulfate and concentrated under vacuum. The residue was purified by flash chromatography on silica gel (0-10% EtOAc/petroleum ether) to afford compound 74b as light yellow oil (1.9 g, 74.2% yield). Mass Spectrum (LCMS, ESI pos.): mass calcd. for C$_{13}$H$_{15}$C$_1$FNO$_2$: 271.1, found: 272.0 [M+H]$^+$.

(C) Methyl (3S)-3-cyclopropyl-2-fluoro-3-(2-(((1r,4S)-4-(2-fluoro-5-methoxyphenyl)cyclohexyl)methoxy)pyridin-4-yl)-2-methylpropanoate, 74c

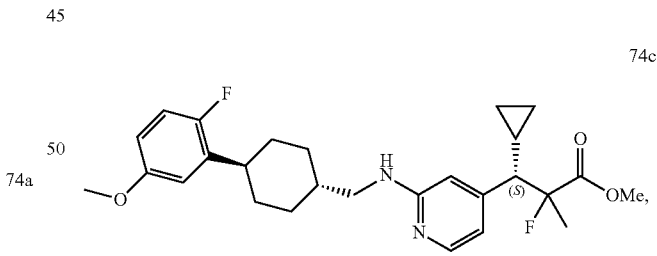

To a solution of ((1r,4r)-4-(2-fluoro-5-methoxyphenyl)cyclohexyl)methanol, 54d (400 mg, 1.68 mmol) in 1,4-dioxane (15 mL) was added methyl (3S)-3-(2-chloropyridin-4-yl)-3-cyclopropyl-2-fluoro-2-methylpropanoate, 74b (502 mg, 1.85 mmol), diacetoxypalladium (7 mg, 0.031 mmol), L-(5-[bis(adamantan-1-yl)phosphanyl]-1',3',5'-triphenyl-1'H-1,4'-bipyrazole) (45 mg, 0.068 mmol) and Cs$_2$CO$_3$ (1.4 g, 4.30 mmol), The resulting solution was stirred overnight under nitrogen at 100° C. in an oil bath. After cooling down, the reaction was quenched by the addition of NH$_4$Cl (satd., aq., 100 mL). The resulting solution was extracted with EtOAc (3×100 mL). The organic layers were combined, and dried over anhydrous sodium sulfate and concentrated under vacuum. The residue was purified by flash chromatography on silica gel (0-10% EtOAc/petroleum ether) to afford compound 74c as light yellow oil (360 mg, 15.4% yield). Mass Spectrum (LCMS, ESI pos.): mass calcd. for $C_{27}H_{33}F_2NO_4$: 473.2, found: 474.1 [M+H]$^+$.

(D) (3S)-3-Cyclopropyl-2-fluoro-3-(2-(((1r,4S)-4-(2-fluoro-5-methoxyphenyl)cyclohexyl)methoxy)pyridin-4-yl)-2-methylpropanoic acid, Cpd 79

To a solution of methyl (3S)-3-cyclopropyl-2-fluoro-3-(2-(((1r,4S)-4-(2-fluoro-5-methoxyphenyl)cyclohexyl)methoxy)pyridin-4-yl)-2-methylpropanoate, 74c (30 mg, 0.063 mmol) in THF (4 mL) was added $H_2O$ (1 mL), methanol (1 mL) and LiOH (11 mg, 0.26 mmol). The reaction mixture was stirred overnight at rt. The mixture was concentrated under vacuum. Water (5 mL) was added and the pH value of the solution was adjusted 4-5 with 1N HCl solution. The resulting solution was extracted with EtOAc (3×100 mL). The organic layers were combined, and dried over anhydrous sodium sulfate and the filtrate concentrated under reduced pressure. The residue was purified by Prep-HPLC with the following conditions: Column: SunFire Prep C18, 5 μM, 19×100 mm; mobile phase: water (0.05% $NH_4HCO_3$) and $CH_3CN$ (30% to 80% $CH_3CN$ in 10 min). The fractions were pooled and lyophilized to afford compound 79 as a white solid (4.4 mg, 14.3% yield). $^1H$ NMR (300 MHz, DMSO-$d_6$) δ (ppm): 8.02-8.12 (m, 1H), 7.00-7.10 (m, 1H), 6.90-6.95 (m, 1H), 6.63-6.89 (m, 3H), 4.10 (d, J=6.3 Hz, 2H), 3.74 (s, 3H), 2.70-2.88 (m, 1H), 2.20-2.40 (m, 1H), 1.71-2.00 (m, 5H), 1.40-1.70 (m, 2H), 1.13-1.39 (m, 6H), 0.52-0.63 (m, 1H), 0.28-0.45 (m, 2H), −0.01-−0.11 (m, 1H). Mass Spectrum (LCMS, ESI neg.): Calcd. for $C_{26}H_{31}F_2NO_4$: 459.2, found: 460.0 [M+H]$^+$.

Example 75

(3S)-3-Cyclopropyl-2-fluoro-3-(2-(((1r,4S)-4-(5-fluoro-2-methoxypyridin-4-yl)cyclohexyl)methoxy)pyridin-4-yl)-2-methylpropanoic acid, Cpd 80

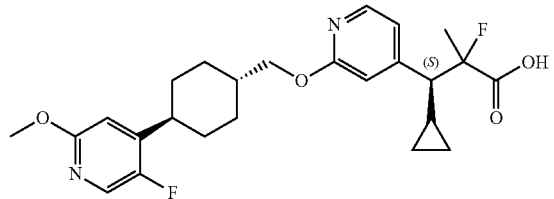

(A) Methyl (3S)-3-cyclopropyl-2-fluoro-3-(2-(((1r,4S)-4-(5-fluoro-2-methoxypyridin-4-yl)cyclohexyl)methoxy)pyridin-4-yl)-2-methylpropanoate, 75a

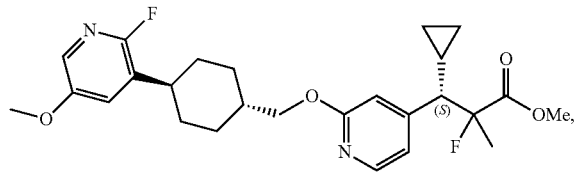

75a

Compound 75a was prepared from ((1r,4r)-4-(5-fluoro-2-methoxypyridin-4-yl)cyclohexyl)methanol, 57c-1 and methyl (3S)-3-(2-chloropyridin-4-yl)-3-cyclopropyl-2-fluoro-2-methylpropanoate, 74b according to the method described in Example 74, Step C. Mass Spectrum (LCMS, ESI pos.): calcd for $C_{26}H_{32}F_2N_2O_4$: 474.2, found: 475.1 [M+H]$^+$.

(B) (3S)-3-Cyclopropyl-2-fluoro-3-(2-(((1r,4S)-4-(5-fluoro-2-methoxypyridin-4-yl)cyclohexyl)methoxy)pyridin-4-yl)-2-methylpropanoic acid, Cpd 80

Compound 80 was prepared from methyl (3S)-3-cyclopropyl-2-fluoro-3-(2-(((1r,4S)-4-(5-fluoro-2-methoxypyridin-4-yl)cyclohexyl)methoxy)pyridin-4-yl)-2-methylpropanoate, 75a according to the method described in Example 74, Step D. $^1H$ NMR (300 MHz, DMSO-$d_6$) δ (ppm): 8.00-8.10 (m, 2H), 6.89-6.94 (m, 1H), 6.68-6.78 (m, 2H), 4.10 (d, J=6.0 Hz, 2H), 3.69 (s, 3H), 2.70-2.85 (m, 1H), 2.20-2.40 (m, 1H), 1.78-1.99 (m, 5H), 1.42-1.61 (m, 2H), 1.15-1.38 (m, 6H), 1.52-1.66 (m, 1H), 1.30-1.46 (m, 2H), −0.01-0.11 (m, 1H). $^{19}F$ NMR (300 MHz, DMSO-$d_6$) δ (ppm): −145.86, −161.49. Mass Spectrum (LCMS, ESI neg.): Calcd. for $C_{25}H_{30}F_2N_2O_4$: 460.2, found: 461.0 [M+H]$^+$.

Biological Examples

In Vitro Assays

Example 1

GPR40 Calcium Flux Assay

Compounds were tested in a calcium flux assay using transfected HEK293 cells stably expressing either human GPR40 or rat GPR40. Human GPR40 expressing cells were cultured in DMEM-High Glucose media supplemented with 10% fetal bovine serum, 1×L-Glutamine, 1×Penicillin/Streptomycin and 500 μg/mL G418. Rat GPR40 expressing cells were cultured in DMEM-High Glucose media supplemented with 10% fetal bovine serum and 1 μg/mL puromycin. Cells were plated into poly-D-lysine coated 384-well plates and cultured overnight in a 37° C. humidified tissue culture incubator under 5% $CO_2$/90% $O_2$ atmosphere. On the day of the experiment, the culture media was replaced with assay buffer (HBSS, 20 mM HEPES, 0.1% BSA) and the cells incubated at 37° C. for 1 h. Calcium-sensitive fluorescent dye (Fluo 8 No-Wash Calcium Dye, ABD Bioquest) was then added and the cells incubated for another 30 min at 37° C. followed by 15 min at room temperature while protected from the light. The cell plate and a plate of diluted compounds of Formula (I) were loaded into a fluorescent plate reader that added compounds onto the cells while measuring the fluorescence intensity of each well. The plate reader recorded fluorescence intensity at 1 second intervals for 8 min and provided the data for analysis in an Excel format. EC50 values were calculated using Prism (GraphPad) software. Resultant data are shown in Table 3.

TABLE 3

| Cpd | hGPR40 $Ca^{2+}$ Assay EC50 (μM) | rGPR40 $Ca^{2+}$ Assay EC50 (μM) |
|---|---|---|
| 1 | 0.0362 | 0.1051 |
| 2 | 0.0008 | 0.0034 |

TABLE 3-continued

| Cpd | hGPR40 Ca$^{2+}$ Assay EC50 (μM) | rGPR40 Ca$^{2+}$ Assay EC50 (μM) |
|---|---|---|
| 3 | 0.0248 | 0.1601 |
| 4 | 0.0007 | 0.0026 |
| 5 | 0.0756 | 0.1463 |
| 6 | 0.3771 | NA |
| 7 | 0.0347 | 0.0798 |
| 8 | 0.0005 | 0.0014 |
| 9 | 0.0005 | 0.0028 |
| 10 | 0.0269 | 0.0760 |
| 11 | 0.0021 | 0.0184 |
| 12 | 0.0138 | 0.1519 |
| 13 | 0.0327 | 0.1430 |
| 14 | 1.5011 | NA |
| 15 | 0.1376 | NA |
| 16 | 3.0818 | NA |
| 17 | 0.0443 | 0.3878 |
| 18 | 0.2257 | NA |
| 19 | 0.0825 | 0.2109 |
| 20 | 0.0099 | 0.0407 |
| 21 | 0.0120 | 0.0353 |
| 22 | 0.0176 | 0.0519 |
| 23 | 0.3073 | NA |
| 24 | 0.0084 | 0.0207 |
| 25 | 0.0053 | 0.0013 |
| 26 | 0.0109 | 0.0198 |
| 27 | 0.0002 | 0.0009 |
| 28 | 0.0026 | 0.0061 |
| 29 | 0.0179 | 0.0409 |
| 30 | 0.0021 | 0.0294 |
| 31 | 0.0261 | 0.0542 |
| 32 | 0.0590 | 0.2557 |
| 33 | 0.0037 | 0.0173 |
| 34 | 0.0624 | 0.2820 |
| 35 | 1.8399 | 5.3248 |
| 36 | 0.0017 | 0.0092 |
| 37 | 0.6868 | 1.3201 |
| 38 | 0.0062 | 0.0156 |
| 39 | 0.5999 | 3.1528 |
| 40 | 0.0220 | 0.0210 |
| 41 | 0.0180 | 0.0430 |
| 42 | 3.1031 | 0.4010 |
| 43 | 0.2810 | 0.4640 |
| 44 | 0.0099 | 0.0290 |
| 45 | 0.2576 | 0.8551 |
| 46 | 5.8036 | >10 |
| 47 | 0.0715 | 0.1470 |
| 48 | 0.2121 | 0.6764 |
| 49 | 0.2442 | 1.1120 |
| 50 | 0.5001 | 0.6555 |
| 51 | 0.0022 | 0.0049 |
| 52 | 0.0002 | 0.0004 |
| 53 | 0.002 | 0.0077 |
| 54 | 0.0005 | 0.0014 |
| 55 | 0.1329 | 0.3458 |
| 56 | 0.003 | 0.0144 |
| 57 | 0.0005 | 0.0012 |
| 58 | 0.0003 | 0.00023 |
| 59 | 0.00027 | 0.00072 |
| 60 | 0.00605 | 0.00688 |
| 61 | 0.00025 | 0.00053 |
| 62 | 0.00025 | 0.00056 |
| 63 | 0.0326 | 0.08666 |
| 64 | 0.00019 | 0.00056 |
| 65 | 0.00059 | 0.00175 |
| 66 | 0.00025 | 0.0004 |
| 67 | 0.0017 | 0.012 |
| 68 | 0.00027 | 0.00222 |
| 69 | 0.0012 | 0.0015 |
| 70 | 0.00016 | 0.00015 |
| 71 | 0.0019 | 0.00236 |
| 72 | 0.00188 | 0.00248 |
| 73 | 0.00022 | 0.00046 |
| 74 | 0.01408 | 0.01621 |
| 75 | 0.00044 | 0.00893 |
| 76 | 0.00018 | 0.00071 |
| 77 | 0.00172 | 0.01036 |
| 78 | 0.0022 | 0.0055 |
| 79 | 0.013 | 0.028 |
| 80 | 0.079 | 0.22 |

In-Vivo Assay

Oral Glucose Tolerance Test. Version A

Male SD rats (200-250 g) were housed 2 per cage in a temperature-controlled room with a 12-hour light/dark cycle. They were allowed ad libitum access to water and fed with normal rodent chow. The night before the oral glucose tolerance test (oGTT), the rats were transferred to clean cages and fasted overnight. On the morning of the oGTT, the rats were weighed and randomized into groups based on fasted blood glucose and body weight. Rats were dosed with vehicle (0.5% methocel) or compounds thirty min prior to the oGTT (glucose, 2 g/kg, po). Blood was collected from the tail vein at 0, 10, 30, 60 and 120 minutes after glucose challenge to measure blood glucose; plasma was used to determine insulin levels. The area under the curve for blood glucose excursion was calculated from t=0 to t=120 minutes. Percent lowering of glucose was calculated from the AUC data with respect to the vehicle-treated group. Resultant data are shown in Table 4.

Oral Glucose Tolerance Test. Version B

Male ZDF rats (7 weeks old, 200-240 g) were housed 2 per cage in a temperature-controlled room with a 12-hour light/dark cycle. They were allowed ad libitum access to water and fed with 5008 rodent chow. The night before the oral glucose tolerance test (OGTT), the rats were transferred to clean cages and fasted overnight. On the morning of the OGTT, the rats were weighed and randomized into groups based on fasted blood glucose and body weight. Rats were dosed with vehicle (0.5% Methocel) or compound (10 mg/kg) 120 min prior to the OGTT (glucose, 1 g/kg, po). Blood was collected from the tail vein at 0, 10, 30, 60 and 120 minutes after glucose challenge to measure blood glucose; plasma was used to determine insulin levels. The area under the curve for blood glucose excursion was calculated from t=0 to t=120 minutes. Percent lowering of glucose was calculated from the AUC data with respect to the vehicle-treated group. Resultant data are shown in Table 4.

TABLE 4

| Cpd No. | Percent Lowering of Glucose (AUC compound vs. AUC Vehicle) | Assay Version |
|---|---|---|
| 1 | 11% | A |
| 2 | 33% | A |
| 25 | 28% | A |
| 27 | 32% | A |
| 59 | 48% | B |

Note:
AUC = Integrated area under the glucose excursion curve from t = 0 to t = 120 minutes.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

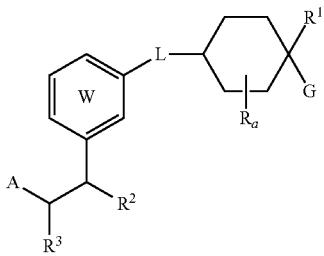

wherein
G is selected from the group consisting of g1, g2, g3, and g4

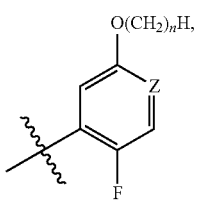

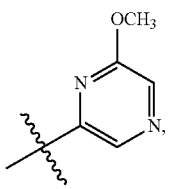

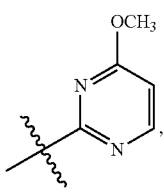

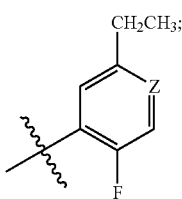

wherein Z is N or CH, and wherein n is an integer from 1 to 3;
$R^1$ is selected from the group consisting of hydrogen, hydroxy, methoxy, and fluoro;
$R_a$ is selected from hydrogen or $C_{1-4}$alkyl;
L is selected from the group consisting of —OCH$_2$—, —NHCH$_2$—, —(CH$_2$)$_2$—, and —CH=CH—;
ring W is phenyl or pyridinyl;
$R^2$ is C3-5cycloalkyl, methylacetylenyl, or ethoxy;
$R^3$ is hydrogen, methyl, trifluoromethyl, or fluoro;
A is carboxy or 1H-tetrazol-5-yl;
or an enantiomer, diastereomer, or pharmaceutically acceptable salt form thereof.

2. The compound of claim 1 wherein G is g1

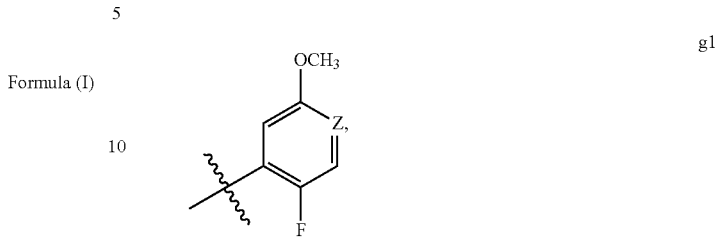

wherein Z is N or CH.

3. The compound of claim 2 wherein G is 2-fluoro-5-methoxyphenyl, 2-ethoxy-5-fluoropyridin-4-yl, or 5-fluoro-2-methoxypyridin-4-yl.

4. The compound of claim 3 wherein G is 2-fluoro-5-methoxyphenyl.

5. The compound of claim 1 wherein $R^1$ is selected from the group consisting of hydrogen, methoxy, and fluoro.

6. The compound of claim 2 wherein $R^1$ is selected from the group consisting of hydrogen, methoxy, and fluoro.

7. The compound of claim 6 wherein $R^1$ is hydrogen.

8. The compound of claim 1 wherein $R_a$ is selected from hydrogen, methyl, or isobutyl.

9. The compound of claim 8 wherein $R_a$ is hydrogen.

10. The compound of claim 1 wherein L is selected from the group consisting of
—OCH$_2$—, —(CH$_2$)$_2$—, and —CH=CH—.

11. The compound of claim 10 wherein L is —OCH$_2$—.

12. The compound of claim 1 wherein $R^2$ is cyclopropyl, methylacetylenyl, or ethoxy.

13. The compound of claim 1 wherein $R^2$ is $C_{3-5}$cycloalkyl.

14. The compound of claim 13 wherein $R^2$ is cyclopropyl.

15. The compound of claim 1 wherein $R^3$ is hydrogen, methyl, or fluoro.

16. The compound of claim 1 wherein ring W is phenyl.

17. The compound of claim 1 wherein ring W is pyridinyl.

18. The compound of claim 1 wherein A is carboxy.

19. A compound selected from the group consisting of
(S)-3-cyclopropyl-3-(3-(((1S,4R)-4-(2-fluoro-5-methoxyphenyl)cyclohexyl)methoxy)phenyl)propanoic acid;
(S)-3-cyclopropyl-3-(3-(((1R,4S)-4-(2-fluoro-5-methoxyphenyl)cyclohexyl)methoxy)phenyl) propanoic acid;
(S)-3-cyclopropyl-3-(3-(((1S,4R)-4-(2-fluoro-5-methoxyphenyl)-4-hydroxycyclohexyl)methoxy)phenyl)propanoic acid;
3-cyclopropyl-3-(2-(((1R,4R)-4-(2-fluoro-5-methoxyphenyl)cyclohexyl)methoxy)pyridin-4-yl)propionic acid;
3-cyclopropyl-3-(2-(((1 S,4S)-4-(2-fluoro-5-methoxyphenyl)cyclohexyl)methoxy)pyridin-4-yl)propionic acid;
(S)-3-cyclopropyl-3-(3-(((1R,4S)-4-(2-fluoro-5-methoxyphenyl)-4-hydroxycyclohexyl)methoxy)phenyl)propanoic acid;
3-cyclopropyl-3-(2-(((1S,4S)-4-(5-fluoro-2-methoxypyridin-4-yl)cyclohexyl)methoxy)pyridin-4-yl)propionic acid;

3-cyclopropyl-3-(2-(((1R,4R)-4-(5-fluoro-2-methoxy-pyridin-4-yl)cyclohexyl)methoxy)pyridin-4-yl)propionic acid;

(S)-3-cyclopropyl-3-(3-(((1R,4S)-4-(5-fluoro-2-methoxypyridin-4-yl)cyclohexyl)methoxy)phenyl)propanoic acid;

(S)-3-cyclopropyl-3-(3-(((1S,4R)-4-(5-fluoro-2-methoxypyridin-4-yl)cyclohexyl)methoxy)phenyl)propanoic acid;

(S)-3-cyclopropyl-3-(3-(((1S,4R)-4-(2-fluoro-5-methoxyphenyl)-4-methoxycyclohexyl)methoxy)phenyl)propanoic acid;

(S)-3-cyclopropyl-3-(3-(((1R,4S)-4-(2-fluoro-5-methoxyphenyl)-4-methoxycyclohexyl)methoxy) phenyl)propanoic acid;

3-cyclopropyl-3-(6-(((1R,4R)-4-(2-fluoro-5-methoxyphenyl) cyclohexyl)methoxy)pyridin-2-yl)propionic acid;

3-cyclopropyl-3-(6-(((1S,4S)-4-(2-fluoro-5-methoxyphenyl)cyclohexyl) methoxy)pyridin-2-yl)propionic acid;

3-cyclopropyl-3-(6-(((1R,4R)-4-(5-fluoro-2-methoxy-pyridin-4-yl)cyclohexyl)methoxy)pyridin-2-yl)propionic acid;

3-cyclopropyl-3-(6-(((1S,4S)-4-(5-fluoro-2-methoxy-pyridin-4-yl)cyclohexyl)methoxy)pyridin-2-yl)propionic acid;

5-((S)-2-cyclopropyl-2-(3-(((1r,4S)-4-(2-fluoro-5-ethoxyphenyl)cyclohexyl)methoxy)phenyl)ethyl)-1H-tetrazole;

3-cyclopropyl-3-(5-(((1S,4S)-4-(2-fluoro-5-methoxyphenyl)cyclohexyl)methoxy)pyridin-3-yl)propanoic acid;

(S)-3-cyclopropyl-3-(3-(((1R,4S)-4-fluoro-4-(2-fluoro-5-methoxyphenyl) cyclohexyl)methoxy)phenyl)propanoic acid;

(S)-3-cyclopropyl-3-(3-(((1R,4S)-4-fluoro-4-(2-fluoro-5-methoxyphenyl) cyclohexyl)methoxy)phenyl)propanoic acid;

3-cyclopropyl-3-(5-(((1R,4R)-4-(2-fluoro-5-methoxyphenyl)cyclohexyl)methoxy) pyridin-3-yl)propionic acid;

3-cyclopropyl-3-(5-(((1R,4R)-4-(5-fluoro-2-methoxy-pyridin-4-yl)cyclohexyl)methoxy)pyridin-3-yl)propionic acid;

3-cyclopropyl-3-(5-(((1S,4S)-4-(5-fluoro-2-methoxy-pyridin-4-yl)cyclohexyl) methoxy)pyridin-3-yl)propionic acid;

(R)-3-cyclopropyl-3-(2-(((1R,4R)-4-(5-fluoro-2-methoxypyridin-4-yl) cyclohexyl)methoxy)pyridin-4-yl)propanoic acid;

(S)-3-cyclopropyl-3-(2-(((1R,4S)-4-(5-fluoro-2-methoxypyridin-4-yl)cyclohexyl) methoxy)pyridin-4-yl)propanoic acid;

(R)-3-cyclopropyl-3-(2-(((1R,4R)-4-(2-fluoro-5-methoxyphenyl)cyclohexyl)methoxy) pyridin-4-yl)propanoic acid;

(S)-3-cyclopropyl-3-(2-(((1R,4S)-4-(2-fluoro-5-methoxyphenyl)cyclohexyl)methoxy) pyridin-4-yl)propanoic acid;

(R)-3-cyclopropyl-3-(3-(((1S,4S)-4-(2-fluoro-5-methoxyphenyl)cyclohexyl)methoxy) phenyl)propanoic acid;

(3S)-3-cyclopropyl-3-(3-((4-(2-fluoro-5-methoxyphenyl)-2-isobutylcyclohexyl) methoxy)phenyl)propanoic acid;

(3S)-3-cyclopropyl-3-(3-((4-(5-fluoro-2-methoxypyridin-4-yl)-2-isobutylcyclohexyl)methoxy)phenyl)propanoic acid;

3-cyclopropyl-3-(4-(((1R,4R)-4-(5-fluoro-2-methoxy-pyridin-4-yl) cyclohexyl)methoxy)pyridin-2-yl)propanoic acid;

3-cyclopropyl-3-(4-(((1S,4S)-4-(5-fluoro-2-methoxy-pyridin-4-yl) cyclohexyl)methoxy)pyridin-2-yl)propanoic acid;

(3S)-3-cyclopropyl-3-(3-((4-(5-fluoro-2-methoxypyridin-4-yl)-2-methylcyclohexyl) methoxy)phenyl)propanoic acid;

3-cyclopropyl-3-(4-(((1R,4R)-4-(2-fluoro-5-methoxy-phenyl)cyclohexyl)methoxy) pyridin-2-yl)propanoic acid;

3-cyclopropyl-3-(4-(((1S,4S)-4-(2-fluoro-5-methoxyphenyl)cyclohexyl)methoxy) pyridin-2-yl)propanoic acid;

(S)-3-cyclopropyl-3-(3-(2-((1R,4R)-4-(2-fluoro-5-methoxyphenyl)cyclohexyl)ethyl)phenyl)propanoic acid;

(R)-3-cyclopropyl-3-(3-(((1S,4S)-4-(2-fluoro-5-methoxyphenyl)cyclohexyl)methoxy) phenyl)propanoic acid;

(R)-3-cyclopropyl-3-(3-(((1R,4R)-4-(2-fluoro-5-methoxyphenyl)cyclohexyl) methoxy)phenyl)propanoic acid;

5-((S)-2-cyclopropyl-2-(3-(((1S,4R)-4-(2-fluoro-5-methoxyphenyl)cyclohexyl) methoxy)phenyl)ethyl)-1H-tetrazole;

(S)-3-cyclopropyl-3-(3-((((1R,4S)-4-(2-fluoro-5-methoxyphenyl)cyclohexyl)methyl) amino)phenyl)propanoic acid;

(R)-3-cyclopropyl-3-(2-(((1S,4S)-4-(2-fluoro-5-methoxyphenyl)cyclohexyl)methoxy) pyridin-4-yl)propanoic acid;

3-(3-(((1S,4S)-4-(2-fluoro-5-methoxyphenyl)cyclohexyl)methoxy)phenyl)hex-4-ynoic acid;

4-((1S,4r)-4-(((4-((S)-1-cyclopropyl-2-(1H-tetrazol-5-yl)ethyl)pyridin-2-yl) oxy)methyl)cyclohexyl)-5-fluoro-2-methoxypyridine;

(S)-3-cyclopropyl-3-(2-(((1S,4R)-4-(5-fluoro-2-methoxypyridin-4-yl)-4-methoxycyclohexyl)methoxy) pyridin-4-yl)propanoic acid;

(S)-3-cyclopropyl-3-(2-(((1R,4S)-4-(5-fluoro-2-methoxypyridin-4-yl)-4-methoxy cyclohexyl) methoxy)pyridin-4-yl)propanoic acid;

(S)-3-cyclopropyl-3-(2-((4-(6-methoxypyrazin-2-yl)cyclohexyl)methoxy)pyridin-4-yl)propanoic acid;

(S)-3-cyclopropyl-3-(3-((((1S,4R)-4-(2-fluoro-5-methoxyphenyl)cyclohexyl)methyl) amino)phenyl) propanoic acid;

(S)-3-cyclopropyl-3-(2-(((1S,4R)-4-(2-ethoxy-5-fluoro-pyridin-4-yl)cyclohexyl)methoxy) pyridin-4-yl)propanoic acid;

(3S)-3-cyclopropyl-3-[2-[[4-(4-methoxypyrimidin-2-yl)cyclohexyl]methoxy]-4-pyridyl]propanoic acid;

3-ethoxy-3-(3-(((1S,4S)-4-(2-fluoro-5-methoxyphenyl) cyclohexyl)methoxy)phenyl)propanoic acid;

(2R,3R)-3-cyclopropyl-3-(3-(((1R,4R)-4-(2-fluoro-5-methoxyphenyl)cyclohexyl) methoxy)phenyl)-2-methylpropanoic acid;

(2S,3R)-3-cyclopropyl-3-(3-(((1R,4R)-4-(2-fluoro-5-methoxyphenyl) cyclohexyl)methoxy)phenyl)-2-methylpropanoic acid;

(2S,3R)-3-cyclopropyl-3-(3-(((1S,4S)-4-(2-fluoro-5-methoxyphenyl)cyclohexyl) methoxy)phenyl)-2-methylpropanoic acid;

(3S)-3-cyclopropyl-2-fluoro-3-(3-(((1R,4S)-4-(2-fluoro-5-methoxyphenyl)cyclohexyl) methoxy)phenyl)propanoic acid;

3-cyclopropyl-3-(3-(((1S,4S)-4-(2-fluoro-5-methoxyphenyl)cyclohexyl)methoxy) phenyl)propanoic acid;

3-cyclopropyl-3-(3-(((1R,4R)-4-(2-fluoro-5-methoxyphenyl)cyclohexyl)methoxy) phenyl)propanoic acid; and (2S,3R)-3-cyclopropyl-3-(3-(((1R,4R)-4-(5-ethyl-2-fluorophenyl)cyclohexyl) methoxy)phenyl)-2-methylpropanoic acid;

or a pharmaceutically acceptable salt form thereof.

20. The compound of claim 19 that is (3S)-3-cyclopropyl-3-[3-[[4-(2-fluoro-5-methoxy-phenyl)cyclohexyl]methoxy]phenyl]propanoic acid, Cpd 2

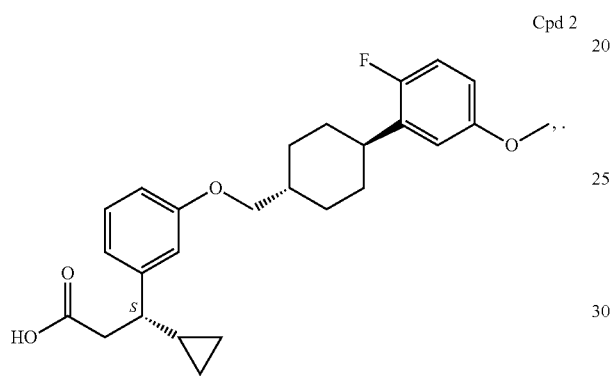

21. A pharmaceutical composition comprising a compound of claim 1 and at least one of a pharmaceutically acceptable carrier, a pharmaceutically acceptable excipient, and a pharmaceutically acceptable diluent.

22. A method of treating a disorder, wherein said disorder is affected by the agonism of the GPR40 receptor, comprising administering to a subject in need thereof a therapeutically effective amount of the compound of claim 1.

23. The method of claim 22 wherein said disorder is selected from the group consisting of Type II diabetes mellitus, obesity, obesity-related disorders, impaired glucose tolerance, insulin resistance, metabolic syndrome, diabetic nephropathy, nonalcoholic steatohepatitis (NASH), hypertension, cardiovascular risk factors related to unmanaged cholesterol and/or lipid levels, osteoporosis, inflammation, and eczema.

24. The method of claim 23 wherein said disorder is Type II diabetes mellitus.

25. A method of treating a disorder selected from the group consisting of Type II diabetes mellitus, obesity, obesity-related disorders, impaired glucose tolerance, insulin resistance, metabolic syndrome, diabetic nephropathy, nonalcoholic steatohepatitis (NASH), hypertension, cardiovascular risk factors related to unmanaged cholesterol and/or lipid levels, osteoporosis, inflammation, and eczema, comprising administering to a subject in need thereof a therapeutically effective amount of the compound of claim 1.

26. A compound of Formula (II)

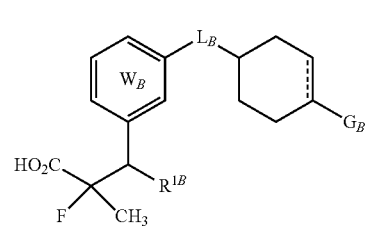

Formula (II)

wherein $G_B$ is selected from the group consisting of g1b, g2b, g3b, and g4b,

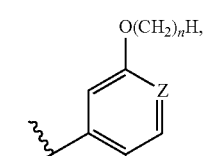

g1b

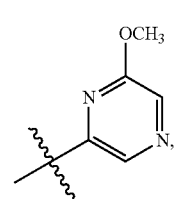

g2b

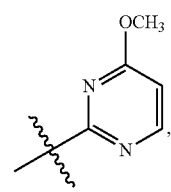

g3b

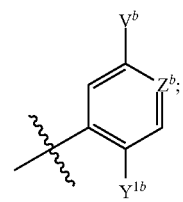

g4b wherein $Z^b$ is N or CH; n is an integer from 1 to 3;

$Y^b$ is independently selected from the group consisting of hydrogen, fluoro, chloro, methyl, trifluoromethoxy, and pyridin-2-ylaminocarbonyl;

$V^b$ is fluoro, trifluoromethoxy, or ethyl;

$Y^{1b}$ is independently selected from the group consisting of hydrogen, fluoro, chloro, methyl, trifluoromethoxy, and pyridin-2-ylaminocarbonyl;

ring $W_B$ is phenyl or pyridinyl, wherein $W_B$ is optionally independently substituted with one substituent selected from fluoro, chloro, or methyl;

$L_B$ is selected from the group consisting of —OCH$_2$—, —CH$_2$O—, —NHCH$_2$—, —(CH$_2$)$_2$—, and —CH═CH—;

‡ is an optional double bond in the $G_B$-substituted cyclohexyl ring;

$R^{1B}$ is $C_{3-5}$cycloalkyl or $C_{1-4}$alkyl;

or an enantiomer, diastereomer, or pharmaceutically acceptable salt form thereof.

27. The compound of claim 26 wherein $G_B$ is g1b

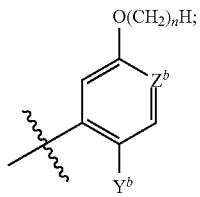

and wherein $Z^b$ is N or CH.

28. The compound of claim 26 wherein $G_B$ is 2-fluoro-5-methoxyphenyl, 2-chloro-5-methoxyphenyl, 2-fluoro-5-methoxypyridin-4-yl, 5-ethyl-2-fluorophenyl, 2,5-difluorophenyl, 2-chloro-5-ethylphenyl, 5-methoxy-2-(pyridin-2-ylcarbamoyl)phenyl, 2-fluoro-5-(trifluoromethoxy)phenyl, 2-ethoxy-5-fluoropyridin-4-yl, or 5-fluoro-2-methoxypyridin-4-yl.

29. The compound of claim 28 wherein $G_B$ is 2-fluoro-5-methoxyphenyl, 2-chloro-5-methoxyphenyl, or 2-fluoro-5-methoxypyridin-4-yl.

30. The compound of claim 26 wherein n is 1.

31. The compound of claim 26 wherein $L_B$ is —OCH$_2$— or —(CH$_2$)$_2$—.

32. The compound of claim 31 wherein $L_B$ is —OCH$_2$—.

33. The compound of claim 26 wherein ‡ is absent.

34. The compound of claim 26 wherein $R^{1B}$ is cyclopropyl.

35. The compound of claim 26 wherein ring $W_B$ is phenyl.

36. The compound of claim 26 wherein ring $W_B$ is pyridinyl.

37. A compound according to claim 26 selected from the group consisting of (3S)-3-cyclopropyl-2-fluoro-3-(3-((1R,4S)-4-(2-fluoro-5-methoxyphenyl)cyclohexyl)methoxy)phenyl)-2-methylpropanoic acid;

(2R,3S)-3-cyclopropyl-2-fluoro-3-(3-(((1R,4S)-4-(2-fluoro-5-methoxyphenyl) cyclohexyl)methoxy)phenyl)-2-methylpropanoic acid;

(2S,3S)-3-cyclopropyl-2-fluoro-3-(3-((1R,4S)-4-(2-fluoro-5-methoxyphenyl) cyclohexyl)methoxy)phenyl)-2-methylpropanoic acid;

(3S)-3-cyclopropyl-2-fluoro-3-(3-(((1R,4S)-4-(2-fluoro-5-methoxypyridin-4-yl)cyclohexyl)methoxy)phenyl)-2-methylpropanoic acid;

(2R,3S)-3-cyclopropyl-2-fluoro-3-(3-(((1R,4S)-4-(2-fluoro-5-methoxypyridin-4-yl)cyclohexyl)methoxy) phenyl)-2-methylpropanoic acid;

(2S,3S)-3-cyclopropyl-2-fluoro-3-(3-((1R,4S)-4-(2-fluoro-5-methoxypyridin-4-yl)cyclohexyl)methoxy) phenyl)-2-methylpropanoic acid;

(2R,3S)-3-(3-((4-(2-chloro-5-methoxyphenyl)cyclohexyl)methoxy)phenyl)-3-cyclopropyl-2-fluoro-2-methylpropanoic acid;

(3S)-3-(3-((4-(2-chloro-5-ethylphenyl)cyclohexyl)methoxy)phenyl)-3-cyclopropyl-2-fluoro-2-methylpropanoic acid;

(3S)-3-cyclopropyl-2-fluoro-3-(3-((4-(3-methoxyphenyl)cyclohexyl)methoxy) phenyl)-2-methylpropanoic acid;

(3S)-3-cyclopropyl-3-(3-((4-(2,5-difluoropyridin-4-yl)cyclohexyl)methoxy)phenyl)-2-fluoro-2-methylpropanoic acid;

(3S)-3-cyclopropyl-3-(3-((1R,4S)-4-(5-ethyl-2-fluorophenyl)cyclohexyl)methoxy)phenyl)-2-fluoro-2-methylpropanoic acid;

(3S)-3-cyclopropyl-2-fluoro-3-(3-((4-(2-methoxypyridin-4-yl)cyclohexyl)methoxy)phenyl)-2-methylpropanoic acid;

(3S)-3-cyclopropyl-2-fluoro-3-(3-((4-(5-methoxy-2-methylphenyl)cyclohexyl)methoxy)phenyl)-2-methylpropanoic acid;

(3S)-3-cyclopropyl-2-fluoro-3-(3-((4-(5-methoxy-2-(pyridin-2-ylcarbamoyl) phenyl)cyclohexyl)methoxy)phenyl)-2-methylpropanoic acid;

(3S)-3-cyclopropyl-2-fluoro-3-(3-((E)-2-((1R,4S)-4-(2-fluoro-5-methoxyphenyl)cyclohexyl)vinyl)phenyl)-2-methylpropanoic acid;

(3S)-3-cyclopropyl-2-fluoro-3-(3-(2-((1R,4R)-4-(2-fluoro-5-methoxyphenyl)cyclohexyl)ethyl)phenyl)-2-methylpropanoic acid;

(2R,3S)-3-cyclopropyl-2-fluoro-3-(3-(((1R,4S)-4-(2-fluoro-5-(trifluoromethoxy) phenyl)cyclohexyl) methoxy)phenyl)-2-methylpropanoic acid;

(2R,3S)-3-cyclopropyl-3-(3-((4-(2,5-difluorophenyl)cyclohexyl) methoxy)phenyl)-2-fluoro-2-methylpropanoic acid;

(2R,3S)-3-cyclopropyl-2-fluoro-3-(3-((2'-fluoro-5'-methoxy-2,3,4,5-tetrahydro-[1,1'-biphenyl]-4-yl) methoxy)phenyl)-2-methylpropanoic acid;

(3S)-3-cyclopropyl-2-fluoro-3-(3-((((1R,4S)-4-(2-fluoro-5-methoxyphenyl) cyclohexyl)methyl)amino)phenyl)-2-methylpropanoic acid;

(3S)-3-cyclopropyl-2-fluoro-3-(3-(((4-(2-fluoro-5-methoxyphenyl) cyclohxyl)oxy)methyl)phenyl)-2-methylpropanoic acid;

(3S)-3-cyclopropyl-2-fluoro-3-(2-(((1R,4S)-4-(2-fluoro-5-methoxyphenyl)cyclohexyl)methoxy)pyridin-4-yl)-2-methylpropanoic acid; and (3S)-3-cyclopropyl-2-fluoro-3-(2-(((1R,4S)-4-(5-fluoro-2-methoxypyridin-4-yl)cyclohexyl)methoxy)pyridin-4-yl)-2-methylpropanoic acid;

or a pharmaceutically acceptable salt form thereof.

38. The compound of claim 37 that is (2R,3S)-3-cyclopropyl-2-fluoro-3-(3-(((1R,4S)-4-(2-fluoro-5-methoxyphenyl)cyclohexyl)methoxy)phenyl)-2-methylpropanoic acid, Cpd 59.

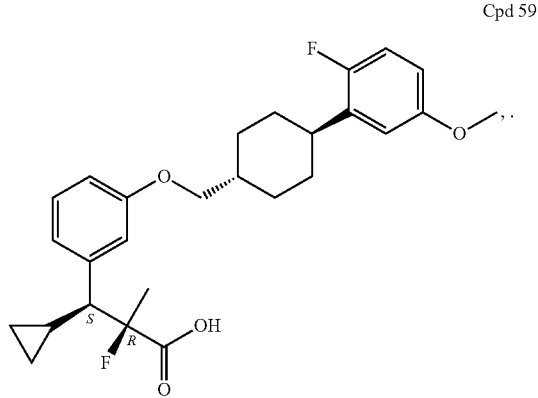

Cpd 59

39. A pharmaceutical composition comprising a compound of claim 26 and at least one of a pharmaceutically acceptable carrier, a pharmaceutically acceptable excipient, and a pharmaceutically acceptable diluent.

40. A pharmaceutical composition comprising a compound of claim 37 and at least one of a pharmaceutically acceptable carrier, a pharmaceutically acceptable excipient, and a pharmaceutically acceptable diluent.

41. A method of treating a disorder, wherein said disorder is affected by the agonism of the GPR40 receptor, comprising administering to a subject in need thereof a therapeutically effective amount of the compound of claim 26.

42. The method of claim 41 wherein said disorder is selected from the group consisting of Type II diabetes mellitus, obesity, obesity-related disorders, impaired glucose tolerance, insulin resistance, metabolic syndrome, diabetic nephropathy, nonalcoholic steatohepatitis (NASH), hypertension, cardiovascular risk factors related to unmanaged cholesterol and/or lipid levels, osteoporosis, inflammation, and eczema.

43. The method of claim 42 wherein said disorder is Type II diabetes mellitus.

44. A method of treating a disorder selected from the group consisting of Type II diabetes mellitus, obesity, obesity-related disorders, impaired glucose tolerance, insulin resistance, metabolic syndrome, diabetic nephropathy, nonalcoholic steatohepatitis (NASH), hypertension, cardiovascular risk factors related to unmanaged cholesterol and/or lipid levels, osteoporosis, inflammation, and eczema, comprising administering to a subject in need thereof a therapeutically effective amount of the compound of claim 26.

* * * * *